United States Patent
Zhang et al.

(10) Patent No.: US 11,673,954 B2
(45) Date of Patent: Jun. 13, 2023

(54) SINGLE-DOMAIN ANTIBODIES AND VARIANTS THEREOF AGAINST PD-L1

(71) Applicant: NANJING LEGEND BIOTECH CO., LTD., Jiangsu (CN)

(72) Inventors: Yafeng Zhang, Jiangsu (CN); Shu Wu, Jiangsu (CN); Shuai Yang, Jiangsu (CN); Chuan-Chu Chou, Westfield, NJ (US)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 227 days.

(21) Appl. No.: 16/764,411

(22) PCT Filed: Nov. 13, 2018

(86) PCT No.: PCT/CN2018/115213
§ 371 (c)(1),
(2) Date: May 15, 2020

(87) PCT Pub. No.: WO2019/096121
PCT Pub. Date: May 23, 2019

(65) Prior Publication Data
US 2021/0221891 A1 Jul. 22, 2021

(30) Foreign Application Priority Data
Nov. 17, 2017 (WO) ................ PCT/CN2017/111712

(51) Int. Cl.
*C07K 16/28* (2006.01)
*A61K 39/00* (2006.01)
*A61P 35/00* (2006.01)
*A61K 39/395* (2006.01)
*A61K 45/06* (2006.01)

(52) U.S. Cl.
CPC ...... *C07K 16/2827* (2013.01); *A61K 39/3955* (2013.01); *A61K 45/06* (2013.01); *A61P 35/00* (2018.01); *A61K 2039/505* (2013.01); *C07K 2317/21* (2013.01); *C07K 2317/22* (2013.01); *C07K 2317/24* (2013.01); *C07K 2317/31* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2017/0198050 A1* 7/2017 Eckelman .......... C07K 16/2827

FOREIGN PATENT DOCUMENTS

| CN | 106243225 A | 12/2016 |
|---|---|---|
| CN | 106939047 A | 7/2017 |
| CN | 107216389 A | 9/2017 |
| WO | 2017020801 A1 | 2/2017 |
| WO | 2017196867 A1 | 11/2017 |

OTHER PUBLICATIONS

International Search Report dated Feb. 12, 2019 in International Application No. PCT/CN2018/115213.
Zhang et al., "Structural basis of a novel PD-L1 nanobody for immune checkpoint blockade," Cell Discovery, vol. 3, No. 17004, pp. 1-12 (2017).

* cited by examiner

*Primary Examiner* — Marianne P Allen
(74) *Attorney, Agent, or Firm* — Fish & Richardson P.C.

(57) ABSTRACT

The present application provides constructs comprising a single-domain antibody (sdAb) moiety that specifically recognizes PD-L1. Also provided are methods of making and using these constructs.

19 Claims, 44 Drawing Sheets
Specification includes a Sequence Listing.

```
                  1         10         20         30         40         50         60         70         80         90        100        110       124
AS06617-WT    (1) DVQLVESGGGLVQPGSLRLSCAASGRTFTSYAVGWFRQAPGKEREFVAGIRWSGIHTDYADSVKGRFTISRDNAKNTVYLQMSLKPEDTAVYYCAAHRTIATIPEKYEYEYWGQGTQVTVSS
AS06617VH11   (1) EVQLVESGGGLVQPGSLRLSCAASGRTFTSYAVGWFRQAPGKEREFVAGIRWSGIHTDYADSVKGRFTISRDNAKNTLYLQMSLRPEDTAVYYCAAHRTIATIPEKYEYEYWGQGTLVTVSS
AS06617VH11   (1) DVQLVESGGGLVQPGSLRLSCAASGRTFTSYAVGWFRQAPGKEREFVSGIRWSGIHTDYADSVKGRFTISRDNAKNTLYLQMSLRPEDTAVYYCAAHRTIATIPEKYEYEYWGQGTLVTVSS
Consensus     (1)  DVQLVESGGGLVQ G SLRLSCAASGRTFTSYAVGWFRQAPG   REFVAGIRW  GIHTDYADSVKGRFTISRDNAKNTL L M SLKPEDTAVYYCAAHRTIATIPEKYEYEYWGQGT VTVSS
```

FIGURE 9D

```
AS06775-WT    (1)  1  VQLVESGGGLVQPGGSLRLSCAASGRTFLTILAVGWFRQAPGKREFVAGIRWSGSGTDYADSVKGRFTISRDNAKNTVYLQMNSLKPEDTAVYYCAAHTIATIPEKYEYEYWGQGTQVTVSS
AS06775VH11   (1)  1  VQLVESGGGLVQPGGSLRLSCAASGRTFLTILAVGWFRQAPGKREFVAGIRWSGSGTDYADSVKGRFTISRDNAKNTVYLQMNSLRPEDTAVYYCAAHTIATIPEKYEYEYWGQGTLVTVSS
AS06775VH11   (1)  1  VQLVESGGGLVQPGGSLRLSCAASGRTFLTILAVGWFRQAPGKREFVAGIRWSGSGTDYADSVKGRFTISRDNAKNTVYLQMNSLRPEDTAVYYCAAHTIATIPEKYEYEYWGQGTLVTVSS
Consensus     (1)     VQLVESGGGLVQ G SLRLSCAASGRTFLTILAVGWFRQAPG  REFVAGIRWSGSGTDYADSVKGRFTISRDNAKNTVYLQMNSL PEDTAVYYCAAHTIATIPEKYEYEYWG  GT VTVSS
```

AS11948SV12M9 ated sequence listing with a file name
SINGLE-DOMAIN ANTIBODIES AND VARIANTS THEREOF AGAINST PD-L1

CROSS-REFERENCE TO RELATED APPLICATION

This application is a Section 371 of International Application No. PCT/CN2018/115213, filed on Nov. 13, 2018, which published in the English language on May 23, 2019 under International Publication No. WO 2019/096121 A1, which claims priority to Chinese Application No. PCT/CN2017/111712, filed on Nov. 17, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII format"065782_4US1_Sequence_Listing" and a creation date of May 1, 2020 and having a size of 277,578 bytes. The sequence listing submitted via EFS-Web is part of the specification and is herein incorporated by reference in its entirety.

FIELD OF THE INVENTION

The present invention relates to constructs comprising a single-domain antibody (sdAb) moiety that specifically recognizes PD-L1, and methods of making and using thereof.

BACKGROUND OF THE INVENTION

An immune inhibitory receptor that is primarily expressed on activated T and B cells, Programmed Cell Death Receptor 1, also referred to as Programmed Death Receptor 1 (PD-1), is a member of the immunoglobulin superfamily related to CD28 and cytotoxic T-lymphocyte associated protein-4 (CTLA-4). PD-1 and like family members are type I transmembrane glycoproteins containing an extracellular Ig Variable-type (V-type) domain that binds its ligands and a cytoplasmic tail that binds signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

PD-1 attenuates T-cell responses when bound to Programmed Cell Death Ligand 1, also referred to as Programmed Death Ligand 1 (PD-L1), and/or Programmed Cell Death Ligand 2, also referred to as Programmed Death Ligand 2 (PD-L2). The binding of either of these ligands to PD-1 negatively regulates antigen receptor signaling. Blocking the binding of PD-L1 to PD-1 enhances tumor-specific CD8+ T-cell immunity, while aiding the clearance of tumor cells by the immune system.

As a result, therapeutic targeting PD-1 and other molecules which signal through interactions with PD-1, such as programmed death ligand 1 (PD-L1) and programmed death ligand 2 (PD-L2) are an area of intense interest. The inhibition of PD-L1 signaling has been proposed as a means to enhance T cell immunity for the treatment of cancer (e.g., tumor immunity) and infection, including both acute and chronic (e.g., persistent) infection. However, as an optimal therapeutic directed to a target in this pathway has yet to be commercialized, a significant unmet medical need exists. Anti-PD-L1 antibody therapy has shown promise in a number of cancers, such as melanoma.

Single-chain antibodies (sdAbs) are different from conventional 4-chain antibodies by having a single monomeric antibody variable domain. For example, camelids and sharks produce single-domain antibodies named heavy chain-only antibodies (HCAbs), which naturally lack light chains. The antigen-binding fragment in each arm of the camelid HCAb has a single heavy chain variable domain ($V_HH$), which can exhibit high affinity to an antigen without the aid of a light chain. Camelid $V_HH$ is known as the smallest functional antigen-binding fragment with a molecular weight of approximately 15 kD.

The disclosures of all publications, patents, patent applications and published patent applications referred to herein are hereby incorporated herein by reference in their entirety.

BRIEF SUMMARY OF THE INVENTION

The present invention relates to constructs comprising a single-domain antibody (sdAb) moiety that specifically recognizes PD-L1, and methods of making and using thereof.

One aspect of the present application provides an isolated anti-PD-L1 construct comprising a sdAb moiety specifically recognizing PD-L1, wherein the sdAb moiety comprises a CDR1 comprising the amino acid sequence of any one of SEQ ID NOs: 51-100, or a variant thereof comprising up to about 3 (such as about any of 1, 2, or 3) amino acid substitutions; a CDR2 comprising the amino acid sequence of any one of SEQ ID NOs: 151-200, or a variant thereof comprising up to about 3 (such as about any of 1, 2, or 3) amino acid substitutions; and a CDR3 comprising the amino acid sequence of any one of SEQ ID NOs: 251-300, or a variant thereof comprising up to about 3 (such as about any of 1, 2, or 3) amino acid substitutions.

In some embodiments according to any one of the isolated anti-PD-L1 constructs described above, the sdAb moiety specifically recognizing PD-L1 comprises a CDR1 comprising the amino acid sequence of any one of SEQ ID NOs: 51-100; a CDR2 comprising the amino acid sequence of any one of SEQ ID NOs: 151-200; and a CDR3 comprising the amino acid sequence of any one of SEQ ID NOs: 251-300.

In some embodiments according to any one of the isolated anti-PD-L1 constructs described above, the sdAb moiety specifically recognizing PD-L1 comprises any one of the following:

(1) a CDR1 comprising the amino acid sequence of SEQ ID NO: 51, or a variant thereof comprising up to about 3 (such as about any of 1, 2, or 3) amino acid substitutions; a CDR2 comprising the amino acid sequence of SEQ ID NO: 151, or a variant thereof comprising up to about 3 (such as about any of 1, 2, or 3) amino acid substitutions; and a CDR3 comprising the amino acid sequence of SEQ ID NO: 251, or a variant thereof comprising up to about 3 (such as about any of 1, 2, or 3) amino acid substitutions;

(2) a CDR1 comprising the amino acid sequence of SEQ ID NO: 52, or a variant thereof comprising up to about 3 (such as about any of 1, 2, or 3) amino acid substitutions; a CDR2 comprising the amino acid sequence of SEQ ID NO: 152, or a variant thereof comprising up to about 3 (such as about any of 1, 2, or 3) amino acid substitutions; and a CDR3 comprising the amino acid sequence of SEQ ID NO: 252, or a variant thereof comprising up to about 3 (such as about any of 1, 2, or 3) amino acid substitutions;

(3) a CDR1 comprising the amino acid sequence of SEQ ID NO: 53, or a variant thereof comprising up to about 3 (such as about any of 1, 2, or 3) amino acid substitutions; a CDR2 comprising the amino acid sequence of SEQ ID NO: 153, or a variant thereof comprising up to about 3 (such as about any of 1, 2, or 3) amino acid substitutions; and a CDR3 comprising the amino acid sequence of SEQ ID NO: 253, or a variant thereof comprising up to about 3 (such as about any of 1, 2, or 3) amino acid substitutions;

(4) a CDR1 comprising the amino acid sequence of SEQ ID NO: 54, or a variant thereof comprising up to about 3 (such as about any of 1, 2, or 3) amino acid substitutions; a CDR2 comprising the amino acid sequence of SEQ ID NO: 154, or a variant thereof comprising up to about 3 (such as about any of 1, 2, or 3) amino acid substitutions; and a CDR3 comprising the amino acid sequence of SEQ ID NO: 254, or a variant thereof comprising up to about 3 (such as about any of 1, 2, or 3) amino acid substitutions;

(5) a CDR1 comprising the amino acid sequence of SEQ ID NO: 55, or a variant thereof comprising up to about 3 (such as about any of 1, 2, or 3) amino acid substitutions; a CDR2 comprising the amino acid sequence of SEQ ID NO: 155, or a variant thereof comprising up to amino acid sequence of SEQ ID NO: 255, or a variant thereof comprising up to about 3 (such as about any of 1, 2, or 3) amino acid substitutions;

(6) a CDR1 comprising the amino acid sequence of SEQ ID NO: 56, or a variant thereof comprising up to about 3 (such as about any of 1, 2, or 3) amino acid substitutions; a CDR2 comprising the amino acid sequence of SEQ ID NO: 156, or a variant thereof comprising up to about 3 (such as about any of 1, 2, or 3) amino acid substitutions; and a CDR3 comprising the amino acid sequence of SEQ ID NO: 256, or a variant thereof comprising up to about 3 (such as about any of 1, 2, or 3) amino acid substitutions;

(7) a CDR1 comprising the amino acid sequence of SEQ ID NO: 57, or a variant thereof comprising up to about 3 (such as about any of 1, 2, or 3) amino acid substitutions; a CDR2 comprising the amino acid sequence of SEQ ID NO: 157, or a variant thereof comprising up to about 3 (such as about any of 1, 2, or 3) amino acid substitutions; and a CDR3 comprising the amino acid sequence of SEQ ID NO: 257, or a variant thereof comprising up to about 3 (such as about any of 1, 2, or 3) amino acid substitutions;

(8) a CDR1 comprising the amino acid sequence of SEQ ID NO: 58, or a variant thereof comprising up to about 3 (such as about any of 1, 2, or 3) amino acid substitutions; a CDR2 comprising the amino acid sequence of SEQ ID NO: 158, or a variant thereof comprising up to about 3 (such as about any of 1, 2, or 3) amino acid substitutions; and a CDR3 comprising the amino acid sequence of SEQ ID NO: 258, or a variant thereof comprising up to about 3 (such as about any of 1, 2, or 3) amino acid substitutions;

(9) a CDR1 comprising the amino acid sequence of SEQ ID NO: 59, or a variant thereof comprising up to about 3 (such as about any of 1, 2, or 3) amino acid substitutions; a CDR2 comprising the amino acid sequence of SEQ ID NO: 159, or a variant thereof comprising up to about 3 (such as about any of 1, 2, or 3) amino acid substitutions; and a CDR3 comprising the amino acid sequence of SEQ ID NO: 259, or a variant thereof comprising up to about 3 (such as about any of 1, 2, or 3) amino acid substitutions;

(10) a CDR1 comprising the amino acid sequence of SEQ ID NO: 60, or a variant thereof comprising up to about 3 (such as about any of 1, 2, or 3) amino acid substitutions; a CDR2 comprising the amino acid sequence of SEQ ID NO: 160, or a variant thereof comprising up to amino acid sequence of SEQ ID NO: 260, or a variant thereof comprising up to about 3 (such as about any of 1, 2, or 3) amino acid substitutions;

(11) a CDR1 comprising the amino acid sequence of SEQ ID NO: 61, or a variant thereof comprising up to about 3 (such as about any of 1, 2, or 3) amino acid substitutions; a CDR2 comprising the amino acid sequence of SEQ ID NO: 161, or a variant thereof comprising up to about 3 (such as about any of 1, 2, or 3) amino acid substitutions; and a CDR3 comprising the amino acid sequence of SEQ ID NO: 261, or a variant thereof comprising up to about 3 (such as about any of 1, 2, or 3) amino acid substitutions;

(12) a CDR1 comprising the amino acid sequence of SEQ ID NO: 62, or a variant thereof comprising up to about 3 (such as about any of 1, 2, or 3) amino acid substitutions; a CDR2 comprising the amino acid sequence of SEQ ID NO: 162, or a variant thereof comprising up to about 3 (such as about any of 1, 2, or 3) amino acid substitutions; and a CDR3 comprising the amino acid sequence of SEQ ID NO: 262, or a variant thereof comprising up to about 3 (such as about any of 1, 2, or 3) amino acid substitutions;

(13) a CDR1 comprising the amino acid sequence of SEQ ID NO: 63, or a variant thereof comprising up to about 3 (such as about any of 1, 2, or 3) amino acid substitutions; a CDR2 comprising the amino acid sequence of SEQ ID NO: 163, or a variant thereof comprising up to about 3 (such as about any of 1, 2, or 3) amino acid substitutions; and a CDR3 comprising the amino acid sequence of SEQ ID NO: 263, or a variant thereof comprising up to about 3 (such as about any of 1, 2, or 3) amino acid substitutions;

(14) a CDR1 comprising the amino acid sequence of SEQ ID NO: 64, or a variant thereof comprising up to about 3 (such as about any of 1, 2, or 3) amino acid substitutions; a CDR2 comprising the amino acid sequence of SEQ ID NO: 164, or a variant thereof comprising up to about 3 (such as about any of 1, 2, or 3) amino acid substitutions; and a CDR3 comprising the amino acid sequence of SEQ ID NO: 264, or a variant thereof comprising up to about 3 (such as about any of 1, 2, or 3) amino acid substitutions;

(15) a CDR1 comprising the amino acid sequence of SEQ ID NO: 65, or a variant thereof comprising up to about 3 (such as about any of 1, 2, or 3) amino acid substitutions; a CDR2 comprising the amino acid sequence of SEQ ID NO: 165, or a variant thereof comprising up to amino acid sequence of SEQ ID NO: 265, or a variant thereof comprising up to about 3 (such as about any of 1, 2, or 3) amino acid substitutions;

(16) a CDR1 comprising the amino acid sequence of SEQ ID NO: 66, or a variant thereof comprising up to about 3 (such as about any of 1, 2, or 3) amino acid substitutions; a CDR2 comprising the amino acid sequence of SEQ ID NO: 166, or a variant thereof comprising up to about 3 (such as about any of 1, 2, or 3) amino acid substitutions; and a CDR3 comprising the amino acid sequence of SEQ ID NO: 266, or a variant thereof comprising up to about 3 (such as about any of 1, 2, or 3) amino acid substitutions;

(17) a CDR1 comprising the amino acid sequence of SEQ ID NO: 67, or a variant thereof comprising up to about 3 (such as about any of 1, 2, or 3) amino acid substitutions; a CDR2 comprising the amino acid sequence of SEQ ID NO: 167, or a variant thereof comprising up to about 3 (such as about any of 1, 2, or 3) amino acid substitutions; and a CDR3 comprising the amino acid sequence of SEQ ID NO: 267, or a variant thereof comprising up to about 3 (such as about any of 1, 2, or 3) amino acid substitutions;

(18) a CDR1 comprising the amino acid sequence of SEQ ID NO: 68, or a variant thereof comprising up to about 3 (such as about any of 1, 2, or 3) amino acid substitutions; a CDR2 comprising the amino acid sequence of SEQ ID NO: 168, or a variant thereof comprising up to about 3 (such as about any of 1, 2, or 3) amino acid substitutions; and a CDR3 comprising the amino acid sequence of SEQ ID NO: 268, or a variant thereof comprising up to about 3 (such as about any of 1, 2, or 3) amino acid substitutions;

(19) a CDR1 comprising the amino acid sequence of SEQ ID NO: 69, or a variant thereof comprising up to about 3 (such as about any of 1, 2, or 3) amino acid substitutions; a CDR2 comprising the amino acid sequence of SEQ ID NO: 169, or a variant thereof comprising up to about 3 (such as about any of 1, 2, or 3) amino acid substitutions; and a CDR3 comprising the amino acid sequence of SEQ ID NO: 269, or a variant thereof comprising up to about 3 (such as about any of 1, 2, or 3) amino acid substitutions;

(20) a CDR1 comprising the amino acid sequence of SEQ ID NO: 70, or a variant thereof comprising up to about 3 (such as about any of 1, 2, or 3) amino acid substitutions; a CDR2 comprising the amino acid sequence of SEQ ID NO: 170, or a variant thereof comprising up to amino acid sequence of SEQ ID NO: 270, or a variant thereof comprising up to about 3 (such as about any of 1, 2, or 3) amino acid substitutions;

(21) a CDR1 comprising the amino acid sequence of SEQ ID NO: 71, or a variant thereof comprising up to about 3 (such as about any of 1, 2, or 3) amino acid substitutions; a CDR2 comprising the amino acid sequence of SEQ ID NO: 171, or a variant thereof comprising up to about 3 (such as about any of 1, 2, or 3) amino acid substitutions; and a CDR3 comprising the amino acid sequence of SEQ ID NO: 271, or a variant thereof comprising up to about 3 (such as about any of 1, 2, or 3) amino acid substitutions;

(22) a CDR1 comprising the amino acid sequence of SEQ ID NO: 72, or a variant thereof comprising up to about 3 (such as about any of 1, 2, or 3) amino acid substitutions; a CDR2 comprising the amino acid sequence of SEQ ID NO: 172, or a variant thereof comprising up to about 3 (such as about any of 1, 2, or 3) amino acid substitutions; and a CDR3 comprising the amino acid sequence of SEQ ID NO: 272, or a variant thereof comprising up to about 3 (such as about any of 1, 2, or 3) amino acid substitutions;

(23) a CDR1 comprising the amino acid sequence of SEQ ID NO: 73, or a variant thereof comprising up to about 3 (such as about any of 1, 2, or 3) amino acid substitutions; a CDR2 comprising the amino acid sequence of SEQ ID NO: 173, or a variant thereof comprising up to about 3 (such as about any of 1, 2, or 3) amino acid substitutions; and a CDR3 comprising the amino acid sequence of SEQ ID NO: 273, or a variant thereof comprising up to about 3 (such as about any of 1, 2, or 3) amino acid substitutions;

(24) a CDR1 comprising the amino acid sequence of SEQ ID NO: 74, or a variant thereof comprising up to about 3 (such as about any of 1, 2, or 3) amino acid substitutions; a CDR2 comprising the amino acid sequence of SEQ ID NO: 174, or a variant thereof comprising up to about 3 (such as about any of 1, 2, or 3) amino acid substitutions; and a CDR3 comprising the amino acid sequence of SEQ ID NO: 274, or a variant thereof comprising up to about 3 (such as about any of 1, 2, or 3) amino acid substitutions;

(25) a CDR1 comprising the amino acid sequence of SEQ ID NO: 75, or a variant thereof comprising up to about 3 (such as about any of 1, 2, or 3) amino acid substitutions; a CDR2 comprising the amino acid sequence of SEQ ID NO: 175, or a variant thereof comprising up to amino acid sequence of SEQ ID NO: 275, or a variant thereof comprising up to about 3 (such as about any of 1, 2, or 3) amino acid substitutions;

(26) a CDR1 comprising the amino acid sequence of SEQ ID NO: 76, or a variant thereof comprising up to about 3 (such as about any of 1, 2, or 3) amino acid substitutions; a CDR2 comprising the amino acid sequence of SEQ ID NO: 176, or a variant thereof comprising up to about 3 (such as about any of 1, 2, or 3) amino acid substitutions; and a CDR3 comprising the amino acid sequence of SEQ ID NO: 276, or a variant thereof comprising up to about 3 (such as about any of 1, 2, or 3) amino acid substitutions;

(27) a CDR1 comprising the amino acid sequence of SEQ ID NO: 77, or a variant thereof comprising up to about 3 (such as about any of 1, 2, or 3) amino acid substitutions; a CDR2 comprising the amino acid sequence of SEQ ID NO: 177, or a variant thereof comprising up to about 3 (such as about any of 1, 2, or 3) amino acid substitutions; and a CDR3 comprising the amino acid sequence of SEQ ID NO: 277, or a variant thereof comprising up to about 3 (such as about any of 1, 2, or 3) amino acid substitutions;

(28) a CDR1 comprising the amino acid sequence of SEQ ID NO: 78, or a variant thereof comprising up to about 3 (such as about any of 1, 2, or 3) amino acid substitutions; a CDR2 comprising the amino acid sequence of SEQ ID NO: 178, or a variant thereof comprising up to about 3 (such as about any of 1, 2, or 3) amino acid substitutions; and a CDR3 comprising the amino acid sequence of SEQ ID NO: 278, or a variant thereof comprising up to about 3 (such as about any of 1, 2, or 3) amino acid substitutions;

(29) a CDR1 comprising the amino acid sequence of SEQ ID NO: 79, or a variant thereof comprising up to about 3 (such as about any of 1, 2, or 3) amino acid substitutions; a CDR2 comprising the amino acid sequence of SEQ ID NO: 179, or a variant thereof comprising up to about 3 (such as about any of 1, 2, or 3) amino acid substitutions; and a CDR3 comprising the amino acid sequence of SEQ ID NO: 279, or a variant thereof comprising up to about 3 (such as about any of 1, 2, or 3) amino acid substitutions;

(30) a CDR1 comprising the amino acid sequence of SEQ ID NO: 80, or a variant thereof comprising up to about 3 (such as about any of 1, 2, or 3) amino acid substitutions; a CDR2 comprising the amino acid sequence of SEQ ID NO: 180, or a variant thereof comprising up to amino acid sequence of SEQ ID NO: 280, or a variant thereof comprising up to about 3 (such as about any of 1, 2, or 3) amino acid substitutions;

(31) a CDR1 comprising the amino acid sequence of SEQ ID NO: 81, or a variant thereof comprising up to about 3 (such as about any of 1, 2, or 3) amino acid substitutions; a CDR2 comprising the amino acid sequence of SEQ ID NO: 181, or a variant thereof comprising up to about 3 (such as about any of 1, 2, or 3) amino acid substitutions; and a CDR3 comprising the amino acid sequence of SEQ ID NO: 281, or a variant thereof comprising up to about 3 (such as about any of 1, 2, or 3) amino acid substitutions;

(32) a CDR1 comprising the amino acid sequence of SEQ ID NO: 82, or a variant thereof comprising up to about 3 (such as about any of 1, 2, or 3) amino acid substitutions; a CDR2 comprising the amino acid sequence of SEQ ID NO: 182, or a variant thereof comprising up to about 3 (such as about any of 1, 2, or 3) amino acid substitutions; and a CDR3 comprising the amino acid sequence of SEQ ID NO: 282, or a variant thereof comprising up to about 3 (such as about any of 1, 2, or 3) amino acid substitutions;

(33) a CDR1 comprising the amino acid sequence of SEQ ID NO: 83, or a variant thereof comprising up to about 3 (such as about any of 1, 2, or 3) amino acid substitutions; a CDR2 comprising the amino acid sequence of SEQ ID NO: 183, or a variant thereof comprising up to about 3 (such as about any of 1, 2, or 3) amino acid substitutions; and a CDR3 comprising the amino acid sequence of SEQ ID NO: 283, or a variant thereof comprising up to about 3 (such as about any of 1, 2, or 3) amino acid substitutions;

(34) a CDR1 comprising the amino acid sequence of SEQ ID NO: 84, or a variant thereof comprising up to about 3 (such as about any of 1, 2, or 3) amino acid substitutions; a CDR2 comprising the amino acid sequence of SEQ ID NO: 184, or a variant thereof comprising up to about 3 (such as about any of 1, 2, or 3) amino acid substitutions; and a CDR3 comprising the amino acid sequence of SEQ ID NO: 284, or a variant thereof comprising up to about 3 (such as about any of 1, 2, or 3) amino acid substitutions;

(35) a CDR1 comprising the amino acid sequence of SEQ ID NO: 85, or a variant thereof comprising up to about 3 (such as about any of 1, 2, or 3) amino acid substitutions; a CDR2 comprising the amino acid sequence of SEQ ID NO: 185, or a variant thereof comprising up to amino acid sequence of SEQ ID NO: 285, or a variant thereof comprising up to about 3 (such as about any of 1, 2, or 3) amino acid substitutions;

(36) a CDR1 comprising the amino acid sequence of SEQ ID NO: 86, or a variant thereof comprising up to about 3 (such as about any of 1, 2, or 3) amino acid substitutions; a CDR2 comprising the amino acid sequence of SEQ ID NO: 186, or a variant thereof comprising up to about 3 (such as about any of 1, 2, or 3) amino acid substitutions; and a CDR3 comprising the amino acid sequence of SEQ ID NO: 286, or a variant thereof comprising up to about 3 (such as about any of 1, 2, or 3) amino acid substitutions;

(37) a CDR1 comprising the amino acid sequence of SEQ ID NO: 87, or a variant thereof comprising up to about 3 (such as about any of 1, 2, or 3) amino acid substitutions; a CDR2 comprising the amino acid sequence of SEQ ID NO: 187, or a variant thereof comprising up to about 3 (such as about any of 1, 2, or 3) amino acid substitutions; and a CDR3 comprising the amino acid sequence of SEQ ID NO: 287, or a variant thereof comprising up to about 3 (such as about any of 1, 2, or 3) amino acid substitutions;

(38) a CDR1 comprising the amino acid sequence of SEQ ID NO: 88, or a variant thereof comprising up to about 3 (such as about any of 1, 2, or 3) amino acid substitutions; a CDR2 comprising the amino acid sequence of SEQ ID NO: 188, or a variant thereof comprising up to about 3 (such as about any of 1, 2, or 3) amino acid substitutions; and a CDR3 comprising the amino acid sequence of SEQ ID NO: 288, or a variant thereof comprising up to about 3 (such as about any of 1, 2, or 3) amino acid substitutions;

(39) a CDR1 comprising the amino acid sequence of SEQ ID NO: 89, or a variant thereof comprising up to about 3 (such as about any of 1, 2, or 3) amino acid substitutions; a CDR2 comprising the amino acid sequence of SEQ ID NO: 189, or a variant thereof comprising up to about 3 (such as about any of 1, 2, or 3) amino acid substitutions; and a CDR3 comprising the amino acid sequence of SEQ ID NO: 289, or a variant thereof comprising up to about 3 (such as about any of 1, 2, or 3) amino acid substitutions;

(40) a CDR1 comprising the amino acid sequence of SEQ ID NO: 90, or a variant thereof comprising up to about 3 (such as about any of 1, 2, or 3) amino acid substitutions; a CDR2 comprising the amino acid sequence of SEQ ID NO: 190, or a variant thereof comprising up to amino acid sequence of SEQ ID NO: 290, or a variant thereof comprising up to about 3 (such as about any of 1, 2, or 3) amino acid substitutions;

(41) a CDR1 comprising the amino acid sequence of SEQ ID NO: 91, or a variant thereof comprising up to about 3 (such as about any of 1, 2, or 3) amino acid substitutions; a CDR2 comprising the amino acid sequence of SEQ ID NO: 191, or a variant thereof comprising up to about 3 (such as about any of 1, 2, or 3) amino acid substitutions; and a CDR3 comprising the amino acid sequence of SEQ ID NO: 291, or a variant thereof comprising up to about 3 (such as about any of 1, 2, or 3) amino acid substitutions;

(42) a CDR1 comprising the amino acid sequence of SEQ ID NO: 92, or a variant thereof comprising up to about 3 (such as about any of 1, 2, or 3) amino acid substitutions; a CDR2 comprising the amino acid sequence of SEQ ID NO: 192, or a variant thereof comprising up to about 3 (such as about any of 1, 2, or 3) amino acid substitutions; and a CDR3 comprising the amino acid sequence of SEQ ID NO: 292, or a variant thereof comprising up to about 3 (such as about any of 1, 2, or 3) amino acid substitutions;

(43) a CDR1 comprising the amino acid sequence of SEQ ID NO: 93, or a variant thereof comprising up to about 3 (such as about any of 1, 2, or 3) amino acid substitutions; a CDR2 comprising the amino acid sequence of SEQ ID NO: 193, or a variant thereof comprising up to about 3 (such as about any of 1, 2, or 3) amino acid substitutions; and a CDR3 comprising the amino acid sequence of SEQ ID NO: 293, or a variant thereof comprising up to about 3 (such as about any of 1, 2, or 3) amino acid substitutions;

(44) a CDR1 comprising the amino acid sequence of SEQ ID NO: 94, or a variant thereof comprising up to about 3 (such as about any of 1, 2, or 3) amino acid substitutions; a CDR2 comprising the amino acid sequence of SEQ ID NO: 194, or a variant thereof comprising up to about 3 (such as about any of 1, 2, or 3) amino acid substitutions; and a CDR3 comprising the amino acid sequence of SEQ ID NO: 294, or a variant thereof comprising up to about 3 (such as about any of 1, 2, or 3) amino acid substitutions;

(45) a CDR1 comprising the amino acid sequence of SEQ ID NO: 95, or a variant thereof comprising up to about 3 (such as about any of 1, 2, or 3) amino acid substitutions; a CDR2 comprising the amino acid sequence of SEQ ID NO: 195, or a variant thereof comprising up to amino acid sequence of SEQ ID NO: 295, or a variant thereof comprising up to about 3 (such as about any of 1, 2, or 3) amino acid substitutions;

(46) a CDR1 comprising the amino acid sequence of SEQ ID NO: 96, or a variant thereof comprising up to about 3 (such as about any of 1, 2, or 3) amino acid substitutions; a CDR2 comprising the amino acid sequence of SEQ ID NO: 196, or a variant thereof comprising up to about 3 (such as about any of 1, 2, or 3) amino acid substitutions; and a CDR3 comprising the amino acid sequence of SEQ ID NO: 296, or a variant thereof comprising up to about 3 (such as about any of 1, 2, or 3) amino acid substitutions;

(47) a CDR1 comprising the amino acid sequence of SEQ ID NO: 97, or a variant thereof comprising up to about 3 (such as about any of 1, 2, or 3) amino acid substitutions; a CDR2 comprising the amino acid sequence of SEQ ID NO: 197, or a variant thereof comprising up to about 3 (such as about any of 1, 2, or 3) amino acid substitutions; and a CDR3 comprising the amino acid sequence of SEQ ID NO: 297, or a variant thereof comprising up to about 3 (such as about any of 1, 2, or 3) amino acid substitutions;

(48) a CDR1 comprising the amino acid sequence of SEQ ID NO: 98, or a variant thereof comprising up to about 3 (such as about any of 1, 2, or 3) amino acid substitutions; a CDR2 comprising the amino acid sequence of SEQ ID NO: 198, or a variant thereof comprising up to about 3 (such as about any of 1, 2, or 3) amino acid substitutions; and a CDR3 comprising the amino acid sequence of SEQ ID NO: 298, or a variant thereof comprising up to about 3 (such as about any of 1, 2, or 3) amino acid substitutions;

(49) a CDR1 comprising the amino acid sequence of SEQ ID NO: 99, or a variant thereof comprising up to about 3 (such as about any of 1, 2, or 3) amino acid substitutions; a CDR2 comprising the amino acid sequence of SEQ ID NO: 199, or a variant thereof comprising up to about 3 (such as about any of 1, 2, or 3) amino acid substitutions; and a CDR3 comprising the amino acid sequence of SEQ ID NO: 299, or a variant thereof comprising up to about 3 (such as about any of 1, 2, or 3) amino acid substitutions;
(50) a CDR1 comprising the amino acid sequence of SEQ ID NO: 100, or a variant thereof comprising up to about 3 (such as about any of 1, 2, or 3) amino acid substitutions; a CDR2 comprising the amino acid sequence of SEQ ID NO: 200, or a variant thereof comprising up to amino acid sequence of SEQ ID NO: 300, or a variant thereof comprising up to about 3 (such as about any of 1, 2, or 3) amino acid substitutions.

In some embodiments according to any one of the isolated anti-PD-L1 construct described above, the sdAb moiety specifically recognizing PD-L1 comprises a $V_HH$ domain having an amino acid sequence containing one or more of the following amino acid residues: a-1) an amino acid residue at position 37 selected from the group consisting of F, Y, L, I, and V, preferably F, V or Y; a-2) an amino acid residue at position 44 selected from the group consisting of A, G, E, D, G, Q, R, S, and L, preferably G, E, or Q; a-3) an amino acid residue at position 45 selected from the group consisting of L, R and C, preferably such as L or R; a-4) an amino acid residue at position 103 selected from the group consisting of G, W, R and S, preferably W or R, more preferably W; and a-5) an amino acid residue at position 108 being Q, wherein the positions are according to the Kabat numbering.

In some embodiments according to any one of the isolated anti-PD-L1 construct described above, the sdAb moiety specifically recognizing PD-L1 comprises a $V_HH$ domain having an amino acid sequence containing one or more of the following amino acid residues: b-1) an amino acid residue at position 37 selected from the group consisting of F, Y, L, I, and V, preferably F, V or Y; b-2) an amino acid residue at position 44 selected from the group consisting of G, E and Q; b-3) an amino acid residue at position 45 being R or L; b-4) an amino acid residue at position 103 selected from the group consisting of G, W, R and S, preferably W and b-5) an amino acid residue at position 108 selected from the group consisting of Q and L, preferably Q, wherein the positions are according to the Kabat numbering.

In some embodiments according to any one of the isolated anti-PD-L1 construct described above, the sdAb moiety specifically recognizing PD-L1 comprises a $V_HH$ domain comprising the amino acid sequence of any one of SEQ ID NOs: 351-400, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 288-328. In some embodiments, the sdAb moiety specifically recognizing PD-L1 comprises a $V_HH$ domain comprising the amino acid sequence of any one of SEQ ID NOs: 351-400, or a variant thereof comprising up to about 3 (such as about any of 1, 2, or 3) amino acid substitutions in the $V_HH$ domain. In some embodiments, the sdAb moiety specifically recognizing PD-L1 comprises a $V_HH$ domain comprising the amino acid sequence of any one of SEQ ID NOs: 351-400.

In some embodiments according to any one of the isolated anti-PD-L1 construct described above, the affinity ($K_D$, dissociation constant) of the binding between the sdAb moiety specifically recognizing PD-L1 and PD-L1 is about $10^{-5}$ M to about $10^{-12}$ M (such as about $10^{-5}$ M to about $10^{-12}$ M, about $10^{-7}$ M to about $10^{-12}$ M, or about $10^{-8}$ M to about $10^{-12}$ M).

In some embodiments according to any one of the isolated anti-PD-L1 construct described above, the sdAb moiety specifically recognizing PD-L1 is camelid, chimeric, human, partially humanized, or fully humanized.

In some embodiments according to any one of the isolated anti-PD-L1 construct described above, the isolated anti-PD-L1 construct is a heavy chain-only antibody (HCAb). In some embodiments, the sdAb moiety specifically recognizing PD-L1 is fused to a human IgG1 Fc. In some embodiments, the HCAb is monomeric or dimeric. In some embodiments, the sdAb moiety specifically recognizing PD-L1 comprises the amino acid sequence of SEQ ID NO: 351-400. In some embodiments, the HCAb comprises the amino acid sequence of any one of SEQ ID NOs: 401-440.

In some embodiments according to any one of the isolated anti-PD-L1 construct described above, the isolated anti-PD-L1 construct further comprises a second antibody moiety specifically recognizing a second antigen. In some embodiments, the second antibody moiety is a full-length antibody, a Fab, a Fab', a (Fab')2, an Fv, a single chain Fv (scFv), an scFv-scFv, a minibody, a diabody, a sdAb, or an antibody mimetics. In some embodiments, the anti-PD-L1 construct is monospecific. In some embodiments, the anti-PD-L1 construct is multispecific. In some embodiments, the second antibody moiety is a sdAb. In some embodiments, the second antigen is PD-L1. In some embodiments, the isolated anti-PD-L1 construct comprises three or more sdAbs that specifically recognize PD-L1. In some embodiments, the second antigen is human serum albumin (HSA). In some embodiments, the sdAb moiety specifically recognizing PD-L1 is amino (N)-terminal and/or carboxyl(C)-terminal to the second antibody moiety. In some embodiments, the sdAb moiety specifically recognizing PD-L1 and the second antibody moiety are optionally connected by a peptide linker (such as SEQ ID NO: 443, 444, or 445).

In some embodiments according to any one of the isolated anti-PD-L1 construct described above, the isolated anti-PD-L1 construct further comprises a second antibody moiety specifically recognizing a second antigen, wherein the second antibody moiety is a full-length antibody. In some embodiments, the amino (N)-terminus of the sdAb moiety specifically recognizing PD-L1 is fused to the carboxy(C)-terminus of at least one of the heavy chains of the full-length antibody. In some embodiments, the C-terminus of the sdAb moiety specifically recognizing PD-L1 is fused to the N-terminus of at least one of the heavy chains of the full-length antibody. In some embodiments, the full-length antibody specifically recognizes TIGIT. In some embodiments, the full-length antibody specifically recognizes TIM-3. In some embodiments, the full-length antibody specifically recognizes LAG-3. In some embodiments, the sdAb moiety specifically recognizing PD-L1 comprises the amino acid sequence of SEQ ID NO: 351-400. In some embodiments, the sdAb moiety specifically recognizing PD-L1 and the second antibody moiety are optionally connected by a peptide linker (SEQ ID NO: 443-445).

Further provided is a second isolated anti-PD-L1 construct that specifically binds to PD-L1 competitively with any one of the isolated anti-PD-L1 construct described above. In some embodiments, the second isolated anti-PD-L1 construct comprises a CDR1 comprising the amino acid sequence of any one of SEQ ID NOs:51-100, or a variant thereof comprising up to about 3 (such as about any of 1, 2, or 3) amino acid substitutions; a CDR2 comprising the amino acid sequence of any one of SEQ ID NOs: 151-200, or a variant thereof comprising up to about 3 (such as about any of 1, 2, or 3) amino acid substitutions; and a CDR3 comprising the amino acid sequence of any one of SEQ ID NOs: 251-300, or a variant thereof comprising up to about 3 (such as about any of 1, 2, or 3) amino acid substitutions.

Further provided is a pharmaceutical composition comprising any one of the isolated anti-PD-L1 constructs described above, and a pharmaceutical acceptable carrier.

Another aspect of the present application provides a method of treating an individual having a PD-L1-related disease, comprising administering to the individual an effective amount of any one of the pharmaceutical composition described above. In some embodiments, the PD-L1 related disease is cancer. In some embodiments, the cancer is a solid tumor, such as a colon cancer. In some embodiments, the method further comprises administering to the individual an additional cancer therapy, such as surgery, radiation, chemotherapy, immunotherapy, hormone therapy, or a combination thereof. In some embodiments, the PD-L1 related disease is a pathogenic infection. In some embodiments, the pharmaceutical composition is administered systemically, such as intravenously (i.v.). In some embodiments, the pharmaceutical composition is administered locally, such as intratumorally. In some embodiments, the individual is a human.

Further provided is an isolated nucleic acid encoding any one of the isolated anti-PD-L1 construct described above. In some embodiments, the isolated nucleic acid encodes an amino acid sequence selected from any one of SEQ ID NOs: 351-400.

Further provided is a vector comprising any one of the isolated nucleic acids described above.

Further provided is an isolated host cell comprising any one of the isolated nucleic acids or vectors described above.

Further provided is a kit comprising any one of the isolated anti-PD-L1 constructs, isolated nucleic acids, vectors, or isolated host cells described above.

Another aspect of the present application provides a method of producing any one of isolated anti-PD-L1 constructs described above, comprising culturing a host cell comprising any one of the isolated nucleic acids or vectors described above, or culturing any one of the isolated host cells described above, under conditions effective to express the encoded anti-PD-L1 construct; and obtaining the expressed anti-PD-L1 construct from said host cell. In some embodiments, the method further comprises producing a host cell comprising any one of the isolated nucleic acids or vectors described above.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiments which are presently preferred. It should be understood, however, that the invention is not limited to the precise arrangements and instrumentalities shown. In the drawings:

Figure 9B:
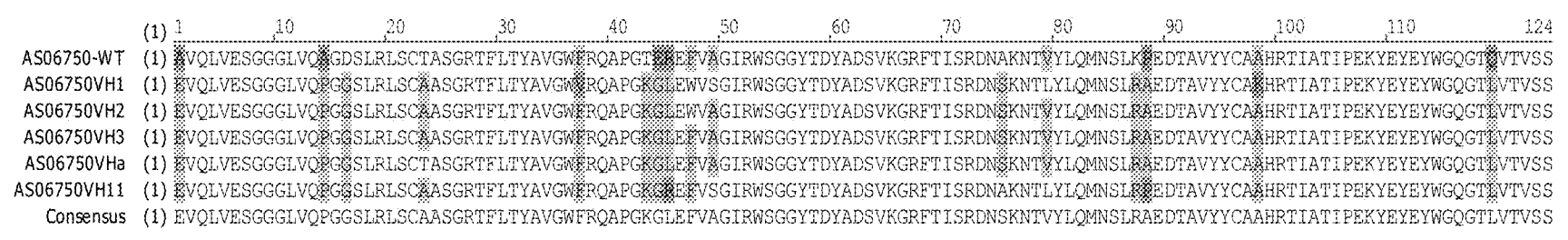
Figure 9C:
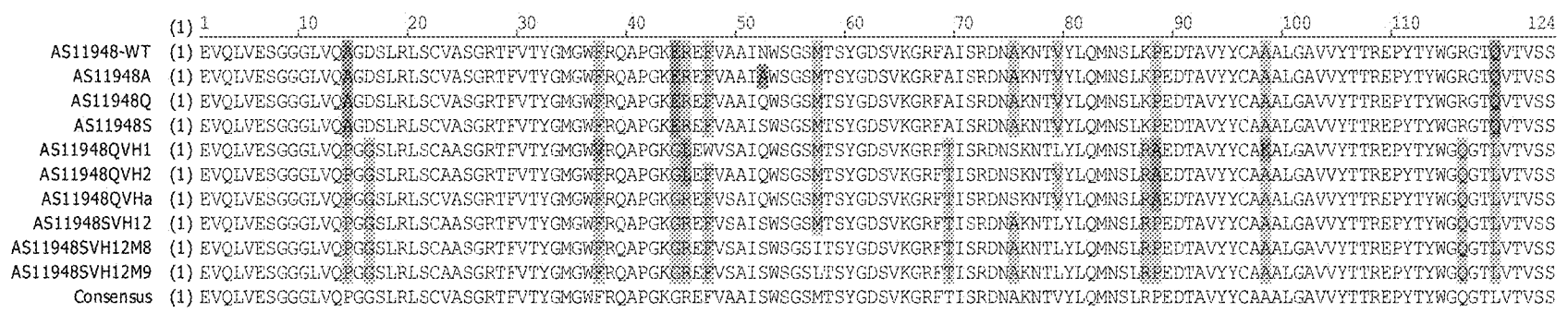

FIGS. 9A-9E depict sdAb sequences alignment of three WT anti-PD-L1 sdAbs and top 1-9 clones after humanization, amino acid differences in the framework regions relative to the human acceptor (best human germline sequence sharing the highest degree of homology with WT sdAb) are shaded in dark grey:

FIG. 9A depicts the sdAb sequences alignment of AS06730 (SEQ ID NO: 360), the top 9 clones after humanization (SEQ ID NOs: 376-384), and the consensus sequence;

FIG. 9B depicts the sdAb sequences alignment of AS06750 (SEQ ID NO: 361), the top 5 clones (SEQ ID NOs: 385-389) after humanization, and the consensus sequence; and FIG. 9C depicts the sdAb sequences alignment of AS11948 (SEQ ID NO: 372), the top 9 clones (SEQ ID NOs: 390-398) after humanization, and the consensus sequence;

FIG. 9D depicts the sdAb sequences alignment of AS06617 (SEQ ID NO: 351), the top 1 clone (SEQ ID NO: 399) after humanization, and the consensus sequence;

FIG. 9E depicts the sdAb sequences alignment of AS06775 (SEQ ID NO: 365), the top 1 clone (SEQ ID NO: 400) after humanization, and the consensus sequence.

FIGS. 10A-10C (AS06730 (FIG. 10A); AS067305 (FIG. 10B); AS06730SVH3a (FIG. 10C)): The affinity determination was done using PD-L1His being immobilized onto the chip and anti-PD-L1 HCAb as analyte at concentrations of 0.11, 0.33, 1, 3, and 9 nM;

FIGS. 10R-10T (AS06775 (FIG. 10R); AS06775VH11 (FIG. 10S); AS06775VH4 (FIG. 10T)): The affinity determination was done using PD-L1 His being immobilized onto the chip and anti-PD-L1 His as analyte at concentrations of 0.11, 0.33, 1, 3, and 9 nM.

DETAILED DESCRIPTION OF THE INVENTION

Figure 1:
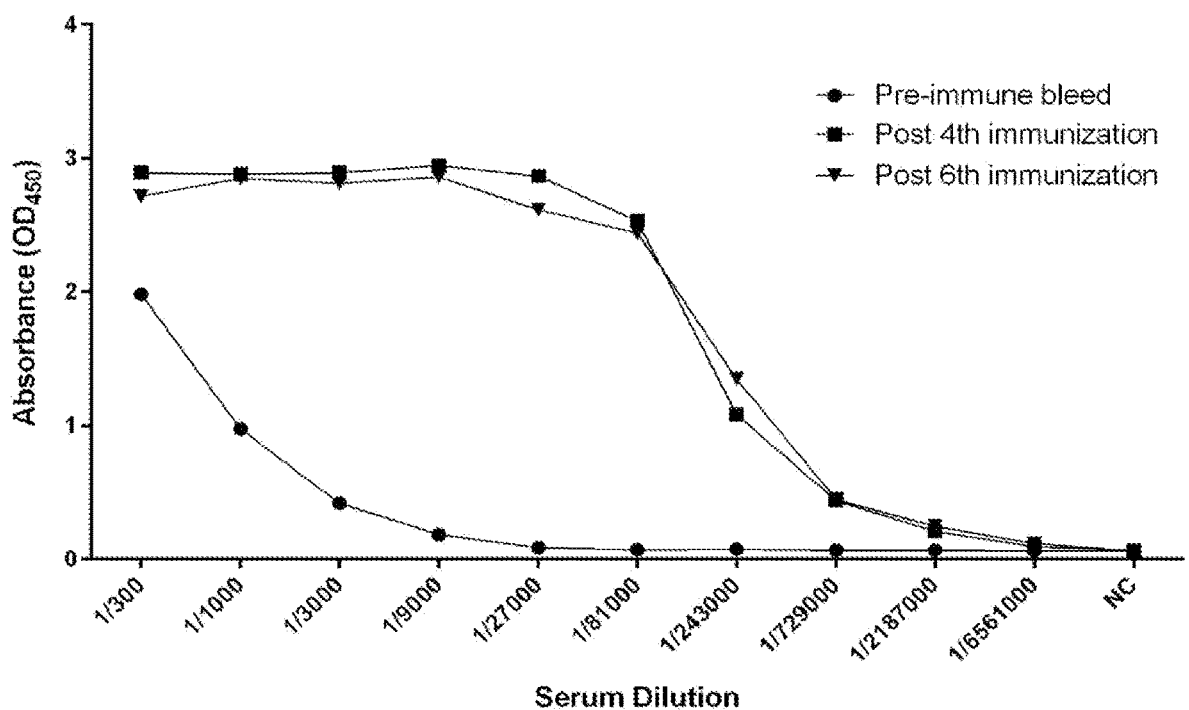
FIG. 1 depicts immune response evaluation of pre-immune serum and immune serum after the $4^{th}$ and $6^{th}$ immunization with recombinant PD-L1 ECD protein.

The present invention provides a single-domain antibody (sdAb) specifically recognizing PD-L1 (hereinafter also referred to as "anti-PD-L1 sdAb") and its antibody variants, including but not limited to, a larger protein or polypeptide comprising the anti-PD-L1 sdAb, such as a heavy chain-only antibody (HCAb), or an anti-PD-L1 sdAb fused to a full-length antibody or an antigen-binding fragment thereof, as a new strategy to treat PD-L1-related diseases, such as cancer.

Single-chain antibodies (sdAbs) are different from conventional 4-chain antibodies by having a single monomeric antibody variable domain, such as heavy chain variable domain ($V_HH$), which can exhibit high affinity to an antigen without the aid of a light chain. Camelid $V_HH$ is known as the smallest functional antigen-binding fragment with a molecular weight of approximately 15 kD.

Accordingly, one aspect of the present application provides an isolated anti-PD-L1 construct comprising a sdAb moiety specifically recognizing PD-L1. The isolated anti-PD-L1 construct can be, for example, an anti-PD-L1 sdAb (e.g. natural or humanized), a polypeptide comprising multiple anti-PD-L1 sdAbs described herein fused together, an HCAb comprising an anti-PD-L1 sdAb described herein fused to a human IgG1 Fc, or an anti-PD-L1 sdAb fused to a full-length antibody, such as an anti-PD-1 antibody, or an anti-PD-L1 antibody, or an antigen-binding fragment thereof. The anti-PD-L1 construct can be monospecific or multispecific, monovalent or multivalent.

Also provided are compositions (such as pharmaceutical compositions), kits and articles of manufacture comprising the construct comprising an anti-PD-L1 sdAb moiety, methods of making the construct comprising an anti-PD-L1 sdAb moiety, and methods of treating PD-L1 related disease (such as cancer) using the construct comprising an anti-PD-L1 sdAb moiety.

I. Definitions

The terms "Programmed cell death 1 ligand 1," "PD-L1," "B7 homolog 1 (B7-H1)," "PD-L1 antigen", "PDCD1 ligand 1" and "CD274" (see, e.g., Chemnitz (2004) J. Immunol. 173:945-954) are used interchangeably, and include variants, isoforms, species homologs of human PD-L1, and analogs having at least one common epitope with PD-L1 (see, e.g., Butte (2008) Mol Immunol. 45:3567-3572). Accordingly, the anti-PD-L1 construct of the invention can, in certain cases, cross-react with PD-L1 from species other than human, or other proteins which are structurally related to human PD-L1 (e.g., human PD-L1 homologs). In other cases, the anti-PD-L1 construct can be completely specific for human PD-L1 and not exhibit species or other types of cross-reactivity.

The term "human PD-L1" refers to human sequence PD-L1, such as the complete amino acid sequence of human PD-L1 having Genbank Accession Number Q9NZQ7. The human PD-L1 sequence can differ from human PD-L1 of Genbank Accession Number Q9NZQ7 by having, for example, conserved mutations or mutations in non-conserved regions and the PD-L1 has substantially the same biological function as the human PD-L1 of Genbank Accession Number Q9NZQ7. For example, a biological function of human PD-L1 is having an epitope in the extracellular domain of PD-L1 that is specifically bound by an anti-PD-L1 construct of the instant disclosure or a biological function of human PD-L1 is modulation of T cell activity.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "Programmed cell death 1 (PD-1)" as used herein is intended to refer to a cell surface receptor that belongs to the immunoglobulin superfamily and is expressed on T cells and pro-B cells. The amino acid sequences of human B7-1 (CD80) are disclosed at Genbank Accession Numbers NP_005009.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

The term "effective amount" used herein refers to an amount of an agent or a combination of agents, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "antibody" or "antibody moiety" is used in the broadest sense and encompasses various antibody structures, including but not limited to monoclonal antibodies, polyclonal antibodies, multi specific antibodies (e.g., bispecific antibodies), full-length antibodies and antigen-binding fragments thereof, so long as they exhibit the desired antigen-binding activity.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen-binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs" (Variable domain of the heavy chain of the Heavy chain antibody). Some $V_H$Hs can also be known as nanobodies. Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody (or construct) is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody (or construct) includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_H H$". $V_H H$ is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called complementary determining regions (CDRs) or hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g. U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The terms "full-length antibody", "intact antibody", or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_H H$) and an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include, but are not limited to Fab, Fab', F(ab')$_2$ and Fv fragments; diabodies; linear antibodies (see U.S. Pat. No. 5,641,870, Example 2; Zapata et al., *Protein Eng.* 8(10): 1057-1062) [1995]; single-chain antibody molecules; single-domain antibodies (such as $V_H H$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H 1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

The term "constant domain" refers to the portion of an immunoglobulin molecule having a more conserved amino acid sequence relative to the other portion of the immunoglobulin, the variable domain, which contains the antigen-binding site. The constant domain contains the $C_H 1$, $C_H 2$ and $C_H3$ domains (collectively, CH) of the heavy chain and the CHL (or CL) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). "Humanized antibody" is used as a subset of "chimeric antibodies".

"Humanized" forms of non-human (e.g., llama or camelid) antibodies are antibodies that contain minimal sequence derived from non-human immunoglobulin. In some embodiments, a humanized antibody is a human immunoglobulin (recipient antibody) in which residues from an CDR (hereinafter defined) of the recipient are replaced by residues from an CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies can comprise residues that are not found in the recipient antibody or in the donor antibody. These modifications can be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest,* 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_HH$) are numbered according to the general numbering for VH domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5$^{th}$ Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the VH, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of CDR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds," "specifically recognizes," or is "specific for" refers to measurable and reproducible interactions such as binding between a target and an antigen binding protein (such as a sdAb), which is determinative of the presence of the target in the presence of a heterogeneous population of molecules including biological molecules. For example, an antigen binding protein (such as a sdAb) that specifically binds a target (which can be an epitope) is an antigen binding protein (such as a sdAb) that binds this target with greater affinity, avidity, more readily, and/or with greater duration than it binds other targets. In some embodiments, the extent of binding of an antigen binding protein (such as a sdAb) to an unrelated target is less than about 10% of the binding of the antigen binding protein (such as sdAb) to the target as measured, e.g., by a radioimmunoassay (RIA). In some embodiments, an antigen binding protein (such as a sdAb) that specifically binds a target has a dissociation constant ($K_d$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antigen binding protein specifically binds an epitope on a protein that is conserved among the protein from different species. In some embodiments, specific binding can include, but does not require exclusive binding.

The term "specificity" refers to selective recognition of an antigen binding protein (such as a sdAb) for a particular epitope of an antigen. Natural antibodies, for example, are monospecific. The term "multispecific" as used herein denotes that an antigen binding protein has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary. That is, for example, the terms "anti-PD-L1/PD-1," "anti-PD-1/PD-L1," "PD-L1×PD-1," "PD-1×PD-L1," "PD-1-PD-L1," and "PD-L1-PD-1" may be used interchangeably to refer to bispecific antibodies that specifically bind to both PD-L1 and PD-1. The term "monospecific" as used herein denotes an antigen binding protein (such as a sdAb) that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

"Antibody effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody—dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effector-less mutation." In one aspect, the effector-less mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair. Binding affinity can be indicated by $K_d$, $K_{off}$, $K_{on}$, or $K_a$. The term "$K_{off}$", as used herein, is intended to refer to the off rate constant for dissociation of an antibody (or antigen-binding domain) from the antibody/antigen complex, as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex, expressed in units of $M^{-1} s^{-1}$. The term equilibrium dissociation constant "$K_D$" or "$K_d$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$, expressed in units of M. The measurement of $K_d$ presupposes that all binding agents are in solution. In the case where the antibody is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$, expressed in units of $M^{-1}$.

The dissociation constant ($K_D$ or $K_d$) is used as an indicator showing affinity of antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (Mols). An antibody or antigen-binding fragment thereof that specifically binds to a target may have a dissociation constant ($K_d$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-10}$ M, $\leq 10^{-11}$ M, or $\leq 10^{-12}$ M.

Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

Half maximal inhibitory concentration ($IC_{50}$) is a measure of the effectiveness of a substance (such as an antibody) in inhibiting a specific biological or biochemical function. It indicates how much of a particular drug or other substance (inhibitor, such as an antibody) is needed to inhibit a given biological process (e.g., the binding between PD-L1 and B7-1, or component of a process, i.e. an enzyme, cell, cell receptor or microorganism) by half. The values are typically expressed as molar concentration. $IC_{50}$ is comparable to an $EC_{50}$ for agonist drug or other substance (such as an antibody). $EC_{50}$ also represents the plasma concentration required for obtaining 50% of a maximum effect in vivo. As used herein, an "$IC_{50}$" is used to indicate the effective concentration of an antibody (such as an anti-PD-L1 sdAb) needed to neutralize 50% of the antigen bioactivity (such as PD-L1 bioactivity) in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid molecules encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

The term "pharmaceutical formulation" of "pharmaceutical composition" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Anti-PD-L1 Construct

Anti-PD-L1 Single-Domain Antibody Moiety

The isolated anti-PD-L1 construct described herein comprises a single-domain antibody (sdAb) moiety that specifically recognizes PD-L1 (or "anti-PD-L1 sdAb"). In some embodiments, the isolated anti-PD-L1 construct is an anti-PD-L1 sdAb.

Single-Domain Antibodies

Exemplary sdAbs include, but are not limited to, heavy chain variable domains from heavy-chain only antibodies (e.g., $V_HH$ (Variable domain of the heavy chain of the Heavy chain antibody) in Camelidae or $V_{NAR}$ (Variable domain of the shark New Antigen Receptor) in cartilaginous fish), binding molecules naturally devoid of light chains, single domains (such as $V_H$ or $V_L$) derived from conventional 4-chain antibodies, humanized heavy-chain only antibodies, human single-domain antibodies produced by transgenic mice or rats expressing human heavy chain segments, and engineered domains and single domain scaffolds other than those derived from antibodies. The sdAbs may be derived from any species including, but not limited to mouse, rat, human, camel, llama, lamprey, fish, shark, goat, rabbit, and bovine. Single-domain antibodies contemplated herein also include naturally occurring single-domain antibody molecules from species other than Camelidae and sharks.

In some embodiments, the sdAb is derived from a naturally occurring single-domain antigen binding molecule known as heavy chain antibody devoid of light chains (also referred herein as "heavy chain-only antibodies", or "HCAb"). Such single domain molecules are disclosed in WO 94/04678 and Hamers-Casterman, C. et al. (1993) *Nature* 363:446-448, for example. For clarity reasons, the variable domain derived from a heavy chain molecule naturally devoid of light chain is known herein as a $V_HH$ to distinguish it from the conventional VH of four chain immunoglobulins. Such a $V_HH$ molecule can be derived from antibodies raised in Camelidae species, for example, camel, llama, vicuna, dromedary, alpaca and guanaco. Other species besides Camelidae may produce heavy chain molecules naturally devoid of light chain, and such $V_HH$s are within the scope of the present application.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) VH domain from a conventional 4-chain antibody by one or more of the amino acid residues that occur at the corresponding position(s) in a $V_HH$ domain of a heavy chain antibody. This can be performed in a manner known per se, which will be clear to the skilled person, for example on the basis of the further description herein. Such "camelizing" substitutions are preferably inserted at amino acid positions that form and/or are present at the VH-VL interface, and/or at the so-called Camelidae hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb is a human sdAb produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb is affinity matured.

In some embodiments, naturally occurring $V_HH$ domains against a particular antigen or target, can be obtained from (naïve or immune) libraries of Camelid $V_{HH}$ sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naïve or immune) $V_HH$ libraries may be used, such as $V_{HH}$ libraries obtained from (naïve or immune) $V_HH$ libraries by techniques such as random mutagenesis and/or CDR shuffling, as for example described in WO 00/43507.

In some embodiments, the sdAbs are generated from conventional four-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

Because of the unique properties of sdAbs, using $V_HH$ domains as single antigen-binding proteins or as antigen-binding domains (i.e. as part of a larger protein or polypeptide) offers a number of significant advantages over the conventional $V_H$ and $V_L$, scFv and conventional antibody fragments (such as Fab or (Fab')2): 1) only a single domain is required to bind an antigen with high affinity, so there is no need to have a second domain, nor to assure that these two domains are present in the correct spatial conformation and configuration (e.g. no need to pair the heavy chain and light chain during folding, no need to use a specially designed linker such as for scFv); 2) $V_HH$ domains and other sdAbs can be expressed from a single gene and require no post-translational folding or modifications; 3) $V_HH$ domains and other sdAbs can be easily engineered into multivalent and/or multispecific formats (such as those described in the present application); 4) $V_HH$ domains and other sdAbs are highly soluble and do not have a tendency to aggregate (as with the mouse-derived "dAbs" described by Ward et al., Nature. 1989 Oct. 12; 341(6242):544-6); 5) $V_HH$ domains and other sdAbs are highly stable against heat, pH, proteases and other denaturing agents or conditions; 6) $V_HH$ domains and other sdAbs are easy and relatively cheap to prepare (even on a large production scale), such as using microbial fermentation, there is no need to use mammalian expression system (required by production of, for example, conventional antibody fragments); 7) $V_HH$ domains and other sdAbs are relatively small (approximately 15 kDa, or 10 times smaller than a conventional IgG) compared to conventional 4-chain antibodies and antigen-binding fragments thereof, thus have high(er) tissue penetration ability, such as for solid tumors and other dense tissues; and 8) $V_HH$ domains and other sdAbs can exhibit so-called "cavity-binding properties" (due to their extended CDR3 loop compared to that of conventional $V_H$ domains) and can therefore access targets and epitopes not accessible to conventional 4-chain antibodies and antigen-binding fragments thereof, for example, it has been shown that $V_HH$ domains and other sdAbs can inhibit enzymes (see for example WO1997049805; Transue et al., *Proteins.* 1998 Sep. 1; 32(4):515-22; Lauwereys et al., EMBO J. 1998 Jul. 1; 17(13):3512-20).

PD-L1

Similar in structure to related B7 family members, PD-L1 protein contains extracellular IgV and IgC domains and a short, cytoplasmic region. PD-L1 has an intracellular domain similar to that of CD28, which lacks intrinsic catalytic activity and contains one YVKM motif able to bind PI3K, PP2A and SHP-2 and one proline-rich motif able to bind SH3 containing proteins.

The amino acid sequence of human PD-L1 is disclosed at Genbank Accession Number Q9NZQ7. The region of amino acids 1-18 is the leader peptide; 19-238 is the extracellular domain; 239-259 is the transmembrane domain; and 260-290 is the cytoplasmic domain.

A particular human PD-L1 sequence will generally be at least 90% identical in amino acids sequence to human PD-L1 of Genbank Accession Number Q9NZQ7 and contains amino acid residues that identify the amino acid sequence as being human when compared to PD-L1 amino acid sequences of other species (e.g., murine). In some embodiments, a human PD-L1 may be at least about 95%, 96%, 97%, 98%, or 99% identical in amino acid sequence to PD-L1 of Genbank Accession Number Q9NZQ7. In some embodiments, a human PD-L1 sequence will display no more than 10 amino acid differences from the PD-L1 of Genbank Accession Number Q9NZQ7. In some embodiments, the human PD-L1 may display no more than 5, 4, 3, 2, or 1 amino acid difference from the PD-L1 of Genbank Accession Number Q9NZQ7. Percent identity can be determined as described herein. In some embodiments, the anti-PD-L1 sdAb moiety described herein specifically recognizes a PD-L1 polypeptide with 100% amino acid sequence identity to the PD-L1 of Genbank Accession Number Q9NZQ7. In some embodiments, the anti-PD-L1 sdAb moiety specifically recognizes a PD-L1 polypeptide comprising an amino acid sequence of SEQ ID NO: 441.

In some embodiments, the anti-PD-L1 sdAb moiety may cross-react with PD-L1 from species other than human, or other proteins which are structurally related to human PD-L1 (e.g., human PD-L1 homologs). In some embodiments, the anti-PD-L1 sdAb moiety is completely specific for human PD-L1 and not exhibit species or other types of cross-reactivity. In some embodiments, the anti-PD-L1 sdAb moiety specifically recognizes a soluble isoform of human PD-L1. In some embodiments, the anti-PD-L1 sdAb moiety specifically recognizes a membrane-bound isoform of human PD-L1 (SEQ ID NO: 441).

In some embodiments, the anti-PD-L1 sdAb moiety described herein specifically recognizes the extracellular domain (ECD) of PD-L1. In some embodiments, the anti- PD-L1 sdAb moiety specifically recognizes the N-terminal portion of the PD-L1 extracellular domain (ECD). In some embodiments, the anti-PD-L1 sdAb moiety specifically recognizes the C-terminal portion of the PD-L1 extracellular domain (ECD). In some embodiments, the anti-PD-L1 sdAb moiety specifically recognizes the middle portion of the PD-L1 extracellular domain (ECD). In some embodiments, the extracellular domain of PD-L1 specifically recognized by the anti-PD-L1 sdAb moiety is at least about 95%, 96%, 97%, 98%, or 99% identical in amino acid sequence to the extracellular domain of the PD-L1 of Genbank Accession Number Q9NZQ7. In some embodiments, the extracellular domain of PD-L1 specifically recognized by the anti-PD-L1 sdAb moiety is 100% identical in amino acid sequence to the extracellular domain of the PD-L1 of Genbank Accession Number Q9NZQ7. In some embodiments, the anti-PD-L1 sdAb moiety specifically recognizes a PD-L1 polypeptide comprising an amino acid sequence of SEQ ID NO: 442.

Antibody Affinity

Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

In some embodiments, the $K_d$ of the binding between the anti-PD-L1 sdAb moiety and PD-L1 is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-5}$ M to about $10^{-12}$ M, about $10^{-6}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-5}$ M to about $10^{-11}$ M, about $10^{-7}$ M to about $10^{-11}$ M, about $10^{-8}$ M to about $10^{-11}$ M, about $10^{-9}$ M to about $10^{-11}$ M, about $10^{-5}$ M to about $10^{-10}$ M, about $10^{-7}$ M to about $10^{-10}$ M, about $10^{-8}$ M to about $10^{-10}$ M, about $10^{-5}$ M to about $10^{-9}$ M, about $10^{-7}$ M to about $10^{-9}$ M, about $10^{-5}$ M to about $10^{-8}$ M, or about $10^{-6}$ M to about $10^{-8}$ M.

In some embodiments, the $K_{on}$ of the binding between the anti-PD-L1 sdAb moiety and PD-L1 is about $10^2$ M$^{-1}$s$^{-1}$ to about $10^4$ M$^{-1}$s$^{-1}$, about $10^4$ M$^{-1}$s$^{-1}$ to about $10^6$ M$^{-1}$s$^{-1}$, about $10^6$ M$^{-1}$s$^{-1}$ to about $10^7$ M$^{-1}$s$^{-1}$, about $10^2$ M$^{-1}$s$^{-1}$ to about $10^7$ M$^{-1}$s$^{-1}$, about $10^3$ M$^{-1}$s$^{-1}$ to about $10^7$ M$^{-1}$s$^{-1}$, about $10^4$ M$^{-1}$s$^{-1}$ to about $10^7$ M$^{-1}$s$^{-1}$, about $10^5$ M$^{-1}$s$^{-1}$ to about $10^7$ M$^{-1}$s$^{-1}$, about $10^3$ M$^{-1}$s$^{-1}$ to about $10^6$ M$^{-1}$s$^{-1}$, or about $10^4$ M$^{-1}$s$^{-1}$ to about $10^6$ M$^{-1}$s$^{-1}$.

In some embodiments, the $K_{off}$ of the binding between the anti-PD-L1 sdAb moiety and PD-L1 is about 1 s$^{-1}$ to about $10^{-2}$ s$^{-1}$, about $10^{-2}$ s$^{-1}$ to about $10^{-4}$ s$^{-1}$, about $10^{-4}$ s$^{-1}$ to about $10^{-5}$ s$^{-1}$, about $10^{-5}$ s$^{-1}$ to about $10^{-6}$ s$^{-1}$, about 1 s$^{-1}$ to about $10^{-6}$ s$^{-1}$, about $10^{-2}$ s$^{-1}$ to about $10^{-6}$ s$^{-1}$, about $10^{-3}$ s$^{-1}$ to about $10^{-6}$ s$^{-1}$, about $10^{-4}$ s$^{-1}$ to about $10^{-6}$ s$^{-1}$, about $10^{-2}$ s$^{-1}$ to about $10^{-5}$ s$^{-1}$, or about $10^{-3}$ s$^{-1}$ to about $10^{-5}$ s$^{-1}$.

In some embodiments, the $IC_{50}$ of the anti-PD-L1 sdAb moiety is less than 10 nM in an amplified luminescent proximity homogeneous assay (AlphaLISA) with 0.12 nM PD-1 and 0.2 nM PD-L1. In some embodiments, the $IC_{50}$ of the anti-PD-L1 sdAb moiety is less than 500 nM in an inhibition of ligand binding by FACS analysis (competition binding assay), or cell based cytokine release assay. In some embodiments, the $IC_{50}$ of the anti-PD-L1 sdAb moiety is less than 1 nM, about 1 nM to about 10 nM, about 10 nM to about 50 nM, about 50 nM to about 100 nM, about 100 nM to about 200 nM, about 200 nM to about 300 nM, about 300 nM to about 400 nM, or about 400 nM to about 500 nM.

Chimeric or Humanized Antibodies

In some embodiments, the anti-PD-L1 antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the sdAbs are modified, such as humanized, without diminishing the native affinity of the domain for antigen and while reducing its immunogenicity with respect to a heterologous species. For example, the amino acid residues of the antibody variable domain ($V_HH$) of an llama antibody can be determined, and one or more of the Camelid amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelid single-domain antibodies requires the introduction and mutagenesis of a limited amount of amino acids in a single polypeptide chain. This is in contrast to humanization of scFv, Fab', (Fab')2 and IgG, which requires the introduction of amino acid changes in two chains, the light and the heavy chain and the preservation of the assembly of both chains.

Single-domain antibodies comprising a $V_HH$ domain can be humanized to have human-like sequences. In some embodiments, the FR regions of the $V_HH$ domain used herein comprise at least about any one of 50%, 60%, 70%, 80%, 90%, 95% or more of amino acid sequence homology to human VH framework regions. One exemplary class of humanized $V_HH$ domains is characterized in that the $V_HH$s carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human VH framework regions and said polypeptides might be administered to a human directly without expectation of an unwanted immune response therefrom, and without the burden of further humanization.

Another exemplary class of humanized Camelid single-domain antibodies has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in $V_H$ from double-chain antibodies. As such, peptides belonging to these two classes show a high amino acid sequence homology to human $V_H$ framework regions and said peptides might be administered to a human directly without expectation of an unwanted immune response therefrom, and without the burden of further humanization.

Human Antibodies

In some embodiments, the anti-PD-L1 sdAb moiety provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Transgenic mice or rats capable of producing fully human single-domain antibodies are known in the art. See, e.g., US20090307787A1, U.S. Pat. No. 8,754,287, US20150289489A1, US20100122358A1, and WO2004049794.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J Immunol. Methods* 284(1-2): 119-132(2004). Methods for constructing single-domain antibody libraries have been described, for example, see U.S. Pat. No. 7,371,849.

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Biological Activities

The biological activity of anti-PD-L1 sdAb moiety described herein can be determined by measuring its half maximal inhibitory concentration ($IC_{50}$), which is a measure of the effectiveness of an antibody in inhibiting a specific biological or biochemical function (such as inhibiting the binding between PD-L1 and its receptor PD-1). For example, here $IC_{50}$ can be used to indicate the effective concentration of anti-PD-L1 sdAb needed to neutralize 50% of PD-L1 bioactivity in vitro. $IC_{50}$ is comparable to an $EC_{50}$ for agonist drug or other substance (such as an antibody). $EC_{50}$ also represents the plasma concentration required for obtaining 50% of a maximum effect in vivo. $IC_{50}$ or $EC_{50}$ can be measured by assays known in the art, for example, bioassays such as inhibition of ligand binding by FACS analysis (competition binding assay), cell based cytokine release assay, or amplified luminescent proximity homogeneous assay (AlphaLISA).

For example, the blockade of ligand binding can be studied using flow cytometry (also see Example 1). CHO cells expressing human PD-L1 can be dissociated from adherent culture flasks and mixed with varying concentrations of anti-PD-L1 sdAb for test, and a constant concentration of labeled-PD-1 protein (such as biotin-labeled hPD-1/Fc protein). An anti-PD-L1 antibody positive control can be employed, such as Tecentriq®. The mixture is equilibrated for 30 minutes at room temperature, washed three times with FACS buffer (PBS containing 1% BSA). Then, an antibody specifically recognizing the labeled PD-1 protein of constant concentration (such as PE/Cy5 Streptavidin secondary antibody) is added and incubated for 15 minutes at room temperature. Cells are washed with FACS buffer and analyzed by flow cytometry. Data can be analyzed with Prism (GraphPad Software, San Diego, Calif.) using non-linear regression to calculate $IC_{50}$. The results from the competition assay will demonstrate the ability of anti-PD-L1 sdAbs in inhibiting the interaction between labeled-PD-1 and PD-L1.

The biological activity of anti-PD-L1 sdAb moiety can also be tested by PD-L1-based blockade assay for cytokine release (also see Example 1). PD-1 signaling typically has a greater effect on cytokine production than on cellular proliferation, with significant effects on IFN-γ, TNF-α and IL-2 production. PD-1 mediated inhibitory signaling also depends on the strength of the TCR signaling, with greater inhibition delivered at low levels of TCR stimulation. This reduction can be overcome by costimulation through CD28 (Freeman et al., J. Exp. Med. 192: 1027-34 (2000)) or the presence of IL-2 (Carter et al., Eur. J. Immunol. 32: 634-43 (2002)). Additionally, several studies show a receptor for PD-L1 or PD-L2 that is independent of PD-1. B7.1 has already been identified as a binding partner for PD-L1 (Butte et al., Immunity 27: 111-22 (2007)). Chemical crosslinking studies suggest that PD-L1 and B7.1 can interact through their IgV-like domains. B7.1:PD-L1 interactions can induce an inhibitory signal into T cells. As a result, the antagonism of signaling through PD-L1, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the present invention, may be combined with antagonists of other components of PD-1:PD-L1 signaling, for example, antagonist anti-PD-1 and anti-PD-L2 antibodies. Thus, blockade of PD-L1 pathways by anti-PD-L1 antibodies can be studied using a variety of bioassays that monitor T cell proliferation, IFN-γ release, or IL-2 secretion.

For examples, PD-1 Effector Cells (Jurkat cell stably transfected with human PD-1 protein and NFAT luciferase) and CHO-K1/human CD274 (CHO-K1 stably expressing human CD80) are mixed in wells. Anti-PD-L1 sdAbs are added into each well at different concentrations. No antibody can be used as a background control. Negative control (such as human IgG1) and positive control (such as Tecentriq®) can be employed. After 24-hour incubation in 37° C./5% $CO_2$ incubator, medium is taken from each testing well for IL-2 secretion measurement (Cisbio). $EC_{50}$ value for each test antibody is measured, which will reflect the ability of test anti-PD-L1 sdAb in blocking the interaction between PD-1 and PD-L1 on Jurkat cells, thus in inhibiting T-cell IL-2 production.

In some embodiments, the anti-PD-L1 sdAb moiety blocks or antagonizes signals transduced by the PD-L1 ligand. In some embodiments, the anti-PD-L1 sdAb moiety can bind to an epitope on PD-L1 so as to inhibit PD-L1 from interacting with a PD-1. In some embodiments, the anti-PD-L1 sdAb moiety can reduce the binding of PD-L1 to it receptor PD-1 by at least about any of 5%, 10%, 20%, 25%, 30%, 40%, 50%, 60%, 70%, 75%, 80%, 90%, 95%, 99% or 99.9% under conditions in which the ratio of antibody combining site to PD-L1 ligand binding site is greater than 1:1 and the concentration of antibody is greater than $10^{-8}$ M.

In some embodiments, there is provided an anti-PD-L1 sdAb moiety comprising a CDR1 comprising the amino acid sequence of any one of SEQ ID NOs: 51-100, or a variant thereof comprising up to about 3 (such as about any of 1, 2, or 3) amino acid substitutions; a CDR2 comprising the amino acid sequence of any one of SEQ ID NOs: 151-200, or a variant thereof comprising up to about 3 (such as about any of 1, 2, or 3) amino acid substitutions; and a CDR3 comprising the amino acid sequence of any one of SEQ ID NOs: 251-300, or a variant thereof comprising up to about 3 (such as about any of 1, 2, or 3) amino acid substitutions. In some embodiments, the $K_d$ of the binding between the anti-PD-L1 sdAb moiety and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 sdAb moiety is camelid, chimeric, human, partially humanized, or fully humanized.

In some embodiments, the anti-PD-L1 sdAb moiety comprises a CDR3 comprising the amino acid sequence of any one of SEQ ID NOs: 251-300, and the amino acid substitutions are in CDR1 and/or CDR2.

Thus, in some embodiments, there is provided an anti-PD-L1 sdAb moiety comprising a CDR1 comprising the amino acid sequence of any one of SEQ ID NOs: 51-100, or a variant thereof comprising up to about 3 (such as about any of 1, 2, or 3) amino acid substitutions; a CDR2 comprising the amino acid sequence of any one of SEQ ID NOs: 151-200, or a variant thereof comprising up to about 3 (such as about any of 1, 2, or 3) amino acid substitutions; and a CDR3 comprising the amino acid sequence of any one of SEQ ID NOs: 251-300. In some embodiments, the $K_d$ of the binding between the anti-PD-L1 sdAb moiety and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 sdAb moiety is camelid, chimeric, human, partially humanized, or fully humanized.

In some embodiments, there is provided an anti-PD-L1 sdAb moiety comprising a CDR1 comprising the amino acid sequence of any one of SEQ ID NOs: 51-100; a CDR2 comprising the amino acid sequence of any one of SEQ ID NOs: 151-200; and a CDR3 comprising the amino acid sequence of any one of SEQ ID NOs: 251-300. In some embodiments, the $K_d$ of the binding between the anti-PD-L1 sdAb moiety and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 sdAb moiety is camelid, chimeric, human, partially humanized, or fully humanized.

The sequences of the CDRs noted herein are provided in Table 15.

The CDRs can be combined in various pair-wise combinations to generate a number of anti-PD-L1 sdAb moieties.

The anti-PD-L1 sdAb moiety may comprise one or more "hallmark residues" in one or more of the FR sequences. In some embodiments, the anti-PD-L1 sdAb moiety may comprise a $V_H H$ domain comprising the amino acid sequence of any one of the following: a-1) the amino acid residue at position 37 is selected from the group consisting of F, Y, L, I, and V (such as Y or such as F); a-2) the amino acid residue at position 44 is selected from the group consisting of A, G, E, D, G, Q, R, S, and L (such as G, E, or Q); a-3) the amino acid residue at position 45 is selected from the group consisting of L, R and C (such as L or R); a-4) the amino acid residue at position 103 is selected from the group consisting of G, W, R and S (such as W or R, or such as W); and a-5) the amino acid residue at position 108 is Q; or b-1) the amino acid residue at position 37 is selected from the group consisting of F, Y, L, I, and V (such as Y or such as F); b-2) the amino acid residue at position 44 is selected from the group consisting of E and Q; b-3) the amino acid residue at position 45 is R; b-4) the amino acid residue at position 103 is selected from the group consisting of G, W, R and S (such as W); and b-5) the amino acid residue at position 108 is selected from the group consisting of Q and L (such as Q); wherein the amino acid position is according to Kabat numbering. It should be noted that these "hallmark residues" at amino acid positions 37, 44, 45, 103 and 108 according to Kabat numbering apply to anti-PD-L1 sdAb moieties of natural $V_H H$ sequences, and can be substituted during humanization. For example, Q at amino acid position 108 according to Kabat numbering can be optionally humanized to L. Other humanized substitutions will be clear to those skilled in the art. For example, potentially useful humanizing substitutions can be determined by comparing the FR sequences of a naturally occurring $V_H H$ with the corresponding FR sequences of one or more closely related human $V_H$, then introducing one or more of such potentially useful humanizing substitutions into said $V_H H$ using methods known in the art (also as described herein). The resulting humanized $V_H H$ sequences can be tested for their PD-L1 binding affinity, for stability, for ease and level of expression, and/or for other desired properties. Possible residue substitutions may also come from an antibody $V_H$ domain wherein the VH/VL interface comprises one or more highly charged amino acid residues. The anti-PD-L1 sdAb moiety described herein can be partially or fully humanized. Preferably, the resulting humanized anti-PD-L1 sdAb binds to PD-L1 with $K_d$, $K_{on}$, $K_{off}$ described herein.

In some embodiments, there is provided an anti-PD-L1 sdAb moiety comprising a $V_H H$ domain comprising the amino acid sequence of any one of SEQ ID NOs: 351-400, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:351-400. In some embodiments, there is provided an anti-PD-L1 sdAb moiety comprising a $V_H H$ domain comprising the amino acid sequence of any one of SEQ ID NOs: 351-400, or a variant thereof comprising up to about 3 (such as about any of 1, 2, or 3) amino acid substitutions in the $V_H H$ domain. In some embodiments, the anti-PD-L1 sdAb moiety comprising the $V_H H$ domain comprising the amino acid sequence of any one of SEQ ID NOs: 351-400 or a variant thereof comprises amino acid substitutions in CDRs, such as the CDR1, and/or the CDR2, and/or the CDR3 of any one of SEQ ID NOs: 351-400. In some embodiments, the anti-PD-L1 sdAb moiety comprising the $V_H H$ domain comprising the amino acid sequence of any one of SEQ ID NOs: 351-400 or a variant thereof comprises CDR1, CDR2, and CDR3 of any one of SEQ ID NOs: 351-400, and the amino acid substitutions are in FRs, such as the FR1, and/or the FR2, and/or the FR3, and/or the FR4 of any one of SEQ ID NOs: 351-400.

In some embodiments, there is provided an anti-PD-L1 sdAb moiety (hereinafter referred to as "competing anti-PD-L1 sdAb moiety" or "competing anti-PD-L1 sdAb") that specifically binds to PD-L1 competitively with any one of the anti-PD-L1 sdAb moiety described herein. In some embodiments, competitive binding may be determined using an ELISA assay. For example, in some embodiments, there is provided an anti-PD-L1 sdAb moiety that specifically binds to PD-L1 competitively with an anti-PD-L1 sdAb moiety comprising the amino acid sequence of any one of SEQ ID NOs: 351-400. For another example, in some embodiments, there is provided an anti-PD-L1 sdAb moiety that specifically binds to PD-L1 competitively with an anti-PD-L1 sdAb moiety comprising a CDR1 comprising the amino acid sequence of any one of SEQ ID NOs: 51-100; a CDR2 comprising the amino acid sequence of any one of SEQ ID NOs: 151-200; and a CDR3 comprising the amino acid sequence of any one of SEQ ID NOs: 251-300. In some embodiments, the $K_d$ of the binding between the competing anti-PD-L1 sdAb moiety and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the competing anti-PD-L1 sdAb moiety is camelid, chimeric, human, partially humanized, or fully humanized.

Construct Comprising the Anti-PD-L1 sdAb Moiety

The anti-PD-L1 construct comprising the anti-PD-L1 sdAb moiety can be of any possible format.

In some embodiments, the anti-PD-L1 construct comprising the anti-PD-L1 sdAb moiety may further comprise additional polypeptide sequences, such as one or more antibody moieties, or Fc fragment of immunoglobulin. Such additional polypeptide sequences may or may not change or otherwise influence the (biological) properties of the sdAb, and may or may not add further functionality to the sdAb described herein. In some embodiments, the additional polypeptide sequences confer one or more desired properties or functionalities to the sdAb of the present invention. In some embodiments, the anti-PD-L1 construct is a chimeric antigen receptor (CAR) comprising an extracellular antigen binding domain comprising one or more anti-PD-L1 sdAb moiety described herein.

In some embodiments, the additional polypeptide sequences may be a second antibody moiety (such as sdAb, scFv, full-length antibody) that specifically recognizes a second antigen. In some embodiments, the second antigen is not PD-L1. In some embodiments, the second antibody moiety specifically recognizes the same epitope on PD-L1 as the anti-PD-L1 sdAb described herein. In some embodiments, the second antibody moiety specifically recognizes a different epitope on PD-L1 as the anti-PD-L1 sdAb described herein.

In some embodiments, the additional polypeptide sequences may increase the antibody construct half-life, solubility, or absorption, reduce immunogenicity or toxicity, eliminate or attenuate undesirable side effects, and/or confer other advantageous properties to and/or reduce undesired properties of the anti-PD-L1 construct of the invention, compared to the anti-PD-L1 sdAb described herein per se. Some non-limiting examples of such additional polypeptide sequences are serum proteins, such as human serum albumin (see for example WO 00/27435) or haptenic molecules (for example haptens that are recognized by circulating antibodies, see for example WO 98/22141). It was shown that linking fragments of immunoglobulins (such as $V_H$ domains) to serum albumin or fragments thereof may increase antibody half-life (see e.g. WO 00/27435 and WO 01/077137). Thus, in some embodiments, the anti-PD-L1 construct of the present invention may comprise an anti-PD-L1 sdAb moiety described herein linked to serum albumin (or to a suitable fragment thereof), optionally via a suitable linker (such as peptide linker). In some embodiments, the anti-PD-L1 sdAb moiety described herein can be linked to a fragment of serum albumin at least comprising serum albumin domain III. (see PCT/EP2007/002817).

Heavy Chain-Only Antibody (HCAb)

In some embodiments, anti-PD-L1 sdAb moiety described herein can be linked to one or more (preferably human) $C_H2$ and/or $C_H3$ domains, optionally via a linker sequence, to increase its half-life in vivo.

Thus in some embodiments, the anti-PD-L1 construct is an HCAb (hereinafter referred to as "anti-PD-L1 HCAb") comprising an anti-PD-L1 sdAb moiety described herein fused to Fc fragment of an immunoglobulin, such as IgA, IgD, IgE, IgG, and IgM. In some embodiments, the anti-PD-L1 HCAb comprises an Fc sequence of IgG, such as any of IgG1, IgG2, IgG3, or IgG4. In some embodiments, the Fc fragment is a human Fc. In some embodiments, the Fc fragment is a human IgG1 Fc. In some embodiments, the anti-PD-L1 HCAb is monomeric. In some embodiments, the anti-PD-L1 HCAb is dimeric. In some embodiments, the anti-PD-L1 sdAb moiety and the Fc fragment are optionally connected by a peptide linker. In some embodiments, the peptide linker is a mutated human IgG1 hinge (SEQ ID NO: 445). In some embodiments, the peptide linker comprises the amino acid sequence of SEQ ID NO: 443 (GGGGSGGGS). In some embodiments, the peptide linker comprises the amino acid sequence of SEQ ID NO: 444 (GGGGSGGGGSGGGGS).

Thus in some embodiments, there is provided an anti-PD-L1 HCAb comprising a sdAb moiety specifically recognizing PD-L1, wherein the sdAb moiety comprises a CDR1 comprising the amino acid sequence of any one of SEQ ID NOs: 51-100, or a variant thereof comprising up to about 3 (such as about any of 1, 2, or 3) amino acid substitutions; a CDR2 comprising the amino acid sequence of any one of SEQ ID NOs: 151-200, or a variant thereof comprising up to about 3 (such as about any of 1, 2, or 3) amino acid substitutions; and a CDR3 comprising the amino acid sequence of any one of SEQ ID NOs: 251-300, or a variant thereof comprising up to about 3 (such as about any of 1, 2, or 3) amino acid substitutions, and wherein the sdAb moiety is fused to an Fc fragment of an immunoglobulin. In some embodiments, there is provided an anti-PD-L1 HCAb comprising a sdAb moiety specifically recognizing PD-L1, wherein the sdAb moiety comprises a CDR1 comprising the amino acid sequence of any one of SEQ ID NOs: 51-100; a CDR2 comprising the amino acid sequence of any one of SEQ ID NOs: 151-200; and a CDR3 comprising the amino acid sequence of any one of SEQ ID NOs: 251-300; or a variant thereof comprising up to about 3 (such as about any of 1, 2, or 3) amino acid substitutions in the CDR regions, and wherein the sdAb moiety is fused to an Fc fragment of an immunoglobulin. In some embodiments, the amino acid substitutions are in CDR1 and/or CDR2. In some embodiments, there is provided an anti-PD-L1 HCAb comprising a sdAb moiety specifically recognizing PD-L1, wherein the sdAb moiety comprises a CDR1 comprising the amino acid sequence of any one of SEQ ID NOs: 51-100; a CDR2 comprising the amino acid sequence of any one of SEQ ID NOs: 151-200; and a CDR3 comprising the amino acid sequence of any one of SEQ ID NOs: 251-300, and wherein the sdAb moiety is fused to an Fc fragment of an immunoglobulin. In some embodiments, the anti-PD-L1 sdAb moiety comprises a $V_HH$ domain comprising the amino acid sequence of any one of the following: a-1) the amino acid residue at position 44 is selected from the group consisting of A, G, E, D, G, Q, R, S, and L (such as G, E, or Q); a-2) the amino acid residue at position 45 is selected from the group consisting of L, R and C (such as L or R); a-3) the amino acid residue at position 103 is selected from the group consisting of W, R and S (such as W or R, or such as W); and a-4) the amino acid residue at position 108 is Q; b-1) the amino acid residue at position 44 is selected from the group consisting of E and Q; b-2) the amino acid residue at position 45 is R; b-3) the amino acid residue at position 103 is selected from the group consisting of W, R and S (such as W); and b-4) the amino acid residue at position 108 is selected from the group consisting of Q and L (such as Q); wherein the amino acid position is according to Kabat numbering, and wherein position 108 can be optionally humanized to L when position 108 is Q. In some embodiments, the Fc fragment is a human IgG1 Fc. In some embodiments, the anti-PD-L1 HCAb is monomeric. In some embodiments, the anti-PD-L1 HCAb is dimeric. In some embodiments, the anti-PD-L1 sdAb moiety and the Fc fragment are optionally connected by a peptide linker. In some embodiments, the peptide linker comprises the amino acid sequence of SEQ ID NO: 443, SEQ ID NO: 444, or SEQ ID NO: 445. In some embodiments, the $K_d$ of the binding between the anti-PD-L1 sdAb moiety and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 sdAb moiety is camelid, chimeric, human, partially humanized, or fully humanized.

In some embodiments, there is provided an anti-PD-L1 HCAb comprising the amino acid sequence of any one of SEQ ID NOs: 401-440.

In some embodiments, there is also provided an anti-PD-L1 HCAb (hereinafter referred to as "competing anti-PD-L1 HCAb") that specifically binds to PD-L1 competitively with any one of the anti-PD-L1 HCAb described herein. Competitive binding may be determined using an ELISA assay. For example, in some embodiments, there is provided an anti-PD-L1 HCAb that specifically binds to PD-L1 competitively with an anti-PD-L1 HCAb comprising the amino acid sequence of any one of SEQ ID NOs: 401-440. For another example, in some embodiments, there is provided an anti-PD-L1 HCAb that specifically binds to PD-L1 competitively with an anti-PD-L1 HCAb comprising a CDR1 comprising the amino acid sequence of any one of SEQ ID NOs: 51-100; a CDR2 comprising the amino acid sequence of any one of SEQ ID NOs: 151-200; and a CDR3 comprising the amino acid sequence of any one of SEQ ID NOs: 251-300. In some embodiments, the $K_d$ of the binding between the competing anti-PD-L1 HCAb and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the competing anti-PD-L1 HCAb is camelid, chimeric, human, partially humanized, or fully humanized.

Multivalent and/or Multispecific Antibodies

In some embodiments, the anti-PD-L1 construct comprises an anti-PD-L1 sdAb moiety described herein fused to one or more other antibody moiety (such as an antibody moiety that specifically recognizes another antigen). The one or more other antibody moiety can be of any antibody or antibody fragment format, such as a multispecific sdAb (such as bispecific sdAb), a full-length antibody, a Fab, a Fab', a (Fab')2, an Fv, a single chain Fv (scFv), an scFv-scFv, a minibody, a diabody, or a sdAb. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. For a review of multispecific antibodies, see Weidle et al., Cancer Genomics Proteomics, 10(1):1-18, 2013; Geering and Fussenegger, Trends Biotechnol., 33(2):65-79, 2015; Stamova et al., Antibodies, 1(2):172-198, 2012. Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003). Antibody fragments can be made by various techniques, including but not limited to proteolytic digestion of an intact antibody as well as production by recombinant host cells (e.g. E. coli or phage), as described herein. In some embodiments, the one or more other antibody moiety is antibody mimetics, which are small engineered proteins comprising antigen-binding domains reminiscent of antibodies (Geering and Fussenegger, Trends Biotechnol., 33(2):65-79, 2015). These molecules are derived from existing human scaffold proteins and comprise a single polypeptide. Exemplary antibody mimetics that can be comprised within the anti-PD-L1 construct described herein can be, but are not limited to, a designed ankyrin repeat protein (DARPin; comprising 3-5 fully synthetic ankyrin repeats flanked by N- and C-terminal Cap domains), an avidity multimer (avimer; a high-affinity protein comprising multiple A domains, each domain with low affinity for a target), or an Anticalin (based on the scaffold of lipocalins, with four accessible loops, the sequence of each can be randomized).

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991); and creating polypeptides comprising tandem single-domain antibodies (see, e.g., U.S. Patent Application No. 20110028695; and Conrath et al. J. Biol. Chem., 2001; 276(10):7346-50). Engineered antibodies with three or more functional antigen binding sites, including "Octopus antibodies," are also included herein (see, e.g., US 2006/0025576A1).

Peptide Linkers

In some embodiments, the two or more antibody moieties within the anti-PD-L1 construct can be optionally connected by a peptide linker. The length, the degree of flexibility and/or other properties of the peptide linker(s) used in the anti-PD-L1 construct may have some influence on properties, including but not limited to the affinity, specificity or avidity for one or more particular antigens or epitopes. For example, longer peptide linkers may be selected to ensure that two adjacent domains do not sterically interfere with one another. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a mutated human IgG1 hinge (SEQ ID NO: 445). In some embodiments, the peptide linker is a flexible linker. Exemplary flexible linkers include glycine polymers $(G)_n$, glycine-serine polymers (including, for example, $(GS)_n$, $(GSGGS)_n$, $(GGGS)_n$, and $(GGGGS)_n$, where n is an integer of at least one), glycine-alanine polymers, alanine-serine polymers, and other flexible linkers known in the art. In some embodiments, the peptide linker comprises the amino acid sequence of GGGGSGGGS (SEQ ID NO: 443). In some embodiments, the peptide linker comprises the amino acid sequence of SEQ ID NO: 444 (GGGGSGGGGSGGGGS). In some embodiments, the peptide linker comprises the amino acid sequence of SEQ ID NO: 445 (EPKS SDKTHT SPP SP).

In some embodiments, the anti-PD-L1 construct comprising an anti-PD-L1 sdAb moiety and one or more other antibody moiety is monospecific. In some embodiments, the anti-PD-L1 construct comprising an anti-PD-L1 sdAb moiety and one or more other antibody moiety is multispecific (such as bispecific). Multispecific molecules are molecules that have binding specificities for at least two different antigens or epitopes (e.g., bispecific antibodies have binding specificities for two antigens or epitopes). Multispecific molecules with more than two valencies and/or specificities are also contemplated. For example, trispecific antibodies can be prepared. Tutt et al. *J. Immunol.* 147: 60 (1991). It is to be appreciated that one of skill in the art could select appropriate features of individual multispecific molecules described herein to combine with one another to form a multi-specific anti-PD-L1 molecule of the invention.

In some embodiments, the anti-PD-L1 construct is multivalent but monospecific, i.e., the anti-PD-L1 construct comprises an anti-PD-L1 sdAb moiety described herein and at least a second antibody moiety specifically recognizing the same PD-L1 epitope as the anti-PD-L1 sdAb moiety. In some embodiments, the one or more antibody moiety specifically recognizing the same PD-L1 epitope as the anti-PD-L1 sdAb moiety described herein may comprise the same CDRs and/or the same $V_HH$ amino acid sequence as the anti-PD-L1 sdAb moiety. For example, the anti-PD-L1 construct may comprise two or more anti-PD-L1 sdAb moieties described herein, wherein the two or more anti-PD-L1 sdAb moieties are the same. In some embodiments, the anti-PD-L1 sdAb moieties are optionally connected by peptide linker(s). In some embodiments, the peptide linker comprises the amino acid sequence of any one of SEQ ID NO: 443-445.

In some embodiments, the anti-PD-L1 construct is multivalent and multispecific, i.e., the anti-PD-L1 construct comprises an anti-PD-L1 sdAb moiety described herein and at least a second antibody moiety specifically recognizing a second antigen other than PD-L1, or a different PD-L1 epitope recognized by the anti-PD-L1 sdAb moiety. In some embodiments, the second antibody moiety is a sdAb. In some embodiments, the second antibody moiety specifically recognizes human serum albumin (HSA). In some embodiments, the sdAb moiety specifically recognizing PD-L1 is N terminal or C terminal to the second antibody moiety. In some embodiments, the anti-PD-L1 construct is trivalent and bispecific. In some embodiments, the anti-PD-L1 construct comprises two anti-PD-L1 sdAbs described herein and a second antibody moiety (such as an anti-HSA sdAb), wherein the second antibody moiety is in between the two anti-PD-L1 sdAbs. In some embodiments, the antibody moieties are optionally connected by peptide linker(s). In some embodiments, the peptide linker comprises the amino acid sequence of any one of SEQ ID NO: 443-445.

The monospecific or multispecific anti-PD-L1 construct comprising two or more sdAb moieties specifically recognizing PD-L1 may have increase avidity compared to that of a single anti-PD-L1 sdAb moiety described here.

Bispecific Antibodies Comprising sdAb Fused to Full-Length Antibody

In some embodiments, the anti-PD-L1 construct comprises an anti-PD-L1 sdAb moiety described herein fused to a second antibody moiety, wherein the second antibody moiety is a full-length antibody (such as anti-TIGIT full-length antibody). The construct comprising bi-specificity against PD-L1 and TIGIT will be hereinafter referred to as "anti-PD-L1/TIGIT antibody", "anti-PD-L1/TIGIT construct", or "PD-L1×TIGIT antibody".

In some embodiments, the anti-PD-L1 construct comprises an anti-PD-L1 sdAb moiety described herein fused to a second antibody moiety, wherein the second antibody moiety is a full-length antibody (such as anti-TIM-3 full-length antibody). The construct comprising bi-specificity against PD-L1 and TIM-3 will be hereinafter referred to as "anti-PD-L1/TIM-3 antibody", "anti-PD-L1/TIM-3 construct", or "PD-L1×TIM-3 antibody".

In some embodiments, the anti-PD-L1 construct comprises an anti-PD-L1 sdAb moiety described herein fused to a second antibody moiety, wherein the second antibody moiety is a full-length antibody (such as anti-LAG-3 full-length antibody). The construct comprising bi-specificity against PD-L1 and LAG-3 will be hereinafter referred to as "anti-PD-L1/LAG-3 antibody", "anti-PD-L1/LAG-3 construct", or "PD-L1×LAG-3 antibody".

TIGIT, TIM-3 and LAG-3, similar to PD-L1, are inhibitory immune checkpoint molecules.

In some embodiments, there is provided an isolated anti-PD-L1 construct comprising a sdAb moiety specifically recognizing PD-L1 and a full length antibody selected from the group consisting of an anti-TIGIT antibody, an anti-TIM-3 antibody, and an anti-LAG-3 antibody, wherein the anti-PD-L1 sdAb moiety comprises a CDR1 comprising the amino acid sequence of any one of SEQ ID NOs: 51-100, or a variant thereof comprising up to about 3 (such as about any of 1, 2, or 3) amino acid substitutions; a CDR2 comprising the amino acid sequence of any one of SEQ ID NOs: 151-200, or a variant thereof comprising up to about 3 (such as about any of 1, 2, or 3) amino acid substitutions; and a CDR3 comprising the amino acid sequence of any one of SEQ ID NOs: 251-300, or a variant thereof comprising up to about 3 (such as about any of 1, 2, or 3) amino acid substitutions. In some embodiments, the N terminus of the sdAb moiety specifically recognizing PD-L1 is fused to the C terminus of at least one of the heavy chains of the full-length antibody. In some embodiments, the C terminus of the sdAb moiety specifically recognizing PD-L1 is fused to the N terminus of at least one of the heavy chains of the full-length antibody. In some embodiments, the sdAb moiety specifically recognizing PD-L1 and the full-length antibody are optionally connected by a peptide linker. In some embodiments, the peptide linker comprises the amino acid sequence of SEQ ID NO: 443-445. In some embodiments, the $K_d$ of the binding between the anti-PD-L1 sdAb moiety and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 sdAb moiety is camelid, chimeric, human, partially humanized, or fully humanized.

In some embodiments, there is provided an isolated anti-PD-L1 construct comprising a sdAb moiety specifically recognizing PD-L1 and a full length antibody selected from the group consisting of an anti-TIGIT antibody, an anti-TIM-3 antibody, and an anti-LAG-3 antibody, wherein the sdAb comprises a $V_HH$ domain comprising the amino acid sequence of any one of SEQ ID NOs: 351-400, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 351-400. In some embodiments, there is provided an isolated anti-PD-L1 construct comprising a sdAb moiety specifically recognizing PD-L1 and a full length antibody selected from the group consisting of an anti-TIGIT antibody, an anti-TIM-3 antibody, and an anti-LAG-3 antibody, wherein the sdAb comprises a $V_HH$ domain comprising the amino acid sequence of any one of SEQ ID NOs: 351-400, or a variant thereof comprising up to about 3 (such as about any of 1, 2, or 3) amino acid substitutions in the $V_HH$ domain. In some embodiments, the anti-PD-L1 sdAb moiety comprising the $V_HH$ domain comprising the amino acid sequence of any one of SEQ ID NOs: 351-400 or a variant thereof comprises amino acid substitutions in CDRs, such as the CDR1, and/or the CDR2, and/or the CDR3 of any one of SEQ ID NOs: 351-400. In some embodiments, the anti-PD-L1 sdAb moiety comprising the $V_HH$ domain comprising the amino acid sequence of any one of SEQ ID NOs: 351-400 or a variant thereof comprises CDR1, CDR2, and CDR3 of any one of SEQ ID NOs: 351-400, and the amino acid substitutions are in FRs, such as the FR1, and/or the FR2, and/or the FR3, and/or the FR4 of any one of SEQ ID NOs: 351-400. In some embodiments, the anti-PD-L1 sdAb moiety comprising the $V_HH$ domain comprising the amino acid sequence of any one of SEQ ID NOs: 351-400 or a variant thereof comprises amino acid substitutions in both CDRs and FRs. In some embodiments, there is provided an isolated anti-PD-L1 construct comprising a sdAb moiety specifically recognizing PD-L1 and a full-length antibody selected from the group consisting of an anti-TIGIT antibody, an anti-TIM-3 antibody, and an anti-LAG-3 antibody, wherein the sdAb comprises a $V_HH$ domain comprising the amino acid sequence of any one of SEQ ID NOs: 351-400. In some embodiments, the N terminus of the sdAb moiety specifically recognizing PD-L1 is fused to the C terminus of at least one of the heavy chains of the full-length antibody. In some embodiments, the C terminus of the sdAb moiety specifically recognizing PD-L1 is fused to the N terminus of at least one of the heavy chains of the full-length antibody. In some embodiments, the sdAb moiety specifically recognizing PD-L1 and the full-length antibody are optionally connected by a peptide linker. In some embodiments, the peptide linker comprises the amino acid sequence of SEQ ID NO: 443-445. In some embodiments, the $K_d$ of the binding between the anti-PD-L1 sdAb moiety and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 sdAb moiety is camelid, chimeric, human, partially humanized, or fully humanized.

In some embodiments, there is also provided an anti-PD-L1 construct comprising a sdAb moiety specifically recognizing PD-L1 (hereinafter referred to as "competing anti-PD-L1 construct") that specifically binds to PD-L1 competitively with any one of the anti-PD-L1/TIGIT constructs, anti-PD-L1/TIM-3 constructs or anti-PD-L1/LAG-3 constructs described herein.

Anti-PD-L1 Antibody Variants

In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, Deletion and Variants

In some embodiments, antibody variants having one or more amino acid substitutions are provided. Sites of interest for substitutional mutagenesis include the HVRs and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;

(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an anti-PD-L1 construct provided herein is altered to increase or decrease the extent to which the construct is glycosylated. Addition or deletion of glycosylation sites to an antibody may be conveniently accomplished by altering the amino acid sequence such that one or more glycosylation sites is created or removed.

Where the anti-PD-L1 construct comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-PD-L1 construct of the present application may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4): 680-688 (2006); and WO2003/085107).

Anti-PD-L1 construct variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of the anti-PD-L1 construct provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an anti-PD-L1 construct variant that possesses some but not all effector functions, which make it a desirable candidate for applications in which the half-life of the anti-PD-L1 construct in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (Cell Technology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In some embodiments, an anti-PD-L1 construct variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, there is provided an anti-PD-L1 construct (e.g., a HCAb) variant comprising a variant Fc region comprising one or more amino acid substitutions which increase half-life and/or improve binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-PD-L1 constructs (such as HCAb or anti-PD-L1 sdAb fused to a full-length antibody) comprising any of the Fc variants described herein, or combinations thereof, are contemplated.

d) Cysteine Engineered Antibody Variants

In some embodiments, it may be desirable to create cysteine engineered anti-PD-L1 constructs, e.g., "thio-MAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered anti-PD-L1 constructs may be generated as described, e.g., in U.S. Pat. No. 7,521,541.

e) Antibody Derivatives

In some embodiments, an anti-PD-L1 construct provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an anti-PD-L1 construct and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an anti-PD-L1 construct provided herein (such as anti-PD-L1 sdAb, anti-PD-L1 HCAb, anti-PD-L1/antiCTLA-4 HCAb, anti-PD-L1/TIGIT bispecific antibody, anti-PD-L1/TIM-3 bispecific antibody or anti-PD-L1/LAG-3 bispecific antibody) may be further modified to contain one or more biologically active protein, polypeptides or fragments thereof. "Bioactive" or "biologically active" as used herein means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof have immunostimulatory/immunoregulatory, membrane transport, or enzymatic activities.

In some embodiments, the bioactive protein or fragments thereof that can be fused with the anti-PD-L1 construct described herein is a ligand, such as lymphokines and cellular factors which interact with specific cellular receptor. Lymphokines are low molecular weight proteins which are secreted by T cells when antigens or lectins stimulate T cell growth. Examples of lymphokines include, but are not limited to, interferon-α, interferon-γ, interleukin-1 (IL-1), interleukin-2 (IL-2), interleukin-3 (IL-3), tumor necrosis factor (TNF), a colony stimulating factor (e.g. CSF-1, G-CSF or GM-CSF), chemotaxins, macrophage migration inhibitory factor (MIF), macrophage-activating factor (MAF), NK cell activating factor, T cell replacing factor, leukocyte-inhibitory factor (LIF), lymphotoxins, osteoclast-activating factor (OAF), soluble immune response suppressor (SIRS), growth-stimulating factor, monocyte growth factor, etc. Cellular factors which may be incorporated into the anti-PD-L1 fusion proteins of the invention include but are not limited to tumor necrosis factor α (TNFα), interferons (IFNs), and nerve growth factor (NGF), etc.

III. Pharmaceutical Compositions

Further provided by the present application are pharmaceutical compositions comprising any one of the anti-PD-L1 constructs comprising a sdAb specifically recognizing PD-L1 as described herein (such as anti-PD-L1 sdAb, anti-PD-L1 HCAb, anti-PD-L1/antiCTLA-4 HCAb, anti-PD-L1/TIGIT bispecific antibody, anti-PD-L1/TIM-3 bispecific antibody or anti-PD-L1/LAG-3 bispecific antibody), and optionally a pharmaceutically acceptable carrier. Pharmaceutical compositions can be prepared by mixing an anti-PD-L1 construct described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the anti-PD-L1 construct comprising anti-PD-L1 sdAb described here essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of anti-PD-L1 construct described herein may comprise less than about 10% (preferably less than about 5%) of the anti-PD-L1 construct present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). The addition of a preservative may, for example, facilitate the production of a multi-use (multiple-dose) formulation. Suitable preservatives for use in the present application include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1% to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

IV. Methods of Treating PD-L1 Related Diseases

The anti-PD-L1 construct comprising sdAb specifically recognizing PD-L1 as described herein (such as anti-PD-L1 sdAb, anti-PD-L1 HCAb, anti-PD-L1/antiCTLA-4 HCAb, anti-PD-L1/TIGIT bispecific antibody, anti-PD-L1/TIM-3 bispecific antibody or anti-PD-L1/LAG-3 bispecific antibody), and the compositions (such as pharmaceutical compositions) thereof are useful for a variety of applications, such as in diagnosis, molecular assays, and therapy.

One aspect of the invention provides a method of treating a PD-L1 related disease or a condition in an individual in need thereof, comprising administering to the individual an effective amount of a pharmaceutical composition comprising the anti-PD-L1 construct described herein. In some embodiments, the PD-L1 related disease is cancer. In some embodiments, the PD-L1 related disease is pathogenic infection, such as viral infection.

The present invention contemplates, in part, protein constructs (such as anti-PD-L1 sdAb, anti-PD-L1 HCAb, anti-PD-L1/antiCTLA-4 HCAb, anti-PD-L1/TIGIT bispecific antibody, anti-PD-L1/TIM-3 bispecific antibody or anti-PD-L1/LAG-3 bispecific antibody), nucleic acid molecules and/or vectors encoding thereof, host cells comprising nucleic acid molecules and/or vectors encoding thereof, that can be administered either alone or in any combination with another therapy, and in at least some aspects, together with a pharmaceutically acceptable carrier or excipient. In some embodiments, prior to administration of the anti-PD-L1 construct, they may be combined with suitable pharmaceutical carriers and excipients that are well known in the art. The compositions prepared according to the disclosure can be used for the treatment or delaying of worsening of cancer.

In some embodiments, there is provided a method of treating cancer comprising administering to the individual an effective amount of a pharmaceutical composition comprising an isolated anti-PD-L1 construct comprising a single-domain antibody (sdAb) moiety specifically recognizing PD-L1 (such as anti-PD-L1 sdAb, anti-PD-L1 HCAb, anti-PD-L1/antiCTLA-4 HCAb, anti-PD-L1/TIGIT bispecific antibody, anti-PD-L1/TIM-3 bispecific antibody or anti-PD-L1/LAG-3 bispecific antibody). In some embodiments, the cancer is a solid tumor (such as colon cancer). In some embodiments, the pharmaceutical composition is administered systemically (such as intravenously). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (uninfected by the oncolytic VV) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as chemotherapy, surgery, hormone therapy, radiation, gene therapy, immunotherapy (such as T-cell therapy), bone marrow transplantation, stem cell transplantation, targeted therapy, cryotherapy, ultrasound therapy, photodynamic therapy, radio-frequency ablation or the like, in an adjuvant setting or a neoadjuvant setting (i.e., the method may be carried out before the primary/definitive therapy). In some embodiments, the method is used to treat an individual who has previously been treated. In some embodiments, the cancer has been refractory to prior therapy. In some embodiments, the method is used to treat an individual who has not previously been treated.

In some embodiments, the method is suitable for treating cancers with aberrant PD-L1 expression, activity and/or signaling include, by way of non-limiting example, melanoma, prostate cancer, lung cancer, colon cancer, gastric cancer, ovarian cancer, breast cancer, and glioblastoma.

Thus in some embodiments, there is provided a method of treating an immunotherapy-responsive solid tumor (such as carcinoma or adenocarcinoma, such as cancers with aberrant PD-L1 expression, activity and/or signaling), comprising administering to the individual an effective amount of a pharmaceutical composition comprising an isolated anti-PD-L1 construct comprising a sdAb moiety specifically recognizing PD-L1 (such as anti-PD-L1 sdAb, anti-PD-L1 HCAb, anti-PD-L1/antiCTLA-4 HCAb, anti-PD-L1/TIGIT bispecific antibody, anti-PD-L1/TIM-3 bispecific antibody or anti-PD-L1/LAG-3 bispecific antibody). In some embodiments, the cancer is a solid tumor (such as colon cancer). In some embodiments, the pharmaceutical composition is administered systemically (such as intravenously). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (uninfected by the oncolytic VV) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

In some embodiments, the method is suitable for treating cancers with aberrant PD-1 or PD-L1/PD-L2 expression, activity and/or signaling include, by way of non-limiting example, hematological cancer and/or solid tumors. Some cancers whose growth may be inhibited using the antibodies of the invention include cancers typically responsive to immunotherapy. Non-limiting examples of other cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention. Examples of other cancers that may be treated using the antibodies of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Immunol.* 17:133-144).

Thus, in some embodiments, there is provided a method of treating an immunotherapy-responsive solid tumor (such as carcinoma or adenocarcinoma, such as cancers with aberrant PD-L1 expression, activity and/or signaling, and/or aberrant TIGIT, TIM-3 and LAG-3 expression, activity and/or signaling), comprising administering to the individual an effective amount of a pharmaceutical composition comprising an isolated anti-PD-L1 construct comprising a single-domain antibody (sdAb) moiety specifically recognizing PD-L1 fused to a TIGIT, TIM-3 or LAG-3 full-length antibody. In some embodiments, there is provided a method of treating an immunotherapy-responsive solid tumor (such as carcinoma or adenocarcinoma, such as cancers with aberrant PD-L1 expression, activity and/or signaling, and/or aberrant TIGIT, TIM-3, LAG-3 expression, activity and/or signaling), comprising administering to the individual an effective amount of a pharmaceutical composition comprising an isolated anti-PD-L1 construct comprising a single-domain antibody (sdAb) moiety specifically recognizing PD-L1 fused to a TIGIT, TIM-3 or LAG-3 full-length antibody.

In some embodiments, the method described herein is suitable for treating a colorectal cancer, such as adenocarcinoma, gastrointestinal carcinoid tumor, gastrointestinal stromal tumor, Leiomyosarcoma, melanoma, or squamous cell carcinoma.

Dosages and desired drug concentrations of pharmaceutical compositions of the present application may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the anti-PD-L1 construct comprising an anti-PD-L1 sdAb moiety described herein are used, normal dosage amounts may vary from about 10 ng/kg up to about 100 mg/kg of mammal body weight or more per day, preferably about 1 mg/kg/day to 10 mg/kg/day, such as about 1-3 mg/kg/day, about 2-4 mg/kg/day, about 3-5 mg/kg/day, about 4-6 mg/kg/day, about 5-7 mg/kg/day, about 6-8 mg/kg/day, about 6-6.5 mg/kg/day, about 6.5-7 mg/kg/day, about 7-9 mg/kg/day, or about 8-10 mg/kg/day, depending upon the route of administration. It is within the scope of the present application that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the pharmaceutical composition is administered for a single time (e.g. bolus injection). In some embodiments, the pharmaceutical composition is administered for multiple times (such as any of 2, 3, 4, 5, 6, or more times). If multiple administrations, they may be performed by the same or different routes and may take place at the same site or at alternative sites. The pharmaceutical composition may be administered twice per week, 3 times per week, 4 times per week, 5 times per week, daily, daily without break, once per week, weekly without break, once per 2 weeks, once per 3 weeks, once per month, once per 2 months, once per 3 months, once per 4 months, once per 5 months, once per 6 months, once per 7 months, once per 8 months, once per 9 months, once per 10 months, once per 11 months, or once per year. The interval between administrations can be about any one of 24 h to 48 h, 2 days to 3 days, 3 days to 5 days, 5 days to 1 week, 1 week to 2 weeks, 2 weeks to 1 month, 1 month to 2 months, 2 month to 3 months, 3 months to 6 months, or 6 months to a year. Intervals can also be irregular (e.g. following tumor progression). In some embodiments, there is no break in the dosing schedule. In some embodiments, the pharmaceutical composition is administered every 4 days for 4 times. The optimal dosage and treatment regime for a particular patient can readily be determined by one skilled in the art of medicine by monitoring the patient for signs of disease and adjusting the treatment accordingly.

The pharmaceutical compositions of the present application, including but not limited to reconstituted and liquid formulations, are administered to an individual in need of treatment with the anti-PD-L1 construct described herein, preferably a human, in accord with known methods, such as intravenous administration as a bolus or by continuous infusion over a period of time, by intramuscular, intraperitoneal, intracerebrospinal, subcutaneous, intravenous (i.v.), intra-articular, intrasynovial, intrathecal, oral, topical, or inhalation routes. A reconstituted formulation can be prepared by dissolving a lyophilized anti-PD-L1 construct described herein in a diluent such that the protein is dispersed throughout. Exemplary pharmaceutically acceptable (safe and non-toxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the individual by subcutaneous (i.e. beneath the skin) administration. For such purposes, the pharmaceutical compositions may be injected using a syringe. However, other devices for administration of the pharmaceutical compositions are available such as injection devices; injector pens; auto-injector devices, needleless devices; and subcutaneous patch delivery systems.

In some embodiments, the pharmaceutical compositions are administered to the individual intravenously. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)).

V. Methods of Preparation

The anti-PD-L1 construct (such as anti-PD-L1 single-domain antibodies) described herein may be prepared using any methods known in the art or as described herein. Also see Examples 1-2.

Methods of preparing single-domain antibodies have been described. See, for example, Els Pardon et al, *Nature Protocol*, 2014; 9(3): 674. Single-domain antibodies (such as $V_H$Hs) may be obtained using methods known in the art such as by immunizing a Camelid species (such as camel or llama) and obtaining hybridomas therefrom, or by cloning a library of single-domain antibodies using molecular biology techniques known in the art and subsequent selection by ELISA with individual clones of unselected libraries or by using phage display.

For recombinant production of the single-domain antibodies, the nucleic acids encoding the single-domain antibodies are isolated and inserted into a replicable vector for further cloning (amplification of the DNA) or for expression. DNA encoding the single-domain antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

EMBODIMENTS

The invention provides also the following non-limiting embodiments.

Embodiment 1 is an isolated anti-PD-L1 construct comprising a single-domain antibody (sdAb) moiety specifically recognizing PD-L1, wherein the sdAb moiety comprises a CDR1 comprising the amino acid sequence of any one of SEQ ID NOs: 51-100, or a variant thereof comprising up to about 3 amino acid substitutions; a CDR2 comprising the amino acid sequence of any one of SEQ ID NOs: 151-200, or a variant thereof comprising up to about 3 amino acid substitutions; and a CDR3 comprising the amino acid sequence of any one of SEQ ID NOs: 251-300, or a variant thereof comprising up to about 3 amino acid substitutions.

Embodiment 2 is the isolated anti-PD-L1 construct of embodiment 1, wherein the sdAb moiety comprises a CDR1 comprising the amino acid sequence of any one of SEQ ID NOs: 51-100; a CDR2 comprising the amino acid sequence of any one of SEQ ID NOs: 151-200; and a CDR3 comprising the amino acid sequence of any one of SEQ ID NOs: 251-300; or a variant thereof comprising up to about 3 amino acid substitutions in the CDR regions.

Embodiment 3 is the isolated anti-PD-L1 construct of any one of embodiments 1-2, wherein the sdAb moiety comprises any one of the following:
  (1) a CDR1 comprising the amino acid sequence of SEQ ID NO: 51; a CDR2 comprising the amino acid sequence of SEQ ID NO: 151; and a CDR3 comprising the amino acid sequence of SEQ ID NO: 251; or a variant thereof comprising up to about 3 amino acid substitutions in the CDR regions;

(2) a CDR1 comprising the amino acid sequence of SEQ ID NO: 52; a CDR2 comprising the amino acid sequence of SEQ ID NO: 152; and a CDR3 comprising the amino acid sequence of SEQ ID NO: 252; or a variant thereof comprising up to about 3 amino acid substitutions in the CDR regions;

(3) a CDR1 comprising the amino acid sequence of SEQ ID NO: 53; a CDR2 comprising the amino acid sequence of SEQ ID NO: 153; and a CDR3 comprising the amino acid sequence of SEQ ID NO: 253; or a variant thereof comprising up to about 3 amino acid substitutions in the CDR regions;

(4) a CDR1 comprising the amino acid sequence of SEQ ID NO: 54; a CDR2 comprising the amino acid sequence of SEQ ID NO: 154; and a CDR3 comprising the amino acid sequence of SEQ ID NO: 254; or a variant thereof comprising up to about 3 amino acid substitutions in the CDR regions;

(5) a CDR1 comprising the amino acid sequence of SEQ ID NO: 55; a CDR2 comprising the amino acid sequence of SEQ ID NO: 155; and a CDR3 comprising the amino acid sequence of SEQ ID NO: 255; or a variant thereof comprising up to about 3 amino acid substitutions in the CDR regions;

(6) a CDR1 comprising the amino acid sequence of SEQ ID NO: 56; a CDR2 comprising the amino acid sequence of SEQ ID NO: 156; and a CDR3 comprising the amino acid sequence of SEQ ID NO: 256; or a variant thereof comprising up to about 3 amino acid substitutions in the CDR regions;

(7) a CDR1 comprising the amino acid sequence of SEQ ID NO: 57; a CDR2 comprising the amino acid sequence of SEQ ID NO: 157; and a CDR3 comprising the amino acid sequence of SEQ ID NO: 257; or a variant thereof comprising up to about 3 amino acid substitutions in the CDR regions;

(8) a CDR1 comprising the amino acid sequence of SEQ ID NO: 58; a CDR2 comprising the amino acid sequence of SEQ ID NO: 158; and a CDR3 comprising the amino acid sequence of SEQ ID NO: 258; or a variant thereof comprising up to about 3 amino acid substitutions in the CDR regions;

(9) a CDR1 comprising the amino acid sequence of SEQ ID NO: 59; a CDR2 comprising the amino acid sequence of SEQ ID NO: 159; and a CDR3 comprising the amino acid sequence of SEQ ID NO: 259; or a variant thereof comprising up to about 3 amino acid substitutions in the CDR regions;

(10) a CDR1 comprising the amino acid sequence of SEQ ID NO: 60; a CDR2 comprising the amino acid sequence of SEQ ID NO: 160; and a CDR3 comprising the amino acid sequence of SEQ ID NO: 260; or a variant thereof comprising up to about 3 amino acid substitutions in the CDR regions;

(11) a CDR1 comprising the amino acid sequence of SEQ ID NO: 61; a CDR2 comprising the amino acid sequence of SEQ ID NO: 161; and a CDR3 comprising the amino acid sequence of SEQ ID NO: 261; or a variant thereof comprising up to about 3 amino acid substitutions in the CDR regions;

(12) a CDR1 comprising the amino acid sequence of SEQ ID NO: 62; a CDR2 comprising the amino acid sequence of SEQ ID NO: 162; and a CDR3 comprising the amino acid sequence of SEQ ID NO: 262; or a variant thereof comprising up to about 3 amino acid substitutions in the CDR regions;

(13) a CDR1 comprising the amino acid sequence of SEQ ID NO: 63; a CDR2 comprising the amino acid sequence of SEQ ID NO: 163; and a CDR3 comprising the amino acid sequence of SEQ ID NO: 263; or a variant thereof comprising up to about 3 amino acid substitutions in the CDR regions;

(14) a CDR1 comprising the amino acid sequence of SEQ ID NO: 64; a CDR2 comprising the amino acid sequence of SEQ ID NO: 164; and a CDR3 comprising the amino acid sequence of SEQ ID NO: 264; or a variant thereof comprising up to about 3 amino acid substitutions in the CDR regions;

(15) a CDR1 comprising the amino acid sequence of SEQ ID NO: 65; a CDR2 comprising the amino acid sequence of SEQ ID NO: 165; and a CDR3 comprising the amino acid sequence of SEQ ID NO: 265; or a variant thereof comprising up to about 3 amino acid substitutions in the CDR regions;

(16) a CDR1 comprising the amino acid sequence of SEQ ID NO: 66; a CDR2 comprising the amino acid sequence of SEQ ID NO: 166; and a CDR3 comprising the amino acid sequence of SEQ ID NO: 266; or a variant thereof comprising up to about 3 amino acid substitutions in the CDR regions;

(17) a CDR1 comprising the amino acid sequence of SEQ ID NO: 67; a CDR2 comprising the amino acid sequence of SEQ ID NO: 167; and a CDR3 comprising the amino acid sequence of SEQ ID NO: 267; or a variant thereof comprising up to about 3 amino acid substitutions in the CDR regions;

(18) a CDR1 comprising the amino acid sequence of SEQ ID NO: 68; a CDR2 comprising the amino acid sequence of SEQ ID NO: 168; and a CDR3 comprising the amino acid sequence of SEQ ID NO: 268; or a variant thereof comprising up to about 3 amino acid substitutions in the CDR regions;

(19) a CDR1 comprising the amino acid sequence of SEQ ID NO: 69; a CDR2 comprising the amino acid sequence of SEQ ID NO: 169; and a CDR3 comprising the amino acid sequence of SEQ ID NO: 269; or a variant thereof comprising up to about 3 amino acid substitutions in the CDR regions;

(20) a CDR1 comprising the amino acid sequence of SEQ ID NO: 70; a CDR2 comprising the amino acid sequence of SEQ ID NO: 170; and a CDR3 comprising the amino acid sequence of SEQ ID NO: 270; or a variant thereof comprising up to about 3 amino acid substitutions in the CDR regions;

(21) a CDR1 comprising the amino acid sequence of SEQ ID NO: 71; a CDR2 comprising the amino acid sequence of SEQ ID NO: 171; and a CDR3 comprising the amino acid sequence of SEQ ID NO: 271; or a variant thereof comprising up to about 3 amino acid substitutions in the CDR regions;

(22) a CDR1 comprising the amino acid sequence of SEQ ID NO: 72; a CDR2 comprising the amino acid sequence of SEQ ID NO: 172; and a CDR3 comprising the amino acid sequence of SEQ ID NO: 272; or a variant thereof comprising up to about 3 amino acid substitutions in the CDR regions;

(23) a CDR1 comprising the amino acid sequence of SEQ ID NO: 73; a CDR2 comprising the amino acid sequence of SEQ ID NO: 173; and a CDR3 comprising the amino acid sequence of SEQ ID NO: 273; or a variant thereof comprising up to about 3 amino acid substitutions in the CDR regions;

(24) a CDR1 comprising the amino acid sequence of SEQ ID NO: 74; a CDR2 comprising the amino acid sequence of SEQ ID NO: 174; and a CDR3 comprising the amino acid sequence of SEQ ID NO: 274; or a variant thereof comprising up to about 3 amino acid substitutions in the CDR regions;

(25) a CDR1 comprising the amino acid sequence of SEQ ID NO: 75; a CDR2 comprising the amino acid sequence of SEQ ID NO: 175; and a CDR3 comprising the amino acid sequence of SEQ ID NO: 275; or a variant thereof comprising up to about 3 amino acid substitutions in the CDR regions;

(26) a CDR1 comprising the amino acid sequence of SEQ ID NO: 76; a CDR2 comprising the amino acid sequence of SEQ ID NO: 176; and a CDR3 comprising the amino acid sequence of SEQ ID NO: 276; or a variant thereof comprising up to about 3 amino acid substitutions in the CDR regions;

(27) a CDR1 comprising the amino acid sequence of SEQ ID NO: 77; a CDR2 comprising the amino acid sequence of SEQ ID NO: 177; and a CDR3 comprising the amino acid sequence of SEQ ID NO: 277; or a variant thereof comprising up to about 3 amino acid substitutions in the CDR regions;

(28) a CDR1 comprising the amino acid sequence of SEQ ID NO: 78; a CDR2 comprising the amino acid sequence of SEQ ID NO: 178; and a CDR3 comprising the amino acid sequence of SEQ ID NO: 278; or a variant thereof comprising up to about 3 amino acid substitutions in the CDR regions;

(29) a CDR1 comprising the amino acid sequence of SEQ ID NO: 79; a CDR2 comprising the amino acid sequence of SEQ ID NO: 179; and a CDR3 comprising the amino acid sequence of SEQ ID NO: 279; or a variant thereof comprising up to about 3 amino acid substitutions in the CDR regions;

(30) a CDR1 comprising the amino acid sequence of SEQ ID NO: 80; a CDR2 comprising the amino acid sequence of SEQ ID NO: 180; and a CDR3 comprising the amino acid sequence of SEQ ID NO: 280; or a variant thereof comprising up to about 3 amino acid substitutions in the CDR regions;

(31) a CDR1 comprising the amino acid sequence of SEQ ID NO: 81; a CDR2 comprising the amino acid sequence of SEQ ID NO: 181; and a CDR3 comprising the amino acid sequence of SEQ ID NO: 281; or a variant thereof comprising up to about 3 amino acid substitutions in the CDR regions;

(32) a CDR1 comprising the amino acid sequence of SEQ ID NO: 82; a CDR2 comprising the amino acid sequence of SEQ ID NO: 182; and a CDR3 comprising the amino acid sequence of SEQ ID NO: 282; or a variant thereof comprising up to about 3 amino acid substitutions in the CDR regions;

(33) a CDR1 comprising the amino acid sequence of SEQ ID NO: 83; a CDR2 comprising the amino acid sequence of SEQ ID NO: 183; and a CDR3 comprising the amino acid sequence of SEQ ID NO: 283; or a variant thereof comprising up to about 3 amino acid substitutions in the CDR regions;

(34) a CDR1 comprising the amino acid sequence of SEQ ID NO: 84; a CDR2 comprising the amino acid sequence of SEQ ID NO: 184; and a CDR3 comprising the amino acid sequence of SEQ ID NO: 284; or a variant thereof comprising up to about 3 amino acid substitutions in the CDR regions;

(35) a CDR1 comprising the amino acid sequence of SEQ ID NO: 85; a CDR2 comprising the amino acid sequence of SEQ ID NO: 185; and a CDR3 comprising the amino acid sequence of SEQ ID NO: 285; or a variant thereof comprising up to about 3 amino acid substitutions in the CDR regions;

(36) a CDR1 comprising the amino acid sequence of SEQ ID NO: 86; a CDR2 comprising the amino acid sequence of SEQ ID NO: 186; and a CDR3 comprising the amino acid sequence of SEQ ID NO: 286; or a variant thereof comprising up to about 3 amino acid substitutions in the CDR regions;

(37) a CDR1 comprising the amino acid sequence of SEQ ID NO: 87; a CDR2 comprising the amino acid sequence of SEQ ID NO: 187; and a CDR3 comprising the amino acid sequence of SEQ ID NO: 287; or a variant thereof comprising up to about 3 amino acid substitutions in the CDR regions;

(38) a CDR1 comprising the amino acid sequence of SEQ ID NO: 88; a CDR2 comprising the amino acid sequence of SEQ ID NO: 188; and a CDR3 comprising the amino acid sequence of SEQ ID NO: 288; or a variant thereof comprising up to about 3 amino acid substitutions in the CDR regions;

(39) a CDR1 comprising the amino acid sequence of SEQ ID NO: 89; a CDR2 comprising the amino acid sequence of SEQ ID NO: 189; and a CDR3 comprising the amino acid sequence of SEQ ID NO: 289; or a variant thereof comprising up to about 3 amino acid substitutions in the CDR regions;

(40) a CDR1 comprising the amino acid sequence of SEQ ID NO: 90; a CDR2 comprising the amino acid sequence of SEQ ID NO: 190; and a CDR3 comprising the amino acid sequence of SEQ ID NO: 290; or a variant thereof comprising up to about 3 amino acid substitutions in the CDR regions; and

(41) a CDR1 comprising the amino acid sequence of SEQ ID NO: 91; a CDR2 comprising the amino acid sequence of SEQ ID NO: 191; and a CDR3 comprising the amino acid sequence of SEQ ID NO: 291; or a variant thereof comprising up to about 3 amino acid substitutions in the CDR regions;

(42) a CDR1 comprising the amino acid sequence of SEQ ID NO: 92; a CDR2 comprising the amino acid sequence of SEQ ID NO: 192; and a CDR3 comprising the amino acid sequence of SEQ ID NO: 292; or a variant thereof comprising up to about 3 amino acid substitutions in the CDR regions;

(43) a CDR1 comprising the amino acid sequence of SEQ ID NO: 93; a CDR2 comprising the amino acid sequence of SEQ ID NO: 193; and a CDR3 comprising the amino acid sequence of SEQ ID NO: 293; or a variant thereof comprising up to about 3 amino acid substitutions in the CDR regions;

(44) a CDR1 comprising the amino acid sequence of SEQ ID NO: 94; a CDR2 comprising the amino acid sequence of SEQ ID NO: 194; and a CDR3 comprising the amino acid sequence of SEQ ID NO: 294; or a variant thereof comprising up to about 3 amino acid substitutions in the CDR regions;

(45) a CDR1 comprising the amino acid sequence of SEQ ID NO: 95; a CDR2 comprising the amino acid sequence of SEQ ID NO: 195; and a CDR3 comprising the amino acid sequence of SEQ ID NO: 295; or a variant thereof comprising up to about 3 amino acid substitutions in the CDR regions;

(46) a CDR1 comprising the amino acid sequence of SEQ ID NO: 96; a CDR2 comprising the amino acid sequence of SEQ ID NO: 196; and a CDR3 comprising the amino acid sequence of SEQ ID NO: 296; or a variant thereof comprising up to about 3 amino acid substitutions in the CDR regions;

(47) a CDR1 comprising the amino acid sequence of SEQ ID NO: 97; a CDR2 comprising the amino acid sequence of SEQ ID NO: 197; and a CDR3 comprising the amino acid sequence of SEQ ID NO: 297; or a variant thereof comprising up to about 3 amino acid substitutions in the CDR regions;

(48) a CDR1 comprising the amino acid sequence of SEQ ID NO: 98; a CDR2 comprising the amino acid sequence of SEQ ID NO: 198; and a CDR3 comprising the amino acid sequence of SEQ ID NO: 298; or a variant thereof comprising up to about 3 amino acid substitutions in the CDR regions;

(49) a CDR1 comprising the amino acid sequence of SEQ ID NO: 99; a CDR2 comprising the amino acid sequence of SEQ ID NO: 199; and a CDR3 comprising the amino acid sequence of SEQ ID NO: 299; or a variant thereof comprising up to about 3 amino acid substitutions in the CDR regions;

(50) a CDR1 comprising the amino acid sequence of SEQ ID NO: 100; a CDR2 comprising the amino acid sequence of SEQ ID NO: 200; and a CDR3 comprising the amino acid sequence of SEQ ID NO: 300; or a variant thereof comprising up to about 3 amino acid substitutions in the CDR regions;

Embodiment 4 is the isolated anti-PD-L1 construct of any one of embodiments 1-3, wherein the sdAb moiety comprises a $V_HH$ domain having the amino acid sequence containing:
  a-1) an amino acid residue at position 37 selected from the group consisting of F, Y, L, I, and V, preferably Y and V, and more preferably F;
  a-2) an amino acid residue at position 44 selected from the group consisting of A, G, E, D, G, Q, R, S, and L, preferably Q and G, and more preferably E;
  a-3) an amino acid residue at position 45 selected from the group consisting of L, R, and C;
  a-4) an amino acid residue at position 103 selected from the group consisting of W, R, G, and S; and
  a-5) an amino acid residue at position 108 being Q,
  wherein each of the amino acid positions is according to the Kabat numbering.

Embodiment 5 is the isolated anti-PD-L1 construct of embodiment 4, wherein the sdAb moiety comprises a $V_HH$ domain having the amino acid sequence containing:
  a-1) the amino acid residue at position 37 selected from the group consisting of F, Y, L, I, and V, preferably Y and V, and more preferably F;
  a-2) the amino acid residue at position 44 selected from the group consisting of G, E and Q;
  a-3) the amino acid residue at position 45 selected from the group consisting of L and R;
  a-4) the amino acid residue at position 103 selected from the group consisting of W, G, and R; and
  a-5) the amino acid residue at position 108 being Q.

Embodiment 6 is the isolated anti-PD-L1 construct of embodiment 5, wherein the sdAb moiety comprises a $V_HH$ domain having the amino acid sequence containing:
  a-1) the amino acid residue at position 37 selected from the group consisting of F, Y, and V;
  a-2) the amino acid residue at position 44 selected from the group consisting of G, E and Q;
  a-3) the amino acid residue at position 45 selected from the group consisting of L and R;
  a-4) the amino acid residue at position 103 being W or G; and
  a-5) the amino acid residue at position 108 being Q, which is optionally humanized to L.

Embodiment 7 is the isolated anti-PD-L1 construct of any one of embodiments 1-3, wherein the sdAb moiety comprises a $V_HH$ domain having the amino acid sequence containing:
  b-1) an amino acid residue at position 37 selected from the group consisting of F, Y, L, I, and V, preferably Y and V, and more preferably F
  b-2) an amino acid residue at position 44 selected from the group consisting of E, Q and G;
  b-3) an amino acid residue at position 45 being R;
  b-4) an amino acid residue at position 103 selected from the group consisting of W, R, and S; and
  b-5) an amino acid residue at position 108 selected from the group consisting of Q and L,
  wherein each of the amino acid positions is according to Kabat numbering.

Embodiment 8 is the isolated anti-PD-L1 construct of embodiment 7, wherein the sdAb moiety comprises a VHH domain having the amino acid sequence containing:
  b-1) the amino acid residue at position 37 selected from the group consisting of F, Y, L, I, and V;
  b-2) the amino acid residue at position 44 selected from the group consisting of E, G and Q;
  b-3) the amino acid residue at position 45 being R;
  b-4) the amino acid residue at position 103 being W or G; and
  b-5) the amino acid residue at position 108 being Q, which is optionally humanized to L.

Embodiment 9 is the isolated anti-PD-L1 construct of any one of embodiments 1-8, wherein the sdAb moiety comprises a $V_HH$ domain comprising the amino acid sequence of any one of SEQ ID NOs: 351-400, or a variant thereof having at least about 80%, at least about 90%, or at least about 95% sequence identity to any one of SEQ ID NOs: 351-400.

Embodiment 10 is the isolated anti-PD-L1 construct of embodiment 9, wherein the sdAb moiety comprises a $V_HH$ domain comprising the amino acid sequence of any one of SEQ ID NOs: 351-400, or a variant thereof comprising up to about 3 amino acid substitutions in the $V_HH$ domain.

Embodiment 11 is the isolated anti-PD-L1 construct of any one of embodiments 1-10, wherein the $K_D$ of the binding between the sdAb moiety and PD-L1 is about $10^{-5}$ M to about $10^{-12}$ M, about $10^{-7}$ M to about $10^{-12}$ M, or about $10^{-8}$ M to about $10^{-12}$ M.

Embodiment 12 is the isolated anti-PD-L1 construct of any one of embodiments 1-11, wherein the sdAb moiety specifically recognizing PD-L1 is camelid, chimeric, human, partially humanized, or fully humanized.

Embodiment 13 is the isolated anti-PD-L1 construct of any one of embodiments 1-12, wherein the isolated anti-PD-L1 construct is a heavy chain-only antibody (HCAb).

Embodiment 14 is the isolated anti-PD-L1 construct of embodiment 13, wherein the sdAb moiety that specifically recognizes PD-L1 is fused to a human IgG1 Fc.

Embodiment 15 is the isolated anti-PD-L1 construct of embodiment 13 or 14, wherein the HCAb is monomeric or dimeric.

Embodiment 16 is the isolated anti-PD-L1 construct of any one of embodiments 13-15, wherein the sdAb moiety specifically recognizing PD-L1 comprises the amino acid sequence of any one of SEQ ID NOs: 351-400.

Embodiment 17 is the isolated anti-PD-L1 construct of any one of embodiments 13-15, wherein the HCAb comprises the amino acid sequence of any one of SEQ ID NOs: 401-440.

Embodiment 18 is the isolated anti-PD-L1 construct of any one of embodiments 1-13, wherein the isolated anti-PD-L1 construct further comprises a second antibody moiety specifically recognizing a second antigen.

Embodiment 19 is the isolated anti-PD-L1 construct of embodiment 18, wherein the second antibody moiety is a full-length antibody, a Fab, a Fab', a (Fab')2, an Fv, a single chain Fv (scFv), an scFv-scFv, a minibody, a diabody, a sdAb, or an antibody mimetics.

Embodiment 20 is the isolated anti-PD-L1 construct of embodiment 18 or 19, wherein the anti-PD-L1 construct is monospecific or multi specific.

Embodiment 21 is the isolated anti-PD-L1 construct of any one of embodiments 18-20, wherein the second antibody moiety is a sdAb.

Embodiment 22 is the isolated anti-PD-L1 construct of any one embodiments 18-21, wherein the second antigen is PD-L1.

Embodiment 23 is the isolated anti-PD-L1 construct of embodiment 22, wherein the isolated anti-PD-L1 construct comprises three or more sdAbs that specifically recognize PD-L1.

Embodiment 24 is the isolated anti-PD-L1 construct of embodiment 22 or 23, wherein the second antibody comprises an amino acid sequence of any one of SEQ ID NOs:351-400.

Embodiment 25 is the isolated anti-PD-L1 construct of any one of embodiments 18-21, wherein the second antigen is human serum albumin (HSA).

Embodiment 26 is the isolated anti-PD-L1 construct of any one of embodiments 18-21, wherein the second antigen is CTLA-4, and the second antibody is anti-CTLA-4 sdAb.

Embodiment 27 is the isolated anti-PD-L1 construct of any one of embodiments 18-26, wherein the sdAb moiety specifically recognizing PD-L1 is amino (N)-terminal and/or carboxy (C)-terminal to the second antibody moiety.

Embodiment 28 is the isolated anti-PD-L1 construct of any one embodiments 18-21, wherein the second antibody moiety is a full-length antibody.

Embodiment 29 is the isolated anti-PD-L1 construct of claim 28, wherein the amino (N)-terminus of the sdAb moiety specifically recognizing PD-L1 is fused to the carboxy (C)-terminus of at least one of the heavy chains of the full-length antibody.

Embodiment 30 is the isolated anti-PD-L1 construct of claim 28, wherein the C-terminus of the sdAb moiety specifically recognizing PD-L1 is fused to the N-terminus of at least one of the heavy chains of the full length antibody.

Embodiment 31 is the isolated anti-PD-L1 construct of any one of embodiments 28-30, wherein the full-length antibody specifically recognizes a polypeptide selected from the group consisting of TIGIT, TIM-3, and LAG-3.

Embodiment 32 is the isolated anti-PD-L1 construct of any one of embodiments 28-30, wherein the PD-L1 specifically recognized by the sdAb moiety comprises the amino acid sequence of SEQ ID NO:441 or SEQ ID NO:442.

Embodiment 33 is the isolated anti-PD-L1 construct of any one of embodiments 28-30, wherein the sdAb moiety specifically recognizing PD-L1 and the second antibody moiety are optionally connected by a peptide linker.

Embodiment 34 is the isolated anti-PD-L1 construct of embodiment 33, wherein the peptide linker comprises the amino acid sequence of SEQ ID NO: 443-445.

Embodiment 35 is a second isolated anti-PD-L1 construct that specifically binds to PD-L1 competitively with the isolated anti-PD-L1 construct of any one of embodiments 1-34.

Embodiment 36 is the second isolated anti-PD-L1 construct of embodiment 35, wherein the second isolated anti-PD-L1 construct comprises a CDR1 comprising the amino acid sequence of any one of SEQ ID NOs: 51-100, or a variant thereof comprising up to about 3 amino acid substitutions; a CDR2 comprising the amino acid sequence of any one of SEQ ID NOs: 151-200, or a variant thereof comprising up to about 3 amino acid substitutions; and a CDR3 comprising the amino acid sequence of any one of SEQ ID NOs: 251-300, or a variant thereof comprising up to about 3 amino acid substitutions.

Embodiment 37 is a pharmaceutical composition comprising the isolated anti-PD-L1 construct of any one of embodiments 1-36 and a pharmaceutical acceptable carrier.

Embodiment 38 is a method of treating an individual having a PD-L1-related disease in a subject in need thereof, comprising administering to the subject an effective amount of the pharmaceutical composition of embodiment 37.

Embodiment 39 is the method of embodiment 38, wherein the PD-L1 related disease is cancer.

Embodiment 40 is the method of embodiment 39, wherein the cancer is a solid tumor.

Embodiment 41 is the method of embodiment 39 or 40, wherein the cancer is a colon cancer.

Embodiment 42 is the method of any one of embodiments 39-41, further comprising administering to the individual an additional cancer therapy.

Embodiment 43 is the method of embodiment 42, wherein the additional cancer therapy is surgery, radiation, chemotherapy, immunotherapy, hormone therapy, or a combination thereof.

Embodiment 44 is the method of embodiment 38, wherein the PD-L1 related disease is a pathogenic infection.

Embodiment 45 is the method of any one of embodiments 38-44, wherein the pharmaceutical composition is administered systemically or locally.

Embodiment 46 is the method of embodiment 45, wherein the pharmaceutical composition is administered intravenously.

Embodiment 47 is the method of embodiment 45, wherein the pharmaceutical composition is administered intratumorally.

Embodiment 48 is the method of any one of embodiments 38-47, wherein the individual is a human.

EXAMPLES

The examples below are intended to be purely exemplary of the invention and should therefore not be considered to limit the invention in any way. The following examples and detailed description are offered by way of illustration and not by way of limitation.

Example 1: Generation of Anti-PD-L1 sdAbs

Immunization

Figure 2:
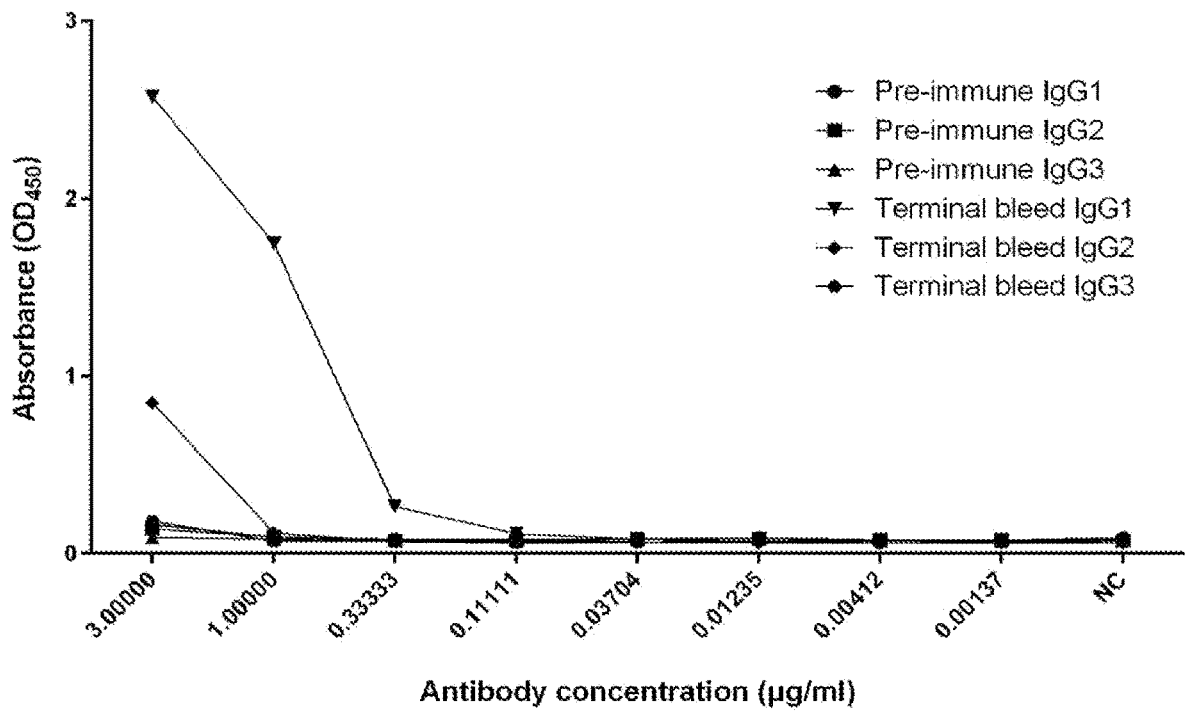
FIG. 2 depicts the immune response evaluation of heavy chain antibodies (IgG2 and IgG3) after the $6^{th}$ immunization (terminal bleed) with recombinant PD-L1 ECD protein; heavy chain antibodies fractionated from pre-immune serum were used as negative controls.
Figure 3A:
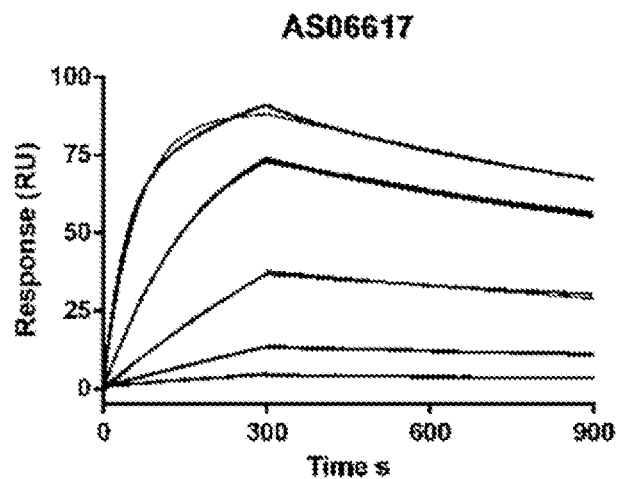
FIGS. 3A-3N depict the affinity determination of selected sdAbs (AS06617 (FIG. 3A); AS06618 (FIG. 3B); AS06628 (FIG. 3C); AS06682 (FIG. 3D); AS06686 (FIG. 3E); AS06703 (FIG. 3F); AS06730 (FIG. 3G); AS06750 (FIG. 3H); AS06775 (FIG. 3I); AS06778 (FIG. 3J); AS06791 (FIG. 3K); AS11947 (FIG. 3L); AS11948 (FIG. 3M); and AS12003 (FIG. 3N)): the PD-L1 was immobilized onto the chip and anti-PD-L1 sdAb was flowed as analyte at concentrations of 0.11, 0.33, 1, 3, and 9 nM.
Figure 3B:
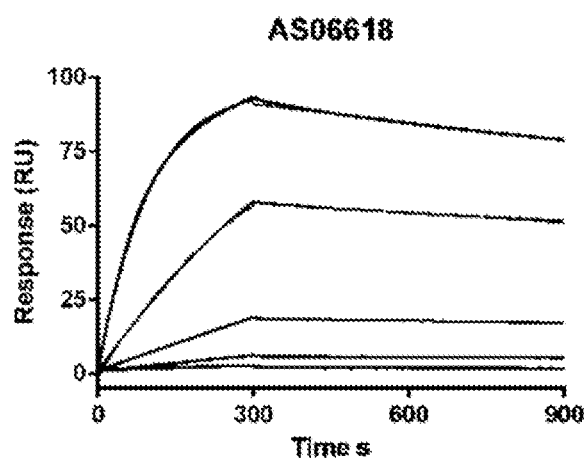
Figure 3C:
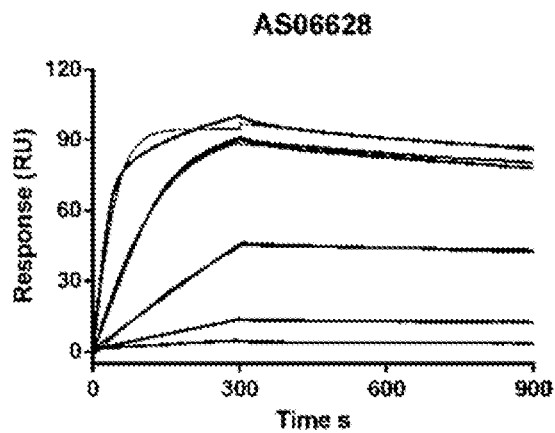
Figure 3D:
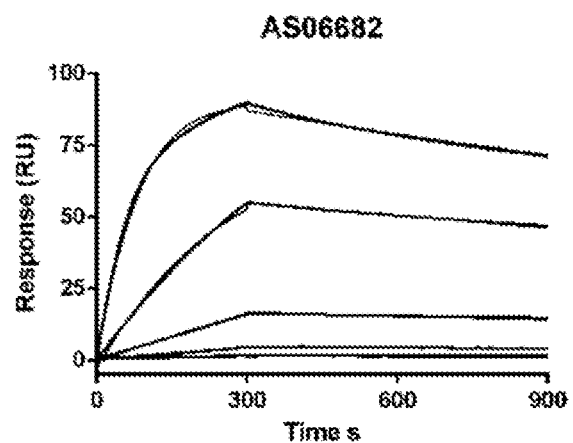
Figure 3E:
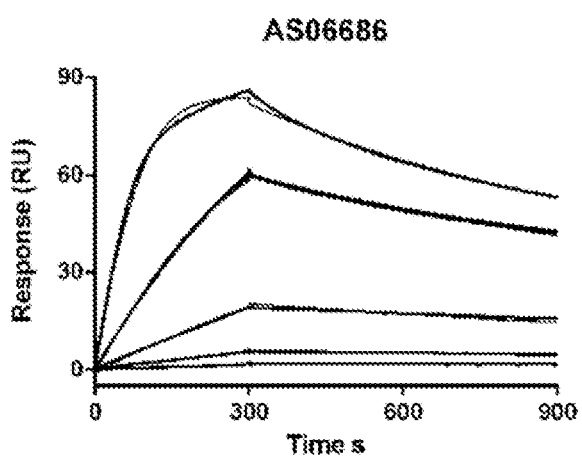
Figure 3F:
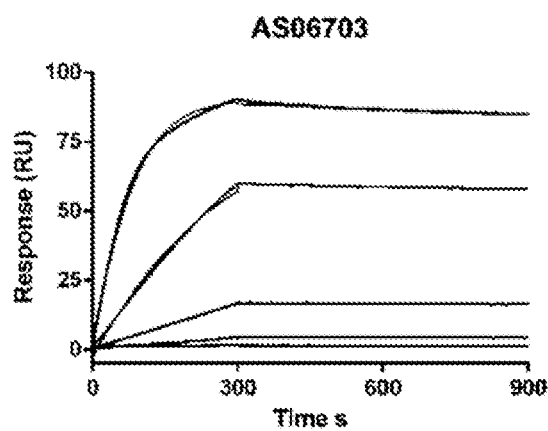
Figure 3G:
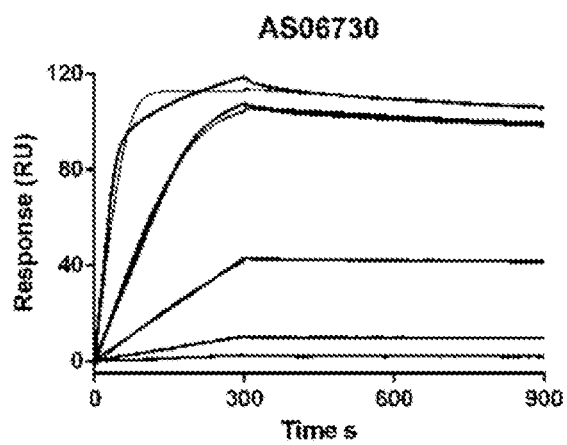
Figure 3H:
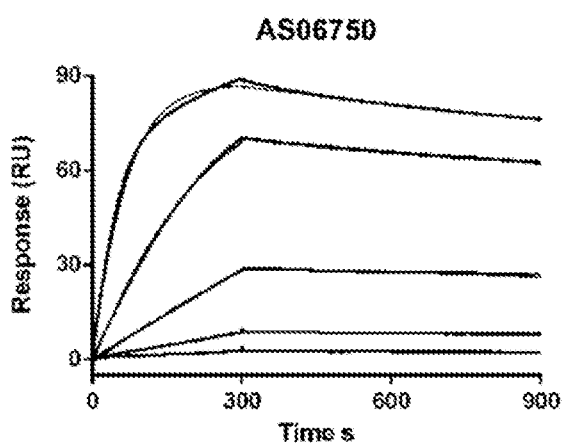
Figure 3I:
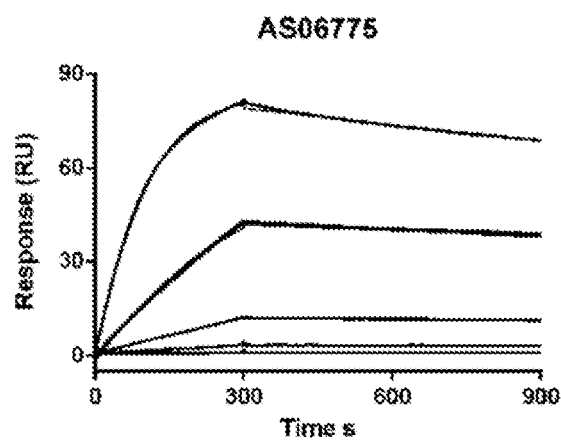
Figure 3J:
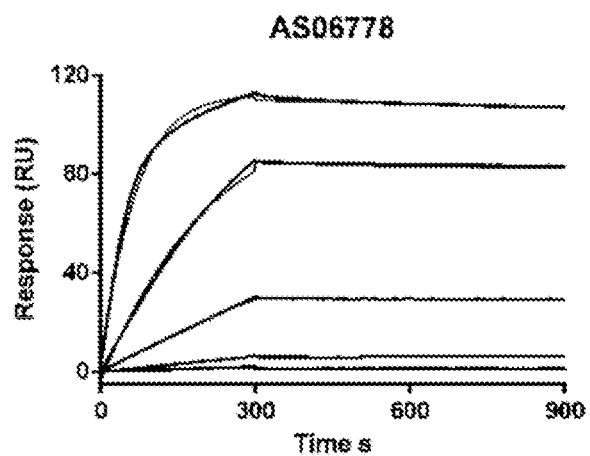
Figure 3K:
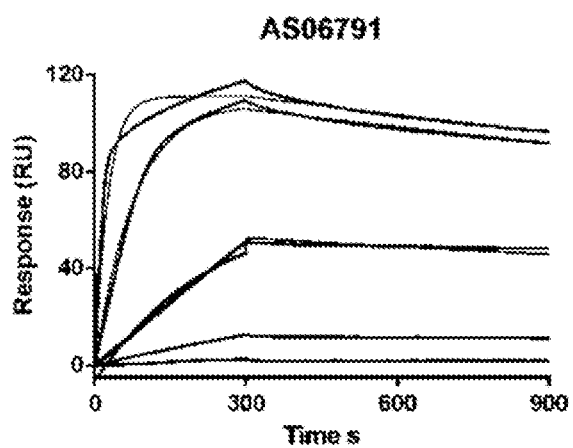
Figure 3L:
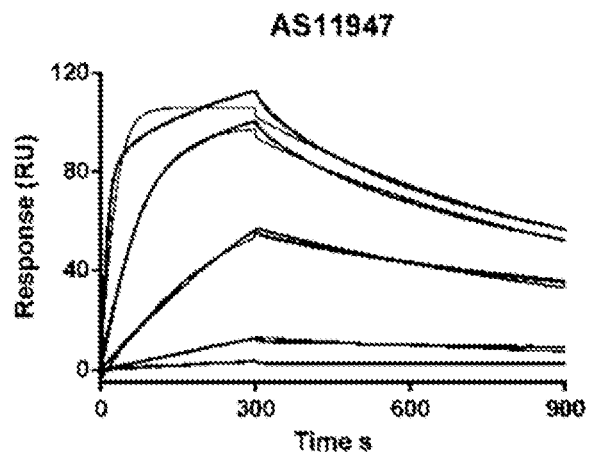
Figure 3M:
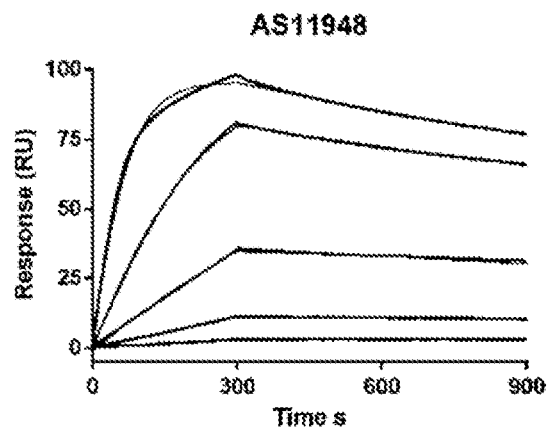
Figure 3N:
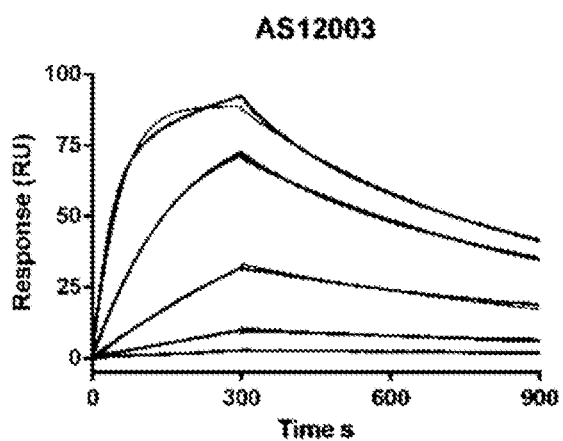
Figure 4A:
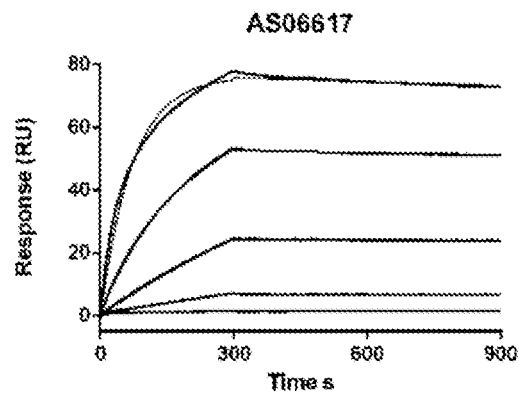
FIGS. 4A-4N depict the affinity determination of selected sdAbs (AS06617 (FIG. 4A); AS06618 (FIG. 4B); AS06628 (FIG. 4C); AS06682 (FIG. 4D); AS06686 (FIG. 4E); AS06703 (FIG. 4F); AS06730 (FIG. 4G); AS06750 (FIG. 4H); AS06775 (FIG. 4I); AS06778 (FIG. 4J); AS06791 (FIG. 4K); AS11947 (FIG. 4L); AS11948 (FIG. 4M); and AS12003 (FIG. 4N)): the PD-L1 was immobilized onto the chip and anti-PD-L1 HCAb was flowed as analyte at concentrations of 0.11, 0.33, 1, 3, and 9 nM.
Figure 4B:
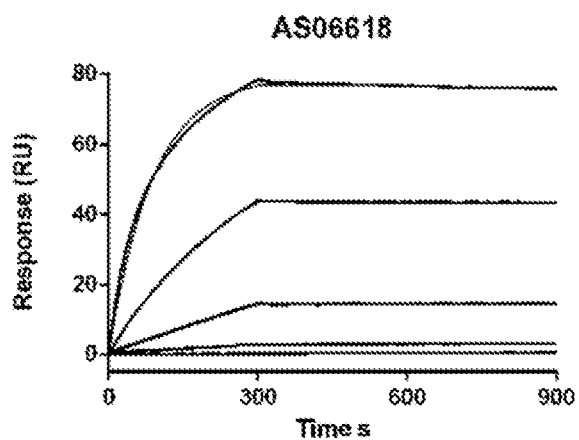
Figure 4C:
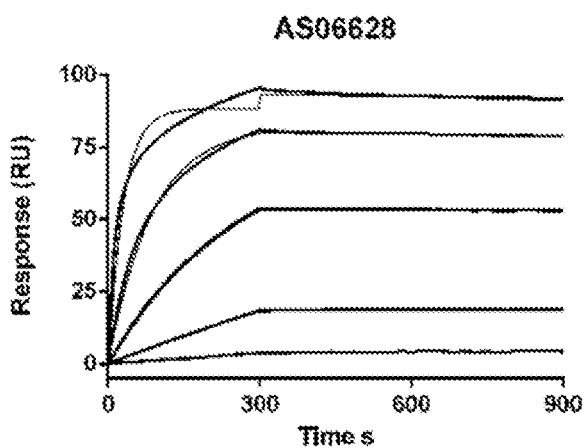
Figure 4D:
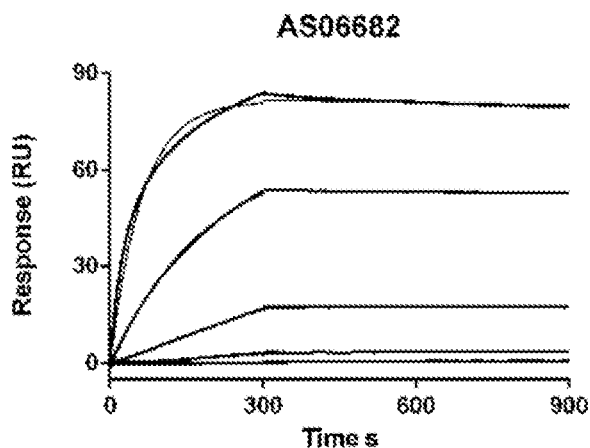
Figure 4E:
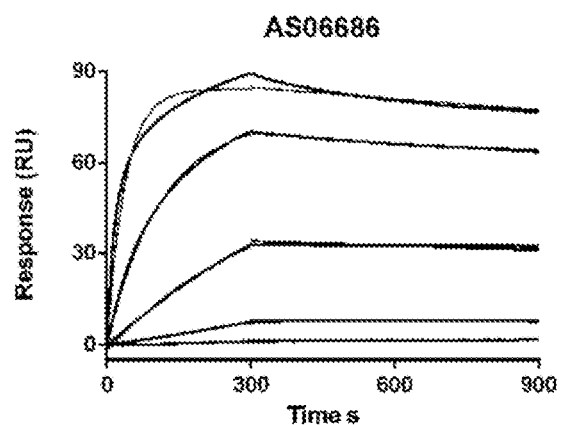
Figure 4F:
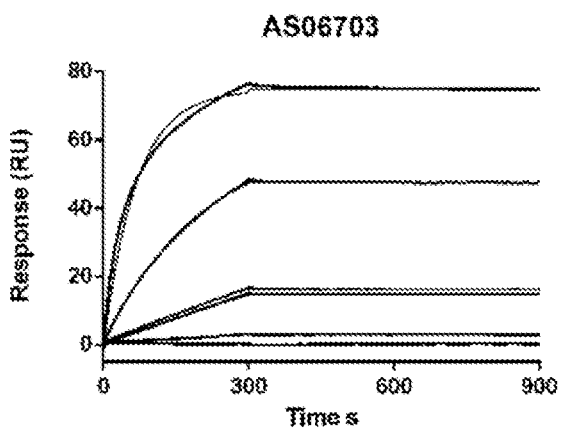
Figure 4G:
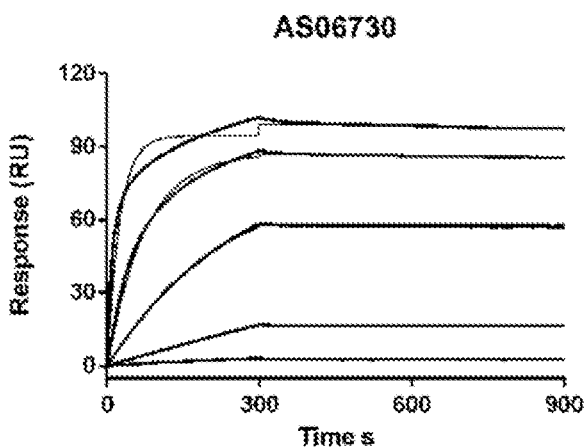
Figure 4H:
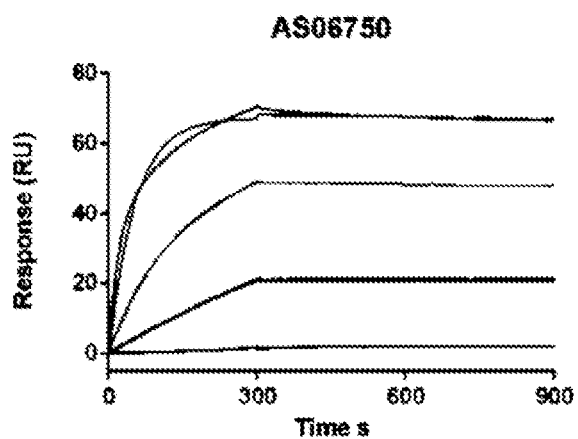
Figure 4I:
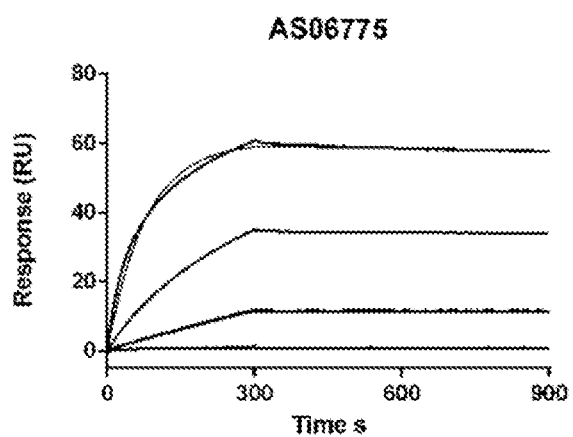
Figure 4J:
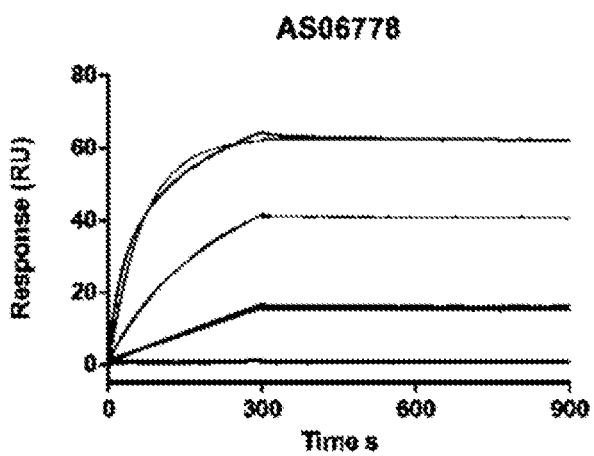
Figure 4K:
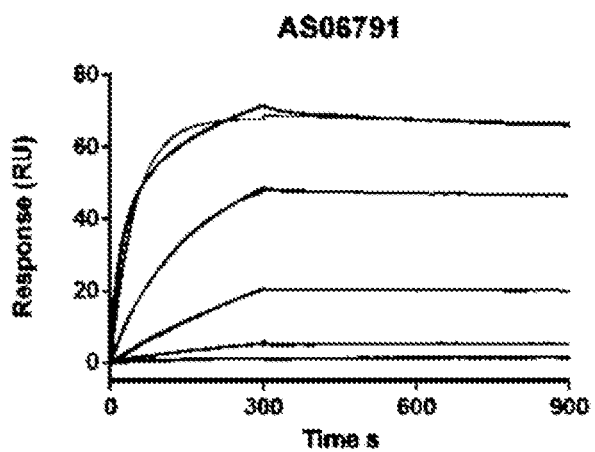
Figure 4L:
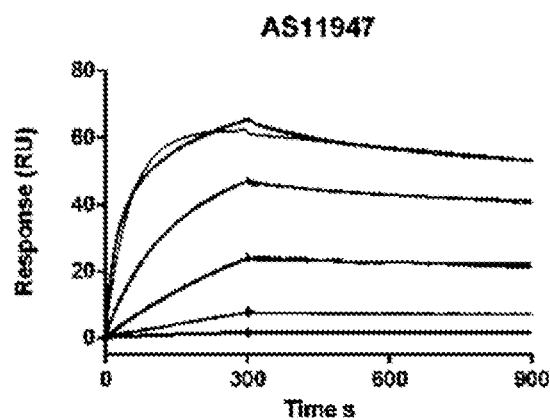
Figure 4M:
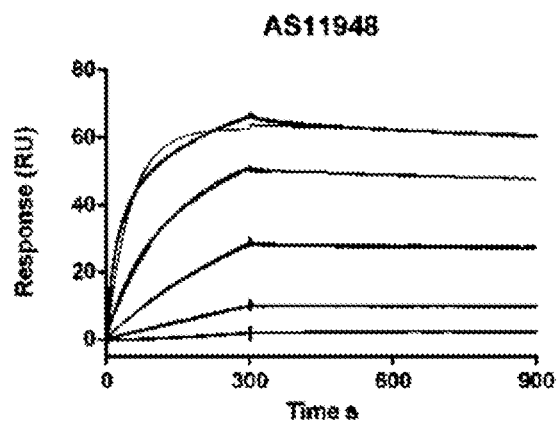
Figure 4N:
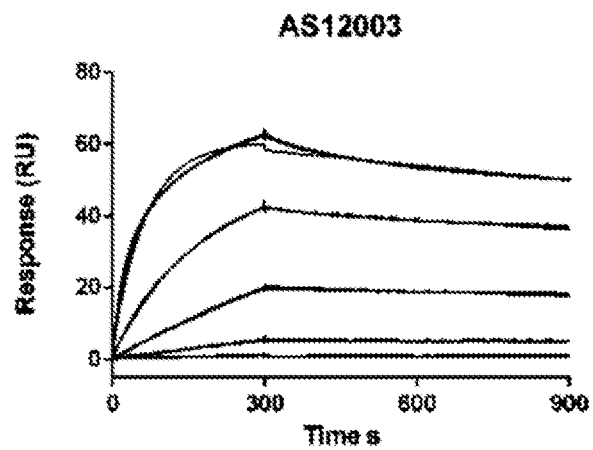

Two llamas were immunized with recombinant PD-L1 ECD protein under all current animal welfare regulations. For immunization, the antigen was formulated as an emulsion with CFA (primary immunization) or IFA (boost immunization). The antigen was administered by double-spot injections intramuscularly at the neck. Each animal received two injections of the emulsion, containing 100 µg of PD-L1 ECD and 4 subsequent injections containing 50 µg of antigen at weekly intervals. At different time points during immunization, 10 ml blood samples were collected from the animal and sera were prepared. The induction of an antigen specific humoral immune response was verified using the serum samples in an ELISA-based experiment with immobilized PD-L1 ECD protein (FIGS. 1 and 2). Five days after the last immunization, a blood sample of 300 ml was collected. Peripheral blood lymphocytes (PBLs), as the genetic source of the llama heavy chain immunoglobulins (HCAbs), were isolated from the 300 ml blood sample using a Ficoll-Paque gradient (Amersham Biosciences), yielding $1 \times 10^9$ PBLs. The maximal diversity of antibodies is expected to be equal to the number of sampled B-lymphocytes, which is about 10% of the number of PBLs ($1 \times 10^8$). The fraction of heavy-chain antibodies in llama is up to 20% of the number of B-lymphocytes. Therefore, the maximal diversity of HCAbs in the 300 ml blood sample is calculated as $2 \times 10^7$ different molecules.

Library Construction

RNA extracted from PBLs and lymph node was used as starting material for RT-PCR to amplify sdAb encoding gene fragments. These fragments were cloned into an in-house phagemid vector. In frame with the sdAb coding sequence, the vector coded for a C-terminal (His)6 tag. The library size is more than $1 \times 10^9$. The library phage was prepared according to a standard protocol and stored after filter sterilization at 4° C. for further use.

Selections and High-Throughput Screening

Selections were carried out with the above libraries using solid panning as well as cell-based panning. Only a single round of selection was performed for both conditions. Each selection output was analyzed for enrichment factor (#phage present in eluate relative to control), diversity and percentage of PD-L1 positive clones (ELISA). Based on these parameters the best selections were chosen for further analysis. To this end, the output from each selection was recloned as a pool into a soluble expression vector for high-throughput screening. In frame with the sdAb coding sequence, the vector coded for a C-terminal (His)6 tag. Colonies were picked and grown in 96 deep well plates (1 ml volume) and induced by adding IPTG and 0.1% Triton for sdAb expression in the supernatant.

The supernatant was analyzed for their ability to bind to PD-L1 ECD protein (by ELISA) and PD-L1 stable cell line (by FACS). The positive binders were sequenced and the unique clones were selected for further characterization.

The unique clones were grown in 2XYT medium and induced by IPTG for sdAb expression in the supernatant. The supernatant of unique binders were analyzed for their ability to inhibit PD-L1-PD-1 interaction. To this end, the supernatant was incubated with PD-L1 ECD protein, then the complex was added to PD-1 stable cell line for binding evaluation. sdAbs with negative signal on PD-1 cell line are considered as PD-L1 inhibitors.

All potential inhibitors were selected for off-rate analysis by surface plasmon resonance (SPR) on a BIAcore T200 instrument. The dissociation phase was used to calculate the $k_{off}$ values for each individual sdAb.

sdAb Production

The His6-tagged sdAbs were purified from periplasmic extracts by ÄKTA. The NTA resin was processed according to the manufacturer's instructions. Periplasmic extracts prepared were incubated with the resin for 30 min at RT on a rotator. The resin was washed with PBS and transferred to a column. The packed resin was washed with 15 mM Imidazole. sdAbs were eluted from the column using 150 mM Imidazole. The eluted fractions were analyzed by spotting on Hybond Membrane and visualized with Ponceau. Fractions containing protein were pooled and dialyzed against PBS. Dialyzed protein was collected, filter sterilized, concentration determined and stored at −20° C.

To determine the purity, protein samples were analyzed on a 12% SDS-PAGE gel. 10 Laemmli sample buffer was added to 10 µl (2 µg) purified protein, then the sample was heated for 10 minutes at 95° C., cooled and loaded onto a 12% SDS-PAGE gel. The gel was processed according to general procedures and stained with Coomassie Brilliant Blue (CBB).

HCAb Production

The HCAb constructs were generated by fusion sdAbs with human Fc region. The maxiprep of the HCAb constructs were prepared for CHO-K1 cell transient expression and purification. The expressed HCAbs were purified by chromatography through a column containing Protein A agarose resin followed by a size exclusion column.

To determine the purity, protein samples were analyzed on a 12% SDS-PAGE gel. 10 µl Laemmli sample buffer was added to 10 µl (2 µg) purified protein, then the sample was heated for 10 minutes at 95° C., cooled and loaded onto a 12% SDS-PAGE gel. The gel was processed according to general procedures and stained with Coomassie Brilliant Blue (CBB). The purity of purified HCAbs are >85%. The data were summarized in Table 20.

TABLE 20

Summary of HCAb purification

| Sample | AS06617 | AS06618 | AS06628 | AS06682 | AS06686 |
| --- | --- | --- | --- | --- | --- |
| Conc. (mg/ml) | 1.50 | 1.70 | 1.58 | 1.55 | 1.48 |
| Amount (mg) | 10.48 | 20.42 | 16.60 | 16.26 | 14.83 |
| Purity | >85% | >85% | >85% | >85% | >85% |
| Endotoxin level (EU/µg) | <0.01 | <0.01 | <0.01 | <0.01 | <0.01 |

| Sample | AS06703 | AS06730 | AS06750 | AS06775 | AS06778 |
| --- | --- | --- | --- | --- | --- |
| Conc. (mg/ml) | 1.35 | 1.81 | 1.81 | 1.63 | 1.41 |
| Amount (mg) | 13.45 | 21.77 | 21.70 | 19.51 | 12.71 |
| Purity | >85% | >85% | >85% | >85% | >85% |
| Endotoxin level (EU/µg) | <0.01 | <0.01 | <0.01 | <0.01 | <0.01 |

TABLE 20-continued

Summary of HCAb purification

| Sample | AS06791 | AS11947 | AS11948 | AS12003 |
|---|---|---|---|---|
| Conc. (mg/ml) | 1.82 | 1.80 | 1.58 | 2.02 |
| Amount (mg) | 21.82 | 19.81 | 17.38 | 24.25 |
| Purity | >85% | >85% | >85% | >85% |
| Endotoxin level (EU/μg) | <0.01 | 0.01~0.1 | <0.01 | <0.01 | sdAb Affinity Determination and HCAb Affinity Determination

Affinity constant ($K_d$) of each sdAbs and HCAbs was determined by surface plasmon resonance (SPR) on a BIAcore T200 instrument. Briefly, PD-L1 His was amine-coupled to a CM5 sensor chip at a density of no higher than 100 RU. Anti-PD-L1 sdAbs or anti-PD-L1 HCAbs were injected at 5 different concentrations between 0.33 and 27 nM. Flow rate was 30 μl/min in all experiments. Association and dissociation phases were 5 and 10 min, respectively. The chip was regenerated using Glycine/HCl pH 1.5. Binding curves at different concentrations of sdAbs and HCAbs were used to calculate the kinetic parameters $k_{on}$, $k_{off}$ and $K_D$ (FIGS. 3A-3N and FIGS. 4A-4N). The kinetics data were summarized in Table 3 and Table 4.

TABLE 3 affinity determination of sdAbs against PD-L1

| Ligand | Analyte | $k_a$ (1/Ms) | $k_d$ (1/s) | $K_D$ (M) |
|---|---|---|---|---|
| PD-L1/His | AS06617 sdAb | 1.86E+06 | 4.64E−04 | 2.49E−10 |
|  | AS06618 sdAb | 1.44E+06 | 2.45E−04 | 1.70E−10 |
|  | AS06628 sdAb | 4.10E+06 | 2.15E−04 | 5.26E−11 |
|  | AS06682 sdAb | 1.68E+06 | 3.42E−04 | 2.03E−10 |
|  | AS06686 sdAb | 2.79E+06 | 9.65E−04 | 3.46E−10 |
|  | AS06703 sdAb | 1.80E+06 | 6.96E−05 | 3.87E−11 |
|  | AS06730 sdAb | 7.11E+06 | 1.39E−04 | 1.95E−11 |
|  | AS06750 sdAb | 2.05E+06 | 2.23E−04 | 1.09E−10 |
|  | AS06775 sdAb | 1.58E+06 | 2.47E−04 | 1.56E−10 |
|  | AS06778 sdAb | 1.90E+06 | 4.42E−05 | 2.33E−11 |
|  | AS06791 sdAb | 1.56E+06 | 2.39E−04 | 1.53E−10 |
|  | AS11947 sdAb | 1.92E+06 | 1.18E−03 | 6.17E−10 |
|  | AS11948 sdAb | 2.37E+06 | 3.94E−04 | 1.67E−10 |
|  | AS12003 sdAb | 2.76E+06 | 1.55E−03 | 5.60E−10 |

TABLE 4 affinity determination of HCAbs against PD-L1

| Ligand | Analyte | $k_a$ (1/Ms) | $k_d$ (1/s) | $K_D$ (M) |
|---|---|---|---|---|
| PD-L1/His | AS06617 HCAb | 5.20E+05 | 5.51E−05 | 1.06E−10 |
|  | AS06618 HCAb | 4.21E+05 | 1.41E−05 | 3.35E−11 |
|  | AS06628 HCAb | 1.27E+06 | 1.98E−05 | 1.55E−11 |
|  | AS06730 HCAb | 1.52E+06 | 2.44E−05 | 1.61E−11 |
|  | AS06682 HCAb | 5.99E+05 | 3.34E−05 | 5.57E−11 |
|  | AS06686 HCAb | 9.79E+05 | 1.53E−04 | 1.56E−10 |
|  | AS06703 HCAb | 5.55E+05 | <1.00E−05* | <1.80E−11* |
|  | AS06750 HCAb | 7.19E+05 | 2.81E−05 | 3.92E−11 |
|  | AS06775 HCAb | 4.76E+05 | 3.29E−05 | 6.90E−11 |
|  | AS06778 HCAb | 5.53E+05 | <1.00E−05* | <1.81E−11* |
|  | AS06791 HCAb | 7.81E+05 | 5.33E−05 | 6.83E−11 |
|  | AS11947 HCAb | 7.30E+05 | 2.26E−04 | 3.10E−10 |
|  | AS11948 HCAb | 7.61E+05 | 8.25E−05 | 1.08E−10 |
|  | AS12003 HCAb | 5.69E+05 | 2.47E−04 | 4.34E−10 |

*kd is outside the limits that can be measured by Biacore T200

Target Binding Assays

The ability of the purified antigen binding proteins to bind PD-L1 is determined using Surface Plasmon Resonance method (e.g., BIACORE®), an enzyme-linked immunosorbent assay, a Fluorescence-Assisted Cell Sorting method (FACS), or a combination thereof. The analyses can be performed on PD-L1 transfected cells.

Figure 5A:
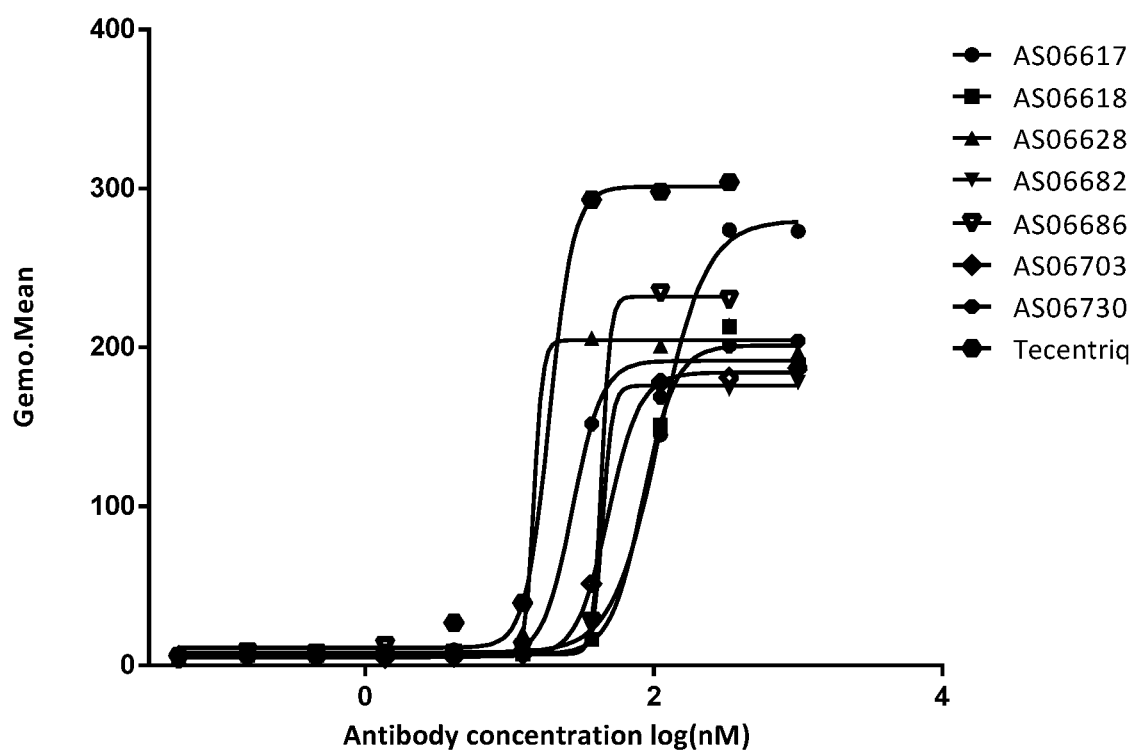
FIGS. 5A and 5B depict the relative binding assay of selected anti-PD-L1 HCAbs based FACS using PD-L1 stably expressing cell line: Tecentriq® was used as a positive anti-PD-L1 antibody control.
Figure 5B:
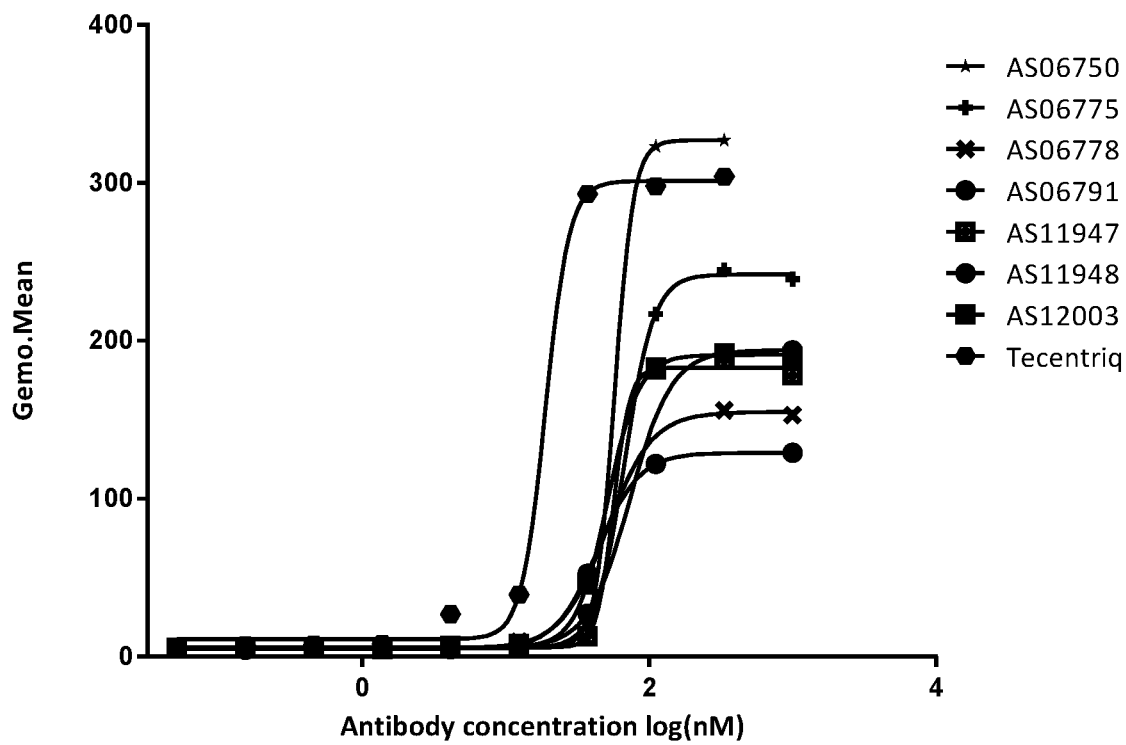

CHO-K1 cells expressing human PD-L1 were dissociated from adherent culture flasks and mixed with varying concentrations of antibodies and a constant concentration of anti-PD-L1 sdAbs or HCAbs (in a 96-well plate). Tecentriq® was used as an anti-PD-L1 antibody positive control. The antibody and cell incubation was equilibrated for 30 minutes at room temperature, washed three times with FACS buffer (PBS containing 1% BSA). FITC conjugated anti-human IgG secondary antibody was then added and incubated for 15 minutes at room temperature. Cells were washed again with FACS buffer and analyzed by flow cytometry. Data were analyzed with Prism (GraphPad Software, San Diego, Calif.) using non-linear regression, and $EC_{50}$ values were calculated (FIGS. 5A and 5B).

Inhibition of Ligand Binding by FACS Analysis

Figure 6A:
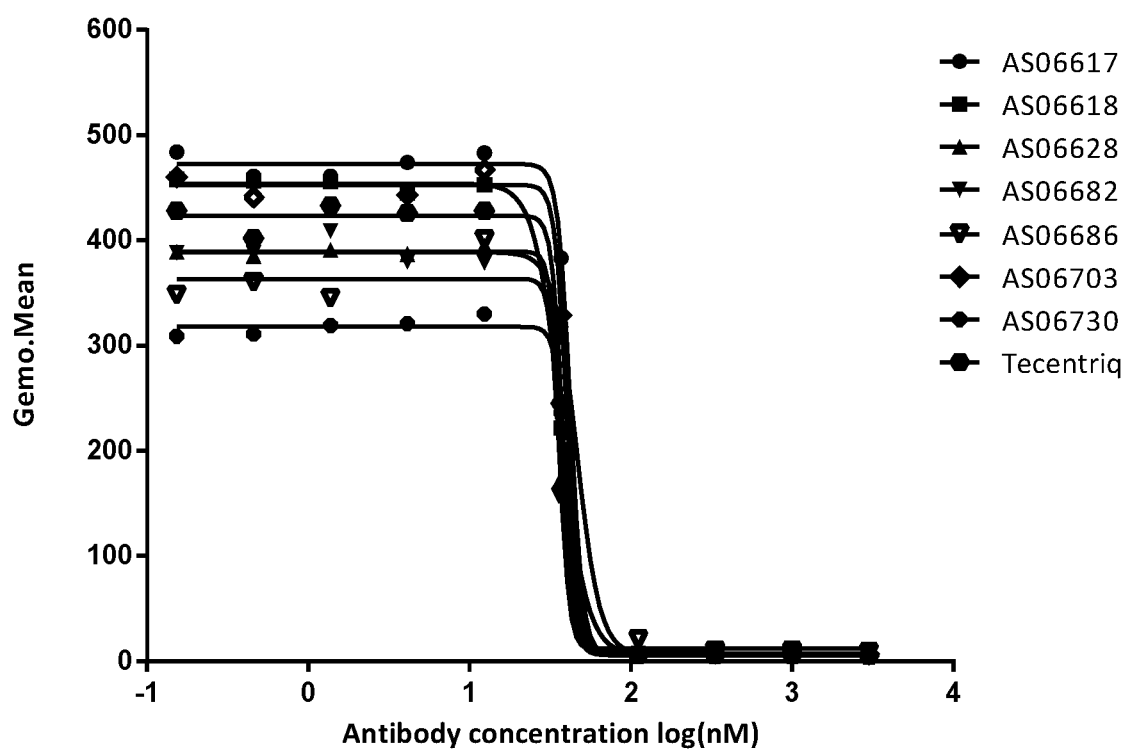
FIGS. 6A and 6B depict FACS-based ligand competition assay of selected anti-PD-L1 HCAbs by using PD-L1 expressing stable cell line and biotin-labeled hPD-1/Fc protein: Tecentriq® was used as a positive anti-PD-L1 antibody control.
Figure 6B:
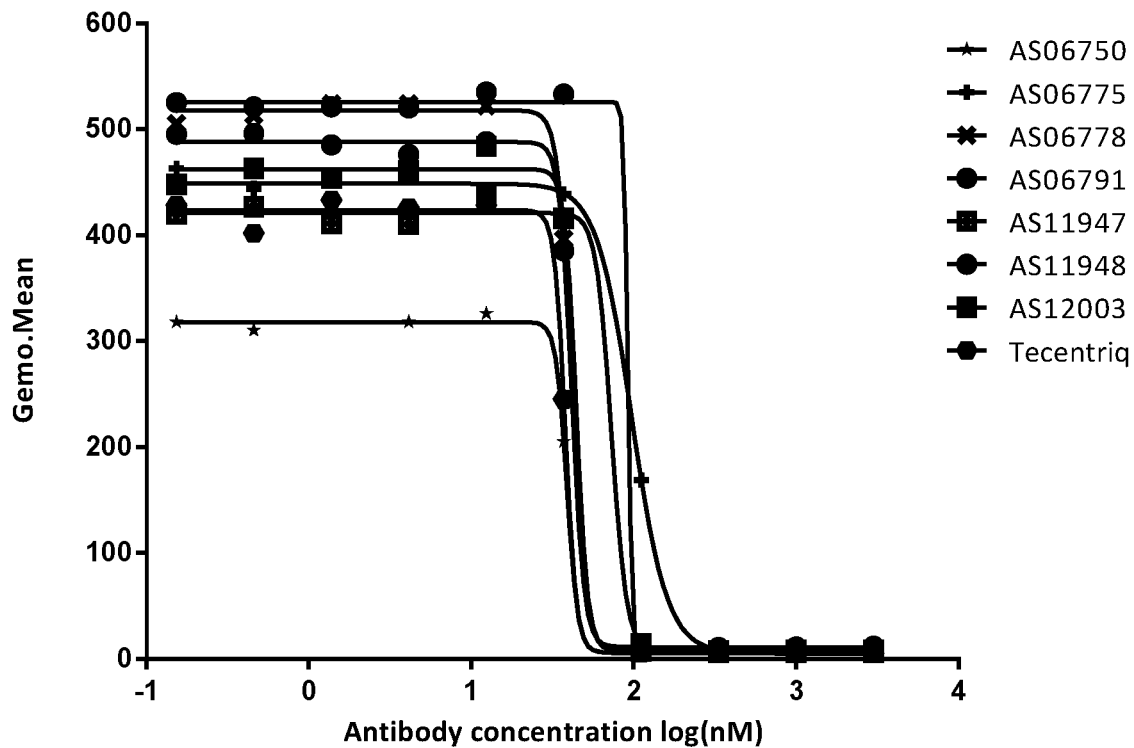
Figure 7A:
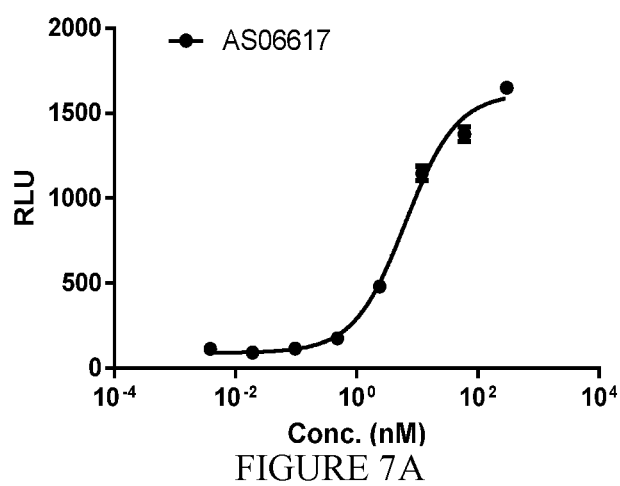
FIGS. 7A-7O depict functional activity evaluation of purified sdAbs (AS06617 (FIG. 7A); AS06618 (FIG. 7B); AS06628 (FIG. 7C); AS06682 (FIG. 7D); AS06686 (FIG. 7E); AS06703 (FIG. 7F); AS06730 (FIG. 7G); AS06750 (FIG. 7H); AS06775 (FIG. 7I); AS06778 (FIG. 7J); AS06791 (FIG. 7K); AS11947 (FIG. 7L); AS11948 (FIG. 7M); AS12003 (FIG. 7N); and Tecentriq (FIG. 7O)) by PD-L1-based blockade assay: Tecentriq® was used as a positive anti-PD-L1 antibody control.
Figure 7B:
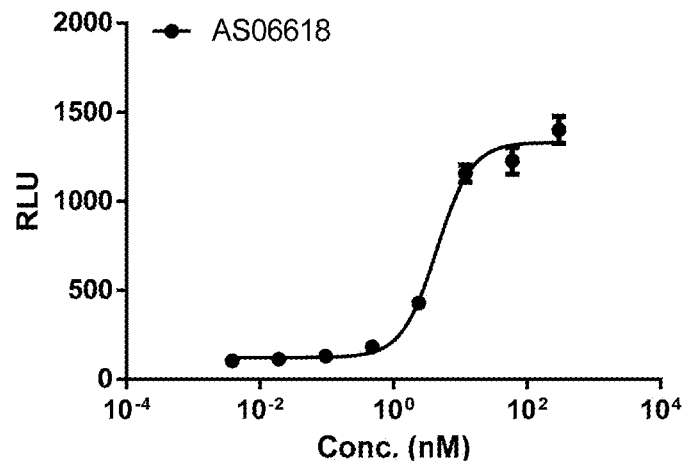
Figure 7C:
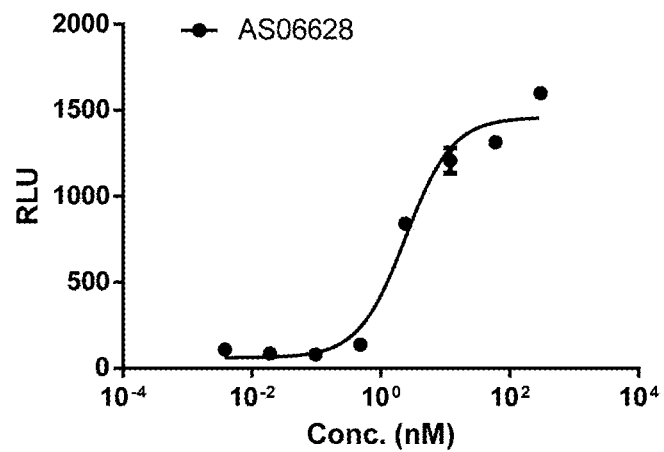
Figure 7D:
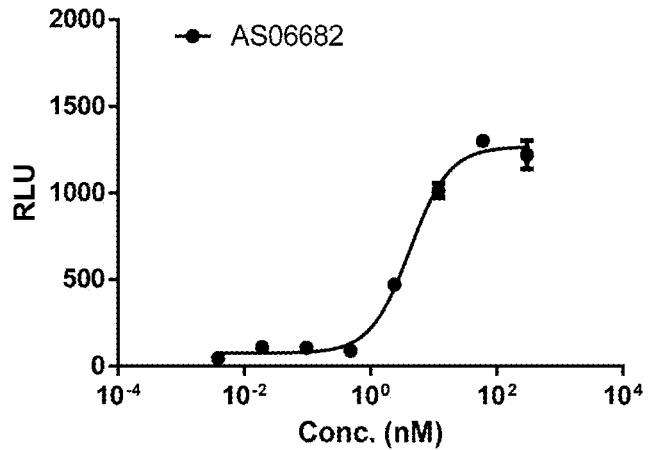
Figure 7E:
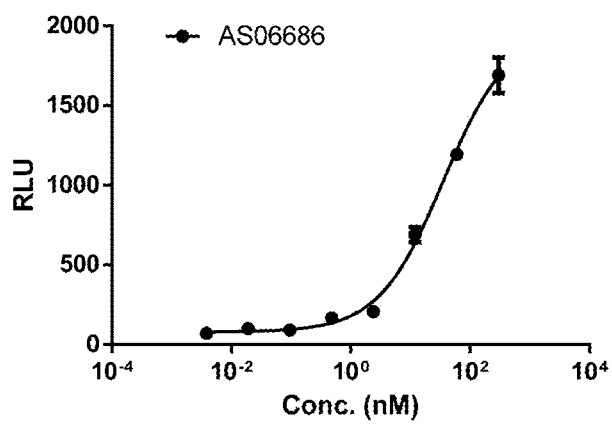
Figure 7F:
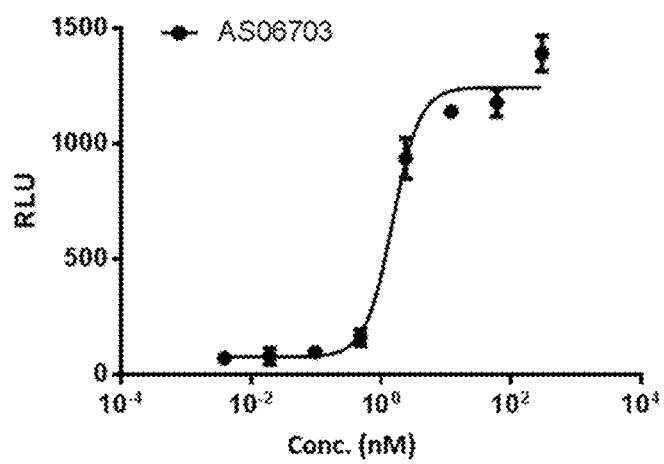
Figure 7G:
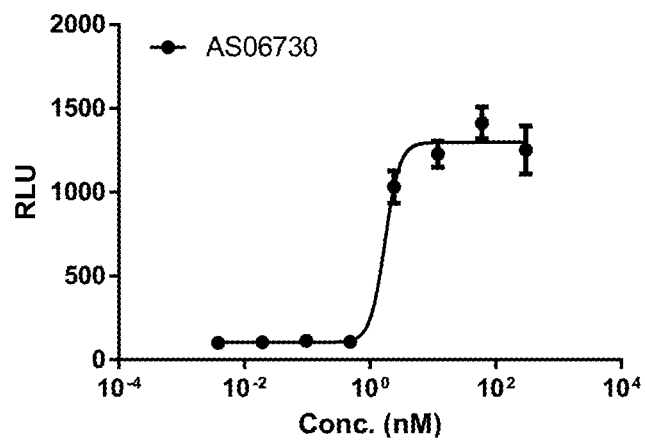
Figure 7H:
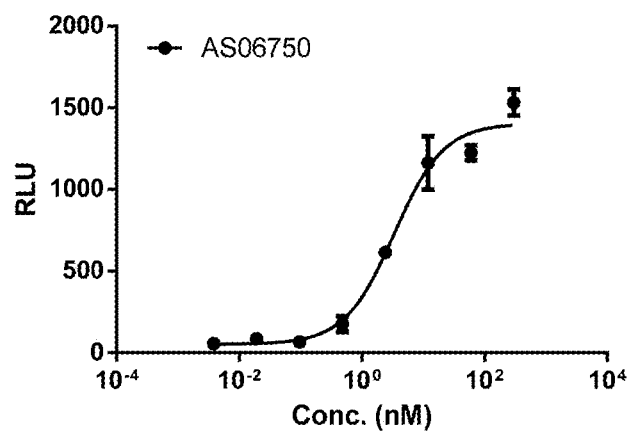
Figure 7I:
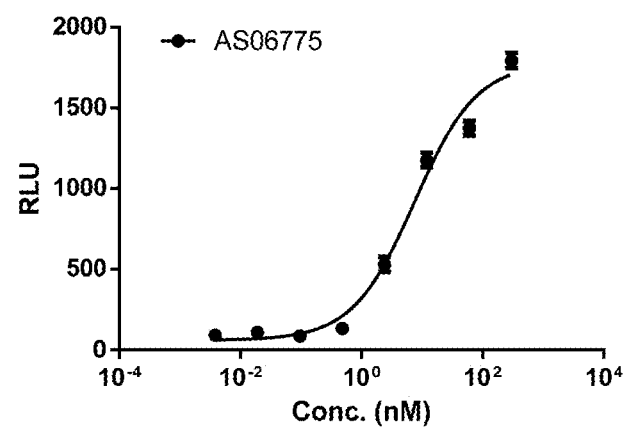
Figure 7J:
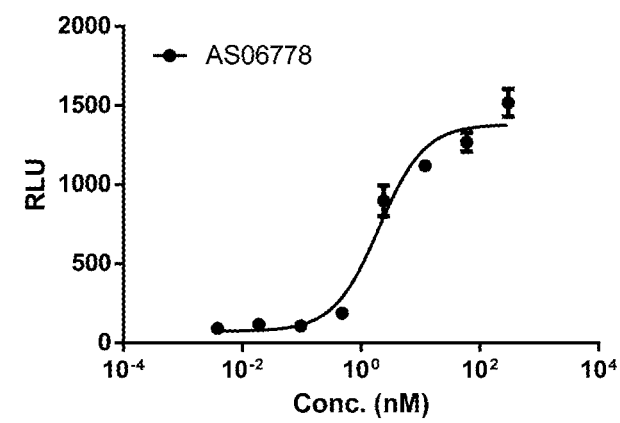
Figure 7K:
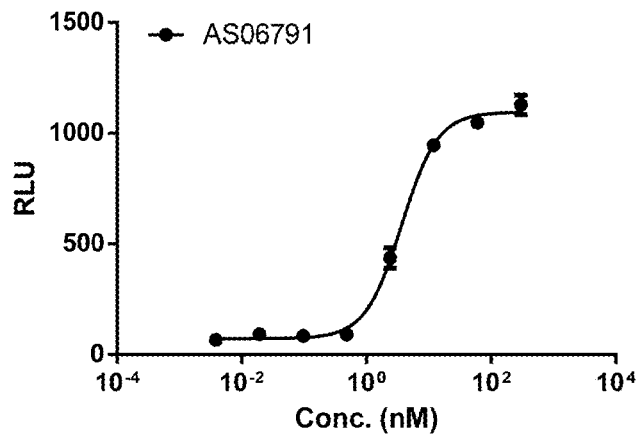
Figure 7L:
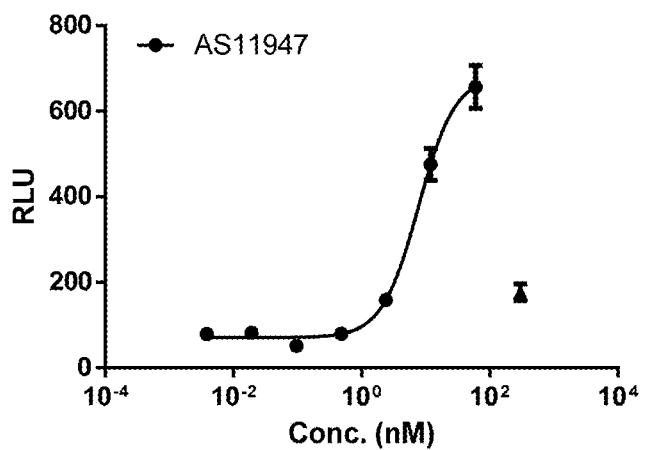
Figure 7M:
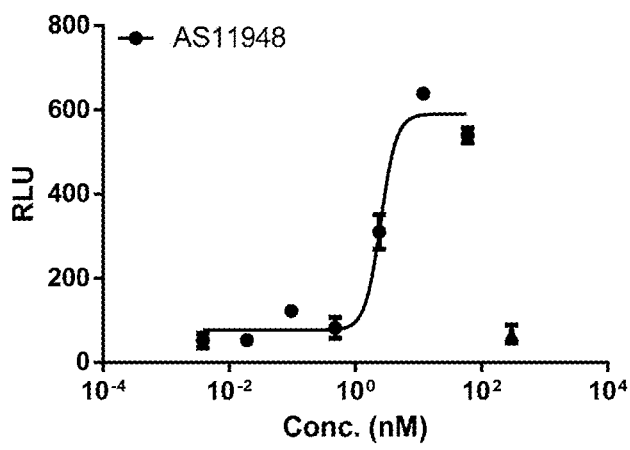
Figure 7N:
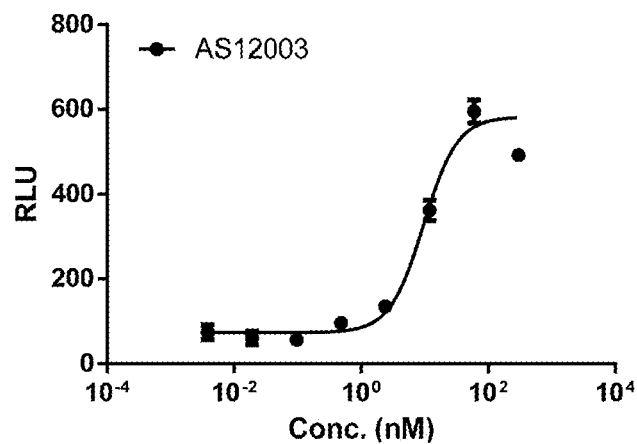
Figure 7O:
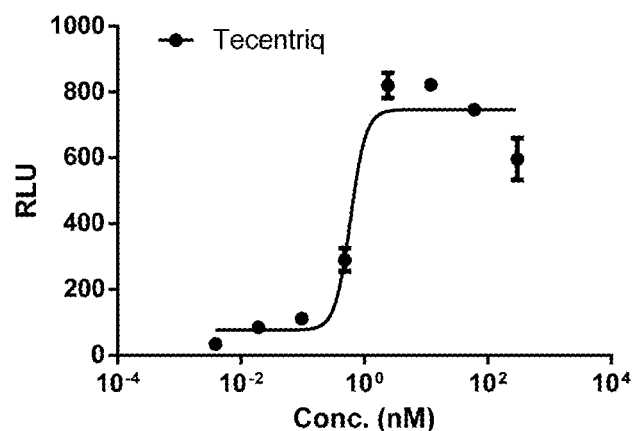
Figure 8A:
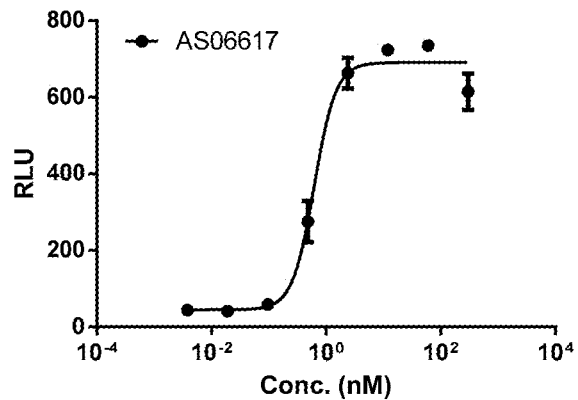
FIGS. 8A-8O depict functional activity evaluation of purified top HCAbs (AS06617 (FIG. 8A); AS06618 (FIG. 8B); AS06628 (FIG. 8C); AS06682 (FIG. 8D); AS06686 (FIG. 8E); AS06703 (FIG. 8F); AS06730 (FIG. 8G); AS06750 (FIG. 8H); AS06775 (FIG. 8I); AS06778 (FIG. 8J); AS06791 (FIG. 8K); AS11947 (FIG. 8L); AS11948 (FIG. 8M); AS12003 (FIG. 8N); and Tecentriq (FIG. 8O)) by PD-L1-based blockade assay: Tecentriq® served as a positive anti-PD-L1 antibody control.
Figure 8B:
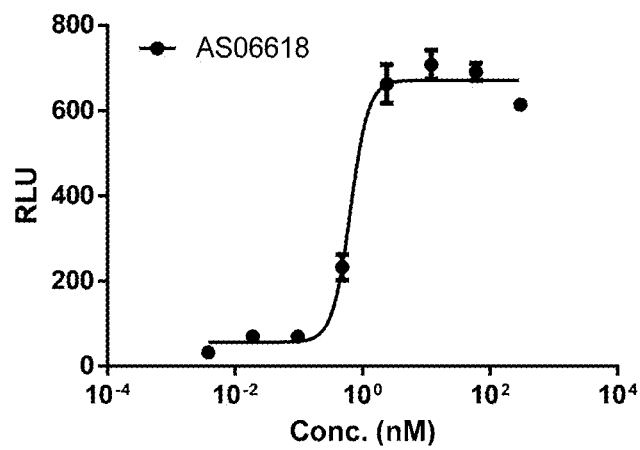
Figure 8C:
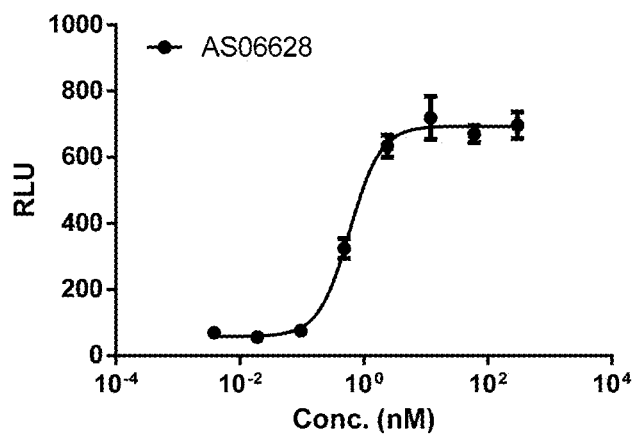
Figure 8D:
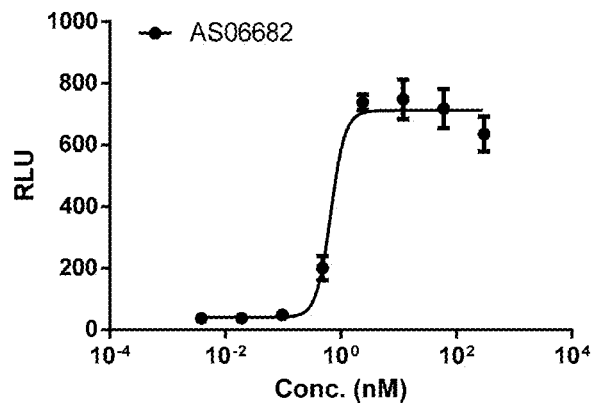
Figure 8E:
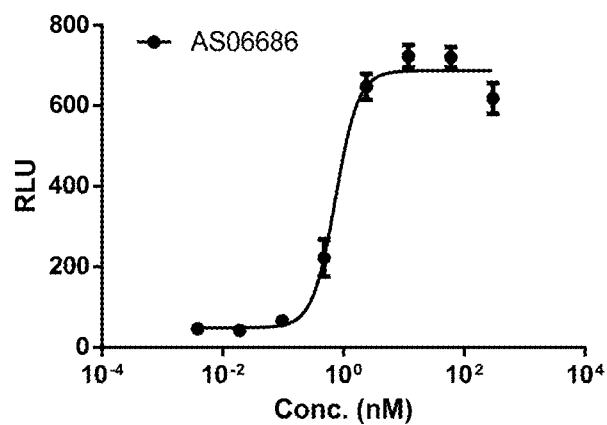
Figure 8F:
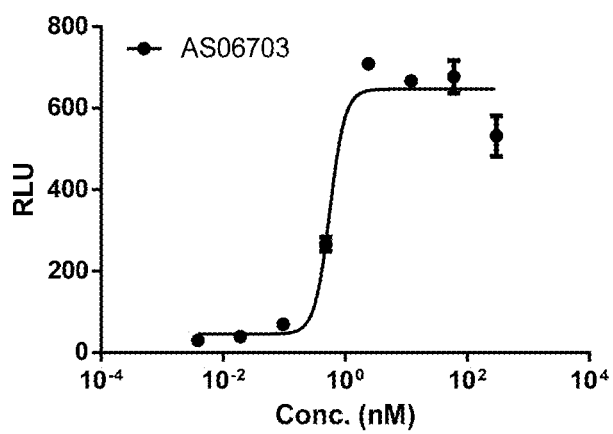
Figure 8G:
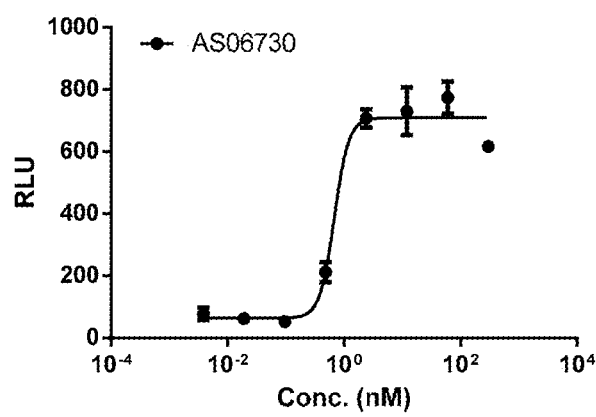
Figure 8H:
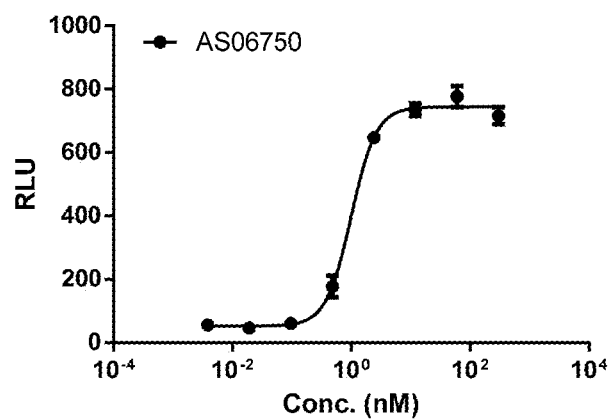
Figure 8I:
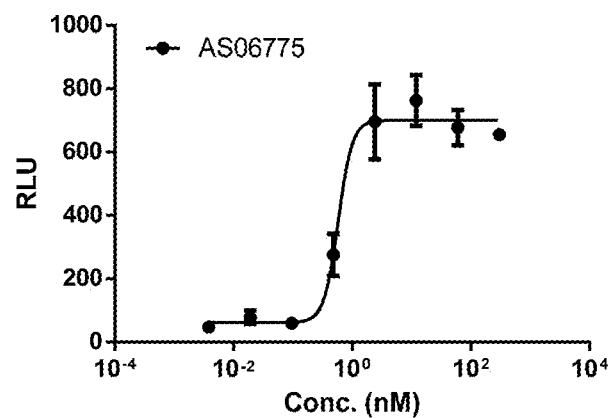
Figure 8J:
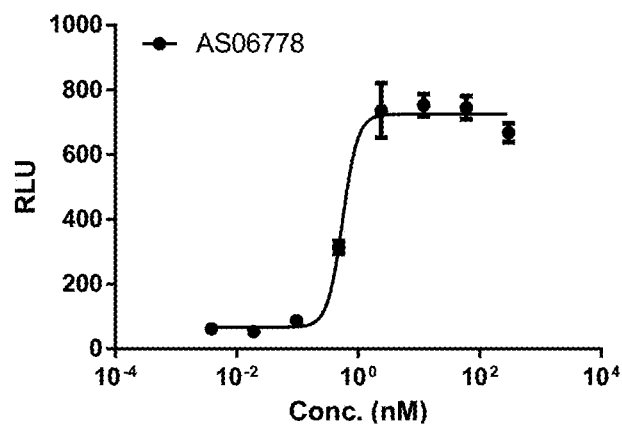
Figure 8K:
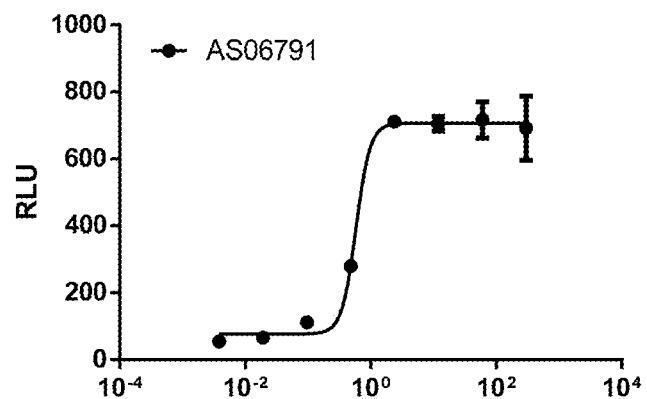
Figure 8L:
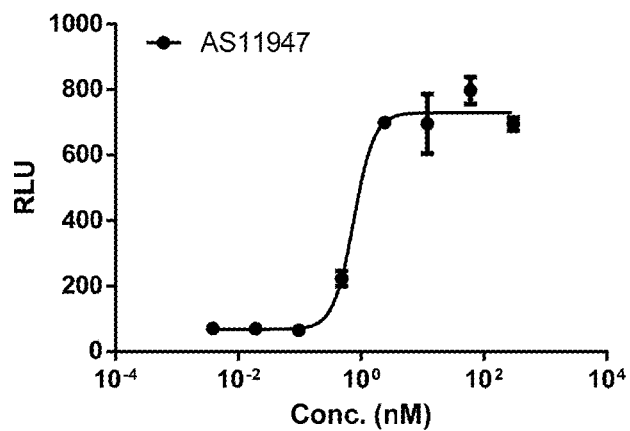
Figure 8M:
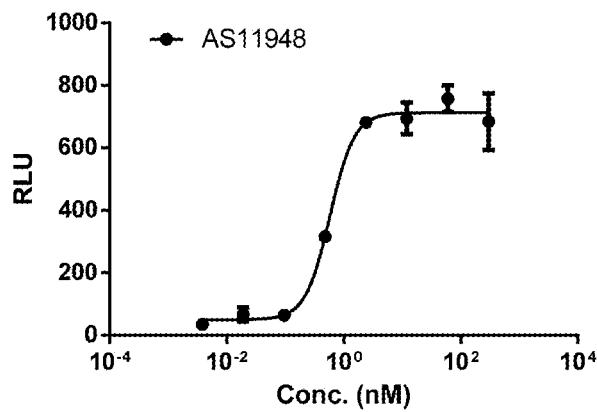
Figure 8N:
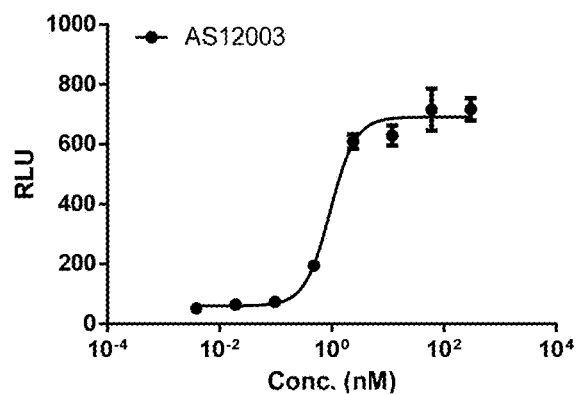
Figure 8O:
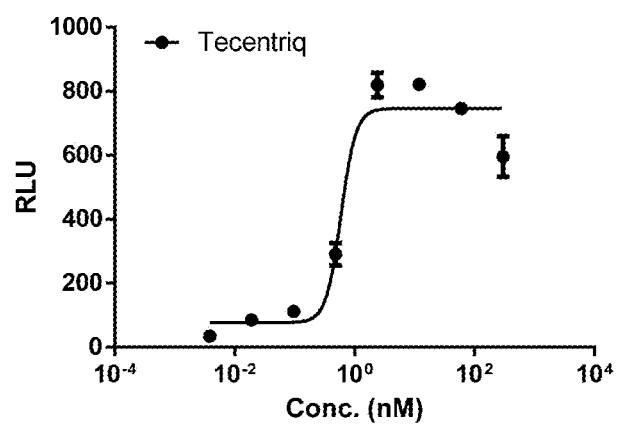
Figure 9A:
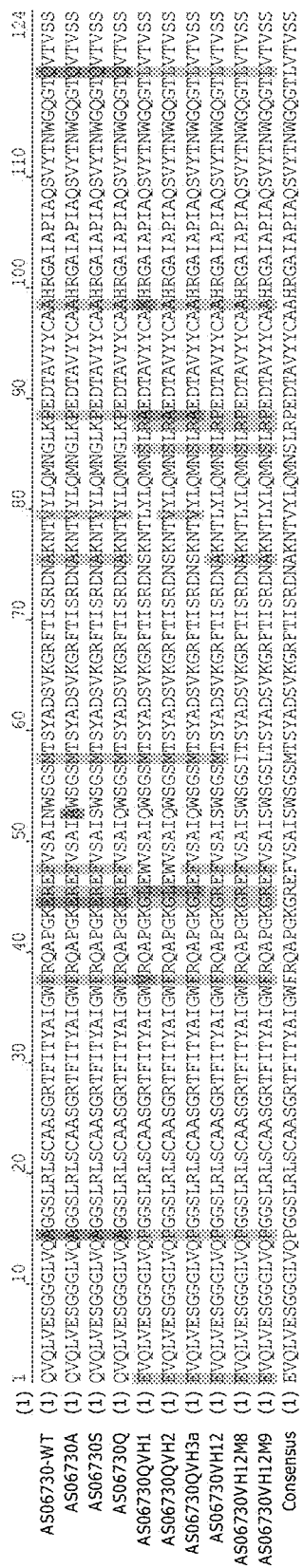

Blockade of ligand binding was studied using flow cytometry. For anti-PD-L1 HCAbs evaluation, CHO-K1 cells expressing human PD-L1 were dissociated from adherent culture flasks and mixed with varying concentrations of antibodies and a constant concentration of biotin-labeled hPD-1/Fc protein (both in a 96-well plate). Tecentriq® was used as an anti-PD-L1 antibody positive control. The mixture was equilibrated for 30 minutes at room temperature, washed three times with FACS buffer (PBS containing 1% BSA). PE/Cy5 Streptavidin secondary antibody was then added and incubated for 15 minutes at room temperature. Cells were washed again with FACS buffer and analyzed by flow cytometry. Data were analyzed with Prism (GraphPad Software, San Diego, Calif.) using non-linear regression, and $IC_{50}$ values were calculated. As can be seen from FIGS. 6A and 6B, the competition assays demonstrated the ability of most anti-PD-L1 HCAbs in efficiently inhibiting PD-L1-PD-1 interactions at low concentrations (1-10 μg/ml), the $IC_{50}$ of most HCAbs are comparable to Tecentriq®.

PD-L1-Based Blockade Assay

CHO-K1 stable expressing PD-L1 cells and Jurkat effector cells are used to assess PD-1 blockade for anti-PD-L1 sdAbs and HCAbs evaluation. The effector cells contain a luciferase construct that is induced upon disruption of the PD-1/PD-L1 receptor-ligand interaction, such as when the PD-L1 cells are mixed with effector cells expressing PD-1. Thus, efficacy of inhibiting PD-L1 on CHO-K1 stable cells by anti-PD-L1 sdAbs and HCAbs can be assessed by measuring luciferase reporter activity. The assay is performed as follows.

On day one, PD-L1 cells are thawed in a 37° C. water bath until cells are just thawed (about 3-4 minutes), and 0.5 mL of thawed cells is transferred to 14.5 mL cell recovery medium (10% FBS/F-12). The cell suspension is mixed well by gently inverting the tube 1-2 times. The cell suspension is then transferred to a sterile reagent reservoir, and dispensed into assay plates with 25 μL of cell suspension per well. 100 μL of assay medium is added per well as blank control. 100 μL of cell recovery medium is added per well for wells serving as blank control. The plates are then lidded and incubated overnight in a $CO_2$ incubator at 37° C.

On the day of assay, fresh assay buffer (RPMI 1640+1% FBS) is prepared. An eight-point serial dilution is performed in assay buffer for each of the control anti-PD-L1 antibody (e.g., Tecentriq®), sdAbs or HCAbs. The starting concentration and dilution scheme is optimized to achieve full dose-response curves. The assay plates containing PD-L1 cells are retrieved from the $CO_2$ incubator. 95 μl of medium is removed per well from all the wells. 40 μL of serial dilutions of the control anti-PD-L1 antibody, or the antigen binding protein, is added per well to wells containing PD-L1 cells. 80 μL assay buffer is added per well to the blank control wells for each plate.

Next, PD-1 effector Cells are thawed in a 37° C. water bath until cells are just thawed (about 3-4 minutes). The cell suspension is gently mixed in the vial by pipetting up and down, and 0.5 mL of the cells is added to 5.9 mL assay buffer. The cell suspension is mixed well by gently inverting the tube 1-2 times. The cell suspension is then transferred to a sterile reagent reservoir, and 40 μL of the cell suspension is dispensed to each well containing the PD-1 cells and control antibody or bispecific antigen binding protein. The plates are lidded and incubated for six hours at 37° C. in a $CO_2$ incubator.

The Luciferase Assay System is reconstituted by transferring one bottle of Buffer to the bottle containing Substrate. The system is stored at room temperature and shielded from light for same day use. After 6 hours induction, assay plates are removed from the $CO_2$ incubator and equilibrated at ambient temperature for 5-10 min. 80 μL of reagent is added to each well. The plates are incubated for 5-10 min at ambient temperature. Luminescence is measured in GloMax® Discover System (Promega, Madison, Wis.) or a plate reader with glow-type luminescence reading capabilities.

Luminescence is expressed as Relative Light Unit (RLU). The RLU values of wells having diluted antibody or bispecific antigen binding protein is normalized to the RLU of no antibody or bispecific antigen binding protein control to provide Fold of Luciferase Induction. Data is graphed as RLU versus $Log_{10}$ of concentration of antibody or bispecific antigen binding protein and as Fold of Induction versus $Log_{10}$ concentration of antibody or bispecific antigen binding protein. The data is fitted to a curve and $EC_{50}$ of each bispecific antigen binding proteins and the control anti-PD-1 antibody is determined using curve fitting software such as GraphPad Prism (FIGS. 7A to 7O and FIGS. 8A to 8O, Tables 5 and 6).

TABLE 5

$EC_{50}$ of PD-L1-based blockade assay for sdAbs

| Sample | AS06617 sdAb | AS06618 sdAb | AS06628 sdAb | AS06682 sdAb | AS06686 sdAb |
|---|---|---|---|---|---|
| $EC_{50}$ (M) | 6.38E−08 | 4.45E−08 | 2.42E−08 | 4.20E−08 | 3.52E−07 |
| Sample | AS06703 sdAb | AS06730 sdAb | AS06750 sdAb | AS06775 sdAb | AS06778 sdAb |
| $EC_{50}$ (M) | 1.50E−08 | 1.72E−08 | 3.36E−08 | 7.55E−08 | 2.01E−08 |
| Sample | AS06791sdAb | AS11947 sdAb | AS11948 sdAb | AS12003 sdAb | Tecentriq |
| $EC_{50}$ (M) | 3.65E−08 | 7.72E−08 | 2.52E−08 | 9.62E−08 | 5.92E−09 |

TABLE 6

$EC_{50}$ of PD-L1-based blockade assay for HCAbs

| Sample | AS06617 HCAb | AS06618 HCAb | AS06628 HCAb | AS06682 HCAb | AS06686 HCAb |
|---|---|---|---|---|---|
| $EC_{50}$ (M) | 6.20E−09 | 6.45E−09 | 5.88E−09 | 6.66E−09 | 7.37E−09 |
| Sample | AS06703 HCAb | AS06730 HCAb | AS06750 HCAb | AS06775 HCAb | AS06778 HCAb |
| $EC_{50}$ (M) | 5.59E−09 | 6.791E−09 | 9.98E−09 | 5.8E−09 | 5.54E−09 |
| Sample | AS06791 HCAb | AS11947 HCAb | AS11948 HCAb | AS12003 HCAb | Tecentriq |
| $EC_{50}$ (M) | 5.82E−09 | 7.55E−09 | 5.80E−09 | 9.34E−09 | 5.92E−09 |

Example 2: Anti-PD-L1 sdAb Humanization

Five anti-PD-L1 sdAbs (AS06730, AS06750, AS11948, AS06617 and AS06675) were selected for humanization. Protein sequences of wildtype camelid sdAb was aligned with the 5 closest human germline sequences sharing the highest degree of homology. The best human germline sequence was selected as human acceptor. Homology model was made. According to the model analysis data, residues potentially critical for antigen binding or antibody scaffold formation were left untouched while the rest were selected for conversion into the human counterpart. Initially a panel of four sequence optimized variants was generated (stage 1). These variants were analyzed for a number of parameters and the results obtained were used to design a second set of sdAbs (stage 2). For each wildtype sdAb, 1-9 humanized sdAbs were designed for binding, stability and functional evaluation, and their sequence alignments are shown in FIGS. 9A-9E.

Humanized HCAb Production

The HCAb constructs were generated by fusion sdAbs with human Fc region. The maxiprep of the HCAb constructs were prepared for CHO-K1 cell transient expression and purification. The expressed HCAbs were purified by chromatography through a column containing Protein A agarose resin followed by a size exclusion column.

Affinity Ranking of Humanized HCAbs

Binding kinetics of each humanized HCAb to PD-L1 are determined using recombinant human PD-L1 His protein (R&D System) coated on a CM5 (Biacore) sensor chip. Each antigen binding protein is flowed over the antigen-coated chip, using surface plasmon resonance. Alternatively, each antigen binding protein is captured on a CM5 sensor chip, over which human PD-1-His protein is applied. Only the binding affinity of humanized clones comparable to that of the parent HCAbs were selected for further characterization (Tables 7-11).

TABLE 7 affinity ranking of humanized sdAbs (AS06730)

| Ligand | Analyte | $k_a$ (1/Ms) | $k_d$ (1/s) | $K_D$ (M) |
|---|---|---|---|---|
| PD-L1/His | AS06730 | 2.34E+05 | 3.35E−04 | 1.43E−09 |
| | AS06730S | 2.29E+05 | 5.73E−04 | 2.51E−09 |
| | AS06730A | 6.96E+05 | 2.41E−02 | 3.46E−08 |
| | AS06730Q | 3.68E+11 | 1.18E+03 | 3.21E−09 |
| | AS06730QVH1 | 2.58E+06 | 5.79E−03 | 2.24E−09 |
| | AS06730QVH2 | 5.30E+05 | 2.19E−03 | 4.14E−09 |
| | AS06730QVH3a | 2.32E+06 | 2.12E−01 | 9.14E−08 |
| | AS06730SVH12 | 3.0E+05 | 1.8E−03 | 6.1E−09 |
| | AS06730SVH12M8 | 3.1E+05 | 6.5E−03 | 2.1E−08 |
| | AS06730SVH12M9 | 3.2E+05 | 1.2E−02 | 3.7E−08 |

TABLE 8 affinity ranking of humanized sdAbs (AS06750)

| Ligand | Analyte | $k_a$ (1/Ms) | $k_d$ (1/s) | $K_D$ (M) |
|---|---|---|---|---|
| PD-L1/His | AS06750 | 1.49E+05 | 3.30E−04 | 2.21E−09 |
| | AS06750VH2 | 2.12E+05 | 3.29E−04 | 1.55E−09 |
| | AS06750VH3 | 2.02E+05 | 3.55E−04 | 1.75E−09 |
| | AS06750VHa | 1.89E+05 | 3.08E−04 | 1.63E−09 |
| | AS06750VH1 | 7.08E+04 | 2.53E−03 | 3.57E−08 |
| | AS06750VH11 | 1.40E+05 | 2.70E−04 | 1.90E−09 |

TABLE 9 affinity ranking of humanized sdAbs (AS11948)

| Ligand | Analyte | $k_a$ (1/Ms) | $k_d$ (1/s) | $K_D$ (M) |
|---|---|---|---|---|
| PD-L1/His | AS11948 | 2.97E+05 | 5.82E−04 | 1.96E−09 |
| | AS11948Q | 3.01E+05 | 4.65E−02 | 1.55E−07 |
| | AS11948QVH1 | 3.32E+05 | 7.99E−04 | 2.41E−09 |
| | AS11948QVH2 | 2.17E+06 | 1.95E−01 | 8.98E−08 |
| | AS11948A | 2.05E+06 | 1.96E−01 | 9.55E−08 |
| | AS11948QVHa | 6.41E+10 | 6.77E+02 | 1.06E−08 |
| | AS11948S | 2.26E+05 | 8.61E−04 | 3.80E−09 |
| | AS11948SVH12 | 4.0E+05 | 1.5E−03 | 3.7E−09 |
| | AS11948SVH12M8 | 4.3E+05 | 9.5E−03 | 2.2E−08 |
| | AS11948SVH12M9 | 4.0E+05 | 6.3E−03 | 1.6E−08 |

TABLE 10 affinity ranking of humanized sdAbs (AS06617)

| Ligand | Analyte | $k_a$ (1/Ms) | $k_d$ (1/s) | $K_D$ (M) |
|---|---|---|---|---|
| PD-L1/His | AS06617 | 3.10E+05 | 4.30E−04 | 1.40E−09 |
| | AS06617VH11 | 4.30E+05 | 1.20E−03 | 2.70E−09 |

TABLE 11 affinity ranking of humanized sdAbs (AS06775)

| Ligand | Analyte | $k_a$ (1/Ms) | $k_d$ (1/s) | $K_D$ (M) |
|---|---|---|---|---|
| PD-L1/His | AS0775 | 2.10E+05 | 3.60E−04 | 1.70E−09 |
| | AS06775VH11 | 3.20E+05 | 5.00E−04 | 1.60E−09 |
| | AS06775VH4 | 2.46E+05 | 7.16E−04 | 2.92E−09 |

Affinity Determination

Figure 10A:
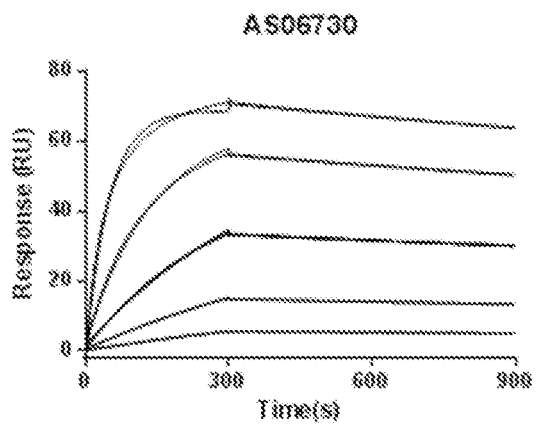
FIGS. 10A-10T depict the affinity determination of selected humanized HCAbs along with the parent HCAbs.
Figure 10B:
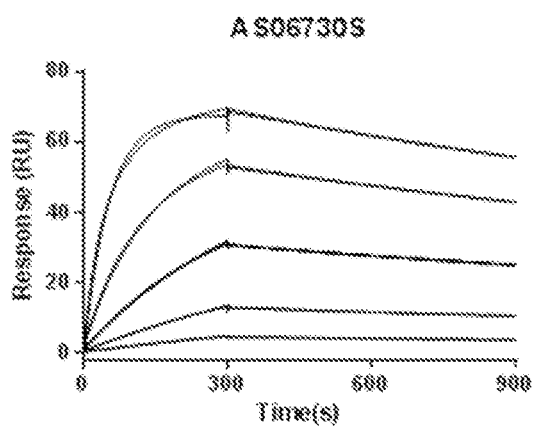
Figure 10C:
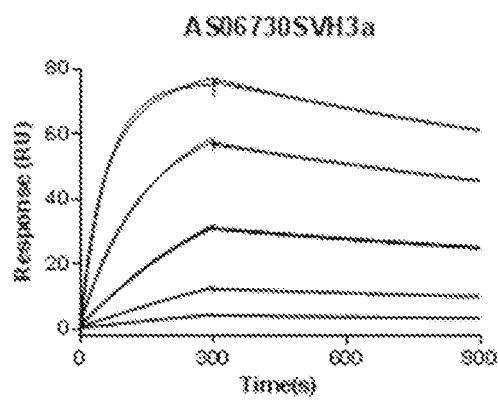
Figure 10D:
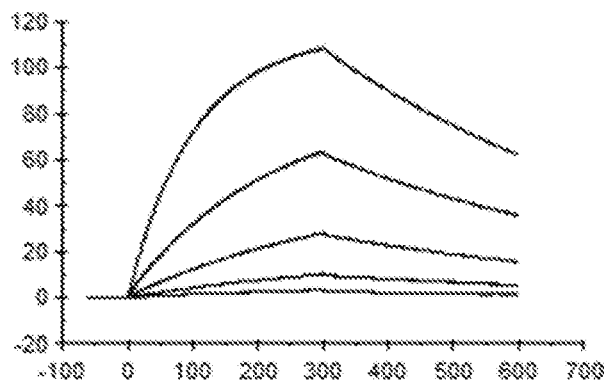
FIGS. 10D-10F (AS06730SVH12 (FIG. 10D); AS06730SVH12M8 (FIG. 10E); AS06730SVH12M9 (FIG. 10F)): The affinity determination was done using HCAbs being captured onto the chip by anti-human IgG and PD-L1 His as analyte at concentrations of 0.33, 1, 3, 9 and 27 nM.
Figure 10E:
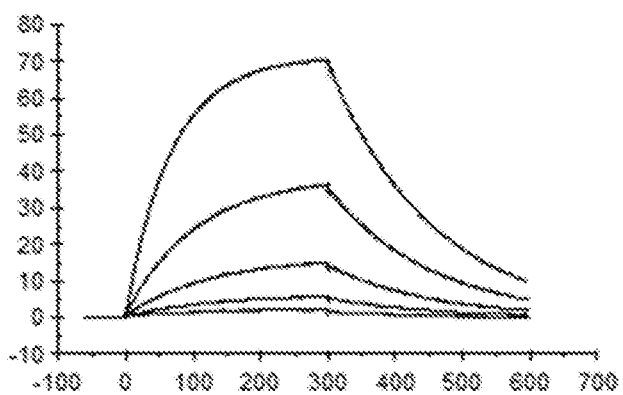
Figure 10F:
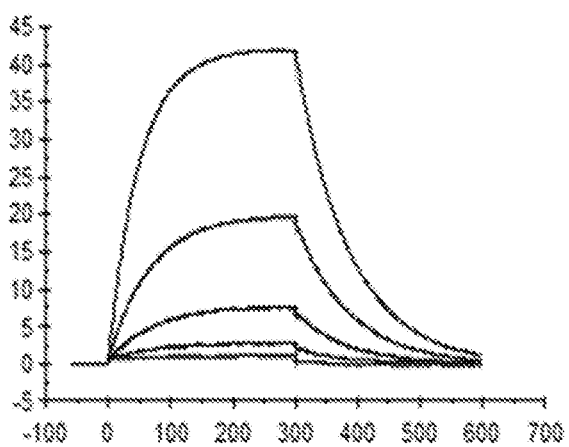
Figure 10G:
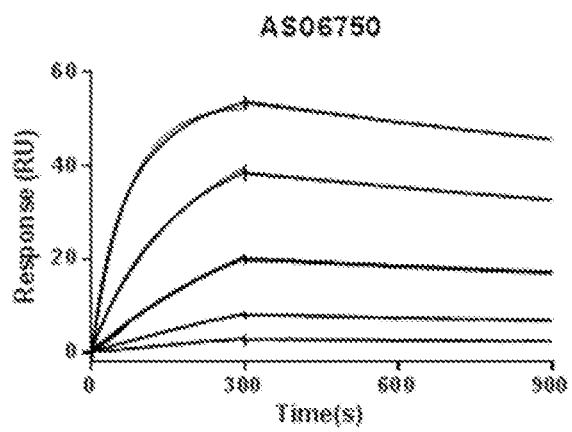
FIGS. 10G-10J (AS06750 (FIG. 10G); AS06750VH2 (FIG. 10H); AS06750VH11 (FIG. 10I); AS06750VH4 (FIG. 10J)), The affinity determination was done using PD-L1 His being immobilized onto the chip and anti-PD-L1 HCAb as analyte at concentrations of 0.11, 0.33, 1, 3, and 9 nM.
Figure 10H:
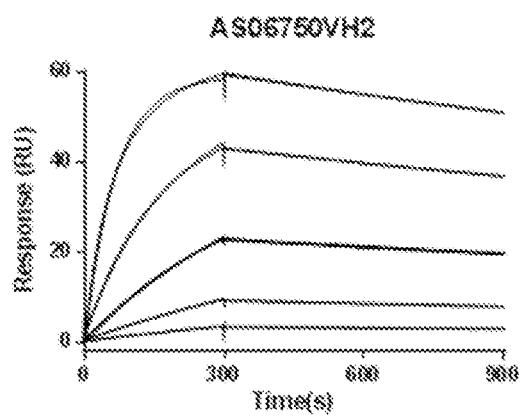
Figure 10I:
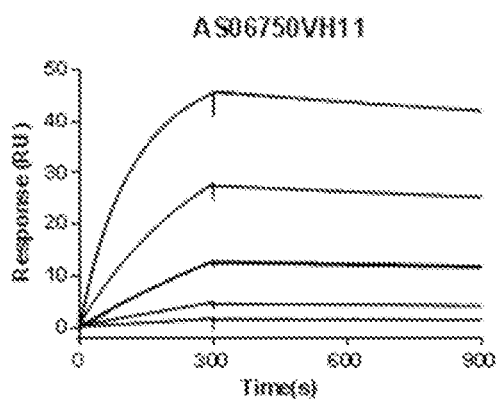
Figure 10J:
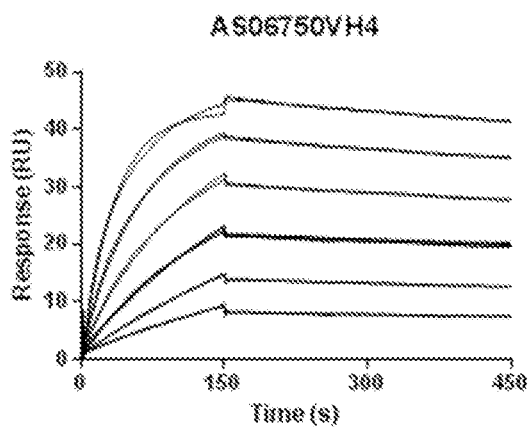
Figure 10K:
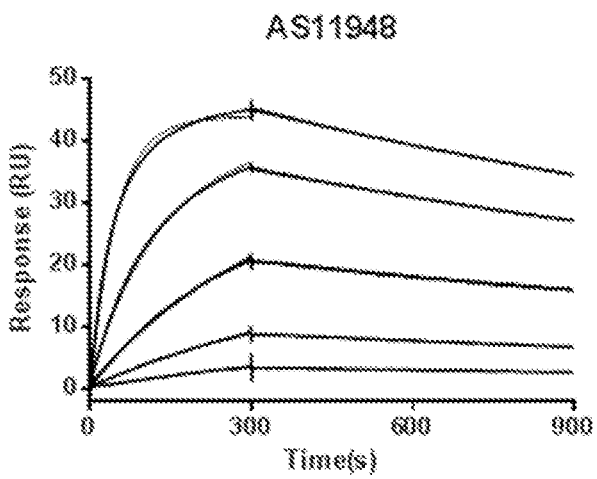
FIGS. 10K-10L (AS11948 (FIG. 10K); AS11948S (FIG. 10L)): The affinity determination was done using PD-L1 His being immobilized onto the chip and anti-PD-L1 HCAb as analyte at concentrations of 0.11, 0.33, 1, 3, and 9 nM.
Figure 10L:
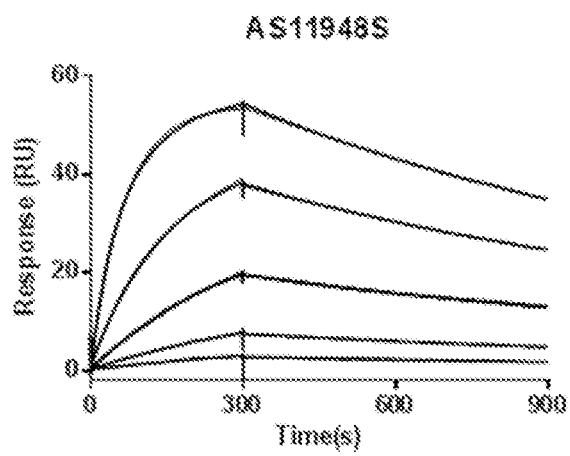
Figure 10M:
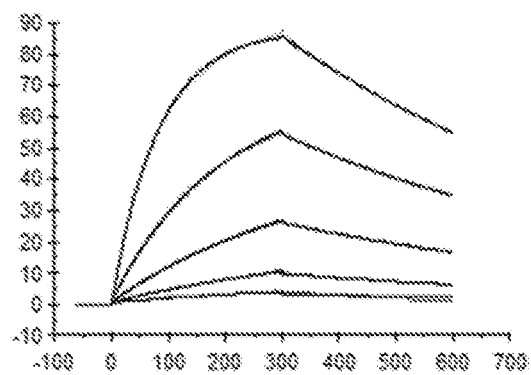
FIGS. 10M-10O (AS11948SV12 (FIG. 10M); AS11948SV12M8 (FIG. 10N); AS11948V12M9 (FIG. 10O)): The affinity determination was done using HCAbs being captured onto the chip by anti-human IgG and PD-L1 His as analyte at concentrations of 0.33, 1, 3, 9 and 27 nM.
Figure 10N:
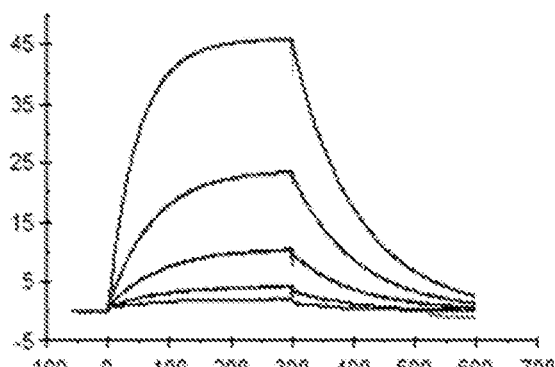
Figure 10O:
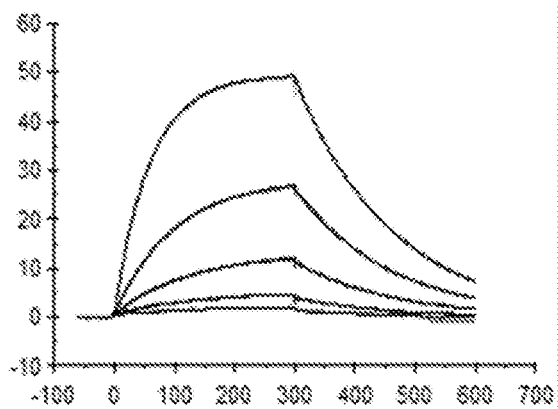
Figure 10P:
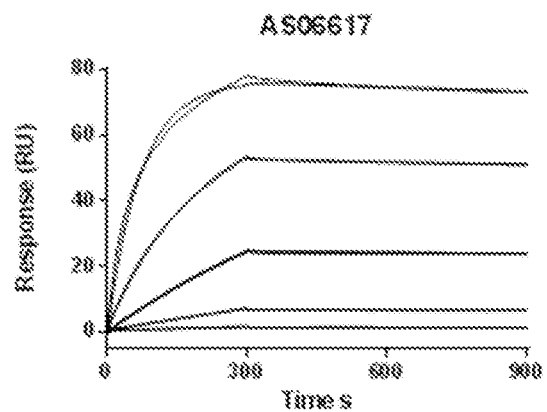
FIGS. 10P-10Q (AS06617 (FIG. 10P); AS06617VH11 (FIG. 10Q)): The affinity determination was done using PD-L1 His being immobilized onto the chip and anti-PD-L1 HCAb as analyte at concentrations of 0.11, 0.33, 1, 3, and 9 nM.
Figure 10Q:
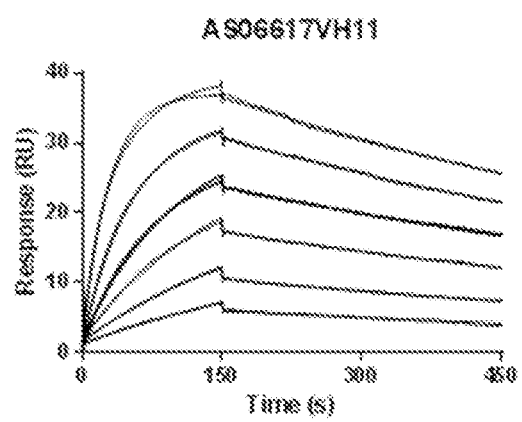
Figure 10R:
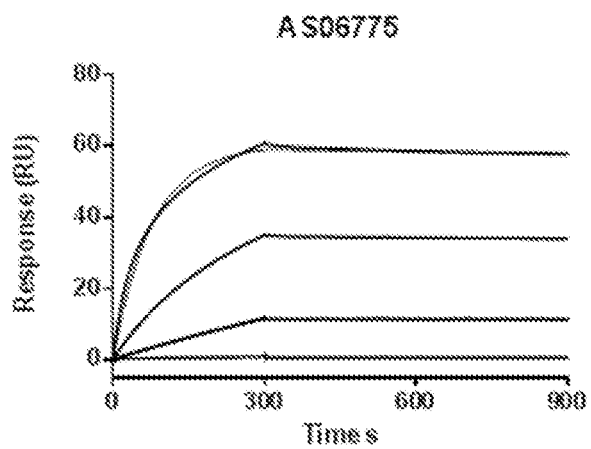
Figure 10S:
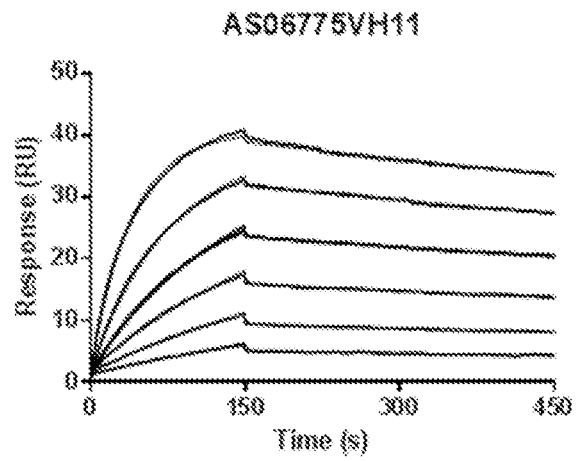
Figure 10T:
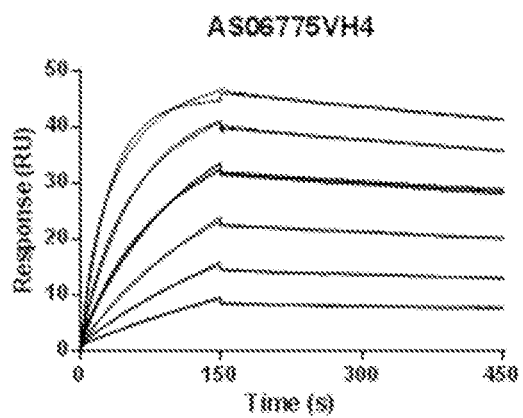

AS06730S, AS06730SVH3a, AS06730SVH12, AS06730AVH12M8, AS06730SVH12M9, AS06750VH2, AS06750VH11, AS06750VH4, AS11948S, AS11948SVH12, AS11948SV12M8, AS11948SV12M9, AS06617VH11, AS06775VH11 and AS06775VH4 were selected for affinity determination. Affinity constant ($K_d$) of each HCAbs was determined by surface plasmon resonance (SPR) on a BIAcore T200 instrument. Briefly, for most of HCAbs affinity determination, PD-L1 His was amine-coupled to a CM5 sensor chip at a density of no higher than 100 RU. Anti-PD-L1 HCAbs were injected at 5 different concentrations between 0.11 nM and 27 nM. Flow rate was 30 μl/min in all experiments. Association and dissociation phases were 5 and 10 min, respectively. The chip was regenerated using Glycine/HCl pH 1.5. For AS06730SVH12, AS06730SVH12M8, AS06730VH12M9, AS11948SV12, AS11948SV12M8 and AS11948SV12M9 HCAbs affinity determination, anti-PD-L1 HCAbs were captured on a CM5 sensor chip at a density of no higher than 100 RU by anti-human IgG antibody. Anti-PD-L1 His was injected at 5 different concentrations between 0.33 and 27 nM. Flow rate was 30 μl/min in all experiments. Association and dissociation phases were 5 min. Binding curves at different concentrations of HCAbs were used to calculate the kinetic parameters $k_{on}$, $k_{off}$ and $K_d$ (FIGS. 10A-10T). The kinetics data were summarized in Table 12 and Table 13.

TABLE 12

Affinity parameters of humanized HCAbs

| Ligand | Analyte | $k_a$ (1/Ms) | $k_d$ (1/s) | $K_D$ (M) |
|---|---|---|---|---|
| PD-L1 His | AS06730 HCAb | 7.6E+04 | 1.7E−04 | 2.2E−09 |
| | AS06730S HCAb | 7.1E+04 | 3.5E−04 | 4.9E−09 |
| | AS06730SVH3a HCAb | 6.2E+04 | 3.7E−04 | 5.9E−09 |
| | AS06750 HCAb | 2.0E+05 | 3.6E−04 | 1.8E−09 |
| | AS06750VH2 HCAb | 2.0E+05 | 3.3E−04 | 1.7E−09 |
| | AS06750VH11 HCAb | 9.5E+04 | 3.0E−04 | 3.2E−09 |
| | AS06750VH4 HCAb | 1.4E+05 | 2.7E−04 | 1.9E−09 |
| | AS11948 HCAb | 3.5E+05 | 6.2E−04 | 1.8E−09 |
| | AS11948S HCAb | 2.9E+05 | 1.1E−03 | 3.8E−09 |
| | AS06617 HCAb | 4.8E+05 | 1.0E−03 | 2.1E−09 |
| | AS06617VH11 HCAb | 4.3E+05 | 1.2E−03 | 2.7E−09 |
| | AS06775 HCAb | 3.1E+05 | 4.3E−04 | 1.4E−09 |
| | AS06775VH4 HCAb | 2.1E+05 | 3.6E−04 | 1.7E−09 |
| | AS06775VH11 HCAb | 3.2E+05 | 5.0E−04 | 1.6E−09 |

TABLE 13

Affinity parameters of humanized HCAbs

| Ligand | Analyte | $k_a$ (1/Ms) | $k_d$ (1/s) | $K_D$ (M) |
|---|---|---|---|---|
| AS06730SVH12 HCAb | PD-L1 His | 3.0E+05 | 1.8E−03 | 6.1E−09 |
| AS06730SVH12M8 HCAb | | 3.6E+05 | 6.5E−03 | 1.8E−08 |
| AS06730SVH12M9 HCAb | | 4.0E+05 | 1.2E−02 | 3.0E−08 |
| AS11948SVH12 HCAb | | 4.0E+05 | 1.5E−03 | 3.7E−09 |
| AS11948SVH12M8 HCAb | | 4.3E+05 | 9.5E−03 | 2.2E−08 |
| AS11948SVH12M9 HCAb | | 4.0E+05 | 6.3E−03 | 1.6E−08 |

PD-L1 Based Blockade Assay

Figure 11A:
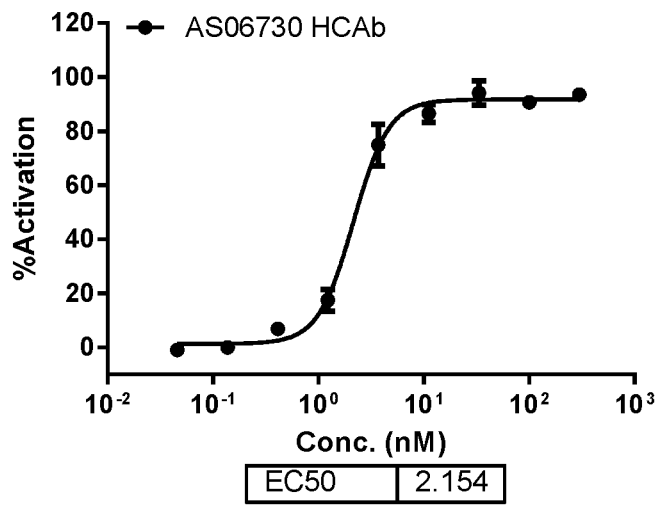
FIGS. 11A-11Q (AS06730 (FIG. 11A); AS06730S (FIG. 11B); AS06730SVH3a (FIG. 11C); AS06730SVH12 (FIG. 11D); AS06750 (FIG. 11E); AS06750VH2 (FIG. 11F); AS06750VH11 (FIG. 11G); AS06750VH4 (FIG. 11H); AS11948 (FIG. 11I); AS11948S (FIG. 11J); AS11948SVH12 (FIG. 11K); AS11948SVH12M8 (FIG. 11L); AS06617 (FIG. 11M); AS06617VH11 (FIG. 11N); AS06775 (FIG. 11O); AS06775VH11 (FIG. 11P); AS06775VH4 (FIG. 11Q)) depict functional activity evaluation of purified top humanized HCAbs along with the parent HCAbs by PD-L1-based blockade assay.
Figure 11B:
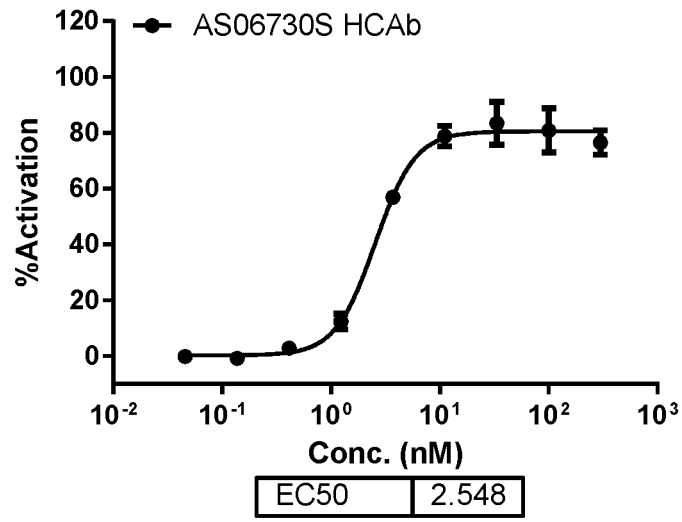
Figure 11C:
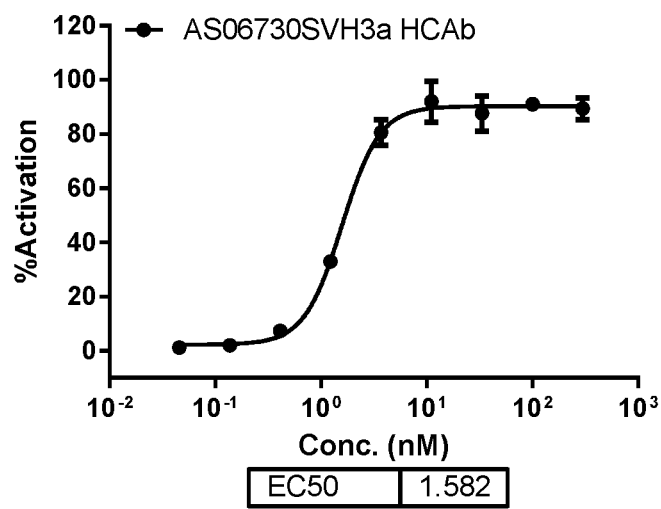
Figure 11D:
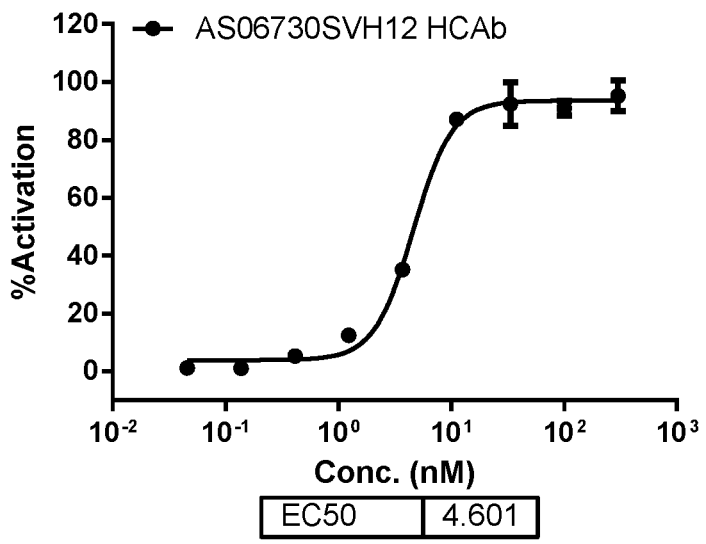
Figure 11E:
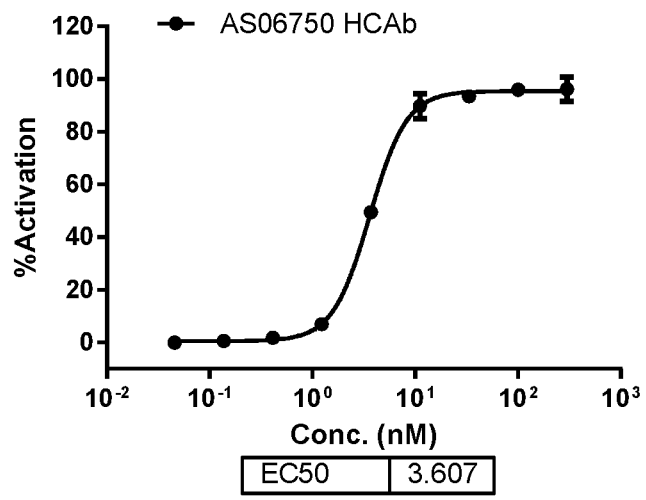
Figure 11F:
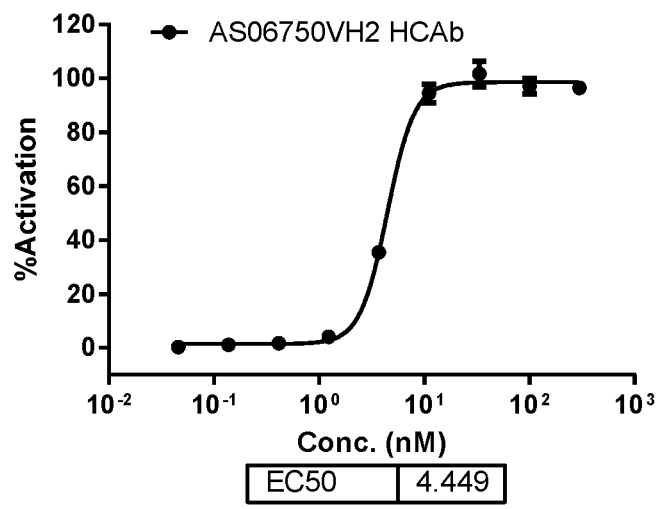
Figure 11G:
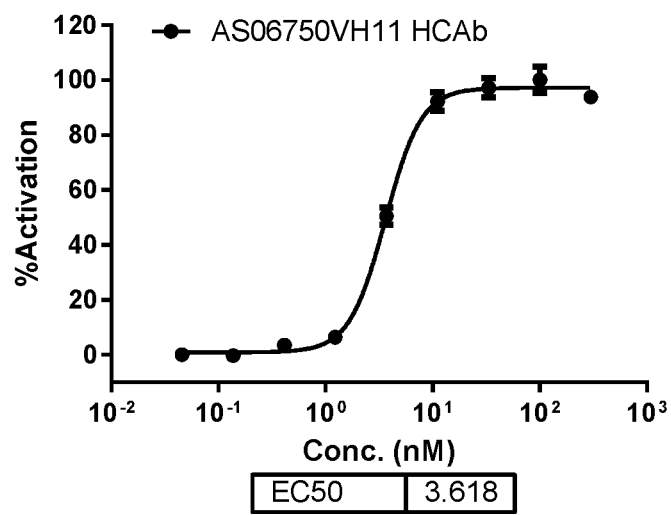
Figure 11H:
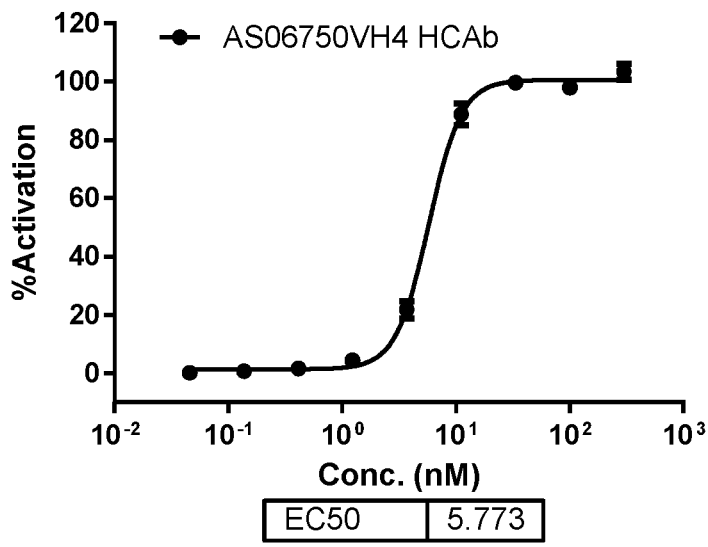
Figure 11I:
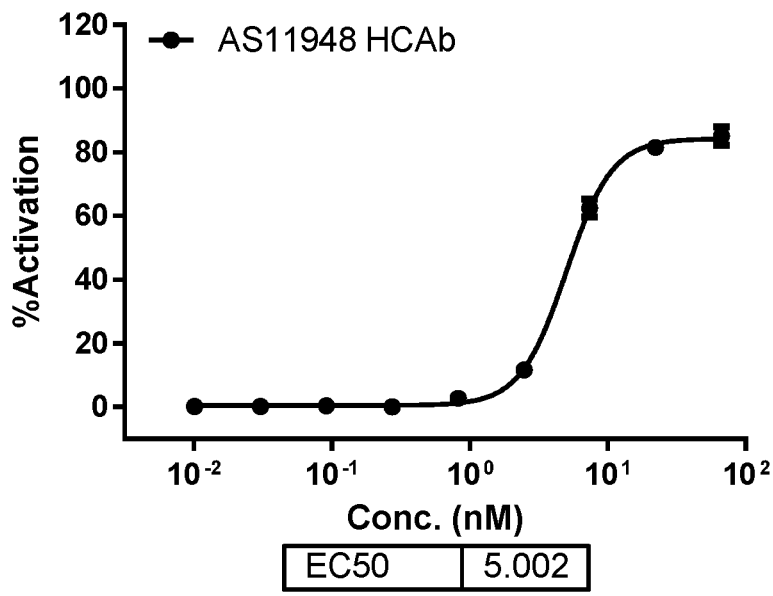
Figure 11J:
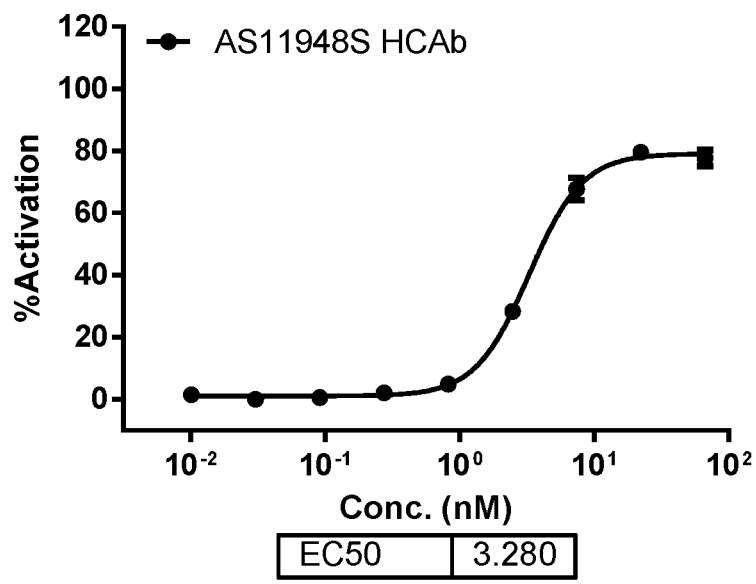
Figure 11K:
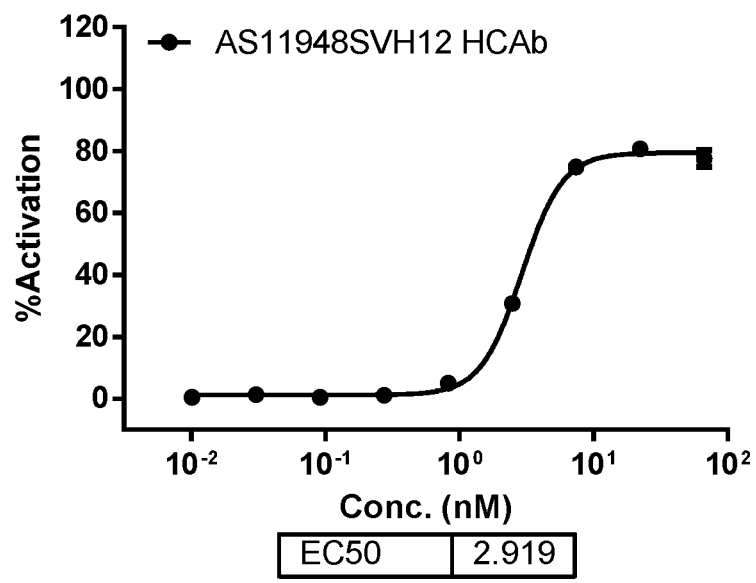
Figure 11L:
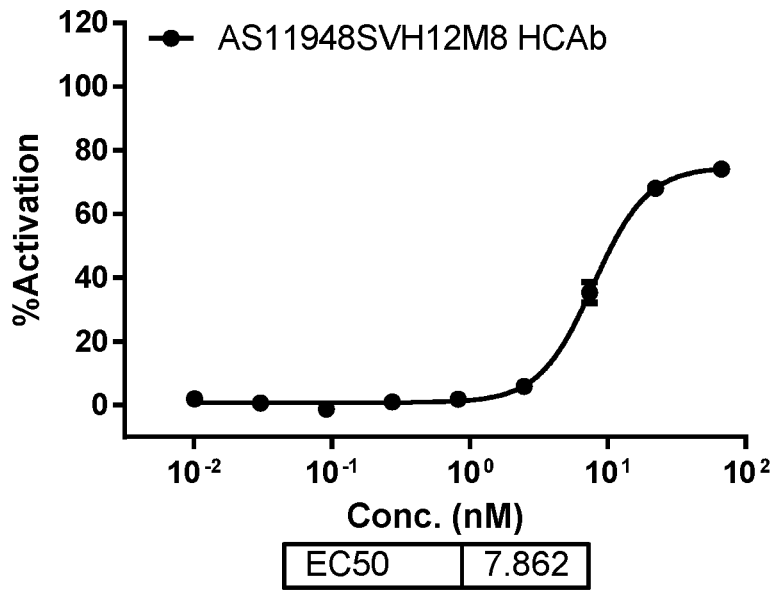
Figure 11M:
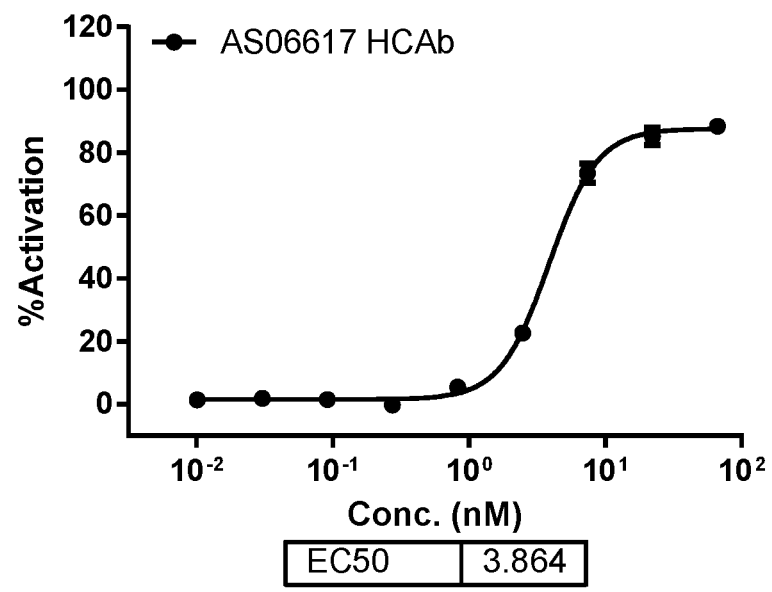
Figure 11N:
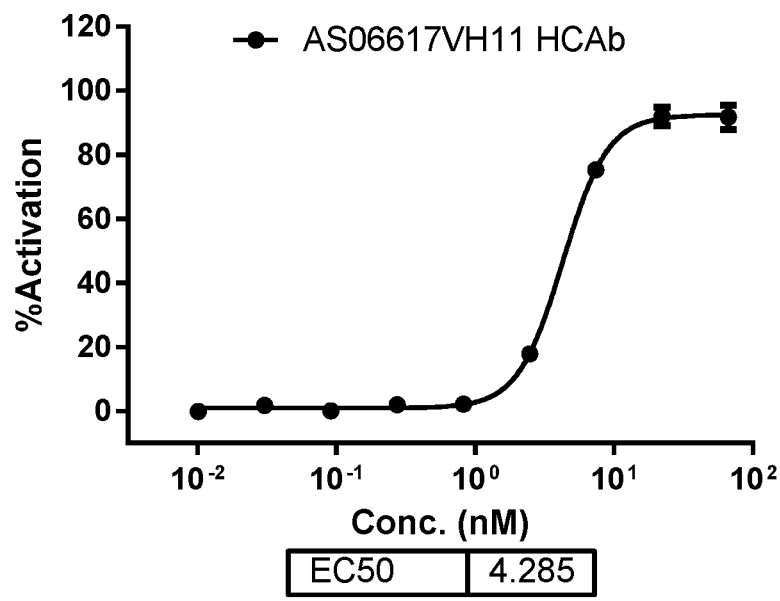
Figure 11O:
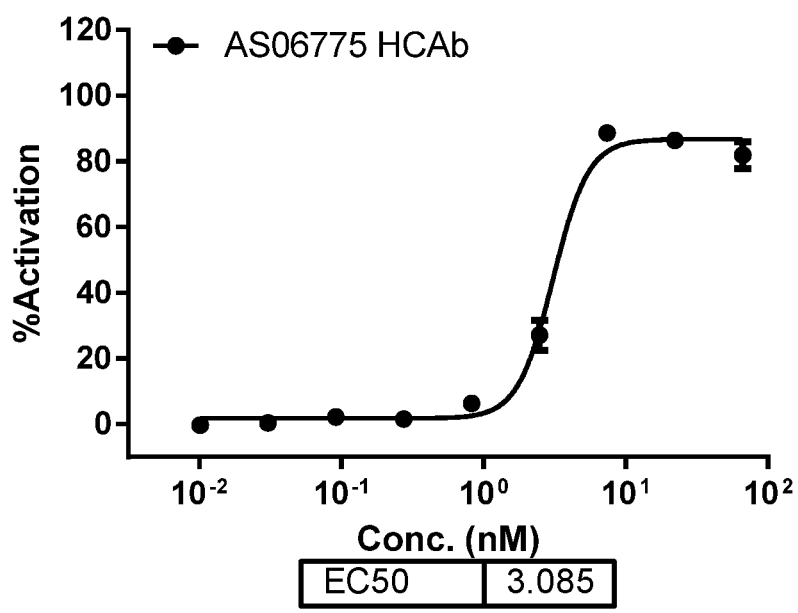
Figure 11P:
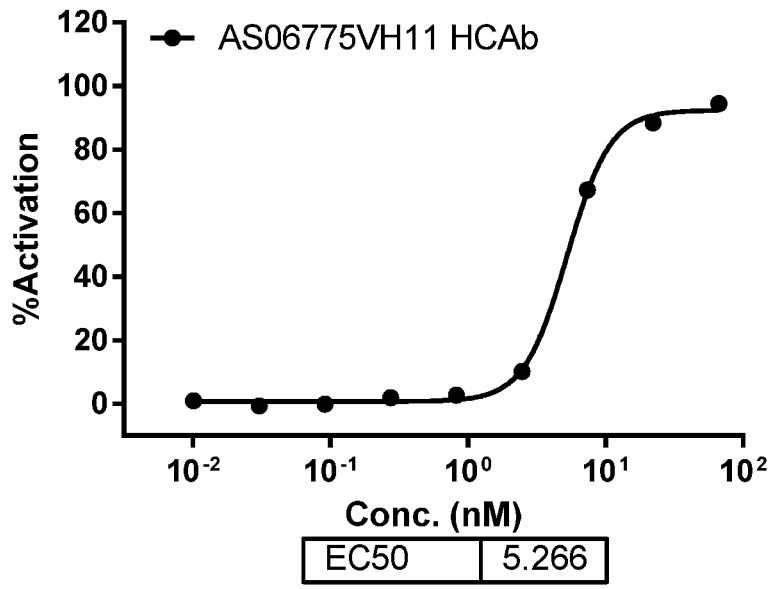
Figure 11Q:
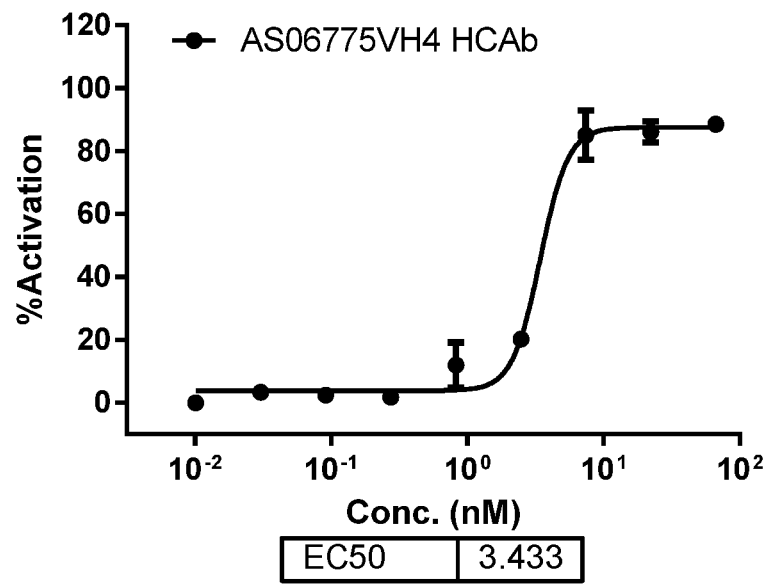

PD-L1 based blockade assay was performed as described in Example 1. As can be seen from FIGS. 11A-11Q, all the selected humanized anti-PD-L1 HCAbs are comparable to Tecentriq® in inhibiting the binding between PD-L1 and PD-1. The $EC_{50}$ data was summarized in Table 14.

TABLE 14

$EC_{50}$ of PD-L1-based blockade assay for HCAbs

| Sample | AS0730 HCAb | AS06730S HCAb | AS06730SVH3a HCAb | AS06730SVH12 HCAb | AS06750 HCAb |
|---|---|---|---|---|---|
| $EC_{50}$ (M) | 2.15E−09 | 2.54E−09 | 1.58E−09 | 4.60E−09 | 3.60E−09 |
| Sample | AS06750VH2 HCAb | AS06750VH11 HCAb | AS06750H4 HCAb | AS11948 HCAb | AS11948S HCAb |
| $EC_{50}$ (M) | 4.44E−09 | 3.61E−09 | 5.77E−09 | 5.00E−09 | 3.28E−09 |
| Sample | AS11948VH12 HCAb | AS11948VH12M8 HCAb | AS06617 HCAb | AS06617VH11 HCAb | AS06775 HCAb |
| $EC_{50}$ (M) | 2.91E−09 | 7.86E−09 | 3.86E−09 | 4.28E−09 | 3.08E−09 |

| Sample | AS06775VH11 HCAb | AS06775VH4 HCAb | Tecentriq |
|---|---|---|---|
| $EC_{50}$ (M) | 5.26E−09 | 3.43E−09 | 5.92E−09 |

In Vivo Activity of Humanized HCAbs

In the studies presented here, the efficacy of PD-L1 HCAb blockade against murine tumor model was investigated. Inhibition of the PD-L1 interaction is proposed to exert a therapeutic effect by restoring anti-tumor CD8+ T cell responses, thus the preclinical efficacy study was conducted in syngeneic murine tumor model in which the immune system of the host is fully intact. The human PD-1 transgenic mice was used.

Figure 12:
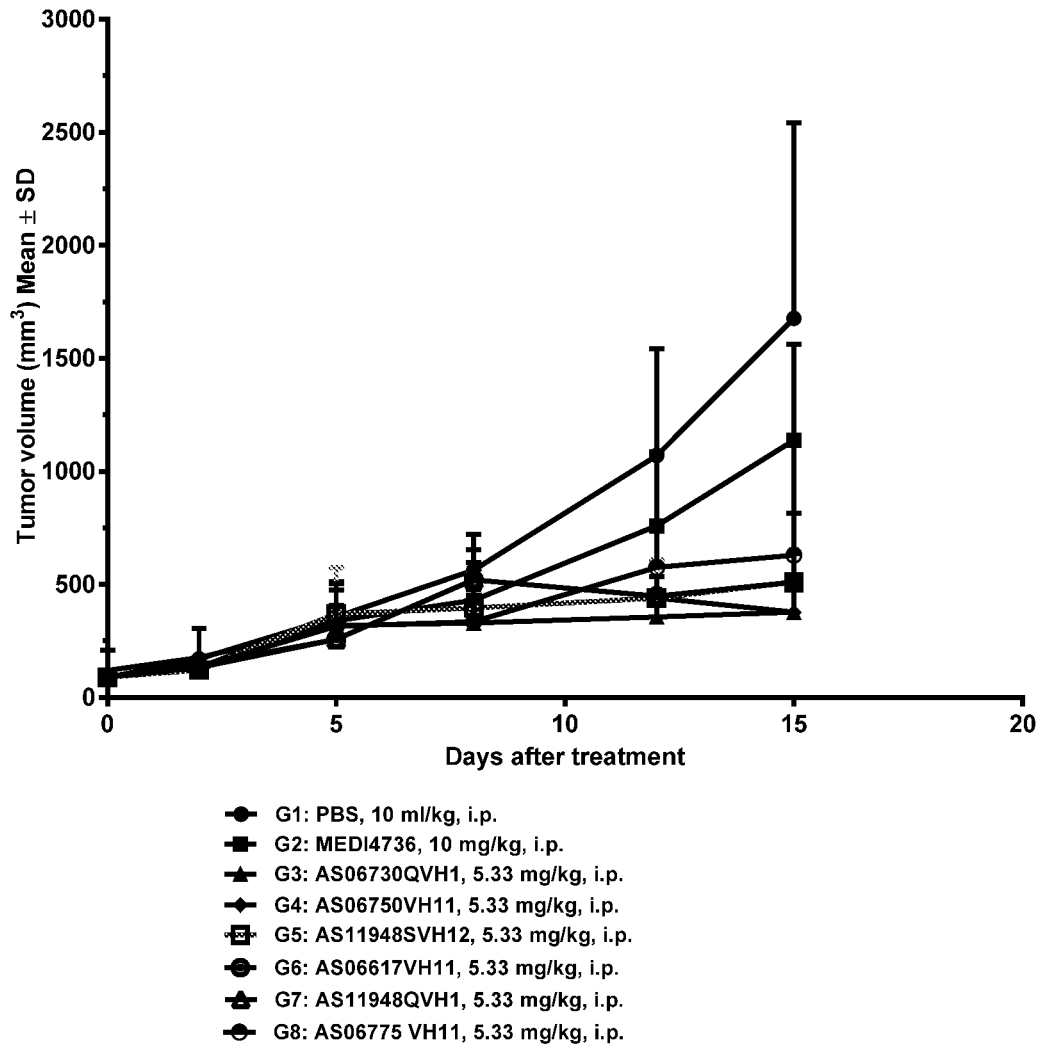
FIG. 12 depicts the in vivo efficacy study of 6 humanized HCAbs (AS06730QVH1, AS06750VH11, AS11948SVH12, AS06617VH11, AS06617VH11, AS11948QVH1 and AS06775VH11).

In this study, mice were inoculated subcutaneously in the right flank with $1 \times 10^6$ human PD-L1 overexpression MC38 colon carcinoma cells. When tumors reached a mean volume of ~100 mm$^3$, mice were sorted into treatment groups (n=5) (defined as study day 0). 6 humanized HCAbs tested in this study were listed: AS06730QVH1, AS06750VH11, AS11948SVH12, AS06617VH11, AS06617VH11, AS11948QVH1 and AS06775VH11. Groups were administered benchmark antibody MEDI4736 (10 mg/kg) or humanized HCAbs (5.33 mg/kg) intravenously days 0, 2, 5, 7, 9 and 12. A control group was treated with 10 ml/kg of PBS. Tumors were measured twice weekly for the study duration. All treatment groups demonstrated significant efficacy (P<0.050) when compared to the control group (FIG. 12). These observations support that anti-PD-L1 therapy as an effective strategy for driving anti-tumor CD8+ T cell responses.

TABLE 15

CDRs of isolated sdAbs

| sdAb | ID | CDR1 | ID | CDR2 | ID | CDR3 |
|---|---|---|---|---|---|---|
| AS06617 | 51 | GRTFISYAVG | 151 | GIRWNGIHTDYADSVKG | 251 | HRTIATIPEKYEYEY |
| AS06618 | 52 | GRTFLSYAVG | 152 | GIRWSGGYTDYAEAVKG | 252 | HRTIATIPEKYEYEY |
| AS06624 | 53 | GRTFLTYALG | 153 | GVSWSGSGTKYADSVKG | 253 | QISAIVPISAHEYEY |
| AS06628 | 54 | GRTFITYAIG | 154 | AINWSGSMTSYADSVKG | 254 | HRGAIAPMTQSVYDY |
| AS06639 | 55 | GRTFITYAIG | 155 | AINWSGSMTSYADSVKG | 255 | HRGAIAPMTQSVYDT |
| AS06682 | 56 | GRTFLSYAVG | 156 | GIRWSGEHTDYAASVKG | 256 | HTTIATIPKKYEYEY |
| AS06686 | 57 | GRTFLTYALG | 157 | GVSWSGSSTKYADSVKG | 257 | QISAIVPISAHEYQY |
| AS06703 | 58 | GRTFITYAIG | 158 | AINWSGSMTSYADSVKG | 258 | HLGAIAPMSQSVYDY |
| AS06709 | 59 | GRTFLSYAVG | 159 | GIRWSGGSTDYSDSVKG | 259 | HRTIATIPEKYEYEY |
| AS06730 | 60 | GRTFITYAIG | 160 | AINWSGSMTSYADSVKG | 260 | HRGAIAPIAQSVYTN |
| AS06750 | 61 | GRTFLTYAVG | 161 | GIRWSGGYTDYADSVKG | 261 | HRTIATIPEKYEYEY |
| AS06752 | 62 | GRTFLTYAVG | 162 | GIRWSGESTDYAESVKG | 262 | HRTIATIPEKYYYEY |
| AS06763 | 63 | GRPVSSAVMG | 163 | RLTSSATSTFYAESVKG | 263 | DVPGTKIWSIQTPDRYNY |
| AS06766 | 64 | GRTLTGLLIG | 164 | IISWTYGSTNYADSVKG | 264 | RDVAVAKYDS |
| AS06775 | 65 | GRTFLTLAVG | 165 | GIRWSGSGTDYADSVKG | 265 | HTTIATIPEKYEYEY |
| AS06778 | 66 | GRTFITYAMG | 166 | AISWSGSSTYSADSVKG | 266 | EVSARTGEHLPKLMGDY |
| AS06786 | 67 | GRTFLTLAVG | 167 | GIRWSGSGTDYADSVKG | 267 | HTTIATIPEKYEYEY |
| AS06791 | 68 | GRTFITYAIG | 168 | AINWSGSMTSYADSVKG | 268 | HRGAIAPMTQSVYDY |
| AS06808 | 69 | GRTFSRYAMG | 169 | TSTGSGGLTSYANSVKG | 269 | NRYNSDSRYMSSYDW |
| AS06810 | 70 | GRTFLSYAVG | 170 | GIRWSGLHTDYADSVKG | 270 | HRTIATIPEKYEYEY |
| AS11947 | 71 | GRTFISYAVG | 171 | GIRWNGISTDYTDSVKG | 271 | HRTIATIPNKYEYDH |
| AS11948 | 72 | GRTFVTYGMG | 172 | AINWSGSMTSYGDSVKG | 272 | ALGAWYTTREPYTY |
| AS12003 | 73 | GRTFLSYAVG | 173 | GIRWSGGSTDYADSVKG | 273 | HRTIATVPNKYEYDT |
| AL22863 | 74 | VSSFSINDMG | 174 | TIAS-GGSTNYADSVKG | 274 | DFRDWTRRRYSY |
| AL23474 | 75 | GRTFSNYTMA | 175 | VVSRGGGATDYADSVKG | 275 | GTDLSYYYSTKKWAY |
| AS06730S | 76 | GRTFITYAIG | 176 | AISWSGSMTSYADSVKG | 276 | HRGAIAPIAQSVYTN |
| AS06730Q | 77 | GRTFITYAIG | 177 | AIQWSGSMTSYADSVKG | 277 | HRGAIAPIAQSVYTN |
| AS06730QVH1 | 78 | GRTFITYAIG | 178 | AIQWSGSMTSYADSVKG | 278 | HRGAIAPIAQSVYTN |
| AS06730QVH2 | 79 | GRTFITYAIG | 179 | AIQWSGSMTSYADSVKG | 279 | HRGAIAPIAQSVYTN |
| AS06730QVH3a | 80 | GRTFITYAIG | 180 | AIQWSGSMTSYADSVKG | 280 | HRGAIAPIAQSVYTN |
| AS06730SVH12 | 81 | GRTFITYAIG | 181 | AISWSGSMTSYADSVKG | 281 | HRGAIAPIAQSVYTN |
| AS06730SVH12M8 | 82 | GRTFITYAIG | 182 | AISWSGSITSYADSVKG | 282 | HRGAIAPIAQSVYTN |
| AS06730SVH12M9 | 83 | GRTFITYAIG | 183 | AISWSGSLTSYADSVKG | 283 | HRGAIAPIAQSVYTN |
| AS06750VH1 | 84 | GRTFLTYAVG | 184 | GIRWSGGYTDYADSVKG | 284 | HRTIATIPEKYEYEY |
| AS06750VH2 | 85 | GRTFLTYAVG | 185 | GIRWSGGYTDYADSVKG | 285 | HRTIATIPEKYEYEY |
| AS06750VH3 | 86 | GRTFLTYAVG | 186 | GIRWSGGYTDYADSVKG | 286 | HRTIATIPEKYEYEY |
| AS06750VHa | 87 | GRTFLTYAVG | 187 | GIRWSGGYTDYADSVKG | 287 | HRTIATIPEKYEYEY |
| AS06750VH11 | 88 | GRTFLTYAVG | 188 | GIRWSGGYTDYADSVKG | 288 | HRTIATIPEKYEYEY |

TABLE 15-continued

CDRs of isolated sdAbs

| sdAb | ID | CDR1 | ID | CDR2 | ID | CDR3 |
|---|---|---|---|---|---|---|
| AS11948A | 89 | GRTFVTYGMG | 189 | AIAWSGSMTSYGDSVKG | 289 | ALGAWYTTREPYTY |
| AS11948S | 90 | GRTFVTYGMG | 190 | AISWSGSMTSYGDSVKG | 290 | ALGAWYTTREPYTY |
| AS11948Q | 91 | GRTFVTYGMG | 191 | AIQWSGSMTSYGDSVKG | 291 | ALGAWYTTREPYTY |
| AS11948QVH1 | 92 | GRTFVTYGMG | 192 | AIQWSGSMTSYGDSVKG | 292 | ALGAWYTTREPYTY |
| AS11948QVH2 | 93 | GRTFVTYGMG | 193 | AIQWSGSMTSYGDSVKG | 293 | ALGAWYTTREPYTY |
| AS11948QVHa | 94 | GRTFVTYGMG | 194 | AIQWSGSMTSYGDSVKG | 294 | ALGAWYTTREPYTY |
| AS11948SVH12 | 95 | GRTFVTYGMG | 195 | AISWSGSMTSYGDSVKG | 295 | ALGAWYTTREPYTY |
| AS11948SVH12M8 | 96 | GRTFVTYGMG | 196 | AISWSGSITSYGDSVKG | 296 | ALGAWYTTREPYTY |
| AS11948SVH12M9 | 97 | GRTFVTYGMG | 197 | AISWSGSLTSYGDSVKG | 297 | ALGAWYTTREPYTY |
| AS06617VH11 | 98 | GRTFISYAVG | 198 | GIRWSGIHTDYADSVKG | 298 | HRTIATIPEKYEYEY |
| AS06775VH11 | 99 | GRTFLTLAVG | 199 | GIRWSGSGTDYADSVKG | 299 | HTTIATIPEKYEYEY |
| AS06775VH4 | 100 | GRTFLTYAVG | 200 | GIRWSGGYTDYADSVKG | 300 | HRTIATIPEKYEYEY |

ID: SEQ ID NO

TABLE 16

Framework Regions 1 and 2

| sdAb | ID | FR-1 | ID | FR-2 |
|---|---|---|---|---|
| AS06617 | 1 | DVQLVESGGGLVQAGDSLRLSCAAS | 101 | WFRQAPGSEREFVA |
| AS06618 | 2 | EVQLVESGGRLVRAGDSLRLSCAAS | 102 | WFRQAPGTEREFVA |
| AS06624 | 3 | QVQLVESGGGLVQAGGSLRLACSAS | 103 | WFRQAPGKEREFVA |
| AS06628 | 4 | QVQLVESGGGLVQAGDSLRLSCAAS | 104 | WFRQAPGKEREFVT |
| AS06639 | 5 | AVQLVESGGGLVQAGGSLRLSCAAS | 105 | WFRQAPGKEREFVS |
| AS06682 | 6 | AVQLVESGGGLVQAGDSLRLSCTAS | 106 | WFRQAPGTEREFVA |
| AS06686 | 7 | AVQLVESGGGLVQAGDSLRLACAAS | 107 | WFRQAPGKEREFVA |
| AS06703 | 8 | EVQLVESGGGLVRAGGSLRLSCAAS | 108 | WFRQAPGKEREFVT |
| AS06709 | 9 | EVQLVESGGGLVQAGDSLRLSCTAS | 109 | WFRQAPGTEREFVA |
| AS06730 | 10 | QVQLVESGGGLVQAGGSLRLSCAAS | 110 | WFRQAPGKEREFVS |
| AS06750 | 11 | AVQLVESGGGLVQAGDSLRLSCTAS | 111 | WFRQAPGTEREFVA |
| AS06752 | 12 | EVQLVESGGGLVQAGDSLRLSCAAS | 112 | WFRQAPGTEREFVA |
| AS06763 | 13 | QVQLVESGGGLVQAGGSLRLSCAVS | 113 | WFRQAPGKEREFVG |
| AS06766 | 14 | EVQLVESGGGLVQAGGSLSLSCAVS | 114 | WFRQAPGKERELVA |
| AS06775 | 15 | QVQLVESGGGLVQAGDSLRLSCAAS | 115 | WFRQAPGTEREFVA |
| AS06778 | 16 | QVQLVESGGGLVQAGDSLRLSCAAS | 116 | WFRQAPGKERELVA |
| AS06786 | 17 | QVQLVESGGGLVQAGDSLRLSCAAS | 117 | WFRQAPGTEREFVA |
| AS06791 | 18 | QVQLVESGGGLVQAGDSLRLSCAAS | 118 | WFRQAPGKEREFVT |
| AS06808 | 19 | QVKLEESGGGLVQAGGSLRLSCVAS | 119 | WFRQAPGKEREFVS |
| AS06810 | 20 | AVQLVESGGGLVQAGDSLRLSCAAS | 120 | WFRQAPGTEREFVA |
| AS11947 | 21 | DVQLVESGGGLVQAGDSLRLTCSAS | 121 | WFRQAPGTEREFVA |

TABLE 16-continued

Framework Regions 1 and 2

| sdAb | ID | FR-1 | ID | FR-2 |
|---|---|---|---|---|
| AS11948 | 22 | EVQLVESGGGLVQAGDSLRLSCVAS | 122 | WFRQAPGKEREFVA |
| AS12003 | 23 | EVQLVESGGGLVQAGDSLRLSCAAS | 123 | WFRQAPGTEREFVA |
| AL22863 | 24 | QVKLEESGGGLVQVGDSLRLSCAAS | 124 | WYRQAPGKQRELVA |
| AL23474 | 25 | QVKLEESGGGLVQVGDSLRLSCAAS | 125 | WFRQFPGKEREFVA |
| AS06730S | 26 | QVQLVESGGGLVQAGGSLRLSCAAS | 126 | WFRQAPGKEREFVS |
| AS06730Q | 27 | QVQLVESGGGLVQAGGSLRLSCAAS | 127 | WFRQAPGKEREFVS |
| AS06730QVH1 | 28 | EVQLVESGGGLVQPGGSLRLSCAAS | 128 | WVRQAPGKGLEWVS |
| AS06730QVH2 | 29 | EVQLVESGGGLVQPGGSLRLSCAAS | 129 | WFRQAPGKGLEWVS |
| AS06730QVH3a | 30 | EVQLVESGGGLVQPGGSLRLSCAAS | 130 | WFRQAPGKGLEFVS |
| AS06730SVH12 | 31 | EVQLVESGGGLVQPGGSLRLSCAAS | 131 | WFRQAPGKGREFVS |
| AS06730SVH12M8 | 32 | EVQLVESGGGLVQPGGSLRLSCAAS | 132 | WFRQAPGKGREFVS |
| AS06730SVH12M9 | 33 | EVQLVESGGGLVQPGGSLRLSCAAS | 133 | WFRQAPGKGREFVS |
| AS06750VH1 | 34 | EVQLVESGGGLVQPGGSLRLSCAAS | 134 | WVRQAPGKGLEWVS |
| AS06750VH2 | 35 | EVQLVESGGGLVQPGGSLRLSCAAS | 135 | WFRQAPGKGLEWVA |
| AS06750VH3 | 36 | EVQLVESGGGLVQPGGSLRLSCAAS | 136 | WFRQAPGKGLEFVA |
| AS06750VHa | 37 | EVQLVESGGGLVQPGGSLRLSCTAS | 137 | WFRQAPGKGLEFVA |
| AS06750VH11 | 38 | EVQLVESGGGLVQPGGSLRLSCAAS | 138 | WFRQAPGKGREFVS |
| AS11948A | 39 | EVQLVESGGGLVQAGDSLRLSCVAS | 139 | WFRQAPGKEREFVA |
| AS11948S | 40 | EVQLVESGGGLVQAGDSLRLSCVAS | 140 | WFRQAPGKEREFVA |
| AS11948Q | 41 | EVQLVESGGGLVQAGDSLRLSCVAS | 141 | WFRQAPGKEREFVA |
| AS11948QVH1 | 42 | EVQLVESGGGLVQPGGSLRLSCAAS | 142 | WVRQAPGKGLEWVS |
| AS11948QVH2 | 43 | EVQLVESGGGLVQPGGSLRLSCAAS | 143 | WFRQAPGKGLEFVA |
| AS11948QVHa | 44 | EVQLVESGGGLVQPGGSLRLSCVAS | 144 | WFRQAPGKGREFVS |
| AS11948SVH12 | 45 | EVQLVESGGGLVQPGGSLRLSCAAS | 145 | WFRQAPGKGREFVS |
| AS11948SVH12M8 | 46 | EVQLVESGGGLVQPGGSLRLSCAAS | 146 | WFRQAPGKGREFVS |
| AS11948SVH12M9 | 47 | EVQLVESGGGLVQPGGSLRLSCAAS | 147 | WFRQAPGKGREFVS |
| AS06617VH11 | 48 | EVQLVESGGGLVQPGGSLRLSCAAS | 148 | WFRQAPGKGREFVS |
| AS06775VH11 | 49 | EVQLVESGGGLVQPGGSLRLSCAAS | 149 | WFRQAPGKGREFVS |
| AS06775VH4 | 50 | EVQLVESGGGLVQPGGSLRLSCAAS | 150 | WFRQAPGKGLEFVS |

ID: SEQ ID NO; R: Framework region

TABLE 17

Framework Regions 3 and 4

| sdAb | ID | FR-3 | ID | FR-4 |
|---|---|---|---|---|
| AS06617 | 201 | RFTISRDNAKNTVTLEMTSLKPEDTAVYYCAA | 301 | WGQGTQVTVSS |
| AS06618 | 202 | RFTISRDNAKNTVYLQMNSLKPEDTAVYYCAA | 302 | WGQGTQVTVSS |
| AS06624 | 203 | RFTISRDNAKNTVYMQMNSLKPEDTAVYYCAA | 303 | WGQGTQVTVSS |
| AS06628 | 204 | RFTISRDNNKNMVYLQMNSLKPEDTAVYYCAA | 304 | WGQGTQVTVSS |

TABLE 17-continued

Framework Regions 3 and 4

| sdAb | ID | FR-3 | ID | FR-4 |
| --- | --- | --- | --- | --- |
| AS06639 | 205 | RFTISRDNAKNTVYLQMNGLKPEDTAVYYCAA | 305 | WGQGTQVTVSS |
| AS06682 | 206 | RFTISRDNAKNTVYLQMNSLKPEDTAVYYCAA | 306 | WGQGTQVTVSS |
| AS06686 | 207 | RFTISRDNAKNTVYMQMNSLKPEDTAVYYCAA | 307 | WGQGTQVTVSS |
| AS06703 | 208 | RFTISRDNNKNTVYLQMNSLKPEDTALYYCAA | 308 | WGQGTQVTVSS |
| AS06709 | 209 | RFTISRDNAKNTVYLQMNSLKPEDTAVYYCAA | 309 | WGQGTQVTVSS |
| AS06730 | 210 | RFTISRDNAKNTVYLQMNGLKPEDTAVYYCAA | 310 | WGQGTQVTVSS |
| AS06750 | 211 | RFTISRDNAKNTVYLQMNSLKPEDTAVYYCAA | 311 | WGQGTQVTVSS |
| AS06752 | 212 | RFTISRDDTKNTVYLQMNSLKPEDTAVYYCAA | 312 | WGQGTQVTVSS |
| AS06763 | 213 | RFTISRDNAKNTVYLQMNNLKPEDTAVYYCAA | 313 | WGQGTQVTVSS |
| AS06766 | 214 | RFTISRDNAKNTVLLQMNSLKPEDTAVYYCSA | 314 | WGQGTQVTVSS |
| AS06775 | 215 | RFTISRDNAKNTVYLQMNSLKPEDTAVYYCAA | 315 | WGRGTQVTVSS |
| AS06778 | 216 | RFTISRDNAKNTVYLQMNSLKPEDTAVYYCAA | 316 | WGQGTQVTVSS |
| AS06786 | 217 | RFTISRDNAANTVYLQMNSLKPEDTAVYYCAA | 317 | WGQGTQVTVSS |
| AS06791 | 218 | RFTISRDNAKNTVYLQINGLKSEDTAVYYCAA | 318 | WGQGTQVTVSS |
| AS06808 | 219 | RFTISRDNAKNTVYLQMNNLKPEDTAIYYCAA | 319 | WGQGTQVTVSS |
| AS06810 | 220 | RFTISRDNAKNTVYLQMNSLKPEDTAIYYCAA | 320 | WGQGTQVTVSS |
| AS11947 | 221 | RFTISRDNAKNTVYLQMNSLKPEDTAIYYCAA | 321 | WGQGTQVTVSS |
| AS11948 | 222 | RFAISRDNAKNTVYLQMNSLKPEDTAVYYCAA | 322 | WGRGTQVTVSS |
| AS12003 | 223 | RFTISRDNAKNTVYLQMNSLKPEDTAVYYCAA | 323 | WGQGTQVTVSS |
| AL22863 | 224 | RFTISRDNVKNTVYLQMNGLKPEDTAVYYCNA | 324 | WGQGTQVTVSS |
| AL23474 | 225 | RFTISRDNAKNTMYLQMNSLKTEDTAVYYCAA | 325 | WGQGTQVTVSS |
| AS06730S | 226 | RFTISRDNAKNTVYLQMNGLKPEDTAVYYCAA | 326 | WGQGTQVTVSS |
| AS06730Q | 227 | RFTISRDNAKNTVYLQMNGLKPEDTAVYYCAA | 327 | WGQGTQVTVSS |
| AS06730QVH1 | 228 | RFTISRDNSKNTLYLQMNSLRAEDTAVYCAK | 328 | WGQGTLVTVSS |
| AS06730QVH2 | 229 | RFTISRDNSKNTVYLQMNSLRAEDTAVYYCAA | 329 | WGQGTLVTVSS |
| AS06730QVH3a | 230 | RFTISRDNSKNTVYLQMNSLRAEDTAVYYCAA | 330 | WGQGTLVTVSS |
| AS06730SVH12 | 231 | RFTISRDNAKNTLYLQMNSLRPEDTAVYYCAA | 331 | WGQGTLVTVSS |
| AS06730SVH12M8 | 232 | RFTISRDNAKNTLYLQMNSLRPEDTAVYYCAA | 332 | WGQGTLVTVSS |
| AS06730SVH12M9 | 233 | RFTISRDNAKNTLYLQMNSLRPEDTAVYYCAA | 333 | WGQGTLVTVSS |
| AS06750VH1 | 234 | RFTISRDNSKNTLYLQMNSLRAEDTAVYYCAK | 334 | WGQGTLVTVSS |
| AS06750VH2 | 235 | RFTISRDNSKNTVYLQMNSLRAEDTAVYYCAA | 335 | WGQGTLVTVSS |
| AS06750VH3 | 236 | RFTISRDNSKNTVYLQMNSLRAEDTAVYYCAA | 336 | WGQGTLVTVSS |
| AS06750VHa | 237 | RFTISRDNSKNTVYLQMNSLRAEDTAVYYCAA | 337 | WGQGTLVTVSS |
| AS06750VH11 | 238 | RFTISRDNAKNTLYLQMNSLRPEDTAVYYCAA | 338 | WGQGTLVTVSS |
| AS11948A | 239 | RFAISRDNAKNTVYLQMNSLKPEDTAVYYCAA | 339 | WGRGTQVTVSS |
| AS11948S | 240 | RFAISRDNAKNTVYLQMNSLKPEDTAVYYCAA | 340 | WGRGTQVTVSS |
| AS11948Q | 241 | RFAISRDNAKNTVYLQMNSLKPEDTAVYYCAA | 341 | WGRGTQVTVSS |
| AS11948QVH1 | 242 | RFTISRDNSKNTLYLQMNSLRAEDTAVYYCAK | 342 | WGQGTLVTVSS |

TABLE 17-continued

Framework Regions 3 and 4

| sdAb | ID | FR-3 | ID | FR-4 |
|---|---|---|---|---|
| AS11948QVH2 | 243 | RFTISRDNSKNTVYLQMNSLRAEDTAVYYCAA | 343 | WGQGTLVTVSS |
| AS11948QVHa | 244 | RFTISRDNSKNTVYLQMNSLRAEDTAVYYCAA | 344 | WGQGTLVTVSS |
| AS11948SVH12 | 245 | RFTISRDNAKNTLYLQMNSLRPEDTAVYYCAA | 345 | WGQGTLVTVSS |
| AS11948SVH12M8 | 246 | RFTISRDNAKNTLYLQMNSLRPEDTAVYYCAA | 346 | WGQGTLVTVSS |
| AS11948SVH12M9 | 247 | RFTISRDNAKNTLYLQMNSLRPEDTAVYYCAA | 347 | WGQGTLVTVSS |
| AS06617VH11 | 248 | RFTISRDNSKNTLYLQMNSLRAEDTAVYYCAA | 348 | WGQGTLVTVSS |
| AS06775VH11 | 249 | RFTISRDNAKNTLYLQMNSLRPEDTAVYYCAA | 349 | WGQGTLVTVSS |
| AS06775VH4 | 250 | RFTISRDNSKNTLYLQMNSLRAEDTAVYYCAA | 350 | WGQGTLVTVSS |

ID: SEQ ID NO; R: Framework region

TABLE 18 sdAbs

| sdAb | ID | Sequence |
|---|---|---|
| AS06617 | 351 | DVQLVESGGGLVQAGDSLRLSCAASGRTFISYAVGWFRQAPGSEREFVAGIR WNGIHTDYADSVKGRFTISRDNAKNTVTLEMTSLKPEDTAVYYCAAHRTIAT IPEKYEYEYWGQGTQVTVSS |
| AS06618 | 352 | EVQLVESGGRLVRAGDSLRLSCAASGRTFLSYAVGWFRQAPGTEREFVAGIR WSGGYTDYAEAVKGRFTISRDNAKNTVYLQMNSLKPEDTAVYYCAAHRTIAT IPEKYEYEYWGQGTQVTVSS |
| AS06624 | 353 | QVQLVESGGGLVQAGGSLRLACSASGRTFLTYALGWFRQAPGKEREFVAGVS WSGSGTKYADSVKGRFTISRDNAKNTVYMQMNSLKPEDTAVYYCAAQISAIV PISAHEYEYWGQGTQVTVSS |
| AS06628 | 354 | QVQLVESGGGLVQAGGSLRLSCAASGRTFITYAIGWFRQAPGKEREFVTAIN WSGSMTSYADSVKGRFTISRDNNKNMVYLQMNSLKPEDTAVYYCAAHRGAIA PMTQSVYDYWGQGTQVTVSS |
| AS06639 | 355 | AVQLVESGGGLVQAGGSLRLSCAASGRTFITYAIGWFRQAPGKEREFVSAIN WSGSMTSYADSVKGRFTISRDNAKNTVYLQMNGLKPEDTAVYYCAAHRGAIA PMTQSVYDTWGQGTQVTVSS |
| AS06682 | 356 | AVQLVESGGGLVQAGGSLRLSCTASGRTFLSYAVGWFRQAPGTEREFVAGIR WSGEHTDYAASVKGRFTISRDNAKNTVYLQMNSLKPEDTAVYYCAAHTTIAT IPKKYEYEYWGQGTQVTVSS |
| AS06686 | 357 | AVQLVESGGGLVQAGDSLRLACAASGRTFLTYALGWFRQAPGKEREFVAGVS WSGSSTKYADSVKGRFTISRDNAKNTVYMQMNSLKPEDTAVYYCAAQISAIV PISAHEYQYWGQGTQVTVSS |
| AS06703 | 358 | EVQLVESGGGLVRAGGSLRLSCAASGRTFITYAIGWFRQAPGKEREFVTAIN WSGSMTSYADSVKGRFTISRDNNKNTVYLQMNSLKPEDTALYYCAAHLGAIA PMSQSVYDYWGQGTQVTVSS |
| AS06709 | 359 | EVQLVESGGGLVQAGDSLRLSCTASGRTFLSYAVGWFRQAPGTEREFVAGIR WSGGSTDYSDSVKGRFTISRDNAKNTVYLQMNSLKPEDTAVYYCAAHRTIAT IPEKYEYEYWGQGTQVTVSS |
| AS06730 | 360 | QVQLVESGGGLVQAGGSLRLSCAASGRTFITYAIGWFRQAPGKEREFVSAIN WSGSMTSYADSVKGRFTISRDNAKNTVYLQMNGLKPEDTAVYYCAAHRGAIA PIAQSVYTNWGQGTQVTVSS |
| AS06750 | 361 | AVQLVESGGGLVQAGDSLRLSCTASGRTFLTYAVGWFRQAPGTEREFVAGIR WSGGYTDYADSVKGRFTISRDNAKNTVYLQMNSLKPEDTAVYYCAAHRTIAT IPEKYEYEYWGQGTQVTVSS |
| AS06752 | 362 | EVQLVESGGGLVQAGDSLRLSCAASGRTFLTYAVGWFRQAPGTEREFVAGIR WSGESTDYAESVKGRFTISRDDTKNTVYLQMNSLKPEDTAVYYCAAHRTIAT IPEKYYYEYWGQGTQVTVSS |

TABLE 18-continued sdAbs

| sdAb | ID | Sequence |
|---|---|---|
| AS06763 | 363 | QVQLVESGGGLVQAGGSLRLSCAVSGRPVSSAVMGWFRQAPGKEREFVGRLT SSATSTFYAESVKGRFTISRDNAKNTVYLQMNNLKPEDTAVYYCAADVPGTK IWSIQTPDRYNYWGQGTQVTVSS |
| AS06766 | 364 | EVQLVESGGGLVQAGGSLSLSCAVSGRTLTGLLIGWFRQAPGKERELVAIIS WTYGSTNYADSVKGRFTISRDNAKNTVLLQMNSLKPEDTAVYYCSARDVAVA KYDSWGQGTQVTVSS |
| AS06775 | 365 | QVQLVESGGGLVQAGDSLRLSCAASGRTFLTLAVGWFRQAPGTEREFVAGIR WSGSGTDYADSVKGRFTISRDNAKNTVYLQMNSLKPEDTAVYYCAAHTTIAT IPEKYEYEYWGRGTQVTVSS |
| AS06778 | 366 | QVQLVESGGGLVQAGGSLKLSCAASGRTFITYAMGWFRQAPGKERELVAAIS WSGSSTYSADSVKGRFTISRDNAKNTVYLQMNSLKPEDTAVYYCAAEVSART GEHLPKLMGDYWGQGTQVTVSS |
| AS06786 | 367 | QVQLVESGGGLVQAGDSLRLSCAASGRTFLTLAVGWFRQAPGTEREFVAGIR WSGSGTDYADSVKGRFTISRDNAANTVYLQMNSLKPEDTAVYYCAAHTTIAT IPEKYEYEYWGQGTQVTVSS |
| AS06791 | 368 | QVQLVESGGGLVQAGGSLRLSCAASGRTFITYAIGWFRQAPGKEREFVTAIN WSGSMTSYADSVKGRFTISRDNAKNTVYLQINGLKSEDTAVYYCAAHRGAIA PMTQSVYDYWGQGTQVTVSS |
| AS06808 | 369 | QVKLEESGGGLVQAGGSLRLSCVASGRTFSRYAMGWFRQAPGKEREFVSTST GSGGLTSYANSVKGRFTISRDNAKNTVYLQMNNLKPEDTAIYYCAANRYNSD SRYMSSYDWWGQGTQVTVSS |
| AS06810 | 370 | AVQLVESGGGLVQAGDSLRLSCAASGRTFLSYAVGWFRQAPGTEREFVAGIR WSGLHTDYADSVKGRFTISRDNAKNTVYLQMNSLKPEDTAIYYCAAHRTIAT IPEKYEYEYWGQGTQVTVSS |
| AS11947 | 371 | DVQLVESGGGLVQAGDSLRLTCSASGRTFISYAVGWFRQAPGTEREFVAGIR WNGISTDYTDSVKGRFTISRDNAKNTVYLQMNSLKPEDTAIYYCAAHRTIAT IPNKYEYDHWGQGTQVTVSS |
| AS11948 | 372 | EVQLVESGGGLVQAGDSLRLSCVASGRTFVTYGMGWFRQAPGKEREFVAAIN WSGSMTSYGDSVKGRFAISRDNAKNTVYLQMNSLKPEDTAVYYCAAALGAVV YTTREPYTYWGRGTQVTVSS |
| AS12003 | 373 | EVQLVESGGGLVQAGDSLRLSCAASGRTFLSYAVGWFRQAPGTEREFVAGIR WSGGSTDYADSVKGRFTISRDNAKNTVYLQMNSLKPEDTAVYYCAAHRTIAT VPNKYEYDTWGQGTQVTVSS |
| AL22863 | 374 | QVKLEESGGGLVQVGDSLRLSCAASVSSFSINDMGWYRQAPGKQRELVATIA SGGSTNYADSVKGRFTISRDNVKNTVYLQMNGLKPEDTAVYYCNADFRDWTR RRYSYWGQGTQVTVSS |
| AL23474 | 375 | QVKLEESGGGLVQVGDSLRLSCAASGRTFSNYTMAWFRQFPGKEREFVAVVS RGGGATDYADSVKGRFTISRDNAKNTMYLQMNSLKTEDTAVYYCAAGTDLSY YYSTKKWAYWGQGTQVTVSS |
| AS06730S | 376 | QVQLVESGGGLVQAGGSLRLSCAASGRTFITYAIGWFRQAPGKEREFVSAIS WSGSMTSYADSVKGRFTISRDNAKNTVYLQMNGLKPEDTAVYYCAAHRGAIA PIAQSVYTNWGQGTQVTVSS |
| AS06730Q | 377 | QVQLVESGGGLVQAGGSLRLSCAASGRTFITYAIGWFRQAPGKEREFVSAIQ WSGSMTSYADSVKGRFTISRDNAKNTVYLQMNGLKPEDTAVYYCAAHRGAIA PIAQSVYTNWGQGTQVTVSS |
| AS06730QVH1 | 378 | EVQLVESGGGLVQPGGSLRLSCAASGRTFITYAIGWVRQAPGKGLEWVSAIQ WSGSMTSYADSVKGRFTISRDNSKNTLYLQMNSLRAEDTAVYYCAKHRGAIA PIAQSVYTNWGQGTLVTVSS |
| AS06730QVH2 | 379 | EVQLVESGGGLVQPGGSLRLSCAASGRTFITYAIGWFRQAPGKGLEWVSAIQ WSGSMTSYADSVKGRFTISRDNSKNTVYLQMNSLRAEDTAVYYCAAHRGAIA PIAQSVYTNWGQGTLVTVSS |
| AS06730QVH3a | 380 | EVQLVESGGGLVQPGGSLRLSCAASGRTFITYAIGWFRQAPGKGLEFVSAIQ WSGSMTSYADSVKGRFTISRDNSKNTVYLQMNSLRAEDTAVYYCAAHRGAIA PIAQSVYTNWGQGTLVTVSS |
| AS06730SVH12 | 381 | EVQLVESGGGLVQPGGSLRLSCAASGRTFITYAIGWFRQAPGKGREFVSAIS WSGSMTSYADSVKGRFTISRDNAKNTLYLQMNSLRPEDTAVYYCAAHRGAIA PIAQSVYTNWGQGTLVTVSS |

TABLE 18-continued sdAbs

| sdAb | ID | Sequence |
|---|---|---|
| AS06730SVH12M8 | 382 | EVQLVESGGGLVQPGGSLRLSCAASGRTFITYAIGWFRQAPGKGREFVSAIS<br>WSGSITSYADSVKGRFTISRDNAKNTLYLQMNSLRPEDTAVYYCAAHRGAIA<br>PIAQSVYTNWGQGTLVTVSS |
| AS06730SVH12M9 | 383 | EVQLVESGGGLVQPGGSLRLSCAASGRTFITYAIGWFRQAPGKGREFVSAIS<br>WSGSLTSYADSVKGRFTISRDNAKNTLYLQMNSLRPEDTAVYYCAAHRGAIA<br>PIAQSVYTNWGQGTLVTVSS |
| AS06750VH1 | 384 | EVQLVESGGGLVQPGGSLRLSCAASGRTFLTYAVGWVRQAPGKGLEWVSGIR<br>WSGGYTDYADSVKGRFTISRDNSKNTLYLQMNSLRAEDTAVYYCAKHRTIAT<br>IPEKYEYEYWGQGTLVTVSS |
| AS06750VH2 | 385 | EVQLVESGGGLVQPGGSLRLSCAASGRTFLTYAVGWFRQAPGKGLEWVAGIR<br>WSGGYTDYADSVKGRFTISRDNSKNTVYLQMNSLRAEDTAVYYCAAHRTIAT<br>IPEKYEYEYWGQGTLVTVSS |
| AS06750VH3 | 386 | EVQLVESGGGLVQPGGSLRLSCAASGRTFLTYAVGWFRQAPGKGLEFVAGIR<br>WSGGYTDYADSVKGRFTISRDNSKNTVYLQMNSLRAEDTAVYYCAAHRTIAT<br>IPEKYEYEYWGQGTLVTVSS |
| AS06750VHa | 387 | EVQLVESGGGLVQPGGSLRLCTASGRTFLTYAVGWFRQAPGKGLEFVAGIR<br>WSGGYTDYADSVKGRFTISRDNSKNTVYLQMNSLRAEDTAVYYCAAHRTIAT<br>IPEKYEYEYWGQGTLVTVSS |
| AS06750VH11 | 388 | EVQLVESGGGLVQPGGSLRLSCAASGRTFLTYAVGWFRQAPGKGREFVSGIR<br>WSGGYTDYADSVKGRFTISRDNAKNTLYLQMNSLRPEDTAVYYCAAHRTIAT<br>IPEKYEYEYWGQGTLVTVSS |
| AS11948A | 389 | EVQLVESGGGLVQAGDSLRLSCVASGRTFVTYGMGWFRQAPGKEREFVAAIA<br>WSGSMTSYGDSVKGRFAISRDNAKNTVYLQMNSLKPEDTAVYYCAAALGAVV<br>YTTREPYTYWGRGTQVTVSS |
| AS11948S | 390 | EVQLVESGGGLVQAGDSLRLSCVASGRTFVTYGMGWFRQAPGKEREFVAAIS<br>WSGSMTSYGDSVKGRFAISRDNAKNTVYLQMNSLKPEDTAVYYCAAALGAVV<br>YTTREPYTYWGRGTQVTVSS |
| AS11948Q | 391 | EVQLVESGGGLVQAGDSLRLSCVASGRTFVTYGMGWFRQAPGKEREFVAAIQ<br>WSGSMTSYGDSVKGRFAISRDNAKNTVYLQMNSLKPEDTAVYYCAAALGAVV<br>YTTREPYTYWGRGTQVTVSS |
| AS11948QVH1 | 392 | EVQLVESGGGLVQPGGSLRLSCAASGRTFVTYGMGWVRQAPGKGLEWVSAIQ<br>WSGSMTSYGDSVKGRFTISRDNSKNTLYLQMNSLRAEDTAVYYCAKALGAVV<br>YTTREPYTYWGQGTLVTVSS |
| AS11948QVH2 | 393 | EVQLVESGGGLVQPGGSLRLSCAASGRTFVTYGMGWFRQAPGKGLEFVAAIQ<br>WSGSMTSYGDSVKGRFTISRDNSKNTVYLQMNSLRAEDTAVYYCAAALGAVV<br>YTTREPYTYWGQGTLVTVSS |
| AS11948QVHa | 394 | EVQLVESGGGLVQPGGSLRLSCVASGRTFVTYGMGWFRQAPGKGREFVSAIQ<br>WSGSMTSYGDSVKGRFTISRDNSKNTVYLQMNSLRAEDTAVYYCAAALGAVV<br>YTTREPYTYWGQGTLVTVSS |
| AS11948SVH12 | 395 | EVQLVESGGGLVQPGGSLRLSCAASGRTFVTYGMGWFRQAPGKGREFVSAIS<br>WSGSMTSYGDSVKGRFTISRDNAKNTLYLQMNSLRPEDTAVYYCAAALGAVV<br>YTTREPYTYWGQGTLVTVSS |
| AS11948SVH12M8 | 396 | EVQLVESGGGLVQPGGSLRLSCAASGRTFVTYGMGWFRQAPGKGREFVSAIS<br>WSGSITSYGDSVKGRFTISRDNAKNTLYLQMNSLRPEDTAVYYCAAALGAVV<br>YTTREPYTYWGQGTLVTVSS |
| AS11948SVH12M9 | 397 | EVQLVESGGGLVQPGGSLRLSCAASGRTFVTYGMGWFRQAPGKGREFVSAIS<br>WSGSLTSYGDSVKGRFTISRDNAKNTLYLQMNSLRPEDTAVYYCAAALGAVV<br>YTTREPYTYWGQGTLVTVSS |
| AS06617VH11 | 398 | EVQLVESGGGLVQPGGSLRLSCAASGRTFISYAVGWFRQAPGKGREFVSGIRWS<br>GIHTDYADSVKGRFTISRDNAKNTLYLQMNSLRPEDTAVYYCAAHRTIATIPEK<br>YEYEYWGQGTLVTVSS |
| AS06775VH11 | 399 | EVQLVESGGGLVQPGGSLRLSCAASGRTFLTLAVGWFRQAPGKGREFVSGIRWS<br>GSGTDYADSVKGRFTISRDNAKNTLYLQMNSLRPEDTAVYYCAAHTTIATIPEK<br>YEYEYWGQGTLVTVSS |

TABLE 18-continued

| sdAbs | | |
|---|---|---|
| sdAb | ID | Sequence |
| AS06775VH4 | 400 | EVQLVESGGGLVQPGGSLRLSCAASGRTFLTYAVGWFRQAPGKGLEFVSGIR<br>WSGGYTDYADSVKGRFTISRDNSKNTLYLQMNSLRAEDTAVYYCAAHRTIAT<br>IPEKYEYEYWGQGTLVTVSS |

ID: SEQ ID NO

TABLE 19

| HCAbs | | |
|---|---|---|
| HCAb | SEQ ID | Sequence |
| AS06617 | 401 | DVQLVESGGGLVQAGDSLRLSCAASGRTFISYAVGWFRQAPGSEREFVAGIRWN<br>GIHTDYADSVKGRFTISRDNAKNTVTLEMTSLKPEDTAVYYCAAHRTIATIPEK<br>YEYEYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06617VH11 | 402 | EVQLVESGGGLVQPGGSLRLSCAASGRTFISYAVGWFRQAPGKGREFVSGIRWS<br>GIHTDYADSVKGRFTISRDNAKNTLYLQMNSLRPEDTAVYYCAAHRTIATIPEK<br>YEYEYWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06618 | 403 | EVQLVESGGRLVRAGDSLRLSCAASGRTFLSYAVGWFRQAPGTEREFVAGIRWS<br>GGYTDYAEAVKGRFTISRDNAKNTVYLQMNSLKPEDTAVYYCAAHRTIATIPEK<br>YEYEYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06628 | 404 | QVQLVESGGGLVQAGGSLRLSCAASGRTFITYAIGWFRQAPGKEREFVTAINWS<br>GSMTSYADSVKGRFTISRDNNKNMVYLQMNSLKPEDTAVYYCAAHRGAIAPMTQ<br>SVYDYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06682 | 405 | AVQLVESGGGLVQAGDSLRLSCTASGRTFLSYAVGWFRQAPGTEREFVAGIRWS<br>GEHTDYAASVKGRFT1SRDNAKNTVYLQMNSLKPEDTAVYYCAAHTTIATIPKK<br>YEYEYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06686 | 406 | AVQLVESGGGLVQAGDSLRLACAASGRTFLTYALGWFRQAPGKEREFVAGVSWS<br>GSSTKYADSVKGRFTISRDNAKNTVMQMNSLKPEDTAVYYCAAQISAIVPISA<br>HEYQYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06703 | 407 | EVQLVESGGGLVRAGGSLRLSCAASGRTFITYAIGWFRQAPGKEREFVTAINWS<br>GSMTSYADSVKGRFTISRDNNKNTVYLQMNSLKPEDTALYYCAAHLGAIAPMSQ<br>SVYDYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730 | 408 | QVQLVESGGGLVQAGGSLRLSCAASGRTFITYAIGWFRQAPGKEREFVSAINWS<br>GSMTSYADSVKGRFTISRDNAKNTVYLQMNGLKPEDTAVYYCAAHRGAIAPIAQ<br>SVYTNWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN |

TABLE 19-continued

| HCAbs | | |
|---|---|---|
| HCAb | SEQ ID | Sequence |
| | | QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06750 | 409 | AVQLVESGGGLVQAGDSLRLSCTASGRTFLTYAVGWFRQAPGTEREFVAGIRWS<br>GGYTDYADSVKGRFTISRDNAKNTVYLQMNSLKPEDTAVYYCAAHRTIATIPEK<br>YEYEYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06775 | 410 | QVQLVESGGGLVQAGDSLRLSCAASGRTFLTLAVGWFRQAPGTEREFVAGIRWS<br>GSGTDYADSVKGRFTISRDNAKNTVYLQMNSLKPEDTAVYYCAAHTTIATIPEK<br>YEYEYWGRGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06775VH4 | 411 | EVQLVESGGGLVQPGGSLRLSCAASGRTFLTLAVGWFRQAPGKGREFVSGIRWS<br>GSGTDYADSVKGRFTISRDNAKNTLYLQMNSLRPEDTAVYYCAAHTTIATIPEK<br>YEYEYWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06775VH11 | 412 | EVQLVESGGGLVQPGGSLRLSCAASGRTFLTYAVGWFRQAPGKGLEFVSGIRWS<br>GGYTDYADSVKGRFTISRDNSKNTLYLQMNSLRAEDTAVYYCAAHTTIATIPEK<br>YEYEYWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06778 | 413 | QVQLVESGGGLVQAGGSLKLSCAASGRTFITYAMGWFRQAPGKERELVAAISWS<br>GSSTYSADSVKGRFTISRDNAKNTVYLQMNSLKPEDTAVYYCAAEVSARTGEHL<br>PKLMGDYWGQGTQVTVSSEPKSCDKTHTCPPCPAPELLGGPSVFLFPPKPKDTL<br>MISRTPEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLTVD<br>KSRWQQGNVFSCSVMHEALHNHYTQKSLSLSPGK |
| AS06791 | 414 | QVQLVESGGGLVQAGGSLRLSCAASGRTFITYAIGWFRQAPGKEREFVTAINWS<br>GSMTSYADSVKGRFTISRDNAKNTVYLQINGLKSEDTAVYYCAAHRGAIAPMTQ<br>SVYDYWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS11947 | 415 | DVQLVESGGGLVQAGDSLRLTCSASGRTFISYAVGWFRQAPGTEREFVAGIRWN<br>GISTDYTDSVKGRFTISRDNAKNTVYLQMNSLKPEDTAIYYCAAHRTIATIPNK<br>YEYDHWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS11948 | 416 | EVQLVESGGGLVQAGDSLRLSCVASGRTFVTYGMGWFRQAPGKEREFVAAINWS<br>GSMTSYGDSVKGRFAISRDNAKNTVYLQMNSLKPEDTAVYYCAAALGAVVYTTR<br>EPYTYWGRGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS12003 | 417 | EVQLVESGGGLVQAGDSLRLSCAASGRTFLSYAVGWFRQAPGTEREFVAGIRWS<br>GGSTDYADSVKGRFTISRDNAKNTVYLQMNSLKPEDTAVYYCAAHRTIATVPNK<br>YEYDTWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |

TABLE 19-continued

| HCAbs | | |
|---|---|---|
| HCAb | SEQ ID | Sequence |
| AS06730A | 418 | QVQLVESGGGLVQAGGSLRLSCAASGRTFITYAIGWFRQAPGKEREFVSAIAWS<br>GSMTSYADSVKGRFTISRDNAKNTVYLQMNGLKPEDTAVYYCAAHRGAIAPIAQ<br>SVYTNWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730S | 419 | QVQLVESGGGLVQAGGSLRLSCAASGRTFITYAIGWFRQAPGKEREFVSAISWS<br>GSMTSYADSVKGRFTISRDNAKNTVYLQMNGLKPEDTAVYYCAAHRGAIAPIAQ<br>SVYTNWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730Q | 420 | QVQLVESGGGLVQAGGSLRLSCAASGRTFITYAIGWFRQAPGKEREFVSAIQWS<br>GSMTSYADSVKGRFTISRDNAKNTVYLQMNGLKPEDTAVYYCAAHRGAIAPIAQ<br>SVYTNWGQGTQVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730QVH1 | 421 | EVQLVESGGGLVQPGGSLRLSCAASGRTFITYAIGWVRQAPGKGLEWVSAIQWS<br>GSMTSYADSVKGRFTISRDNSKNTLYLQMNSLRAEDTAVYYCAKHRGAIAPIAQ<br>SVYTNWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730QVH2 | 422 | EVQLVESGGGLVQPGGSLRLSCAASGRTFITYAIGWVRQAPGKGLEWVSAIQWS<br>GSMTSYADSVKGRFTISRDNSKNTVYLQMNSLRAEDTAVYYCAKHRGAIAPIAQ<br>SVYTNWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730QVH3a | 423 | EVQLVESGGGLVQPGGSLRLSCAASGRTFITYAIGWVRQAPGKGLEFVSAIQWS<br>GSMTSYADSVKGRFTISRDNSKNTVYLQMNSLRAEDTAVYYCAKHRGAIAPIAQ<br>SVYTNWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730SVH12 | 424 | EVQLVESGGGLVQPGGSLRLSCAASGRTFITYAIGWVRQAPGKGREFVSAISWS<br>GSMTSYADSVKGRFTISRDNAKNTLYLQMNSLRPEDTAVYYCAAHRGAIAPIAQ<br>SVYTNWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730SVH12M8 | 425 | EVQLVESGGGLVQPGGSLRLSCAASGRTFITYAIGWVRQAPGKGREFVSAISWS<br>GSITSYADSVKGRFTISRDNAKNTLYLQMNSLRPEDTAVYYCAAHRGAIAPIAQ<br>SVYTNWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06730SVH12M9 | 426 | EVQLVESGGGLVQPGGSLRLSCAASGRTFITYAIGWVRQAPGKGREFVSAISWS<br>GSLTSYADSVKGRFTISRDNAKNTLYLQMNSLRPEDTAVYYCAAHRGAIAPIAQ<br>SVYTNWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS06750VH1 | 427 | EVQLVESGGGLVQPGGSLRLSCAASGRTFLTYAVGWVRQAPGKGLEWVSGIRWS<br>GGYTDYADSVKGRFTISRDNSKNTLYLQMNSLRAEDTAVYYCAKHRTIATIPEK<br>YEYEYWGQGTLVTVSSEPKSCDKTHTCPPCPAPELLGGPSVFLFPPKPKDTLMI |

TABLE 19-continued

HCAbs

| HCAb | SEQ ID | Sequence |
|---|---|---|
| | | SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS06750VH2 | 428 | EVQLVESGGGLVQPGGSLRLSCAASGRTFLTYAVGWFRQAPGKGLEWVAGIRWS GGYTDYADSVKGRFTISRDNSKNTVYLQMNSLRAEDTAVYYCAAHRTIATIPEK YEYEYWGQGTLVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS06750VH3 | 429 | EVQLVESGGGLVQPGGSLRLSCAASGRTFLTYAVGWFRQAPGKGLEFVAGIRWS GGYTDYADSVKGRFTISRDNSKNTVYLQMNSLRAEDTAVYYCAAHRTIATIPEK YEYEYWGQGTLVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS06750VHa | 430 | EVQLVESGGGLVQPGGSLRLSCTASGRTFLTYAVGWFRQAPGKGLEFVAGIRWS GGYTDYADSVKGRFTISRDNSKNTVYLQMNSLRAEDTAVYYCAAHRTIATIPEK YEYEYWGQGTLVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS06750VH11 | 431 | EVQLVESGGGLVQPGGSLRLSCAASGRTFLTYAVGWFRQAPGKGREFVSGIRWS GGYTDYADSVKGRFTISRDNAKNTLYLQMNSLRPEDTAVYYCAAHRTIATIPEK YEYEYWGQGTLVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS11948A | 432 | EVQLVESGGGLVQAGDSLRLSCVASGRTFVTYGMGWFRQAPGKEREFVAAIAWS GSMTSYGDSVKGRFAISRDNAKNTVYLQMNSLKPEDTAVYYCAAALGAVVYTTR EPYTYWGRGTQVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS11948S | 433 | EVQLVESGGGLVQAGDSLRLSCVASGRTFVTYGMGWFRQAPGKEREFVAAISWS GSMTSYGDSVKGRFAISRDNAKNTVYLQMNSLKPEDTAVYYCAAALGAVVYTTR EPYTYWGRGTQVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS11948Q | 434 | EVQLVESGGGLVQAGDSLRLSCVASGRTFVTYGMGWFRQAPGKEREFVAAIQWS GSMTSYGDSVKGRFAISRDNAKNTVYLQMNSLKPEDTAVYYCAAALGAVVYTTR EPYTYWGRGTQVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS11948QVH1 | 435 | EVQLVESGGGLVQPGGSLRLSCAASGRTFVTYGMGWVRQAPGKGLEWVSAIQWS GSMTSYGDSVKGRFTISRDNSKNTLYLQMNSLRAEDTAVYYCAKALGAVVYTTR EPYTYWGQGTLVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |
| AS11948QVH2 | 436 | EVQLVESGGGLVQPGGSLRLSCAASGRTFVTYGMGWFRQAPGKGLEFVAAIQWS GSMTSYGDSVKGRFTISRDNSKNTVYLQMNSLRAEDTAVYYCAAALGAVVYTTR EPYTYWGQGTLVTVSSEPKSCDKTHTCPPCPAPELLGGPSVFLFPPKPKDTLMI SRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKS RWQQGNVFSCSVMHEALHNHYTQKSLSLSPGK |

TABLE 19-continued

| HCAbs | | |
|---|---|---|
| HCAb | SEQ ID | Sequence |
| AS11948QVHa | 437 | EVQLVESGGGLVQPGGSLRLSCVASGRTFVTYGMGWFRQAPGKGREFVSAIQWS<br>GSMTSYGDSVKGRFTISRDNSKNTVYLQMNSLRAEDTAVYYCAAALGAVVYTTR<br>EPYTYWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS11948SVH12 | 438 | EVQLVESGGGLVQPGGSLRLSCAASGRTFVTYGMGWFRQAPGKGREFVSAISWS<br>GSMTSYGDSVKGRFTISRDNAKNTLYLQMNSLRPEDTAVYYCAAALGAVVYTTR<br>EPYTYWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS11948SVH12M8 | 439 | EVQLVESGGGLVQPGGSLRLSCAASGRTFVTYGMGWFRQAPGKGREFVSAISWS<br>GSITSYGDSVKGRFTISRDNAKNTLYLQMNSLRPEDTAVYYCAAALGAVVYTTR<br>EPYTYWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |
| AS11948SVH12M9 | 440 | EVQLVESGGGLVQPGGSLRLSCAASGRTFVTYGMGWFRQAPGKGREFVSAISWS<br>GSLTSYGDSVKGRFTISRDNAKNTLYLQMNSLRPEDTAVYYCAAALGAVVYTTR<br>EPYTYWGQGTLVTVSSEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK |

What is claimed is:

1. An isolated anti-PD-L1 construct comprising a single-domain antibody (sdAb) moiety specifically recognizing PD-L1, wherein the sdAb moiety comprises
  (1) a CDR1 comprising the amino acid sequence of GRTFVTYGMG (SEQ ID NO: 95); a CDR2 comprising the amino acid sequence of AISWSGSMTSYGDSVKG (SEQ ID NO: 195); and a CDR3 comprising the amino acid sequence of ALGAVVYTTREPYTY (SEQ ID NO: 295);
  (2) a CDR1 comprising the amino acid sequence of GRTFVTYGMG (SEQ ID NO: 96); a CDR2 comprising the amino acid sequence of AISWSGSITSYGDSVKG (SEQ ID NO: 196); and a CDR3 comprising the amino acid sequence of ALGAVVYTTREPYTY (SEQ ID NO: 296);
  (3) a CDR1 comprising the amino acid sequence of GRTFVTYGMG (SEQ ID NO: 97); a CDR2 comprising the amino acid sequence of AISWSGSLTSYGDSVKG (SEQ ID NO: 197); and a CDR3 comprising the amino acid sequence of ALGAVVYTTREPYTY (SEQ ID NO: 297);
  (4) a CDR1 comprising the amino acid sequence of GRTFVTYGMG (SEQ ID NO: 72); a CDR2 comprising the amino acid sequence of AINWSGSMTSYGDSVKG (SEQ ID NO: 172); and a CDR3 comprising the amino acid sequence of ALGAVVYTTREPYTY (SEQ ID NO: 272);
  (5) a CDR1 comprising the amino acid sequence of GRTFVTYGMG (SEQ ID NO: 89); a CDR2 comprising the amino acid sequence of AIAWSGSMTSYGDSVKG (SEQ ID NO: 189); and a CDR3 comprising the amino acid sequence of ALGAVVYTTREPYTY (SEQ ID NO: 289); or
  (6) a CDR1 comprising the amino acid sequence of GRTFVTYGMG (SEQ ID NO: 91); a CDR2 comprising the amino acid sequence of AIQWSGSMTSYGDSVKG (SEQ ID NO: 191); and a CDR3 comprising the amino acid sequence of ALGAVVYTTREPYTY (SEQ ID NO: 291).

2. The isolated anti-PD-L1 construct of claim 1, wherein the sdAb moiety comprises any one of the following:
(1) a $V_HH$ domain comprising the amino acid sequence of SEQ ID NO: 390 or 395, or a variant thereof comprising a CDR1 comprising the amino acid sequence of GRTFVTYGMG (SEQ ID NO: 95); a CDR2 comprising the amino acid sequence of AISWSGSMTSYGDSVKG (SEQ ID NO: 195); and a CDR3 comprising the amino acid sequence of ALGAVVYTTREPYTY (SEQ ID NO: 295) and having at least about 90% or at least about 95% sequence identity to SEQ ID NO: 390 or 395;
(2) a $V_HH$ domain comprising the amino acid sequence of SEQ ID NO: 396, or a variant thereof comprising a CDR1 comprising the amino acid sequence of GRTFVTYGMG (SEQ ID NO: 96); a CDR2 comprising the amino acid sequence of AISWSGSITSYGDSVKG (SEQ ID NO: 196); and a CDR3 comprising the amino acid sequence of ALGAVVYTTREPYTY (SEQ ID NO: 296) and having at least about 90% or at least about 95% sequence identity to SEQ ID NO: 396;
(3) a $V_HH$ domain comprising the amino acid sequence of SEQ ID NO: 397, or a variant thereof comprising a CDR1 comprising the amino acid sequence of GRTFVTYGMG (SEQ ID NO: 97); a CDR2 comprising the amino acid sequence of AISWSGSLTSYGDSVKG (SEQ ID NO: 197); and a CDR3 comprising the amino acid sequence of ALGAVVYTTREPYTY (SEQ ID NO: 297) and having at least about 90% or at least about 95% sequence identity to SEQ ID NO: 397;
(4) a $V_HH$ domain comprising the amino acid sequence of SEQ ID NO: 372, or a variant thereof comprising a CDR1 comprising the amino acid sequence of GRTFVTYGMG (SEQ ID NO: 72); a CDR2 comprising the amino acid sequence of AINWSGSMTSYGDSVKG (SEQ ID NO: 172); and a CDR3 comprising the amino acid sequence of ALGAVVYTTREPYTY (SEQ ID NO: 272) and having at least about 90% or at least about 95% sequence identity to SEQ ID NO: 372;
(5) a $V_HH$ domain comprising the amino acid sequence of SEQ ID NO: 389, or a variant thereof comprising a CDR1 comprising the amino acid sequence of GRTFVTYGMG (SEQ ID NO: 89); a CDR2 comprising the amino acid sequence of AIAWSGSMTSYGDSVKG (SEQ ID NO: 189); and a CDR3 comprising the amino acid sequence of ALGAVVYTTREPYTY (SEQ ID NO: 289) and having at least about 90% or at least about 95% sequence identity to SEQ ID NO: 389; or
(6) a $V_HH$ domain comprising the amino acid sequence of any one of SEQ ID NOs: 391-394, or a variant thereof comprising a CDR1 comprising the amino acid sequence of GRTFVTYGMG (SEQ ID NO: 91); a CDR2 comprising the amino acid sequence of AIQWSGSMTSYGDSVKG (SEQ ID NO: 191); and a CDR3 comprising the amino acid sequence of ALGAVVYTTREPYTY (SEQ ID NO: 291) and having at least about 90% or at least about 95% sequence identity to any one of SEQ ID NOs: 391-394.

3. The isolated anti-PD-L1 construct of claim 1, wherein the $K_d$ of the binding between the sdAb moiety and PD-L1 is about $10^{-7}$ M to about $10^{-12}$ M.

4. The isolated anti-PD-L1 construct of claim 1, wherein the sdAb moiety specifically recognizing PD-L1 is camelid, chimeric, partially humanized, or fully humanized.

5. The isolated anti-PD-L1 construct of claim 4, wherein the sdAb moiety that specifically recognizes PD-L1 is fused to a human IgG1 Fc.

6. The isolated anti-PD-L1 construct of claim 1, wherein the isolated anti-PD-L1 construct is a heavy chain-only antibody (HCAb).

7. The isolated anti-PD-L1 construct of claim 6, wherein the sdAb moiety specifically recognizing PD-L1 comprises the amino acid sequence of any one of SEQ ID NOs: 372, 389, 390, 391, 392, 393, 394, 395, 396, or 397.

8. The isolated anti-PD-L1 construct of claim 6, wherein the HCAb comprises the amino acid sequence of any one of SEQ ID NOs: 416, 432, 433, 434, 435, 436, 437, 438, 439, or 440.

9. The isolated anti-PD-L1 construct of claim 1, wherein the isolated anti-PD-L1 construct is fused to a second antibody moiety specifically recognizing a second antigen, wherein the second antibody moiety is a full-length antibody, a Fab, a Fab', a (Fab')$_2$, an Fv, a single chain Fv (scFv), an scFv-scFv, a minibody, a diabody, a sdAb, or an antibody mimetic.

10. The isolated anti-PD-L1 construct of claim 9, wherein the second antigen is PD-L1, human serum albumin, or CTLA-4.

11. The isolated anti-PD-L1 construct of claim 10, wherein the isolated anti-PD-L1 construct comprises three or more sdAbs that specifically recognize PD-L1.

12. The isolated anti-PD-L1 construct of claim 10, wherein the second antigen is PD-L1, and wherein the second antibody moiety comprises an amino acid sequence of any one of SEQ ID NOs: 351, 352, 353, 354, 355, 356, 357, 358, 359, 360, 361, 362, 363, 364, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400.

13. The isolated anti-PD-L1 construct of claim 9, wherein the sdAb moiety specifically recognizing PD-L1 is amino (N)-terminal and/or carboxy (C)-terminal to the second antibody moiety.

14. The isolated anti-PD-L1 construct of claim 9, wherein the second antibody moiety is a full-length antibody, and wherein the amino (N)-terminus of the sdAb moiety specifically recognizing PD-L1 is fused to the carboxy (C)-terminus of a heavy chain of the full-length antibody or the carboxy (C)-terminus of the sdAb moiety specifically recognizing PD-L1 is fused to the amino (N)-terminus of a heavy chain of the full-length antibody.

15. The isolated anti-PD-L1 construct of claim 9, wherein the second antibody moiety is a full-length antibody, and wherein the full-length antibody specifically recognizes a polypeptide selected from the group consisting of TIGIT, TIM-3, and LAG-3.

16. The isolated anti-PD-L1 construct of claim 9, wherein the PD-L1 specifically recognized by the sdAb moiety comprises the amino acid sequence of SEQ ID NO: 441-442.

17. The isolated anti-PD-L1 construct of claim 9, wherein the sdAb moiety specifically recognizing PD-L1 and the second antibody moiety are connected by a peptide linker.

18. The isolated anti-PD-L1 construct of claim 17, wherein the peptide linker comprises the amino acid sequence of SEQ ID NO: 443-445.

19. A pharmaceutical composition comprising the isolated anti-PD-L1 construct of claim 1 and a pharmaceutical acceptable carrier.

* * * * *

UNITED STATES PATENT AND TRADEMARK OFFICE
CERTIFICATE OF CORRECTION

PATENT NO. : 11,673,954 B2
APPLICATION NO. : 16/764411
DATED : June 13, 2023
INVENTOR(S) : Yafeng Zhang et al.

It is certified that error appears in the above-identified patent and that said Letters Patent is hereby corrected as shown below:

In the Claims

In Column 356, Line 23, In Claim 9, delete "(Fab')$_2$," and insert -- (Fab')2, --.

In Column 356, Line 37, In Claim 12, delete "364, 364," and insert -- 364, --.

Signed and Sealed this
Eighth Day of August, 2023

Katherine Kelly Vidal
*Director of the United States Patent and Trademark Office*

SEQUENCE LISTING

```
<160> NUMBER OF SEQ ID NOS: 445

<210> SEQ ID NO 1
<211> LENGTH: 25
<212> TYPE: PRT
<213> ORGANISM: Artificial Sequence
<220> FEATURE:
<223> OTHER INFORMATION: Synthesized FR1

<400> SEQUENCE: 1

Asp Val Gln Leu Val Glu Ser Gly Gly Gly Leu Val Gln Ala Gly Asp
1               5                   10                  15

Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Synthesized FR1

<400> SEQUENCE: 2

Glu Val Gln Leu Val Glu Ser Gly Gly Arg Leu Val Arg Ala Gly Asp
1               5                   10                  15

Ser Leu Arg Leu Ser Cys Ala Ala Ser
            20                  25

<210> SEQ ID NO 3
<211> LENGTH: 25
```

```
<212> TYPE: PRT
<213> ORGANISM: Artificial Sequence
<220> FEATURE:
<223> OTHER INFORMATION: Synthesized FR1

<400> SEQUENCE: 3

Gln Val Gln Leu Val Glu Ser Gly Gly Gly Leu Val Gln Ala Gly Gly
1               5                   10                  15

Ser Leu Arg Leu Ala Cys Ser Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthesized FR1

<400> SEQUENCE: 4

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthesized FR1

<400> SEQUENCE: 5

Ala Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthesized FR1

<400> SEQUENCE: 6

Ala Val Gln Leu Val Glu Ser Gly Gly Gly Leu Val Gln Ala Gly Asp
1               5                   10                  15

Ser Leu Arg Leu Ser Cys Thr Ala Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthesized FR1

<400> SEQUENCE: 7

Ala Val Gln Leu Val Glu Ser Gly Gly Gly Leu Val Gln Ala Gly Asp
1               5                   10                  15

Ser Leu Arg Leu Ala Cys Ala Ala Ser
            20                  25

<210> SEQ ID NO 8
```

```
<211> LENGTH: 25
<212> TYPE: PRT
<213> ORGANISM: Artificial Sequence
<220> FEATURE:
<223> OTHER INFORMATION: Synthesized FR1

<400> SEQUENCE: 8

Glu Val Gln Leu Val Glu Ser Gly Gly Gly Leu Val Arg Ala Gly Gly
1               5                   10                  15

Ser Leu Arg Leu Ser Cys Ala Ala Ser
            20                  25

<210> SEQ ID NO 9
<211> LENGTH: 25
<212> TYPE: PRT
<213> ORGANISM: Artificial Sequence
<220> FEATURE:
<223> OTHER INFORMATION: Synthesized FR1

<400> SEQUENCE: 9

Glu Val Gln Leu Val Glu Ser Gly Gly Gly Leu Val Gln Ala Gly Asp
1               5                   10                  15

Ser Leu Arg Leu Ser Cys Thr Ala Ser
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthesized FR1

<400> SEQUENCE: 10

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthesized FR1

<400> SEQUENCE: 11

Ala Val Gln Leu Val Glu Ser Gly Gly Gly Leu Val Gln Ala Gly Asp
1               5                   10                  15

Ser Leu Arg Leu Ser Cys Thr Ala Ser
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthesized FR1

<400> SEQUENCE: 12

Glu Val Gln Leu Val Glu Ser Gly Gly Gly Leu Val Gln Ala Gly Asp
1               5                   10                  15

Ser Leu Arg Leu Ser Cys Ala Ala Ser
            20                  25
```

```
<210> SEQ ID NO 13
<211> LENGTH: 25
<212> TYPE: PRT
<213> ORGANISM: Artificial Sequence
<220> FEATURE:
<223> OTHER INFORMATION: Synthesized FR1

<400> SEQUENCE: 13

Gln Val Gln Leu Val Glu Ser Gly Gly Gly Leu Val Gln Ala Gly Gly
1               5                   10                  15

Ser Leu Arg Leu Ser Cys Ala Val Ser
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthesized FR1

<400> SEQUENCE: 14

Glu Val Gln Leu Val Glu Ser Gly Gly Gly Leu Val Gln Ala Gly Gly
1               5                   10                  15

Ser Leu Ser Leu Ser Cys Ala Val Ser
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthesized FR1

<400> SEQUENCE: 15

Gln Val Gln Leu Val Glu Ser Gly Gly Gly Leu Val Gln Ala Gly Asp
1               5                   10                  15

Ser Leu Arg Leu Ser Cys Ala Ala Ser
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthesized FR1

<400> SEQUENCE: 16

Gln Val Gln Leu Val Glu Ser Gly Gly Gly Leu Val Gln Ala Gly Gly
1               5                   10                  15

Ser Leu Lys Leu Ser Cys Ala Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: Synthesized FR1

<400> SEQUENCE: 17

Gln Val Gln Leu Val Glu Ser Gly Gly Gly Leu Val Gln Ala Gly Asp
1               5                   10                  15

Ser Leu Arg Leu Ser Cys Ala Ala Ser
            20                  25
```

<210> SEQ ID NO 18
<211> LENGTH: 25
<212> TYPE: PRT
<213> ORGANISM: Artificial Sequence
<220> FEATURE:
<223> OTHER INFORMATION: Synthesized FR1

<400> SEQUENCE: 18

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthesized FR1

<400> SEQUENCE: 19

Gln Val Lys Leu Glu Glu Ser Gly Gly Gly Leu Val Gln Ala Gly Gly
1               5                   10                  15

Ser Leu Arg Leu Ser Cys Val Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: Synthesized FR1

<400> SEQUENCE: 20

Ala Val Gln Leu Val Glu Ser Gly Gly Gly Leu Val Gln Ala Gly Asp
1               5                   10                  15

Ser Leu Arg Leu Ser Cys Ala Ala Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: Synthesized FR1

<400> SEQUENCE: 21

Asp Val Gln Leu Val Glu Ser Gly Gly Gly Leu Val Gln Ala Gly Asp
1               5                   10                  15

Ser Leu Arg Leu Thr Cys Ser Ala Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: Synthesized FR1

<400> SEQUENCE: 22

Glu Val Gln Leu Val Glu Ser Gly Gly Gly Leu Val Gln Ala Gly Asp
1               5                   10                  15

Ser Leu Arg Leu Ser Cys Val Ala Ser
            20                  25

<210> SEQ ID NO 23
<211> LENGTH: 25
<212> TYPE: PRT
<213> ORGANISM: Artificial Sequence
<220> FEATURE:
<223> OTHER INFORMATION: Synthesized FR1

<400> SEQUENCE: 23

Glu Val Gln Leu Val Glu Ser Gly Gly Gly Leu Val Gln Ala Gly Asp
1               5                   10                  15

Ser Leu Arg Leu Ser Cys Ala Ala Ser
            20                  25

<210> SEQ ID NO 24
<211> LENGTH: 25
<212> TYPE: PRT
<213> ORGANISM: Artificial Sequence
<220> FEATURE:
<223> OTHER INFORMATION: Synthesized FR1

<400> SEQUENCE: 24

Gln Val Lys Leu Glu Glu Ser Gly Gly Gly Leu Val Gln Val Gly Asp
1               5                   10                  15

Ser Leu Arg Leu Ser Cys Ala Ala Ser
            20                  25

<210> SEQ ID NO 25
<211> LENGTH: 25
<212> TYPE: PRT
<213> ORGANISM: Artificial Sequence
<220> FEATURE:
<223> OTHER INFORMATION: Synthesized FR1

<400> SEQUENCE: 25

Gln Val Lys Leu Glu Glu Ser Gly Gly Gly Leu Val Gln Val Gly Asp
1               5                   10                  15

Ser Leu Arg Leu Ser Cys Ala Ala Ser
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthesized FR1

<400> SEQUENCE: 26

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 27
<211> LENGTH: 25
<212> TYPE: PRT
<213> ORGANISM: Artificial Sequence
<220> FEATURE:
<223> OTHER INFORMATION: Synthesized FR1

<400> SEQUENCE: 27

Gln Val Gln Leu Val Glu Ser Gly Gly Gly Leu Val Gln Ala Gly Gly
1               5                   10                  15

Ser Leu Arg Leu Ser Cys Ala Ala Ser 20                  25

<210> SEQ ID NO 28
<211> LENGTH: 25
<212> TYPE: PRT
<213> ORGANISM: Artificial Sequence
<220> FEATURE:
<223> OTHER INFORMATION: Synthesized FR1

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 29
<211> LENGTH: 25
<212> TYPE: PRT
<213> ORGANISM: Artificial Sequence
<220> FEATURE:
<223> OTHER INFORMATION: Synthesized FR1

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthesized FR1

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 25
<212> TYPE: PRT
<213> ORGANISM: Artificial Sequence
<220> FEATURE:
<223> OTHER INFORMATION: Synthesized FR1

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 32
<211> LENGTH: 25
<212> TYPE: PRT
<213> ORGANISM: Artificial Sequence
<220> FEATURE:
<223> OTHER INFORMATION: Synthesized FR1

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthesized FR1

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 34
<211> LENGTH: 25
<212> TYPE: PRT
<213> ORGANISM: Artificial Sequence
<220> FEATURE:
<223> OTHER INFORMATION: Synthesized FR1

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 35
<211> LENGTH: 25
<212> TYPE: PRT
<213> ORGANISM: Artificial Sequence
<220> FEATURE:
<223> OTHER INFORMATION: Synthesized FR1

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 36
<211> LENGTH: 25
<212> TYPE: PRT
<213> ORGANISM: Artificial Sequence
<220> FEATURE:
<223> OTHER INFORMATION: Synthesized FR1

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 37
<211> LENGTH: 25
<212> TYPE: PRT
<213> ORGANISM: Artificial Sequence
<220> FEATURE:
<223> OTHER INFORMATION: Synthesized FR1

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 38
<211> LENGTH: 25
<212> TYPE: PRT
<213> ORGANISM: Artificial Sequence
<220> FEATURE:
<223> OTHER INFORMATION: Synthesized FR1

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 39
<211> LENGTH: 25
<212> TYPE: PRT
<213> ORGANISM: Artificial Sequence
<220> FEATURE:
<223> OTHER INFORMATION: Synthesized FR1

<400> SEQUENCE: 39

Glu Val Gln Leu Val Glu Ser Gly Gly Gly Leu Val Gln Ala Gly Asp
1               5                   10                  15

Ser Leu Arg Leu Ser Cys Val Ala Ser
            20                  25

<210> SEQ ID NO 40
<211> LENGTH: 25
<212> TYPE: PRT
<213> ORGANISM: Artificial Sequence
<220> FEATURE:
<223> OTHER INFORMATION: Synthesized FR1

<400> SEQUENCE: 40

Glu Val Gln Leu Val Glu Ser Gly Gly Gly Leu Val Gln Ala Gly Asp
1               5                   10                  15

Ser Leu Arg Leu Ser Cys Val Ala Ser
            20                  25

<210> SEQ ID NO 41
<211> LENGTH: 25
<212> TYPE: PRT
<213> ORGANISM: Artificial Sequence
<220> FEATURE:
<223> OTHER INFORMATION: Synthesized FR1

<400> SEQUENCE: 41

Glu Val Gln Leu Val Glu Ser Gly Gly Gly Leu Val Gln Ala Gly Asp
1               5                   10                  15

Ser Leu Arg Leu Ser Cys Val Ala Ser
            20                  25

<210> SEQ ID NO 42
<211> LENGTH: 25
<212> TYPE: PRT
<213> ORGANISM: Artificial Sequence
<220> FEATURE:
<223> OTHER INFORMATION: Synthesized FR1

<400> SEQUENCE: 42

Glu Val Gln Leu Val Glu Ser Gly Gly Gly Leu Val Gln Pro Gly Gly

```
<210> SEQ ID NO 43
<211> LENGTH: 25
<212> TYPE: PRT
<213> ORGANISM: Artificial Sequence
<220> FEATURE:
<223> OTHER INFORMATION: Synthesized FR1

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 44
<211> LENGTH: 25
<212> TYPE: PRT
<213> ORGANISM: Artificial Sequence
<220> FEATURE:
<223> OTHER INFORMATION: Synthesized FR1

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 45
<211> LENGTH: 25
<212> TYPE: PRT
<213> ORGANISM: Artificial Sequence
<220> FEATURE:
<223> OTHER INFORMATION: Synthesized FR1

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthesized FR1

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 47
<211> LENGTH: 25
<212> TYPE: PRT
<213> ORGANISM: Artificial Sequence
<220> FEATURE:
<223> OTHER INFORMATION: Synthesized FR1

<400> SEQUENCE: 47
```

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 48
<211> LENGTH: 25
<212> TYPE: PRT
<213> ORGANISM: Artificial Sequence
<220> FEATURE:
<223> OTHER INFORMATION: Synthesized FR1

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 49
<211> LENGTH: 25
<212> TYPE: PRT
<213> ORGANISM: Artificial Sequence
<220> FEATURE:
<223> OTHER INFORMATION: Synthesized FR1

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 50
<211> LENGTH: 25
<212> TYPE: PRT
<213> ORGANISM: Artificial Sequence
<220> FEATURE:
<223> OTHER INFORMATION: Synthesized FR1

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 51
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 51

Gly Arg Thr Phe Ile Ser Tyr Ala Val Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 52

Gly Arg Thr Phe Leu Ser Tyr Ala Val Gly
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 53

Gly Arg Thr Phe Leu Thr Tyr Ala Leu Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 54

Gly Arg Thr Phe Ile Thr Tyr Ala Ile Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 55

Gly Arg Thr Phe Ile Thr Tyr Ala Ile Gly
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 56

Gly Arg Thr Phe Leu Ser Tyr Ala Val Gly
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 57

Gly Arg Thr Phe Leu Thr Tyr Ala Leu Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 58

Gly Arg Thr Phe Ile Thr Tyr Ala Ile Gly
1               5                   10

```
<210> SEQ ID NO 59
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 59

Gly Arg Thr Phe Leu Ser Tyr Ala Val Gly
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 60

Gly Arg Thr Phe Ile Thr Tyr Ala Ile Gly
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 61

Gly Arg Thr Phe Leu Thr Tyr Ala Val Gly
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 62

Gly Arg Thr Phe Leu Thr Tyr Ala Val Gly
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 63

Gly Arg Pro Val Ser Ser Ala Val Met Gly
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 64

Gly Arg Thr Leu Thr Gly Leu Leu Ile Gly
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 65

Gly Arg Thr Phe Leu Thr Leu Ala Val Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 66

Gly Arg Thr Phe Ile Thr Tyr Ala Met Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 67

Gly Arg Thr Phe Leu Thr Leu Ala Val Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 68

Gly Arg Thr Phe Ile Thr Tyr Ala Ile Gly
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 69

Gly Arg Thr Phe Ser Arg Tyr Ala Met Gly
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 70

Gly Arg Thr Phe Leu Ser Tyr Ala Val Gly
1               5                   10

<210> SEQ ID NO 71

```
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 71

Gly Arg Thr Phe Ile Ser Tyr Ala Val Gly
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 72

Gly Arg Thr Phe Val Thr Tyr Gly Met Gly
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 73

Gly Arg Thr Phe Leu Ser Tyr Ala Val Gly
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 74

Val Ser Ser Phe Ser Ile Asn Asp Met Gly
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 75

Gly Arg Thr Phe Ser Asn Tyr Thr Met Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 76

Gly Arg Thr Phe Ile Thr Tyr Ala Ile Gly
1               5                   10

<210> SEQ ID NO 77
<211> LENGTH: 10
```

<212> TYPE: PRT
<213> ORGANISM: Artificial Sequence
<220> FEATURE:
<223> OTHER INFORMATION: Synthesized CDR1

<400> SEQUENCE: 77

Gly Arg Thr Phe Ile Thr Tyr Ala Ile Gly
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 78

Gly Arg Thr Phe Ile Thr Tyr Ala Ile Gly
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 79

Gly Arg Thr Phe Ile Thr Tyr Ala Ile Gly
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 80

Gly Arg Thr Phe Ile Thr Tyr Ala Ile Gly
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 81

Gly Arg Thr Phe Ile Thr Tyr Ala Ile Gly
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 82

Gly Arg Thr Phe Ile Thr Tyr Ala Ile Gly
1               5                   10

<210> SEQ ID NO 83
<211> LENGTH: 10
<212> TYPE: PRT

```
<213> ORGANISM: Artificial Sequence
<220> FEATURE:
<223> OTHER INFORMATION: Synthesized CDR1

<400> SEQUENCE: 83

Gly Arg Thr Phe Ile Thr Tyr Ala Ile Gly
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 84

Gly Arg Thr Phe Leu Thr Tyr Ala Val Gly
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 85

Gly Arg Thr Phe Leu Thr Tyr Ala Val Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 86

Gly Arg Thr Phe Leu Thr Tyr Ala Val Gly
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 87

Gly Arg Thr Phe Leu Thr Tyr Ala Val Gly
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 88

Gly Arg Thr Phe Leu Thr Tyr Ala Val Gly
1               5                   10

<210> SEQ ID NO 89
<211> LENGTH: 10
<212> TYPE: PRT
<213> ORGANISM: Artificial Sequence
```

<220> FEATURE:
<223> OTHER INFORMATION: Synthesized CDR1

<400> SEQUENCE: 89

Gly Arg Thr Phe Val Thr Tyr Gly Met Gly
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 90

Gly Arg Thr Phe Val Thr Tyr Gly Met Gly
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 91

Gly Arg Thr Phe Val Thr Tyr Gly Met Gly
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 92

Gly Arg Thr Phe Val Thr Tyr Gly Met Gly
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 93

Gly Arg Thr Phe Val Thr Tyr Gly Met Gly
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 94

Gly Arg Thr Phe Val Thr Tyr Gly Met Gly
1               5                   10

<210> SEQ ID NO 95
<211> LENGTH: 10
<212> TYPE: PRT
<213> ORGANISM: Artificial Sequence
<220> FEATURE:

<223> OTHER INFORMATION: Synthesized CDR1

<400> SEQUENCE: 95

Gly Arg Thr Phe Val Thr Tyr Gly Met Gly
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 96

Gly Arg Thr Phe Val Thr Tyr Gly Met Gly
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 97

Gly Arg Thr Phe Val Thr Tyr Gly Met Gly
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 98

Gly Arg Thr Phe Ile Ser Tyr Ala Val Gly
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 99

Gly Arg Thr Phe Leu Thr Leu Ala Val Gly
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthesized CDR1

<400> SEQUENCE: 100

Gly Arg Thr Phe Leu Thr Tyr Ala Val Gly
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthesized FR2

```
<400> SEQUENCE: 101

Trp Phe Arg Gln Ala Pro Gly Ser Glu Arg Glu Phe Val Ala
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthesized FR2

<400> SEQUENCE: 102

Trp Phe Arg Gln Ala Pro Gly Thr Glu Arg Glu Phe Val Ala
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthesized FR2

<400> SEQUENCE: 103

Trp Phe Arg Gln Ala Pro Gly Lys Glu Arg Glu Phe Val Ala
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthesized FR2

<400> SEQUENCE: 104

Trp Phe Arg Gln Ala Pro Gly Lys Glu Arg Glu Phe Val Thr
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Synthesized FR2

<400> SEQUENCE: 105

Trp Phe Arg Gln Ala Pro Gly Lys Glu Arg Glu Phe Val Ser
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Synthesized FR2

<400> SEQUENCE: 106

Trp Phe Arg Gln Ala Pro Gly Thr Glu Arg Glu Phe Val Ala
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Synthesized FR2
```

<400> SEQUENCE: 107

Trp Phe Arg Gln Ala Pro Gly Lys Glu Arg Glu Phe Val Ala
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthesized FR2

<400> SEQUENCE: 108

Trp Phe Arg Gln Ala Pro Gly Lys Glu Arg Glu Phe Val Thr
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Synthesized FR2

<400> SEQUENCE: 109

Trp Phe Arg Gln Ala Pro Gly Thr Glu Arg Glu Phe Val Ala
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Synthesized FR2

<400> SEQUENCE: 110

Trp Phe Arg Gln Ala Pro Gly Lys Glu Arg Glu Phe Val Ser
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthesized FR2

<400> SEQUENCE: 111

Trp Phe Arg Gln Ala Pro Gly Thr Glu Arg Glu Phe Val Ala
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthesized FR2

<400> SEQUENCE: 112

Trp Phe Arg Gln Ala Pro Gly Thr Glu Arg Glu Phe Val Ala
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Synthesized FR2

<400> SEQUENCE: 113

Trp Phe Arg Gln Ala Pro Gly Lys Glu Arg Glu Phe Val Gly
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Synthesized FR2

<400> SEQUENCE: 114

Trp Phe Arg Gln Ala Pro Gly Lys Glu Arg Glu Leu Val Ala
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Synthesized FR2

<400> SEQUENCE: 115

Trp Phe Arg Gln Ala Pro Gly Thr Glu Arg Glu Phe Val Ala
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Synthesized FR2

<400> SEQUENCE: 116

Trp Phe Arg Gln Ala Pro Gly Lys Glu Arg Glu Leu Val Ala
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Synthesized FR2

<400> SEQUENCE: 117

Trp Phe Arg Gln Ala Pro Gly Thr Glu Arg Glu Phe Val Ala
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Synthesized FR2

<400> SEQUENCE: 118

Trp Phe Arg Gln Ala Pro Gly Lys Glu Arg Glu Phe Val Thr
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Synthesized FR2

<400> SEQUENCE: 119

-continued

Trp Phe Arg Gln Ala Pro Gly Lys Glu Arg Glu Phe Val Ser
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Synthesized FR2

<400> SEQUENCE: 120

Trp Phe Arg Gln Ala Pro Gly Thr Glu Arg Glu Phe Val Ala
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Synthesized FR2

<400> SEQUENCE: 121

Trp Phe Arg Gln Ala Pro Gly Thr Glu Arg Glu Phe Val Ala
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Synthesized FR2

<400> SEQUENCE: 122

Trp Phe Arg Gln Ala Pro Gly Lys Glu Arg Glu Phe Val Ala
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Synthesized FR2

<400> SEQUENCE: 123

Trp Phe Arg Gln Ala Pro Gly Thr Glu Arg Glu Phe Val Ala
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Synthesized FR2

<400> SEQUENCE: 124

Trp Tyr Arg Gln Ala Pro Gly Lys Gln Arg Glu Leu Val Ala
1               5                   10

<210> SEQ ID NO 125
<211> LENGTH: 14
<212> TYPE: PRT
<213> ORGANISM: Artificial Sequence
<220> FEATURE:
<223> OTHER INFORMATION: Synthesized FR2

<400> SEQUENCE: 125

Trp Phe Arg Gln Phe Pro Gly Lys Glu Arg Glu Phe Val Ala

```
1               5                  10
```

<210> SEQ ID NO 126
<211> LENGTH: 14
<212> TYPE: PRT
<213> ORGANISM: Artificial Sequence
<220> FEATURE:
<223> OTHER INFORMATION: Synthesized FR2

<400> SEQUENCE: 126

```
Trp Phe Arg Gln Ala Pro Gly Lys Glu Arg Glu Phe Val Ser
1               5                  10
```

<210> SEQ ID NO 127
<211> LENGTH: 14
<212> TYPE: PRT
<213> ORGANISM: Artificial Sequence
<220> FEATURE:
<223> OTHER INFORMATION: Synthesized FR2

<400> SEQUENCE: 127

```
Trp Phe Arg Gln Ala Pro Gly Lys Glu Arg Glu Phe Val Ser
1               5                  10
```

<210> SEQ ID NO 128
<211> LENGTH: 14
<212> TYPE: PRT
<213> ORGANISM: Artificial Sequence
<220> FEATURE:
<223> OTHER INFORMATION: Synthesized FR2

<400> SEQUENCE: 128

```
Trp Val Arg Gln Ala Pro Gly Lys Gly Leu Glu Trp Val Ser
1               5                  10
```

<210> SEQ ID NO 129
<211> LENGTH: 14
<212> TYPE: PRT
<213> ORGANISM: Artificial Sequence
<220> FEATURE:
<223> OTHER INFORMATION: Synthesized FR2

<400> SEQUENCE: 129

```
Trp Phe Arg Gln Ala Pro Gly Lys Gly Leu Glu Trp Val Ser
1               5                  10
```

<210> SEQ ID NO 130
<211> LENGTH: 14
<212> TYPE: PRT
<213> ORGANISM: Artificial Sequence
<220> FEATURE:
<223> OTHER INFORMATION: Synthesized FR2

<400> SEQUENCE: 130

```
Trp Phe Arg Gln Ala Pro Gly Lys Gly Leu Glu Phe Val Ser
1               5                  10
```

<210> SEQ ID NO 131
<211> LENGTH: 14
<212> TYPE: PRT
<213> ORGANISM: Artificial Sequence
<220> FEATURE:
<223> OTHER INFORMATION: Synthesized FR2

<400> SEQUENCE: 131

```
Trp Phe Arg Gln Ala Pro Gly Lys Gly Arg Glu Phe Val Ser
1               5                  10
```

```
<210> SEQ ID NO 132
<211> LENGTH: 14
<212> TYPE: PRT
<213> ORGANISM: Artificial Sequence
<220> FEATURE:
<223> OTHER INFORMATION: Synthesized FR2

<400> SEQUENCE: 132

Trp Phe Arg Gln Ala Pro Gly Lys Gly Arg Glu Phe Val Ser
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthesized FR2

<400> SEQUENCE: 133

Trp Phe Arg Gln Ala Pro Gly Lys Gly Arg Glu Phe Val Ser
1               5                   10

<210> SEQ ID NO 134
<211> LENGTH: 14
<212> TYPE: PRT
<213> ORGANISM: Artificial Sequence
<220> FEATURE:
<223> OTHER INFORMATION: Synthesized FR2

<400> SEQUENCE: 134

Trp Val Arg Gln Ala Pro Gly Lys Gly Leu Glu Trp Val Ser
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Synthesized FR2

<400> SEQUENCE: 135

Trp Phe Arg Gln Ala Pro Gly Lys Gly Leu Glu Trp Val Ala
1               5                   10

<210> SEQ ID NO 136
<211> LENGTH: 14
<212> TYPE: PRT
<213> ORGANISM: Artificial Sequence
<220> FEATURE:
<223> OTHER INFORMATION: Synthesized FR2

<400> SEQUENCE: 136

Trp Phe Arg Gln Ala Pro Gly Lys Gly Leu Glu Phe Val Ala
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Synthesized FR2

<400> SEQUENCE: 137

Trp Phe Arg Gln Ala Pro Gly Lys Gly Leu Glu Phe Val Ala
1               5                   10
```

<210> SEQ ID NO 138
<211> LENGTH: 14
<212> TYPE: PRT
<213> ORGANISM: Artificial Sequence
<220> FEATURE:
<223> OTHER INFORMATION: Synthesized FR2

<400> SEQUENCE: 138

Trp Phe Arg Gln Ala Pro Gly Lys Gly Arg Glu Phe Val Ser
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Synthesized FR2

<400> SEQUENCE: 139

Trp Phe Arg Gln Ala Pro Gly Lys Glu Arg Glu Phe Val Ala
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Synthesized FR2

<400> SEQUENCE: 140

Trp Phe Arg Gln Ala Pro Gly Lys Glu Arg Glu Phe Val Ala
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthesized FR2

<400> SEQUENCE: 141

Trp Phe Arg Gln Ala Pro Gly Lys Glu Arg Glu Phe Val Ala
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Synthesized FR2

<400> SEQUENCE: 142

Trp Val Arg Gln Ala Pro Gly Lys Gly Leu Glu Trp Val Ser
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Synthesized FR2

<400> SEQUENCE: 143

Trp Phe Arg Gln Ala Pro Gly Lys Gly Leu Glu Phe Val Ala
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Synthesized FR2

<400> SEQUENCE: 144

Trp Phe Arg Gln Ala Pro Gly Lys Gly Arg Glu Phe Val Ser
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Synthesized FR2

<400> SEQUENCE: 145

Trp Phe Arg Gln Ala Pro Gly Lys Gly Arg Glu Phe Val Ser
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Synthesized FR2

<400> SEQUENCE: 146

Trp Phe Arg Gln Ala Pro Gly Lys Gly Arg Glu Phe Val Ser
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Synthesized FR2

<400> SEQUENCE: 147

Trp Phe Arg Gln Ala Pro Gly Lys Gly Arg Glu Phe Val Ser
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthesized FR2

<400> SEQUENCE: 148

Trp Phe Arg Gln Ala Pro Gly Lys Gly Arg Glu Phe Val Ser
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Synthesized FR2

<400> SEQUENCE: 149

Trp Phe Arg Gln Ala Pro Gly Lys Gly Arg Glu Phe Val Ser
1               5                   10

<210> SEQ ID NO 150

```
<211> LENGTH: 14
<212> TYPE: PRT
<213> ORGANISM: Artificial Sequence
<220> FEATURE:
<223> OTHER INFORMATION: Synthesized FR2

<400> SEQUENCE: 150

Trp Phe Arg Gln Ala Pro Gly Lys Gly Leu Glu Phe Val Ser
1               5                   10

<210> SEQ ID NO 151
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 151

Gly Ile Arg Trp Asn Gly Ile His Thr Asp Tyr Ala Asp Ser Val Lys
1               5                   10                  15

Gly

<210> SEQ ID NO 152
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 152

Gly Ile Arg Trp Ser Gly Gly Tyr Thr Asp Tyr Ala Glu Ala Val Lys
1               5                   10                  15

Gly

<210> SEQ ID NO 153
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 153

Gly Val Ser Trp Ser Gly Ser Gly Thr Lys Tyr Ala Asp Ser Val Lys
1               5                   10                  15

Gly

<210> SEQ ID NO 154
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 154

Ala Ile Asn Trp Ser Gly Ser Met Thr Ser Tyr Ala Asp Ser Val Lys
1               5                   10                  15

Gly

<210> SEQ ID NO 155
<211> LENGTH: 17
<212> TYPE: PRT
<213> ORGANISM: Artificial Sequence
<220> FEATURE:
<223> OTHER INFORMATION: Synthesized CDR2
```

```
<400> SEQUENCE: 155

Ala Ile Asn Trp Ser Gly Ser Met Thr Ser Tyr Ala Asp Ser Val Lys
1               5                   10                  15

Gly

<210> SEQ ID NO 156
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 156

Gly Ile Arg Trp Ser Gly Glu His Thr Asp Tyr Ala Ala Ser Val Lys
1               5                   10                  15

Gly

<210> SEQ ID NO 157
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 157

Gly Val Ser Trp Ser Gly Ser Ser Thr Lys Tyr Ala Asp Ser Val Lys
1               5                   10                  15

Gly

<210> SEQ ID NO 158
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 158

Ala Ile Asn Trp Ser Gly Ser Met Thr Ser Tyr Ala Asp Ser Val Lys
1               5                   10                  15

Gly

<210> SEQ ID NO 159
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 159

Gly Ile Arg Trp Ser Gly Gly Ser Thr Asp Tyr Ser Asp Ser Val Lys
1               5                   10                  15

Gly

<210> SEQ ID NO 160
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 160

Ala Ile Asn Trp Ser Gly Ser Met Thr Ser Tyr Ala Asp Ser Val Lys
1               5                   10                  15
```

Gly

<210> SEQ ID NO 161
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 161

Gly Ile Arg Trp Ser Gly Gly Tyr Thr Asp Tyr Ala Asp Ser Val Lys
1               5                   10                  15

Gly

<210> SEQ ID NO 162
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 162

Gly Ile Arg Trp Ser Gly Glu Ser Thr Asp Tyr Ala Glu Ser Val Lys
1               5                   10                  15

Gly

<210> SEQ ID NO 163
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 163

Arg Leu Thr Ser Ser Ala Thr Ser Thr Phe Tyr Ala Glu Ser Val Lys
1               5                   10                  15

Gly

<210> SEQ ID NO 164
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 164

Ile Ile Ser Trp Thr Tyr Gly Ser Thr Asn Tyr Ala Asp Ser Val Lys
1               5                   10                  15

Gly

<210> SEQ ID NO 165
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 165

Gly Ile Arg Trp Ser Gly Ser Gly Thr Asp Tyr Ala Asp Ser Val Lys
1               5                   10                  15

Gly

```
<210> SEQ ID NO 166
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 166

Ala Ile Ser Trp Ser Gly Ser Ser Thr Tyr Ser Ala Asp Ser Val Lys
1               5                   10                  15
Gly

<210> SEQ ID NO 167
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 167

Gly Ile Arg Trp Ser Gly Ser Gly Thr Asp Tyr Ala Asp Ser Val Lys
1               5                   10                  15
Gly

<210> SEQ ID NO 168
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 168

Ala Ile Asn Trp Ser Gly Ser Met Thr Ser Tyr Ala Asp Ser Val Lys
1               5                   10                  15
Gly

<210> SEQ ID NO 169
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 169

Thr Ser Thr Gly Ser Gly Gly Leu Thr Ser Tyr Ala Asn Ser Val Lys
1               5                   10                  15
Gly

<210> SEQ ID NO 170
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 170

Gly Ile Arg Trp Ser Gly Leu His Thr Asp Tyr Ala Asp Ser Val Lys
1               5                   10                  15
Gly

<210> SEQ ID NO 171
<211> LENGTH: 17
<212> TYPE: PRT
<213> ORGANISM: Artificial Sequence
```

```
<220> FEATURE:
<223> OTHER INFORMATION: Synthesized CDR2

<400> SEQUENCE: 171

Gly Ile Arg Trp Asn Gly Ile Ser Thr Asp Tyr Thr Asp Ser Val Lys
1               5                   10                  15

Gly

<210> SEQ ID NO 172
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 172

Ala Ile Asn Trp Ser Gly Ser Met Thr Ser Tyr Gly Asp Ser Val Lys
1               5                   10                  15

Gly

<210> SEQ ID NO 173
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 173

Gly Ile Arg Trp Ser Gly Gly Ser Thr Asp Tyr Ala Asp Ser Val Lys
1               5                   10                  15

Gly

<210> SEQ ID NO 174
<211> LENGTH: 16
<212> TYPE: PRT
<213> ORGANISM: Artificial Sequence
<220> FEATURE:
<223> OTHER INFORMATION: Synthesized CDR2

<400> SEQUENCE: 174

Thr Ile Ala Ser Gly Gly Ser Thr Asn Tyr Ala Asp Ser Val Lys Gly
1               5                   10                  15

<210> SEQ ID NO 175
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 175

Val Val Ser Arg Gly Gly Gly Ala Thr Asp Tyr Ala Asp Ser Val Lys
1               5                   10                  15

Gly

<210> SEQ ID NO 176
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 176

Ala Ile Ser Trp Ser Gly Ser Met Thr Ser Tyr Ala Asp Ser Val Lys
```

-continued

```
1               5                   10                  15

Gly

<210> SEQ ID NO 177
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 177

Ala Ile Gln Trp Ser Gly Ser Met Thr Ser Tyr Ala Asp Ser Val Lys
1               5                   10                  15

Gly

<210> SEQ ID NO 178
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 178

Ala Ile Gln Trp Ser Gly Ser Met Thr Ser Tyr Ala Asp Ser Val Lys
1               5                   10                  15

Gly

<210> SEQ ID NO 179
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 179

Ala Ile Gln Trp Ser Gly Ser Met Thr Ser Tyr Ala Asp Ser Val Lys
1               5                   10                  15

Gly

<210> SEQ ID NO 180
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 180

Ala Ile Gln Trp Ser Gly Ser Met Thr Ser Tyr Ala Asp Ser Val Lys
1               5                   10                  15

Gly

<210> SEQ ID NO 181
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 181

Ala Ile Ser Trp Ser Gly Ser Met Thr Ser Tyr Ala Asp Ser Val Lys
1               5                   10                  15

Gly
```

<210> SEQ ID NO 182
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 182

Ala Ile Ser Trp Ser Gly Ser Ile Thr Ser Tyr Ala Asp Ser Val Lys
1               5                   10                  15

Gly

<210> SEQ ID NO 183
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 183

Ala Ile Ser Trp Ser Gly Ser Leu Thr Ser Tyr Ala Asp Ser Val Lys
1               5                   10                  15

Gly

<210> SEQ ID NO 184
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 184

Gly Ile Arg Trp Ser Gly Gly Tyr Thr Asp Tyr Ala Asp Ser Val Lys
1               5                   10                  15

Gly

<210> SEQ ID NO 185
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 185

Gly Ile Arg Trp Ser Gly Gly Tyr Thr Asp Tyr Ala Asp Ser Val Lys
1               5                   10                  15

Gly

<210> SEQ ID NO 186
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 186

Gly Ile Arg Trp Ser Gly Gly Tyr Thr Asp Tyr Ala Asp Ser Val Lys
1               5                   10                  15

Gly

<210> SEQ ID NO 187
<211> LENGTH: 17
<212> TYPE: PRT

```
<213> ORGANISM: Artificial Sequence
<220> FEATURE:
<223> OTHER INFORMATION: Synthesized CDR2

<400> SEQUENCE: 187

Gly Ile Arg Trp Ser Gly Gly Tyr Thr Asp Tyr Ala Asp Ser Val Lys
1               5                   10                  15

Gly

<210> SEQ ID NO 188
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 188

Gly Ile Arg Trp Ser Gly Gly Tyr Thr Asp Tyr Ala Asp Ser Val Lys
1               5                   10                  15

Gly

<210> SEQ ID NO 189
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 189

Ala Ile Ala Trp Ser Gly Ser Met Thr Ser Tyr Gly Asp Ser Val Lys
1               5                   10                  15

Gly

<210> SEQ ID NO 190
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 190

Ala Ile Ser Trp Ser Gly Ser Met Thr Ser Tyr Gly Asp Ser Val Lys
1               5                   10                  15

Gly

<210> SEQ ID NO 191
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 191

Ala Ile Gln Trp Ser Gly Ser Met Thr Ser Tyr Gly Asp Ser Val Lys
1               5                   10                  15

Gly

<210> SEQ ID NO 192
<211> LENGTH: 17
<212> TYPE: PRT
<213> ORGANISM: Artificial Sequence
<220> FEATURE:
<223> OTHER INFORMATION: Synthesized CDR2
```

```
<400> SEQUENCE: 192

Ala Ile Gln Trp Ser Gly Ser Met Thr Ser Tyr Gly Asp Ser Val Lys
1               5                   10                  15

Gly

<210> SEQ ID NO 193
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 193

Ala Ile Gln Trp Ser Gly Ser Met Thr Ser Tyr Gly Asp Ser Val Lys
1               5                   10                  15

Gly

<210> SEQ ID NO 194
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 194

Ala Ile Gln Trp Ser Gly Ser Met Thr Ser Tyr Gly Asp Ser Val Lys
1               5                   10                  15

Gly

<210> SEQ ID NO 195
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 195

Ala Ile Ser Trp Ser Gly Ser Met Thr Ser Tyr Gly Asp Ser Val Lys
1               5                   10                  15

Gly

<210> SEQ ID NO 196
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 196

Ala Ile Ser Trp Ser Gly Ser Ile Thr Ser Tyr Gly Asp Ser Val Lys
1               5                   10                  15

Gly

<210> SEQ ID NO 197
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 197

Ala Ile Ser Trp Ser Gly Ser Leu Thr Ser Tyr Gly Asp Ser Val Lys
1               5                   10                  15
```

-continued

Gly

<210> SEQ ID NO 198
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 198

Gly Ile Arg Trp Ser Gly Ile His Thr Asp Tyr Ala Asp Ser Val Lys
1               5                   10                  15

Gly

<210> SEQ ID NO 199
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 199

Gly Ile Arg Trp Ser Gly Ser Gly Thr Asp Tyr Ala Asp Ser Val Lys
1               5                   10                  15

Gly

<210> SEQ ID NO 200
<211> LENGTH: 17
<212> TYPE: PRT
<213> ORGANISM: Artificial Sequence
<220> FEATURE:
<223> OTHER INFORMATION: Synthesized CDR2

<400> SEQUENCE: 200

Gly Ile Arg Trp Ser Gly Gly Tyr Thr Asp Tyr Ala Asp Ser Val Lys
1               5                   10                  15

Gly

<210> SEQ ID NO 201
<211> LENGTH: 32
<212> TYPE: PRT
<213> ORGANISM: Artificial Sequence
<220> FEATURE:
<223> OTHER INFORMATION: Synthesized FR3

<400> SEQUENCE: 201

Arg Phe Thr Ile Ser Arg Asp Asn Ala Lys Asn Thr Val Thr Leu Glu
1               5                   10                  15

Met Thr Ser Leu Lys Pro Glu Asp Thr Ala Val Tyr Tyr Cys Ala Ala
            20                  25                  30

<210> SEQ ID NO 202
<211> LENGTH: 32
<212> TYPE: PRT
<213> ORGANISM: Artificial Sequence
<220> FEATURE:
<223> OTHER INFORMATION: Synthesized FR3

<400> SEQUENCE: 202

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

```
<210> SEQ ID NO 203
<211> LENGTH: 32
<212> TYPE: PRT
<213> ORGANISM: Artificial Sequence
<220> FEATURE:
<223> OTHER INFORMATION: Synthesized FR3

<400> SEQUENCE: 203

Arg Phe Thr Ile Ser Arg Asp Asn Ala Lys Asn Thr Val Tyr Met Gln
1               5                   10                  15

Met Asn Ser Leu Lys Pro Glu Asp Thr Ala Val Tyr Tyr Cys Ala Ala
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: Synthesized FR3

<400> SEQUENCE: 204

Arg Phe Thr Ile Ser Arg Asp Asn Asn Lys Asn Met Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: Synthesized FR3

<400> SEQUENCE: 205

Arg Phe Thr Ile Ser Arg Asp Asn Ala Lys Asn Thr Val Tyr Leu Gln
1               5                   10                  15

Met Asn Gly Leu Lys Pro Glu Asp Thr Ala Val Tyr Tyr Cys Ala Ala
            20                  25                  30

<210> SEQ ID NO 206
<211> LENGTH: 32
<212> TYPE: PRT
<213> ORGANISM: Artificial Sequence
<220> FEATURE:
<223> OTHER INFORMATION: Synthesized FR3

<400> SEQUENCE: 206

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 207
<211> LENGTH: 32
<212> TYPE: PRT
<213> ORGANISM: Artificial Sequence
<220> FEATURE:
<223> OTHER INFORMATION: Synthesized FR3

<400> SEQUENCE: 207

Arg Phe Thr Ile Ser Arg Asp Asn Ala Lys Asn Thr Val Tyr Met Gln
1               5                   10                  15

Met Asn Ser Leu Lys Pro Glu Asp Thr Ala Val Tyr Tyr Cys Ala Ala
```

<210> SEQ ID NO 208
<211> LENGTH: 32
<212> TYPE: PRT
<213> ORGANISM: Artificial Sequence
<220> FEATURE:
<223> OTHER INFORMATION: Synthesized FR3

<400> SEQUENCE: 208

Arg Phe Thr Ile Ser Arg Asp Asn Asn Lys Asn Thr Val Tyr Leu Gln
1               5                   10                  15

Met Asn Ser Leu Lys Pro Glu Asp Thr Ala Leu Tyr Tyr Cys Ala Ala
            20                  25                  30

<210> SEQ ID NO 209
<211> LENGTH: 32
<212> TYPE: PRT
<213> ORGANISM: Artificial Sequence
<220> FEATURE:
<223> OTHER INFORMATION: Synthesized FR3

<400> SEQUENCE: 209

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Synthesized FR3

<400> SEQUENCE: 210

Arg Phe Thr Ile Ser Arg Asp Asn Ala Lys Asn Thr Val Tyr Leu Gln
1               5                   10                  15

Met Asn Gly Leu Lys Pro Glu Asp Thr Ala Val Tyr Tyr Cys Ala Ala
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Synthesized FR3

<400> SEQUENCE: 211

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Synthesized FR3

<400> SEQUENCE: 212

Arg Phe Thr Ile Ser Arg Asp Asp Thr Lys Asn Thr Val Tyr Leu Gln
1               5                   10                  15

```
Met Asn Ser Leu Lys Pro Glu Asp Thr Ala Val Tyr Tyr Cys Ala Ala
            20                  25                  30
```

<210> SEQ ID NO 213
<211> LENGTH: 32
<212> TYPE: PRT
<213> ORGANISM: Artificial Sequence
<220> FEATURE:
<223> OTHER INFORMATION: Synthesized FR3

<400> SEQUENCE: 213

```
Arg Phe Thr Ile Ser Arg Asp Asn Ala Lys Asn Thr Val Tyr Leu Gln
1               5                   10                  15

Met Asn Asn Leu Lys Pro Glu Asp Thr Ala Val Tyr Tyr Cys Ala Ala
            20                  25                  30
```

<210> SEQ ID NO 214
<211> LENGTH: 32
<212> TYPE: PRT
<213> ORGANISM: Artificial Sequence
<220> FEATURE:
<223> OTHER INFORMATION: Synthesized FR3

<400> SEQUENCE: 214

```
Arg Phe Thr Ile Ser Arg Asp Asn Ala Lys Asn Thr Val Leu Leu Gln
1               5                   10                  15

Met Asn Ser Leu Lys Pro Glu Asp Thr Ala Val Tyr Tyr Cys Ser Ala
            20                  25                  30
```

<210> SEQ ID NO 215
<211> LENGTH: 32
<212> TYPE: PRT
<213> ORGANISM: Artificial Sequence
<220> FEATURE:
<223> OTHER INFORMATION: Synthesized FR3

<400> SEQUENCE: 215

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 216
<211> LENGTH: 32
<212> TYPE: PRT
<213> ORGANISM: Artificial Sequence
<220> FEATURE:
<223> OTHER INFORMATION: Synthesized FR3

<400> SEQUENCE: 216

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 217
<211> LENGTH: 32
<212> TYPE: PRT
<213> ORGANISM: Artificial Sequence
<220> FEATURE:
<223> OTHER INFORMATION: Synthesized FR3

<400> SEQUENCE: 217

```
Arg Phe Thr Ile Ser Arg Asp Asn Ala Ala Asn Thr Val Tyr Leu Gln
1               5                   10                  15
```

```
Met Asn Ser Leu Lys Pro Glu Asp Thr Ala Val Tyr Tyr Cys Ala Ala
            20                  25                  30

<210> SEQ ID NO 218
<211> LENGTH: 32
<212> TYPE: PRT
<213> ORGANISM: Artificial Sequence
<220> FEATURE:
<223> OTHER INFORMATION: Synthesized FR3

<400> SEQUENCE: 218

Arg Phe Thr Ile Ser Arg Asp Asn Ala Lys Asn Thr Val Tyr Leu Gln
1               5                   10                  15

Ile Asn Gly Leu Lys Ser Glu Asp Thr Ala Val Tyr Tyr Cys Ala Ala
            20                  25                  30

<210> SEQ ID NO 219
<211> LENGTH: 32
<212> TYPE: PRT
<213> ORGANISM: Artificial Sequence
<220> FEATURE:
<223> OTHER INFORMATION: Synthesized FR3

<400> SEQUENCE: 219

Arg Phe Thr Ile Ser Arg Asp Asn Ala Lys Asn Thr Val Tyr Leu Gln
1               5                   10                  15

Met Asn Asn Leu Lys Pro Glu Asp Thr Ala Ile Tyr Tyr Cys Ala Ala
            20                  25                  30

<210> SEQ ID NO 220
<211> LENGTH: 32
<212> TYPE: PRT
<213> ORGANISM: Artificial Sequence
<220> FEATURE:
<223> OTHER INFORMATION: Synthesized FR3

<400> SEQUENCE: 220

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Ile Tyr Tyr Cys Ala Ala
            20                  25                  30

<210> SEQ ID NO 221
<211> LENGTH: 32
<212> TYPE: PRT
<213> ORGANISM: Artificial Sequence
<220> FEATURE:
<223> OTHER INFORMATION: Synthesized FR3

<400> SEQUENCE: 221

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Ile Tyr Tyr Cys Ala Ala
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: Synthesized FR3

<400> SEQUENCE: 222

Arg Phe Ala Ile Ser Arg Asp Asn Ala Lys Asn Thr Val Tyr Leu Gln
```

```
                1               5                  10                  15
Met Asn Ser Leu Lys Pro Glu Asp Thr Ala Val Tyr Tyr Cys Ala Ala
                20                  25                  30

<210> SEQ ID NO 223
<211> LENGTH: 32
<212> TYPE: PRT
<213> ORGANISM: Artificial Sequence
<220> FEATURE:
<223> OTHER INFORMATION: Synthesized FR3

<400> SEQUENCE: 223

Arg Phe Thr Ile Ser Arg Asp Asn Ala Lys Asn Thr Val Tyr Leu Gln
1               5                  10                  15
Met Asn Ser Leu Lys Pro Glu Asp Thr Ala Val Tyr Tyr Cys Ala Ala
                20                  25                  30

<210> SEQ ID NO 224
<211> LENGTH: 32
<212> TYPE: PRT
<213> ORGANISM: Artificial Sequence
<220> FEATURE:
<223> OTHER INFORMATION: Synthesized FR3

<400> SEQUENCE: 224

Arg Phe Thr Ile Ser Arg Asp Asn Val Lys Asn Thr Val Tyr Leu Gln
1               5                  10                  15
Met Asn Gly Leu Lys Pro Glu Asp Thr Ala Val Tyr Tyr Cys Asn Ala
                20                  25                  30

<210> SEQ ID NO 225
<211> LENGTH: 32
<212> TYPE: PRT
<213> ORGANISM: Artificial Sequence
<220> FEATURE:
<223> OTHER INFORMATION: Synthesized FR3

<400> SEQUENCE: 225

Arg Phe Thr Ile Ser Arg Asp Asn Ala Lys Asn Thr Met Tyr Leu Gln
1               5                  10                  15
Met Asn Ser Leu Lys Thr Glu Asp Thr Ala Val Tyr Tyr Cys Ala Ala
                20                  25                  30

<210> SEQ ID NO 226
<211> LENGTH: 32
<212> TYPE: PRT
<213> ORGANISM: Artificial Sequence
<220> FEATURE:
<223> OTHER INFORMATION: Synthesized FR3

<400> SEQUENCE: 226

Arg Phe Thr Ile Ser Arg Asp Asn Ala Lys Asn Thr Val Tyr Leu Gln
1               5                  10                  15
Met Asn Gly Leu Lys Pro Glu Asp Thr Ala Val Tyr Tyr Cys Ala Ala
                20                  25                  30

<210> SEQ ID NO 227
<211> LENGTH: 32
<212> TYPE: PRT
<213> ORGANISM: Artificial Sequence
<220> FEATURE:
<223> OTHER INFORMATION: Synthesized FR3

<400> SEQUENCE: 227
```

Arg Phe Thr Ile Ser Arg Asp Asn Ala Lys Asn Thr Val Tyr Leu Gln
1               5                   10                  15

Met Asn Gly Leu Lys Pro Glu Asp Thr Ala Val Tyr Tyr Cys Ala Ala
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: Synthesized FR3

<400> SEQUENCE: 228

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: Synthesized FR3

<400> SEQUENCE: 229

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: Synthesized FR3

<400> SEQUENCE: 230

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Synthesized FR3

<400> SEQUENCE: 231

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: Synthesized FR3

<400> SEQUENCE: 232

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 233
<211> LENGTH: 32
<212> TYPE: PRT
<213> ORGANISM: Artificial Sequence
<220> FEATURE:
<223> OTHER INFORMATION: Synthesized FR3

<400> SEQUENCE: 233

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Synthesized FR3

<400> SEQUENCE: 234

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Synthesized FR3

<400> SEQUENCE: 235

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Synthesized FR3

<400> SEQUENCE: 236

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Synthesized FR3

<400> SEQUENCE: 237

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Synthesized FR3

<400> SEQUENCE: 238

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: Synthesized FR3

<400> SEQUENCE: 239

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Synthesized FR3

<400> SEQUENCE: 240

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Synthesized FR3

<400> SEQUENCE: 241

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 242
<211> LENGTH: 32
<212> TYPE: PRT
<213> ORGANISM: Artificial Sequence
<220> FEATURE:
<223> OTHER INFORMATION: Synthesized FR3

<400> SEQUENCE: 242

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 243
<211> LENGTH: 32
<212> TYPE: PRT
<213> ORGANISM: Artificial Sequence
<220> FEATURE:
<223> OTHER INFORMATION: Synthesized FR3

<400> SEQUENCE: 243

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 244
<211> LENGTH: 32
<212> TYPE: PRT
<213> ORGANISM: Artificial Sequence
<220> FEATURE:
<223> OTHER INFORMATION: Synthesized FR3

<400> SEQUENCE: 244

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 245
<211> LENGTH: 32
<212> TYPE: PRT
<213> ORGANISM: Artificial Sequence
<220> FEATURE:
<223> OTHER INFORMATION: Synthesized FR3

<400> SEQUENCE: 245

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: Synthesized FR3

<400> SEQUENCE: 246

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 247
<211> LENGTH: 32
<212> TYPE: PRT
<213> ORGANISM: Artificial Sequence
<220> FEATURE:

<223> OTHER INFORMATION: Synthesized FR3

<400> SEQUENCE: 247

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: Synthesized FR3

<400> SEQUENCE: 248

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: Synthesized FR3

<400> SEQUENCE: 249

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: Synthesized FR3

<400> SEQUENCE: 250

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 251
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 251

His Arg Thr Ile Ala Thr Ile Pro Glu Lys Tyr Glu Tyr Glu Tyr
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 252

His Arg Thr Ile Ala Thr Ile Pro Glu Lys Tyr Glu Tyr Glu Tyr
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 253

Gln Ile Ser Ala Ile Val Pro Ile Ser Ala His Glu Tyr Glu Tyr
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 254

His Arg Gly Ala Ile Ala Pro Met Thr Gln Ser Val Tyr Asp Tyr
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 255

His Arg Gly Ala Ile Ala Pro Met Thr Gln Ser Val Tyr Asp Thr
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 256

His Thr Thr Ile Ala Thr Ile Pro Lys Lys Tyr Glu Tyr Glu Tyr
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 257

Gln Ile Ser Ala Ile Val Pro Ile Ser Ala His Glu Tyr Gln Tyr
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 258

His Leu Gly Ala Ile Ala Pro Met Ser Gln Ser Val Tyr Asp Tyr
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 259

His Arg Thr Ile Ala Thr Ile Pro Glu Lys Tyr Glu Tyr Glu Tyr
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 260

His Arg Gly Ala Ile Ala Pro Ile Ala Gln Ser Val Tyr Thr Asn
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 261

His Arg Thr Ile Ala Thr Ile Pro Glu Lys Tyr Glu Tyr Glu Tyr
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 262

His Arg Thr Ile Ala Thr Ile Pro Glu Lys Tyr Tyr Tyr Glu Tyr
1               5                   10                  15

<210> SEQ ID NO 263
<211> LENGTH: 18
<212> TYPE: PRT
<213> ORGANISM: Artificial Sequence
<220> FEATURE:
<223> OTHER INFORMATION: Synthesized CDR3

<400> SEQUENCE: 263

Asp Val Pro Gly Thr Lys Ile Trp Ser Ile Gln Thr Pro Asp Arg Tyr
1               5                   10                  15

Asn Tyr

<210> SEQ ID NO 264
<211> LENGTH: 10
<212> TYPE: PRT
<213> ORGANISM: Artificial Sequence
<220> FEATURE:
<223> OTHER INFORMATION: Synthesized CDR3

```
<400> SEQUENCE: 264

Arg Asp Val Ala Val Ala Lys Tyr Asp Ser
1               5                   10

<210> SEQ ID NO 265
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 265

His Thr Thr Ile Ala Thr Ile Pro Glu Lys Tyr Glu Tyr Glu Tyr
1               5                   10                  15

<210> SEQ ID NO 266
<211> LENGTH: 17
<212> TYPE: PRT
<213> ORGANISM: Artificial Sequence
<220> FEATURE:
<223> OTHER INFORMATION: Synthesized CDR3

<400> SEQUENCE: 266

Glu Val Ser Ala Arg Thr Gly Glu His Leu Pro Lys Leu Met Gly Asp
1               5                   10                  15

Tyr

<210> SEQ ID NO 267
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 267

His Thr Thr Ile Ala Thr Ile Pro Glu Lys Tyr Glu Tyr Glu Tyr
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 268

His Arg Gly Ala Ile Ala Pro Met Thr Gln Ser Val Tyr Asp Tyr
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 269

Asn Arg Tyr Asn Ser Asp Ser Arg Tyr Met Ser Ser Tyr Asp Trp
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Synthesized CDR3
```

<400> SEQUENCE: 270

His Arg Thr Ile Ala Thr Ile Pro Glu Lys Tyr Glu Tyr Glu Tyr
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 271

His Arg Thr Ile Ala Thr Ile Pro Asn Lys Tyr Glu Tyr Asp His
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 272

Ala Leu Gly Ala Val Val Tyr Thr Thr Arg Glu Pro Tyr Thr Tyr
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 273

His Arg Thr Ile Ala Thr Val Pro Asn Lys Tyr Glu Tyr Asp Thr
1               5                   10                  15

<210> SEQ ID NO 274
<211> LENGTH: 12
<212> TYPE: PRT
<213> ORGANISM: Artificial Sequence
<220> FEATURE:
<223> OTHER INFORMATION: Synthesized CDR3

<400> SEQUENCE: 274

Asp Phe Arg Asp Trp Thr Arg Arg Tyr Ser Tyr
1               5                   10

<210> SEQ ID NO 275
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 275

Gly Thr Asp Leu Ser Tyr Tyr Tyr Ser Thr Lys Lys Trp Ala Tyr
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Synthesized CDR3

```
<400> SEQUENCE: 276

His Arg Gly Ala Ile Ala Pro Ile Ala Gln Ser Val Tyr Thr Asn
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 277

His Arg Gly Ala Ile Ala Pro Ile Ala Gln Ser Val Tyr Thr Asn
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 278

His Arg Gly Ala Ile Ala Pro Ile Ala Gln Ser Val Tyr Thr Asn
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 279

His Arg Gly Ala Ile Ala Pro Ile Ala Gln Ser Val Tyr Thr Asn
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 280

His Arg Gly Ala Ile Ala Pro Ile Ala Gln Ser Val Tyr Thr Asn
1               5                   10                  15

<210> SEQ ID NO 281
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 281

His Arg Gly Ala Ile Ala Pro Ile Ala Gln Ser Val Tyr Thr Asn
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 282
```

His Arg Gly Ala Ile Ala Pro Ile Ala Gln Ser Val Tyr Thr Asn
1               5                   10                  15

<210> SEQ ID NO 283
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 283

His Arg Gly Ala Ile Ala Pro Ile Ala Gln Ser Val Tyr Thr Asn
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 284

His Arg Thr Ile Ala Thr Ile Pro Glu Lys Tyr Glu Tyr Glu Tyr
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 285

His Arg Thr Ile Ala Thr Ile Pro Glu Lys Tyr Glu Tyr Glu Tyr
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 286

His Arg Thr Ile Ala Thr Ile Pro Glu Lys Tyr Glu Tyr Glu Tyr
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 287

His Arg Thr Ile Ala Thr Ile Pro Glu Lys Tyr Glu Tyr Glu Tyr
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 288

His Arg Thr Ile Ala Thr Ile Pro Glu Lys Tyr Glu Tyr Glu Tyr
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 289

Ala Leu Gly Ala Val Val Tyr Thr Thr Arg Glu Pro Tyr Thr Tyr
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 290

Ala Leu Gly Ala Val Val Tyr Thr Thr Arg Glu Pro Tyr Thr Tyr
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 291

Ala Leu Gly Ala Val Val Tyr Thr Thr Arg Glu Pro Tyr Thr Tyr
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 292

Ala Leu Gly Ala Val Val Tyr Thr Thr Arg Glu Pro Tyr Thr Tyr
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 293

Ala Leu Gly Ala Val Val Tyr Thr Thr Arg Glu Pro Tyr Thr Tyr
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 294

Ala Leu Gly Ala Val Val Tyr Thr Thr Arg Glu Pro Tyr Thr Tyr

```
1               5                  10                  15

<210> SEQ ID NO 295
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 295

Ala Leu Gly Ala Val Val Tyr Thr Thr Arg Glu Pro Tyr Thr Tyr
1               5                  10                  15

<210> SEQ ID NO 296
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 296

Ala Leu Gly Ala Val Val Tyr Thr Thr Arg Glu Pro Tyr Thr Tyr
1               5                  10                  15

<210> SEQ ID NO 297
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 297

Ala Leu Gly Ala Val Val Tyr Thr Thr Arg Glu Pro Tyr Thr Tyr
1               5                  10                  15

<210> SEQ ID NO 298
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 298

His Arg Thr Ile Ala Thr Ile Pro Glu Lys Tyr Glu Tyr Glu Tyr
1               5                  10                  15

<210> SEQ ID NO 299
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 299

His Thr Thr Ile Ala Thr Ile Pro Glu Lys Tyr Glu Tyr Glu Tyr
1               5                  10                  15

<210> SEQ ID NO 300
<211> LENGTH: 15
<212> TYPE: PRT
<213> ORGANISM: Artificial Sequence
<220> FEATURE:
<223> OTHER INFORMATION: Synthesized CDR3

<400> SEQUENCE: 300

His Arg Thr Ile Ala Thr Ile Pro Glu Lys Tyr Glu Tyr Glu Tyr
1               5                  10                  15
```

<210> SEQ ID NO 301
<211> LENGTH: 11
<212> TYPE: PRT
<213> ORGANISM: Artificial Sequence
<220> FEATURE:
<223> OTHER INFORMATION: Synthesized FR4

<400> SEQUENCE: 301

Trp Gly Gln Gly Thr Gln Val Thr Val Ser Ser
1               5                   10

<210> SEQ ID NO 302
<211> LENGTH: 11
<212> TYPE: PRT
<213> ORGANISM: Artificial Sequence
<220> FEATURE:
<223> OTHER INFORMATION: Synthesized FR4

<400> SEQUENCE: 302

Trp Gly Gln Gly Thr Gln Val Thr Val Ser Ser
1               5                   10

<210> SEQ ID NO 303
<211> LENGTH: 11
<212> TYPE: PRT
<213> ORGANISM: Artificial Sequence
<220> FEATURE:
<223> OTHER INFORMATION: Synthesized FR4

<400> SEQUENCE: 303

Trp Gly Gln Gly Thr Gln Val Thr Val Ser Ser
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Synthesized FR4

<400> SEQUENCE: 304

Trp Gly Gln Gly Thr Gln Val Thr Val Ser Ser
1               5                   10

<210> SEQ ID NO 305
<211> LENGTH: 11
<212> TYPE: PRT
<213> ORGANISM: Artificial Sequence
<220> FEATURE:
<223> OTHER INFORMATION: Synthesized FR4

<400> SEQUENCE: 305

Trp Gly Gln Gly Thr Gln Val Thr Val Ser Ser
1               5                   10

<210> SEQ ID NO 306
<211> LENGTH: 11
<212> TYPE: PRT
<213> ORGANISM: Artificial Sequence
<220> FEATURE:
<223> OTHER INFORMATION: Synthesized FR4

<400> SEQUENCE: 306

Trp Gly Gln Gly Thr Gln Val Thr Val Ser Ser
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Synthesized FR4

<400> SEQUENCE: 307

Trp Gly Gln Gly Thr Gln Val Thr Val Ser Ser
1               5                   10

<210> SEQ ID NO 308
<211> LENGTH: 11
<212> TYPE: PRT
<213> ORGANISM: Artificial Sequence
<220> FEATURE:
<223> OTHER INFORMATION: Synthesized FR4

<400> SEQUENCE: 308

Trp Gly Gln Gly Thr Gln Val Thr Val Ser Ser
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Synthesized FR4

<400> SEQUENCE: 309

Trp Gly Gln Gly Thr Gln Val Thr Val Ser Ser
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Synthesized FR4

<400> SEQUENCE: 310

Trp Gly Gln Gly Thr Gln Val Thr Val Ser Ser
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Synthesized FR4

<400> SEQUENCE: 311

Trp Gly Gln Gly Thr Gln Val Thr Val Ser Ser
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Synthesized FR4

<400> SEQUENCE: 312

Trp Gly Gln Gly Thr Gln Val Thr Val Ser Ser
1               5                   10

```
<210> SEQ ID NO 313
<211> LENGTH: 11
<212> TYPE: PRT
<213> ORGANISM: Artificial Sequence
<220> FEATURE:
<223> OTHER INFORMATION: Synthesized FR4

<400> SEQUENCE: 313

Trp Gly Gln Gly Thr Gln Val Thr Val Ser Ser
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthesized FR4

<400> SEQUENCE: 314

Trp Gly Gln Gly Thr Gln Val Thr Val Ser Ser
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Synthesized FR4

<400> SEQUENCE: 315

Trp Gly Arg Gly Thr Gln Val Thr Val Ser Ser
1               5                   10

<210> SEQ ID NO 316
<211> LENGTH: 11
<212> TYPE: PRT
<213> ORGANISM: Artificial Sequence
<220> FEATURE:
<223> OTHER INFORMATION: Synthesized FR4

<400> SEQUENCE: 316

Trp Gly Gln Gly Thr Gln Val Thr Val Ser Ser
1               5                   10

<210> SEQ ID NO 317
<211> LENGTH: 11
<212> TYPE: PRT
<213> ORGANISM: Artificial Sequence
<220> FEATURE:
<223> OTHER INFORMATION: Synthesized FR4

<400> SEQUENCE: 317

Trp Gly Gln Gly Thr Gln Val Thr Val Ser Ser
1               5                   10

<210> SEQ ID NO 318
<211> LENGTH: 11
<212> TYPE: PRT
<213> ORGANISM: Artificial Sequence
<220> FEATURE:
<223> OTHER INFORMATION: Synthesized FR4

<400> SEQUENCE: 318

Trp Gly Gln Gly Thr Gln Val Thr Val Ser Ser
1               5                   10

<210> SEQ ID NO 319
```

```
<211> LENGTH: 11
<212> TYPE: PRT
<213> ORGANISM: Artificial Sequence
<220> FEATURE:
<223> OTHER INFORMATION: Synthesized FR4

<400> SEQUENCE: 319

Trp Gly Gln Gly Thr Gln Val Thr Val Ser Ser
1               5                   10

<210> SEQ ID NO 320
<211> LENGTH: 11
<212> TYPE: PRT
<213> ORGANISM: Artificial Sequence
<220> FEATURE:
<223> OTHER INFORMATION: Synthesized FR4

<400> SEQUENCE: 320

Trp Gly Gln Gly Thr Gln Val Thr Val Ser Ser
1               5                   10

<210> SEQ ID NO 321
<211> LENGTH: 11
<212> TYPE: PRT
<213> ORGANISM: Artificial Sequence
<220> FEATURE:
<223> OTHER INFORMATION: Synthesized FR4

<400> SEQUENCE: 321

Trp Gly Gln Gly Thr Gln Val Thr Val Ser Ser
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Synthesized FR4

<400> SEQUENCE: 322

Trp Gly Arg Gly Thr Gln Val Thr Val Ser Ser
1               5                   10

<210> SEQ ID NO 323
<211> LENGTH: 11
<212> TYPE: PRT
<213> ORGANISM: Artificial Sequence
<220> FEATURE:
<223> OTHER INFORMATION: Synthesized FR4

<400> SEQUENCE: 323

Trp Gly Gln Gly Thr Gln Val Thr Val Ser Ser
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Synthesized FR4

<400> SEQUENCE: 324

Trp Gly Gln Gly Thr Gln Val Thr Val Ser Ser
1               5                   10

<210> SEQ ID NO 325
<211> LENGTH: 11
```

```
<212> TYPE: PRT
<213> ORGANISM: Artificial Sequence
<220> FEATURE:
<223> OTHER INFORMATION: Synthesized FR4

<400> SEQUENCE: 325

Trp Gly Gln Gly Thr Gln Val Thr Val Ser Ser
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Synthesized FR4

<400> SEQUENCE: 326

Trp Gly Gln Gly Thr Gln Val Thr Val Ser Ser
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Synthesized FR4

<400> SEQUENCE: 327

Trp Gly Gln Gly Thr Gln Val Thr Val Ser Ser
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Synthesized FR4

<400> SEQUENCE: 328

Trp Gly Gln Gly Thr Leu Val Thr Val Ser Ser
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Synthesized FR4

<400> SEQUENCE: 329

Trp Gly Gln Gly Thr Leu Val Thr Val Ser Ser
1               5                   10

<210> SEQ ID NO 330
<211> LENGTH: 11
<212> TYPE: PRT
<213> ORGANISM: Artificial Sequence
<220> FEATURE:
<223> OTHER INFORMATION: Synthesized FR4

<400> SEQUENCE: 330

Trp Gly Gln Gly Thr Leu Val Thr Val Ser Ser
1               5                   10

<210> SEQ ID NO 331
<211> LENGTH: 11
<212> TYPE: PRT
```

<213> ORGANISM: Artificial Sequence
<220> FEATURE:
<223> OTHER INFORMATION: Synthesized FR4

<400> SEQUENCE: 331

Trp Gly Gln Gly Thr Leu Val Thr Val Ser Ser
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Synthesized FR4

<400> SEQUENCE: 332

Trp Gly Gln Gly Thr Leu Val Thr Val Ser Ser
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Synthesized FR4

<400> SEQUENCE: 333

Trp Gly Gln Gly Thr Leu Val Thr Val Ser Ser
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Synthesized FR4

<400> SEQUENCE: 334

Trp Gly Gln Gly Thr Leu Val Thr Val Ser Ser
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Synthesized FR4

<400> SEQUENCE: 335

Trp Gly Gln Gly Thr Leu Val Thr Val Ser Ser
1               5                   10

<210> SEQ ID NO 336
<211> LENGTH: 11
<212> TYPE: PRT
<213> ORGANISM: Artificial Sequence
<220> FEATURE:
<223> OTHER INFORMATION: Synthesized FR4

<400> SEQUENCE: 336

Trp Gly Gln Gly Thr Leu Val Thr Val Ser Ser
1               5                   10

<210> SEQ ID NO 337
<211> LENGTH: 11
<212> TYPE: PRT
<213> ORGANISM: Artificial Sequence

```
<220> FEATURE:
<223> OTHER INFORMATION: Synthesized FR4

<400> SEQUENCE: 337

Trp Gly Gln Gly Thr Leu Val Thr Val Ser Ser
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Synthesized FR4

<400> SEQUENCE: 338

Trp Gly Gln Gly Thr Leu Val Thr Val Ser Ser
1               5                   10

<210> SEQ ID NO 339
<211> LENGTH: 11
<212> TYPE: PRT
<213> ORGANISM: Artificial Sequence
<220> FEATURE:
<223> OTHER INFORMATION: Synthesized FR4

<400> SEQUENCE: 339

Trp Gly Arg Gly Thr Gln Val Thr Val Ser Ser
1               5                   10

<210> SEQ ID NO 340
<211> LENGTH: 11
<212> TYPE: PRT
<213> ORGANISM: Artificial Sequence
<220> FEATURE:
<223> OTHER INFORMATION: Synthesized FR4

<400> SEQUENCE: 340

Trp Gly Arg Gly Thr Gln Val Thr Val Ser Ser
1               5                   10

<210> SEQ ID NO 341
<211> LENGTH: 11
<212> TYPE: PRT
<213> ORGANISM: Artificial Sequence
<220> FEATURE:
<223> OTHER INFORMATION: Synthesized FR4

<400> SEQUENCE: 341

Trp Gly Arg Gly Thr Gln Val Thr Val Ser Ser
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Synthesized FR4

<400> SEQUENCE: 342

Trp Gly Gln Gly Thr Leu Val Thr Val Ser Ser
1               5                   10

<210> SEQ ID NO 343
<211> LENGTH: 11
<212> TYPE: PRT
<213> ORGANISM: Artificial Sequence
<220> FEATURE:
```

<223> OTHER INFORMATION: Synthesized FR4

<400> SEQUENCE: 343

Trp Gly Gln Gly Thr Leu Val Thr Val Ser Ser
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Synthesized FR4

<400> SEQUENCE: 344

Trp Gly Gln Gly Thr Leu Val Thr Val Ser Ser
1               5                   10

<210> SEQ ID NO 345
<211> LENGTH: 11
<212> TYPE: PRT
<213> ORGANISM: Artificial Sequence
<220> FEATURE:
<223> OTHER INFORMATION: Synthesized FR4

<400> SEQUENCE: 345

Trp Gly Gln Gly Thr Leu Val Thr Val Ser Ser
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Synthesized FR4

<400> SEQUENCE: 346

Trp Gly Gln Gly Thr Leu Val Thr Val Ser Ser
1               5                   10

<210> SEQ ID NO 347
<211> LENGTH: 11
<212> TYPE: PRT
<213> ORGANISM: Artificial Sequence
<220> FEATURE:
<223> OTHER INFORMATION: Synthesized FR4

<400> SEQUENCE: 347

Trp Gly Gln Gly Thr Leu Val Thr Val Ser Ser
1               5                   10

<210> SEQ ID NO 348
<211> LENGTH: 11
<212> TYPE: PRT
<213> ORGANISM: Artificial Sequence
<220> FEATURE:
<223> OTHER INFORMATION: Synthesized FR4

<400> SEQUENCE: 348

Trp Gly Gln Gly Thr Leu Val Thr Val Ser Ser
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Synthesized FR4

<400> SEQUENCE: 349

Trp Gly Gln Gly Thr Leu Val Thr Val Ser Ser
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Synthesized FR4

<400> SEQUENCE: 350

Trp Gly Gln Gly Thr Leu Val Thr Val Ser Ser
1               5                   10

<210> SEQ ID NO 351
<211> LENGTH: 124
<212> TYPE: PRT
<213> ORGANISM: Artificial Sequence
<220> FEATURE:
<223> OTHER INFORMATION: AS06617 synthesized sdAb

<400> SEQUENCE: 351

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ile Ser Tyr
            20                  25                  30

Ala Val Gly Trp Phe Arg Gln Ala Pro Gly Ser Glu Arg Glu Phe Val
        35                  40                  45

Ala Gly Ile Arg Trp Asn Gly Ile His Thr Asp Tyr Ala Asp Ser Val
    50                  55                  60

Lys Gly Arg Phe Thr Ile Ser Arg Asp Asn Ala Lys Asn Thr Val Thr
65                  70                  75                  80

Leu Glu Met Thr Ser Leu Lys Pro Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Gln Val Thr Val Ser Ser
        115                 120

<210> SEQ ID NO 352
<211> LENGTH: 124
<212> TYPE: PRT
<213> ORGANISM: Artificial Sequence
<220> FEATURE:
<223> OTHER INFORMATION: AS06618 synthesized sdAb

<400> SEQUENCE: 352

Glu Val Gln Leu Val Glu Ser Gly Gly Arg Leu Val Arg Ala Gly Asp
1               5                   10                  15

Ser Leu Arg Leu Ser Cys Ala Ala Ser Gly Arg Thr Phe Leu Ser Tyr
            20                  25                  30

Ala Val Gly Trp Phe Arg Gln Ala Pro Gly Thr Glu Arg Glu Phe Val
        35                  40                  45

Ala Gly Ile Arg Trp Ser Gly Tyr Thr Asp Tyr Ala Glu Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys 85                  90                  95
Ala Ala His Arg Thr Ile Ala Thr Ile Pro Glu Lys Tyr Glu Tyr Glu
                100                 105                 110

Tyr Trp Gly Gln Gly Thr Gln Val Thr Val Ser Ser
        115                 120

<210> SEQ ID NO 353
<211> LENGTH: 124
<212> TYPE: PRT
<213> ORGANISM: Artificial Sequence
<220> FEATURE:
<223> OTHER INFORMATION: AS06624 synthesized sdAb

<400> SEQUENCE: 353

Gln Val Gln Leu Val Glu Ser Gly Gly Gly Leu Val Gln Ala Gly Gly
1               5                   10                  15

Ser Leu Arg Leu Ala Cys Ser Ala Ser Gly Arg Thr Phe Leu Thr Tyr
            20                  25                  30

Ala Leu Gly Trp Phe Arg Gln Ala Pro Gly Lys Glu Arg Glu Phe Val
        35                  40                  45

Ala Gly Val Ser Trp Ser Gly Ser Gly Thr Lys Tyr Ala Asp Ser Val
    50                  55                  60

Lys Gly Arg Phe Thr Ile Ser Arg Asp Asn Ala Lys Asn Thr Val Tyr
65                  70                  75                  80

Met Gln Met Asn Ser Leu Lys Pro Glu Asp Thr Ala Val Tyr Tyr Cys
                85                  90                  95

Ala Ala Gln Ile Ser Ala Ile Val Pro Ile Ser Ala His Glu Tyr Glu
                100                 105                 110

Tyr Trp Gly Gln Gly Thr Gln Val Thr Val Ser Ser
        115                 120

<210> SEQ ID NO 354
<211> LENGTH: 124
<212> TYPE: PRT
<213> ORGANISM: Artificial Sequence
<220> FEATURE:
<223> OTHER INFORMATION: AS06628 synthesized sdAb

<400> SEQUENCE: 354

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Glu Arg Glu Phe Val
        35                  40                  45

Thr Ala Ile Asn Trp Ser Gly Ser Met Thr Ser Tyr Ala Asp Ser Val
    50                  55                  60

Lys Gly Arg Phe Thr Ile Ser Arg Asp Asn Asn Lys Asn Met Val Tyr
65                  70                  75                  80

Leu Gln Met Asn Ser Leu Lys Pro Glu Asp Thr Ala Val Tyr Tyr Cys
                85                  90                  95

Ala Ala His Arg Gly Ala Ile Ala Pro Met Thr Gln Ser Val Tyr Asp
                100                 105                 110

Tyr Trp Gly Gln Gly Thr Gln Val Thr Val Ser Ser
        115                 120

<210> SEQ ID NO 355
<211> LENGTH: 124

```
<212> TYPE: PRT
<213> ORGANISM: Artificial Sequence
<220> FEATURE:
<223> OTHER INFORMATION: AS06639 synthesized sdAb

<400> SEQUENCE: 355

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Glu Arg Glu Phe Val
        35                  40                  45

Ser Ala Ile Asn Trp Ser Gly Ser Met Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Ala His Arg Gly Ala Ile Ala Pro Met Thr Gln Ser Val Tyr Asp
            100                 105                 110

Thr Trp Gly Gln Gly Thr Gln Val Thr Val Ser Ser
        115                 120

<210> SEQ ID NO 356
<211> LENGTH: 124
<212> TYPE: PRT
<213> ORGANISM: Artificial Sequence
<220> FEATURE:
<223> OTHER INFORMATION: AS06682 synthesized sdAb

<400> SEQUENCE: 356

Ala Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Leu Ser Tyr
            20                  25                  30

Ala Val Gly Trp Phe Arg Gln Ala Pro Gly Thr Glu Arg Glu Phe Val
        35                  40                  45

Ala Gly Ile Arg Trp Ser Gly Glu His Thr Asp Tyr Ala Ala Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ile Ala Thr Ile Pro Lys Lys Tyr Glu Tyr Glu
            100                 105                 110

Tyr Trp Gly Gln Gly Thr Gln Val Thr Val Ser Ser
        115                 120

<210> SEQ ID NO 357
<211> LENGTH: 124
<212> TYPE: PRT
<213> ORGANISM: Artificial Sequence
<220> FEATURE:
<223> OTHER INFORMATION: AS06686 synthesized sdAb

<400> SEQUENCE: 357

Ala Val Gln Leu Val Glu Ser Gly Gly Gly Leu Val Gln Ala Gly Asp
1               5                   10                  15

Ser Leu Arg Leu Ala Cys Ala Ala Ser Gly Arg Thr Phe Leu Thr Tyr
```

```
                    20                  25                  30

Ala Leu Gly Trp Phe Arg Gln Ala Pro Gly Lys Glu Arg Glu Phe Val
            35                  40                  45

Ala Gly Val Ser Trp Ser Gly Ser Thr Lys Tyr Ala Asp Ser Val
        50                  55                  60

Lys Gly Arg Phe Thr Ile Ser Arg Asp Asn Ala Lys Asn Thr Val Tyr
 65                  70                  75                  80

Met Gln Met Asn Ser Leu Lys Pro Glu Asp Thr Ala Val Tyr Tyr Cys
                85                  90                  95

Ala Ala Gln Ile Ser Ala Ile Val Pro Ile Ser Ala His Glu Tyr Gln
            100                 105                 110

Tyr Trp Gly Gln Gly Thr Gln Val Thr Val Ser Ser
            115                 120
```

```
<210> SEQ ID NO 358
<211> LENGTH: 124
<212> TYPE: PRT
<213> ORGANISM: Artificial Sequence
<220> FEATURE:
<223> OTHER INFORMATION: AS06703 synthesized sdAb

<400> SEQUENCE: 358

Glu Val Gln Leu Val Glu Ser Gly Gly Gly Leu Val Arg Ala Gly Gly
 1               5                  10                  15

Ser Leu Arg Leu Ser Cys Ala Ala Ser Gly Arg Thr Phe Ile Thr Tyr
                20                  25                  30

Ala Ile Gly Trp Phe Arg Gln Ala Pro Gly Lys Glu Arg Glu Phe Val
            35                  40                  45

Thr Ala Ile Asn Trp Ser Gly Ser Met Thr Ser Tyr Ala Asp Ser Val
        50                  55                  60

Lys Gly Arg Phe Thr Ile Ser Arg Asp Asn Asn Lys Asn Thr Val Tyr
 65                  70                  75                  80

Leu Gln Met Asn Ser Leu Lys Pro Glu Asp Thr Ala Leu Tyr Tyr Cys
                85                  90                  95

Ala Ala His Leu Gly Ala Ile Ala Pro Met Ser Gln Ser Val Tyr Asp
            100                 105                 110

Tyr Trp Gly Gln Gly Thr Gln Val Thr Val Ser Ser
            115                 120
```

```
<210> SEQ ID NO 359
<211> LENGTH: 124
<212> TYPE: PRT
<213> ORGANISM: Artificial Sequence
<220> FEATURE:
<223> OTHER INFORMATION: AS06709 synthesized sdAb

<400> SEQUENCE: 359

Glu Val Gln Leu Val Glu Ser Gly Gly Gly Leu Val Gln Ala Gly Asp
 1               5                  10                  15

Ser Leu Arg Leu Ser Cys Thr Ala Ser Gly Arg Thr Phe Leu Ser Tyr
                20                  25                  30

Ala Val Gly Trp Phe Arg Gln Ala Pro Gly Thr Glu Arg Glu Phe Val
            35                  40                  45

Ala Gly Ile Arg Trp Ser Gly Gly Ser Thr Asp Tyr Ser Asp Ser Val
        50                  55                  60

Lys Gly Arg Phe Thr Ile Ser Arg Asp Asn Ala Lys Asn Thr Val Tyr
 65                  70                  75                  80
```

```
Leu Gln Met Asn Ser Leu Lys Pro Glu Asp Thr Ala Val Tyr Tyr Cys
                 85                  90                  95

Ala Ala His Arg Thr Ile Ala Thr Ile Pro Glu Lys Tyr Glu Tyr Glu
            100                 105                 110

Tyr Trp Gly Gln Gly Thr Gln Val Thr Val Ser Ser
        115                 120

<210> SEQ ID NO 360
<211> LENGTH: 124
<212> TYPE: PRT
<213> ORGANISM: Artificial Sequence
<220> FEATURE:
<223> OTHER INFORMATION: AS06730 synthesized sdAb

<400> SEQUENCE: 360

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Glu Arg Glu Phe Val
        35                  40                  45

Ser Ala Ile Asn Trp Ser Gly Ser Met Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Gln Val Thr Val Ser Ser
        115                 120

<210> SEQ ID NO 361
<211> LENGTH: 124
<212> TYPE: PRT
<213> ORGANISM: Artificial Sequence
<220> FEATURE:
<223> OTHER INFORMATION: AS06750 synthesized sdAb

<400> SEQUENCE: 361

Ala Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Leu Thr Tyr
            20                  25                  30

Ala Val Gly Trp Phe Arg Gln Ala Pro Gly Thr Glu Arg Glu Phe Val
        35                  40                  45

Ala Gly Ile Arg Trp Ser Gly Gly Tyr Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Gln Val Thr Val Ser Ser
        115                 120

<210> SEQ ID NO 362
```

-continued

```
<211> LENGTH: 124
<212> TYPE: PRT
<213> ORGANISM: Artificial Sequence
<220> FEATURE:
<223> OTHER INFORMATION: AS06752 synthesized sdAb

<400> SEQUENCE: 362

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Leu Thr Tyr
            20                  25                  30

Ala Val Gly Trp Phe Arg Gln Ala Pro Gly Thr Glu Arg Glu Phe Val
        35                  40                  45

Ala Gly Ile Arg Trp Ser Gly Glu Ser Thr Asp Tyr Ala Glu Ser Val
    50                  55                  60

Lys Gly Arg Phe Thr Ile Ser Arg Asp Asp Thr Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Arg Thr Ile Ala Thr Ile Pro Glu Lys Tyr Tyr Tyr Glu
            100                 105                 110

Tyr Trp Gly Gln Gly Thr Gln Val Thr Val Ser Ser
        115                 120

<210> SEQ ID NO 363
<211> LENGTH: 127
<212> TYPE: PRT
<213> ORGANISM: Artificial Sequence
<220> FEATURE:
<223> OTHER INFORMATION: AS06763 synthesized sdAb

<400> SEQUENCE: 363

Gln Val Gln Leu Val Glu Ser Gly Gly Gly Leu Val Gln Ala Gly Gly
1               5                   10                  15

Ser Leu Arg Leu Ser Cys Ala Val Ser Gly Arg Pro Val Ser Ser Ala
            20                  25                  30

Val Met Gly Trp Phe Arg Gln Ala Pro Gly Lys Glu Arg Glu Phe Val
        35                  40                  45

Gly Arg Leu Thr Ser Ser Ala Thr Ser Thr Phe Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Asp Val Pro Gly Thr Lys Ile Trp Ser Ile Gln Thr Pro Asp
            100                 105                 110

Arg Tyr Asn Tyr Trp Gly Gln Gly Thr Gln Val Thr Val Ser Ser
        115                 120                 125

<210> SEQ ID NO 364
<211> LENGTH: 119
<212> TYPE: PRT
<213> ORGANISM: Artificial Sequence
<220> FEATURE:
<223> OTHER INFORMATION: AS06766 synthesized sdAb

<400> SEQUENCE: 364

Glu Val Gln Leu Val Glu Ser Gly Gly Gly Leu Val Gln Ala Gly Gly
1               5                   10                  15
```

Ser Leu Ser Leu Ser Cys Ala Val Ser Gly Arg Thr Leu Thr Gly Leu
            20                  25                  30

Leu Ile Gly Trp Phe Arg Gln Ala Pro Gly Lys Glu Arg Glu Leu Val
        35                  40                  45

Ala Ile Ile Ser Trp Thr Tyr Gly Ser Thr Asn Tyr Ala Asp Ser Val
    50                  55                  60

Lys Gly Arg Phe Thr Ile Ser Arg Asp Asn Ala Lys Asn Thr Val Leu
65                  70                  75                  80

Leu Gln Met Asn Ser Leu Lys Pro Glu Asp Thr Ala Val Tyr Tyr Cys
                85                  90                  95

Ser Ala Arg Asp Val Ala Val Ala Lys Tyr Asp Ser Trp Gly Gln Gly
                100                 105                 110

Thr Gln Val Thr Val Ser Ser
            115

<210> SEQ ID NO 365
<211> LENGTH: 124
<212> TYPE: PRT
<213> ORGANISM: Artificial Sequence
<220> FEATURE:
<223> OTHER INFORMATION: AS06775 synthesized sdAb

<400> SEQUENCE: 365

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Leu Thr Leu
            20                  25                  30

Ala Val Gly Trp Phe Arg Gln Ala Pro Gly Thr Glu Arg Glu Phe Val
        35                  40                  45

Ala Gly Ile Arg Trp Ser Gly Ser Gly Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ile Ala Thr Ile Pro Glu Lys Tyr Glu Tyr Glu
                100                 105                 110

Tyr Trp Gly Arg Gly Thr Gln Val Thr Val Ser Ser
            115                 120

<210> SEQ ID NO 366
<211> LENGTH: 126
<212> TYPE: PRT
<213> ORGANISM: Artificial Sequence
<220> FEATURE:
<223> OTHER INFORMATION: AS06778 synthesized sdAb

<400> SEQUENCE: 366

Gln Val Gln Leu Val Glu Ser Gly Gly Gly Leu Val Gln Ala Gly Gly
1               5                   10                  15

Ser Leu Lys Leu Ser Cys Ala Ala Ser Gly Arg Thr Phe Ile Thr Tyr
            20                  25                  30

Ala Met Gly Trp Phe Arg Gln Ala Pro Gly Lys Glu Arg Glu Leu Val
        35                  40                  45

Ala Ala Ile Ser Trp Ser Gly Ser Ser Thr Tyr Ser Ala Asp Ser Val
    50                  55                  60

Lys Gly Arg Phe Thr Ile Ser Arg Asp Asn Ala Lys Asn Thr Val Tyr
65                  70                  75                  80

-continued

```
Leu Gln Met Asn Ser Leu Lys Pro Glu Asp Thr Ala Val Tyr Tyr Cys
                85                  90                  95

Ala Ala Glu Val Ser Ala Arg Thr Gly Glu His Leu Pro Lys Leu Met
            100                 105                 110

Gly Asp Tyr Trp Gly Gln Gly Thr Gln Val Thr Val Ser Ser
        115                 120                 125
```

<210> SEQ ID NO 367
<211> LENGTH: 124
<212> TYPE: PRT
<213> ORGANISM: Artificial Sequence
<220> FEATURE:
<223> OTHER INFORMATION: AS06786 synthesized sdAb

<400> SEQUENCE: 367

```
Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Leu Thr Leu
            20                  25                  30

Ala Val Gly Trp Phe Arg Gln Ala Pro Gly Thr Glu Arg Glu Phe Val
        35                  40                  45

Ala Gly Ile Arg Trp Ser Gly Ser Gly Thr Asp Tyr Ala Asp Ser Val
    50                  55                  60

Lys Gly Arg Phe Thr Ile Ser Arg Asp Asn Ala Ala Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ile Ala Thr Ile Pro Glu Lys Tyr Glu Tyr Glu
            100                 105                 110

Tyr Trp Gly Gln Gly Thr Gln Val Thr Val Ser Ser
        115                 120
```

<210> SEQ ID NO 368
<211> LENGTH: 124
<212> TYPE: PRT
<213> ORGANISM: Artificial Sequence
<220> FEATURE:
<223> OTHER INFORMATION: AS06791 synthesized sdAb

<400> SEQUENCE: 368

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Glu Arg Glu Phe Val
        35                  40                  45

Thr Ala Ile Asn Trp Ser Gly Ser Met Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Ile Asn Gly Leu Lys Ser Glu Asp Thr Ala Val Tyr Tyr Cys
                85                  90                  95

Ala Ala His Arg Gly Ala Ile Ala Pro Met Thr Gln Ser Val Tyr Asp
            100                 105                 110

Tyr Trp Gly Gln Gly Thr Gln Val Thr Val Ser Ser
        115                 120
```

<210> SEQ ID NO 369
<211> LENGTH: 124
<212> TYPE: PRT
<213> ORGANISM: Artificial Sequence
<220> FEATURE:
<223> OTHER INFORMATION: AS06808 synthesized sdAb

<400> SEQUENCE: 369

```
Gln Val Lys Leu Glu Glu Ser Gly Gly Gly Leu Val Gln Ala Gly Gly
1               5                   10                  15

Ser Leu Arg Leu Ser Cys Val Ala Ser Gly Arg Thr Phe Ser Arg Tyr
            20                  25                  30

Ala Met Gly Trp Phe Arg Gln Ala Pro Gly Lys Glu Arg Glu Phe Val
        35                  40                  45

Ser Thr Ser Thr Gly Ser Gly Gly Leu Thr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Ile Tyr Tyr Cys
                85                  90                  95

Ala Ala Asn Arg Tyr Asn Ser Asp Ser Arg Tyr Met Ser Ser Tyr Asp
            100                 105                 110

Trp Trp Gly Gln Gly Thr Gln Val Thr Val Ser Ser
        115                 120
```

<210> SEQ ID NO 370
<211> LENGTH: 124
<212> TYPE: PRT
<213> ORGANISM: Artificial Sequence
<220> FEATURE:
<223> OTHER INFORMATION: AS06810 synthesized sdAb

<400> SEQUENCE: 370

```
Ala Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Leu Ser Tyr
            20                  25                  30

Ala Val Gly Trp Phe Arg Gln Ala Pro Gly Thr Glu Arg Glu Phe Val
        35                  40                  45

Ala Gly Ile Arg Trp Ser Gly Leu His Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Gln Val Thr Val Ser Ser
        115                 120
```

<210> SEQ ID NO 371
<211> LENGTH: 124
<212> TYPE: PRT
<213> ORGANISM: Artificial Sequence
<220> FEATURE:
<223> OTHER INFORMATION: AS11947 synthesized sdAb

<400> SEQUENCE: 371

```
Asp Val Gln Leu Val Glu Ser Gly Gly Gly Leu Val Gln Ala Gly Asp
1               5                   10                  15
```

-continued

Ser Leu Arg Leu Thr Cys Ser Ala Ser Gly Arg Thr Phe Ile Ser Tyr
            20                  25                  30

Ala Val Gly Trp Phe Arg Gln Ala Pro Gly Thr Glu Arg Glu Phe Val
            35                  40                  45

Ala Gly Ile Arg Trp Asn Gly Ile Ser Thr Asp Tyr Thr Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala His Arg Thr Ile Ala Thr Ile Pro Asn Lys Tyr Glu Tyr Asp
            100                 105                 110

His Trp Gly Gln Gly Thr Gln Val Thr Val Ser Ser
        115                 120

<210> SEQ ID NO 372
<211> LENGTH: 124
<212> TYPE: PRT
<213> ORGANISM: Artificial Sequence
<220> FEATURE:
<223> OTHER INFORMATION: AS11948 synthesized sdAb

<400> SEQUENCE: 372

Glu Val Gln Leu Val Glu Ser Gly Gly Gly Leu Val Gln Ala Gly Asp
1               5                   10                  15

Ser Leu Arg Leu Ser Cys Val Ala Ser Gly Arg Thr Phe Val Thr Tyr
            20                  25                  30

Gly Met Gly Trp Phe Arg Gln Ala Pro Gly Lys Glu Arg Glu Phe Val
            35                  40                  45

Ala Ala Ile Asn Trp Ser Gly Ser Met Thr Ser Tyr Gly Asp Ser Val
        50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Arg Gly Thr Gln Val Thr Val Ser Ser
        115                 120

<210> SEQ ID NO 373
<211> LENGTH: 124
<212> TYPE: PRT
<213> ORGANISM: Artificial Sequence
<220> FEATURE:
<223> OTHER INFORMATION: AS12003 synthesized sdAb

<400> SEQUENCE: 373

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Leu Ser Tyr
            20                  25                  30

Ala Val Gly Trp Phe Arg Gln Ala Pro Gly Thr Glu Arg Glu Phe Val
            35                  40                  45

Ala Gly Ile Arg Trp Ser Gly Gly Ser Thr Asp Tyr Ala Asp Ser Val
        50                  55                  60

Lys Gly Arg Phe Thr Ile Ser Arg Asp Asn Ala Lys Asn Thr Val Tyr

```
                65                  70                  75                  80
Leu Gln Met Asn Ser Leu Lys Pro Glu Asp Thr Ala Val Tyr Tyr Cys
                    85                  90                  95

Ala Ala His Arg Thr Ile Ala Thr Val Pro Asn Lys Tyr Glu Tyr Asp
                100                 105                 110

Thr Trp Gly Gln Gly Thr Gln Val Thr Val Ser Ser
            115                 120

<210> SEQ ID NO 374
<211> LENGTH: 120
<212> TYPE: PRT
<213> ORGANISM: Artificial Sequence
<220> FEATURE:
<223> OTHER INFORMATION: AL22863 synthesized sdAb

<400> SEQUENCE: 374

Gln Val Lys Leu Glu Glu Ser Gly Gly Gly Leu Val Gln Val Gly Asp
1               5                   10                  15

Ser Leu Arg Leu Ser Cys Ala Ala Ser Val Ser Ser Phe Ser Ile Asn
                20                  25                  30

Asp Met Gly Trp Tyr Arg Gln Ala Pro Gly Lys Gln Arg Glu Leu Val
            35                  40                  45

Ala Thr Ile Ala Ser Gly Gly Ser Thr Asn Tyr Ala Asp Ser Val Lys
        50                  55                  60

Gly Arg Phe Thr Ile Ser Arg Asp Asn Val Lys Asn Thr Val Tyr Leu
65                  70                  75                  80

Gln Met Asn Gly Leu Lys Pro Glu Asp Thr Ala Val Tyr Tyr Cys Asn
                85                  90                  95

Ala Asp Phe Arg Asp Trp Thr Arg Arg Arg Tyr Ser Tyr Trp Gly Gln
                100                 105                 110

Gly Thr Gln Val Thr Val Ser Ser
            115                 120

<210> SEQ ID NO 375
<211> LENGTH: 124
<212> TYPE: PRT
<213> ORGANISM: Artificial Sequence
<220> FEATURE:
<223> OTHER INFORMATION: AL23474 synthesized sdAb

<400> SEQUENCE: 375

Gln Val Lys Leu Glu Glu Ser Gly Gly Gly Leu Val Gln Val Gly Asp
1               5                   10                  15

Ser Leu Arg Leu Ser Cys Ala Ala Ser Gly Arg Thr Phe Ser Asn Tyr
                20                  25                  30

Thr Met Ala Trp Phe Arg Gln Phe Pro Gly Lys Glu Arg Glu Phe Val
            35                  40                  45

Ala Val Val Ser Arg Gly Gly Gly Ala Thr Asp Tyr Ala Asp Ser Val
        50                  55                  60

Lys Gly Arg Phe Thr Ile Ser Arg Asp Asn Ala Lys Asn Thr Met Tyr
65                  70                  75                  80

Leu Gln Met Asn Ser Leu Lys Thr Glu Asp Thr Ala Val Tyr Tyr Cys
                85                  90                  95

Ala Ala Gly Thr Asp Leu Ser Tyr Tyr Tyr Ser Thr Lys Lys Trp Ala
                100                 105                 110

Tyr Trp Gly Gln Gly Thr Gln Val Thr Val Ser Ser
            115                 120
```

<210> SEQ ID NO 376
<211> LENGTH: 124
<212> TYPE: PRT
<213> ORGANISM: Artificial Sequence
<220> FEATURE:
<223> OTHER INFORMATION: AS06730S synthesized sdAb

<400> SEQUENCE: 376

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Glu Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Gln Val Thr Val Ser Ser
        115                 120
```

<210> SEQ ID NO 377
<211> LENGTH: 124
<212> TYPE: PRT
<213> ORGANISM: Artificial Sequence
<220> FEATURE:
<223> OTHER INFORMATION: AS06730Q synthesized sdAb

<400> SEQUENCE: 377

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Glu Arg Glu Phe Val
        35                  40                  45

Ser Ala Ile Gln Trp Ser Gly Ser Met Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Gln Val Thr Val Ser Ser
        115                 120
```

<210> SEQ ID NO 378
<211> LENGTH: 124
<212> TYPE: PRT
<213> ORGANISM: Artificial Sequence
<220> FEATURE:
<223> OTHER INFORMATION: AS06730QVH1 synthesized sdAb

<400> SEQUENCE: 378

```
Glu Val Gln Leu Val Glu Ser Gly Gly Gly Leu Val Gln Pro Gly Gly
```

```
  1               5                  10                  15
Ser Leu Arg Leu Ser Cys Ala Ala Ser Gly Arg Thr Phe Ile Thr Tyr
            20                  25                  30

Ala Ile Gly Trp Val Arg Gln Ala Pro Gly Lys Gly Leu Glu Trp Val
        35                  40                  45

Ser Ala Ile Gln Trp Ser Gly Ser Met Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys His Arg Gly Ala Ile Ala Pro Ile Ala Gln Ser Val Tyr Thr
            100                 105                 110

Asn Trp Gly Gln Gly Thr Leu Val Thr Val Ser Ser
            115                 120
```

<210> SEQ ID NO 379
<211> LENGTH: 124
<212> TYPE: PRT
<213> ORGANISM: Artificial Sequence
<220> FEATURE:
<223> OTHER INFORMATION: AS06730QVH2 synthesized sdAb

<400> SEQUENCE: 379

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Leu Glu Trp Val
        35                  40                  45

Ser Ala Ile Gln Trp Ser Gly Ser Met Thr Ser Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
            85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser
            115                 120
```

<210> SEQ ID NO 380
<211> LENGTH: 124
<212> TYPE: PRT
<213> ORGANISM: Artificial Sequence
<220> FEATURE:
<223> OTHER INFORMATION: AS06730QVH3a synthesized sdAb

<400> SEQUENCE: 380

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Leu Glu Phe Val
        35                  40                  45

Ser Ala Ile Gln Trp Ser Gly Ser Met Thr Ser Tyr Ala Asp Ser Val
    50                  55                  60
```

```
Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser
        115                 120
```

<210> SEQ ID NO 381
<211> LENGTH: 124
<212> TYPE: PRT
<213> ORGANISM: Artificial Sequence
<220> FEATURE:
<223> OTHER INFORMATION: AS06730SVH12 synthesized sdAb

<400> SEQUENCE: 381

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ile Thr Tyr
             20                  25                  30

Ala Ile Gly Trp Phe Arg Gln Ala Pro Gly Lys Gly Arg Glu Phe Val
         35                  40                  45

Ser Ala Ile Ser Trp Ser Gly Ser Met Thr Ser Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser
        115                 120
```

<210> SEQ ID NO 382
<211> LENGTH: 124
<212> TYPE: PRT
<213> ORGANISM: Artificial Sequence
<220> FEATURE:
<223> OTHER INFORMATION: AS06730SVH12M8 synthesized sdAb

<400> SEQUENCE: 382

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ile Thr Tyr
             20                  25                  30

Ala Ile Gly Trp Phe Arg Gln Ala Pro Gly Lys Gly Arg Glu Phe Val
         35                  40                  45

Ser Ala Ile Ser Trp Ser Gly Ser Ile Thr Ser Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser
        115                 120
```

<210> SEQ ID NO 383
<211> LENGTH: 124
<212> TYPE: PRT
<213> ORGANISM: Artificial Sequence
<220> FEATURE:
<223> OTHER INFORMATION: AS06730SVH12M9 synthesized sdAb

<400> SEQUENCE: 383

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Leu Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser
        115                 120

<210> SEQ ID NO 384
<211> LENGTH: 124
<212> TYPE: PRT
<213> ORGANISM: Artificial Sequence
<220> FEATURE:
<223> OTHER INFORMATION: AS06750VH1 synthesized sdAb

<400> SEQUENCE: 384

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
            20                  25                  30

Ala Val Gly Trp Val Arg Gln Ala Pro Gly Lys Gly Leu Glu Trp Val
        35                  40                  45

Ser Gly Ile Arg Trp Ser Gly Gly Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Arg Thr Ile Ala Thr Ile Pro Glu Lys Tyr Glu Tyr Glu
            100                 105                 110

Tyr Trp Gly Gln Gly Thr Leu Val Thr Val Ser Ser
        115                 120

<210> SEQ ID NO 385
<211> LENGTH: 124
<212> TYPE: PRT
<213> ORGANISM: Artificial Sequence
<220> FEATURE:
<223> OTHER INFORMATION: AS06750VH2 synthesized sdAb

<400> SEQUENCE: 385

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
            20                  25                  30

Ala Val Gly Trp Phe Arg Gln Ala Pro Gly Lys Gly Leu Glu Trp Val
        35                  40                  45

Ala Gly Ile Arg Trp Ser Gly Gly Tyr Thr Asp Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser
            115                 120

<210> SEQ ID NO 386
<211> LENGTH: 124
<212> TYPE: PRT
<213> ORGANISM: Artificial Sequence
<220> FEATURE:
<223> OTHER INFORMATION: AS06750VH3 synthesized sdAb

<400> SEQUENCE: 386

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
            20                  25                  30

Ala Val Gly Trp Phe Arg Gln Ala Pro Gly Lys Gly Leu Glu Phe Val
        35                  40                  45

Ala Gly Ile Arg Trp Ser Gly Gly Tyr Thr Asp Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser
            115                 120

<210> SEQ ID NO 387
<211> LENGTH: 124
<212> TYPE: PRT
<213> ORGANISM: Artificial Sequence
<220> FEATURE:
<223> OTHER INFORMATION: AS06750VHa synthesized sdAb

<400> SEQUENCE: 387

Glu Val Gln Leu Val Glu Ser Gly Gly Gly Leu Val Gln Pro Gly Gly
1               5                   10                  15

Ser Leu Arg Leu Ser Cys Thr Ala Ser Gly Arg Thr Phe Leu Thr Tyr
            20                  25                  30

Ala Val Gly Trp Phe Arg Gln Ala Pro Gly Lys Gly Leu Glu Phe Val
        35                  40                  45

Ala Gly Ile Arg Trp Ser Gly Gly Tyr Thr Asp Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser
        115                 120

<210> SEQ ID NO 388
<211> LENGTH: 124
<212> TYPE: PRT
<213> ORGANISM: Artificial Sequence
<220> FEATURE:
<223> OTHER INFORMATION: AS06750VH11 synthesized sdAb

<400> SEQUENCE: 388

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
                20                  25                  30

Ala Val Gly Trp Phe Arg Gln Ala Pro Gly Lys Gly Arg Glu Phe Val
            35                  40                  45

Ser Gly Ile Arg Trp Ser Gly Tyr Thr Asp Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser
        115                 120

<210> SEQ ID NO 389
<211> LENGTH: 124
<212> TYPE: PRT
<213> ORGANISM: Artificial Sequence
<220> FEATURE:
<223> OTHER INFORMATION: AS11948A synthesized sdAb

<400> SEQUENCE: 389

Glu Val Gln Leu Val Glu Ser Gly Gly Gly Leu Val Gln Ala Gly Asp
1               5                   10                  15

Ser Leu Arg Leu Ser Cys Val Ala Ser Gly Arg Thr Phe Val Thr Tyr
                20                  25                  30

Gly Met Gly Trp Phe Arg Gln Ala Pro Gly Lys Glu Arg Glu Phe Val
            35                  40                  45

Ala Ala Ile Ala Trp Ser Gly Ser Met Thr Ser Tyr Gly Asp Ser Val
        50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Arg Gly Thr Gln Val Thr Val Ser Ser

<210> SEQ ID NO 390
<211> LENGTH: 124
<212> TYPE: PRT
<213> ORGANISM: Artificial Sequence
<220> FEATURE:
<223> OTHER INFORMATION: AS11948S synthesized sdAb

<400> SEQUENCE: 390

Glu Val Gln Leu Val Glu Ser Gly Gly Gly Leu Val Gln Ala Gly Asp
1               5                   10                  15

Ser Leu Arg Leu Ser Cys Val Ala Ser Gly Arg Thr Phe Val Thr Tyr
            20                  25                  30

Gly Met Gly Trp Phe Arg Gln Ala Pro Gly Lys Glu Arg Glu Phe Val
        35                  40                  45

Ala Ala Ile Ser Trp Ser Gly Ser Met Thr Ser Tyr Gly Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Arg Gly Thr Gln Val Thr Val Ser Ser
        115                 120

<210> SEQ ID NO 391
<211> LENGTH: 124
<212> TYPE: PRT
<213> ORGANISM: Artificial Sequence
<220> FEATURE:
<223> OTHER INFORMATION: AS11948Q synthesized sdAb

<400> SEQUENCE: 391

Glu Val Gln Leu Val Glu Ser Gly Gly Gly Leu Val Gln Ala Gly Asp
1               5                   10                  15

Ser Leu Arg Leu Ser Cys Val Ala Ser Gly Arg Thr Phe Val Thr Tyr
            20                  25                  30

Gly Met Gly Trp Phe Arg Gln Ala Pro Gly Lys Glu Arg Glu Phe Val
        35                  40                  45

Ala Ala Ile Gln Trp Ser Gly Ser Met Thr Ser Tyr Gly Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Arg Gly Thr Gln Val Thr Val Ser Ser
        115                 120

<210> SEQ ID NO 392
<211> LENGTH: 124
<212> TYPE: PRT
<213> ORGANISM: Artificial Sequence
<220> FEATURE:
<223> OTHER INFORMATION: AS11948QVH1 synthesized sdAb

<400> SEQUENCE: 392

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Val Arg Gln Ala Pro Gly Lys Gly Leu Glu Trp Val
        35                  40                  45

Ser Ala Ile Gln Trp Ser Gly Ser Met Thr Ser Tyr Gly Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Leu Gly Ala Val Val Tyr Thr Thr Arg Glu Pro Tyr Thr
                100                 105                 110

Tyr Trp Gly Gln Gly Thr Leu Val Thr Val Ser Ser
            115                 120

<210> SEQ ID NO 393
<211> LENGTH: 124
<212> TYPE: PRT
<213> ORGANISM: Artificial Sequence
<220> FEATURE:
<223> OTHER INFORMATION: AS11948QVH2 synthesized sdAb

<400> SEQUENCE: 393

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Leu Glu Phe Val
        35                  40                  45

Ala Ala Ile Gln Trp Ser Gly Ser Met Thr Ser Tyr Gly Asp Ser Val
50                      55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Ala Leu Gly Ala Val Val Tyr Thr Thr Arg Glu Pro Tyr Thr
                100                 105                 110

Tyr Trp Gly Gln Gly Thr Leu Val Thr Val Ser Ser
            115                 120

<210> SEQ ID NO 394
<211> LENGTH: 124
<212> TYPE: PRT
<213> ORGANISM: Artificial Sequence
<220> FEATURE:
<223> OTHER INFORMATION: AS11948QVHa synthesized sdAb

<400> SEQUENCE: 394

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Gln Trp Ser Gly Ser Met Thr Ser Tyr Gly Asp Ser Val

```
                50                  55                  60
Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110

Tyr Trp Gly Gln Gly Thr Leu Val Thr Val Ser Ser
                115                 120

<210> SEQ ID NO 395
<211> LENGTH: 124
<212> TYPE: PRT
<213> ORGANISM: Artificial Sequence
<220> FEATURE:
<223> OTHER INFORMATION: AS11948SVH12 synthesized sdAb

<400> SEQUENCE: 395

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Val Thr Tyr
                 20                  25                  30

Gly Met Gly Trp Phe Arg Gln Ala Pro Gly Lys Gly Arg Glu Phe Val
                 35                  40                  45

Ser Ala Ile Ser Trp Ser Gly Ser Met Thr Ser Tyr Gly Asp Ser Val
                 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110

Tyr Trp Gly Gln Gly Thr Leu Val Thr Val Ser Ser
                115                 120

<210> SEQ ID NO 396
<211> LENGTH: 124
<212> TYPE: PRT
<213> ORGANISM: Artificial Sequence
<220> FEATURE:
<223> OTHER INFORMATION: AS11948SVH12M8 synthesized sdAb

<400> SEQUENCE: 396

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Val Thr Tyr
                 20                  25                  30

Gly Met Gly Trp Phe Arg Gln Ala Pro Gly Lys Gly Arg Glu Phe Val
                 35                  40                  45

Ser Ala Ile Ser Trp Ser Gly Ser Ile Thr Ser Tyr Gly Asp Ser Val
                 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110
```

Tyr Trp Gly Gln Gly Thr Leu Val Thr Val Ser Ser
            115                 120

<210> SEQ ID NO 397
<211> LENGTH: 124
<212> TYPE: PRT
<213> ORGANISM: Artificial Sequence
<220> FEATURE:
<223> OTHER INFORMATION: AS11948SVH12M9 synthesized sdAb

<400> SEQUENCE: 397

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Leu Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser
            115                 120

<210> SEQ ID NO 398
<211> LENGTH: 124
<212> TYPE: PRT
<213> ORGANISM: Artificial Sequence
<220> FEATURE:
<223> OTHER INFORMATION: AS06617VH11 synthesized sdAb

<400> SEQUENCE: 398

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Ser Tyr
            20                  25                  30

Ala Val Gly Trp Phe Arg Gln Ala Pro Gly Lys Gly Arg Glu Phe Val
        35                  40                  45

Ser Gly Ile Arg Trp Ser Gly Ile His Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser
            115                 120

<210> SEQ ID NO 399
<211> LENGTH: 124
<212> TYPE: PRT
<213> ORGANISM: Artificial Sequence
<220> FEATURE:
<223> OTHER INFORMATION: AS06775VH11 synthesized sdAb

<400> SEQUENCE: 399

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Leu
            20                  25                  30

Ala Val Gly Trp Phe Arg Gln Ala Pro Gly Lys Gly Arg Glu Phe Val
        35                  40                  45

Ser Gly Ile Arg Trp Ser Gly Ser Gly Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Thr Thr Ile Ala Thr Ile Pro Glu Lys Tyr Glu Tyr Glu
            100                 105                 110

Tyr Trp Gly Gln Gly Thr Leu Val Thr Val Ser Ser
            115                 120

<210> SEQ ID NO 400
<211> LENGTH: 124
<212> TYPE: PRT
<213> ORGANISM: Artificial Sequence
<220> FEATURE:
<223> OTHER INFORMATION: AS06775VH4 synthesized sdAb

<400> SEQUENCE: 400

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
            20                  25                  30

Ala Val Gly Trp Phe Arg Gln Ala Pro Gly Lys Gly Leu Glu Phe Val
        35                  40                  45

Ser Gly Ile Arg Trp Ser Gly Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser
            115                 120

<210> SEQ ID NO 401
<211> LENGTH: 356
<212> TYPE: PRT
<213> ORGANISM: Artificial Sequence
<220> FEATURE:
<223> OTHER INFORMATION: AS06617 synthesized HCAb

<400> SEQUENCE: 401

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ile Ser Tyr
            20                  25                  30

Ala Val Gly Trp Phe Arg Gln Ala Pro Gly Ser Glu Arg Glu Phe Val
        35                  40                  45

```
Ala Gly Ile Arg Trp Asn Gly Ile His Thr Asp Tyr Ala Asp Ser Val
 50                  55                  60
Lys Gly Arg Phe Thr Ile Ser Arg Asp Asn Ala Lys Asn Thr Val Thr
 65                  70                  75                  80
Leu Glu Met Thr Ser Leu Lys Pro Glu Asp Thr Ala Val Tyr Tyr Cys
                 85                  90                  95
Ala Ala His Arg Thr Ile Ala Thr Ile Pro Glu Lys Tyr Glu Tyr Glu
            100                 105                 110
Tyr Trp Gly Gln Gly Thr Gln Val Thr Val Ser Ser Glu Pro Lys Ser
            115                 120                 125
Cys Asp Lys Thr His Thr Cys Pro Pro Cys Pro Ala Pro Glu Leu Leu
130                 135                 140
Gly Gly Pro Ser Val Phe Leu Phe Pro Pro Lys Pro Lys Asp Thr Leu
145                 150                 155                 160
Met Ile Ser Arg Thr Pro Glu Val Thr Cys Val Val Val Asp Val Ser
                165                 170                 175
His Glu Asp Pro Glu Val Lys Phe Asn Trp Tyr Val Asp Gly Val Glu
            180                 185                 190
Val His Asn Ala Lys Thr Lys Pro Arg Glu Glu Gln Tyr Asn Ser Thr
            195                 200                 205
Tyr Arg Val Val Ser Val Leu Thr Val Leu His Gln Asp Trp Leu Asn
210                 215                 220
Gly Lys Glu Tyr Lys Cys Lys Val Ser Asn Lys Ala Leu Pro Ala Pro
225                 230                 235                 240
Ile Glu Lys Thr Ile Ser Lys Ala Lys Gly Gln Pro Arg Glu Pro Gln
                245                 250                 255
Val Tyr Thr Leu Pro Pro Ser Arg Asp Glu Leu Thr Lys Asn Gln Val
            260                 265                 270
Ser Leu Thr Cys Leu Val Lys Gly Phe Tyr Pro Ser Asp Ile Ala Val
            275                 280                 285
Glu Trp Glu Ser Asn Gly Gln Pro Glu Asn Asn Tyr Lys Thr Thr Pro
290                 295                 300
Pro Val Leu Asp Ser Asp Gly Ser Phe Phe Leu Tyr Ser Lys Leu Thr
305                 310                 315                 320
Val Asp Lys Ser Arg Trp Gln Gln Gly Asn Val Phe Ser Cys Ser Val
                325                 330                 335
Met His Glu Ala Leu His Asn His Tyr Thr Gln Lys Ser Leu Ser Leu
            340                 345                 350
Ser Pro Gly Lys
            355
```

<210> SEQ ID NO 402
<211> LENGTH: 356
<212> TYPE: PRT
<213> ORGANISM: Artificial Sequence
<220> FEATURE:
<223> OTHER INFORMATION: AS06617VH11 synthesized HCAb

<400> SEQUENCE: 402

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Arg Thr Phe Ile Ser Tyr
                 20                  25                  30
Ala Val Gly Trp Phe Arg Gln Ala Pro Gly Lys Gly Arg Glu Phe Val
             35                  40                  45
```

Ser Gly Ile Arg Trp Ser Gly Ile His Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 403
<211> LENGTH: 356
<212> TYPE: PRT
<213> ORGANISM: Artificial Sequence
<220> FEATURE:
<223> OTHER INFORMATION: AS06618 synthesized HCAb

<400> SEQUENCE: 403

Glu Val Gln Leu Val Glu Ser Gly Gly Arg Leu Val Arg Ala Gly Asp
1               5                   10                  15

Ser Leu Arg Leu Ser Cys Ala Ala Ser Gly Arg Thr Phe Leu Ser Tyr
            20                  25                  30

Ala Val Gly Trp Phe Arg Gln Ala Pro Gly Thr Glu Arg Glu Phe Val
        35                  40                  45

Ala Gly Ile Arg Trp Ser Gly Gly Tyr Thr Asp Tyr Ala Glu Ala Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala His Arg Thr Ile Ala Thr Ile Pro Glu Lys Tyr Glu Tyr Glu
            100                 105                 110

Tyr Trp Gly Gln Gly Thr Gln Val Thr Val Ser Ser Glu Pro Lys Ser
        115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 404
<211> LENGTH: 356
<212> TYPE: PRT
<213> ORGANISM: Artificial Sequence
<220> FEATURE:
<223> OTHER INFORMATION: AS06628 synthesized HCAb

<400> SEQUENCE: 404

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Glu Arg Glu Phe Val
        35                  40                  45

Thr Ala Ile Asn Trp Ser Gly Ser Met Thr Ser Tyr Ala Asp Ser Val
 50                  55                  60

Lys Gly Arg Phe Thr Ile Ser Arg Asp Asn Lys Asn Met Val Tyr
 65                  70                  75                  80

Leu Gln Met Asn Ser Leu Lys Pro Glu Asp Thr Ala Val Tyr Tyr Cys
                 85                  90                  95

Ala Ala His Arg Gly Ala Ile Ala Pro Met Thr Gln Ser Val Tyr Asp
             100                 105                 110

Tyr Trp Gly Gln Gly Thr Gln Val Thr Val Ser Ser Glu Pro Lys Ser
             115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
             180                 185                 190

Val His Asn Ala Lys Thr Lys Pro Arg Glu Glu Gln Tyr Asn Ser Thr
             195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
             260                 265                 270

Ser Leu Thr Cys Leu Val Lys Gly Phe Tyr Pro Ser Asp Ile Ala Val
             275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
             340                 345                 350

Ser Pro Gly Lys
        355

<210> SEQ ID NO 405
<211> LENGTH: 356
<212> TYPE: PRT
<213> ORGANISM: Artificial Sequence
<220> FEATURE:
<223> OTHER INFORMATION: AS06682 synthesized HCAb

<400> SEQUENCE: 405

Ala Val Gln Leu Val Glu Ser Gly Gly Gly Leu Val Gln Ala Gly Asp
1                5                  10                  15

Ser Leu Arg Leu Ser Cys Thr Ala Ser Gly Arg Thr Phe Leu Ser Tyr
                 20                  25                  30

Ala Val Gly Trp Phe Arg Gln Ala Pro Gly Thr Glu Arg Glu Phe Val
             35                  40                  45

```
Ala Gly Ile Arg Trp Ser Gly Glu His Thr Asp Tyr Ala Ala Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala His Thr Thr Ile Ala Thr Ile Pro Lys Lys Tyr Glu Tyr Glu
            100                 105                 110

Tyr Trp Gly Gln Gly Thr Gln Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 406
<211> LENGTH: 356
<212> TYPE: PRT
<213> ORGANISM: Artificial Sequence
<220> FEATURE:
<223> OTHER INFORMATION: AS06686 synthesized HCAb

<400> SEQUENCE: 406

Ala Val Gln Leu Val Glu Ser Gly Gly Gly Leu Val Gln Ala Gly Asp
 1               5                  10                  15

Ser Leu Arg Leu Ala Cys Ala Ala Ser Gly Arg Thr Phe Leu Thr Tyr
                 20                  25                  30

Ala Leu Gly Trp Phe Arg Gln Ala Pro Gly Lys Glu Arg Glu Phe Val
             35                  40                  45
```

```
Ala Gly Val Ser Trp Ser Gly Ser Ser Thr Lys Tyr Ala Asp Ser Val
 50                  55                  60

Lys Gly Arg Phe Thr Ile Ser Arg Asp Asn Ala Lys Asn Thr Val Tyr
 65                  70                  75                  80

Met Gln Met Asn Ser Leu Lys Pro Glu Asp Thr Ala Val Tyr Tyr Cys
                 85                  90                  95

Ala Ala Gln Ile Ser Ala Ile Val Pro Ile Ser Ala His Glu Tyr Gln
            100                 105                 110

Tyr Trp Gly Gln Gly Thr Gln Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 407
<211> LENGTH: 356
<212> TYPE: PRT
<213> ORGANISM: Artificial Sequence
<220> FEATURE:
<223> OTHER INFORMATION: AS06703 synthesized HCAb

<400> SEQUENCE: 407

Glu Val Gln Leu Val Glu Ser Gly Gly Gly Leu Val Arg Ala Gly Gly
 1               5                  10                  15

Ser Leu Arg Leu Ser Cys Ala Ala Ser Gly Arg Thr Phe Ile Thr Tyr
                 20                  25                  30

Ala Ile Gly Trp Phe Arg Gln Ala Pro Gly Lys Glu Arg Glu Phe Val
             35                  40                  45
```

Thr Ala Ile Asn Trp Ser Gly Ser Met Thr Ser Tyr Ala Asp Ser Val
            50                  55                  60

Lys Gly Arg Phe Thr Ile Ser Arg Asp Asn Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala His Leu Gly Ala Ile Ala Pro Met Ser Gln Ser Val Tyr Asp
             100                 105                 110

Tyr Trp Gly Gln Gly Thr Gln Val Thr Val Ser Ser Glu Pro Lys Ser
             115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 408
<211> LENGTH: 356
<212> TYPE: PRT
<213> ORGANISM: Artificial Sequence
<220> FEATURE:
<223> OTHER INFORMATION: AS06730 synthesized HCAb

<400> SEQUENCE: 408

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
                20                  25                  30

Ala Ile Gly Trp Phe Arg Gln Ala Pro Gly Lys Glu Arg Glu Phe Val
            35                  40                  45

Ser Ala Ile Asn Trp Ser Gly Ser Met Thr Ser Tyr Ala Asp Ser Val
    50                  55                  60

Lys Gly Arg Phe Thr Ile Ser Arg Asp Asn Ala Lys Asn Thr Val Tyr
 65                  70                  75                  80

Leu Gln Met Asn Gly Leu Lys Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Gln Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
            290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 409
<211> LENGTH: 356
<212> TYPE: PRT
<213> ORGANISM: Artificial Sequence
<220> FEATURE:
<223> OTHER INFORMATION: AS06750 synthesized HCAb

<400> SEQUENCE: 409

Ala Val Gln Leu Val Glu Ser Gly Gly Gly Leu Val Gln Ala Gly Asp
 1               5                  10                  15

Ser Leu Arg Leu Ser Cys Thr Ala Ser Gly Arg Thr Phe Leu Thr Tyr
                20                  25                  30

Ala Val Gly Trp Phe Arg Gln Ala Pro Gly Thr Glu Arg Glu Phe Val
            35                  40                  45

```
Ala Gly Ile Arg Trp Ser Gly Gly Tyr Thr Asp Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala His Arg Thr Ile Ala Thr Ile Pro Glu Lys Tyr Glu Tyr Glu
            100                 105                 110

Tyr Trp Gly Gln Gly Thr Gln Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 410
<211> LENGTH: 356
<212> TYPE: PRT
<213> ORGANISM: Artificial Sequence
<220> FEATURE:
<223> OTHER INFORMATION: AS06775 synthesized HCAb

<400> SEQUENCE: 410

Gln Val Gln Leu Val Glu Ser Gly Gly Gly Leu Val Gln Ala Gly Asp
 1               5                  10                  15

Ser Leu Arg Leu Ser Cys Ala Ala Ser Gly Arg Thr Phe Leu Thr Leu
                 20                  25                  30

Ala Val Gly Trp Phe Arg Gln Ala Pro Gly Thr Glu Arg Glu Phe Val
             35                  40                  45
```

Ala Gly Ile Arg Trp Ser Gly Ser Gly Thr Asp Tyr Ala Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala His Thr Thr Ile Ala Thr Ile Pro Glu Lys Tyr Glu Tyr Glu
                100                 105                 110

Tyr Trp Gly Arg Gly Thr Gln Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 411
<211> LENGTH: 356
<212> TYPE: PRT
<213> ORGANISM: Artificial Sequence
<220> FEATURE:
<223> OTHER INFORMATION: AS06775VH4 synthesized HCAb

<400> SEQUENCE: 411

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Leu Thr Leu
                20                  25                  30

Ala Val Gly Trp Phe Arg Gln Ala Pro Gly Lys Gly Arg Glu Phe Val
            35                  40                  45

```
Ser Gly Ile Arg Trp Ser Gly Ser Gly Thr Asp Tyr Ala Asp Ser Val
    50              55              60

Lys Gly Arg Phe Thr Ile Ser Arg Asp Asn Ala Lys Asn Thr Leu Tyr
65              70              75              80

Leu Gln Met Asn Ser Leu Arg Pro Glu Asp Thr Ala Val Tyr Tyr Cys
                85              90              95

Ala Ala His Thr Thr Ile Ala Thr Ile Pro Glu Lys Tyr Glu Tyr Glu
            100             105             110

Tyr Trp Gly Gln Gly Thr Leu Val Thr Val Ser Ser Glu Pro Lys Ser
            115             120             125

Cys Asp Lys Thr His Thr Cys Pro Pro Cys Pro Ala Pro Glu Leu Leu
130             135             140

Gly Gly Pro Ser Val Phe Leu Phe Pro Pro Lys Pro Lys Asp Thr Leu
145             150             155             160

Met Ile Ser Arg Thr Pro Glu Val Thr Cys Val Val Val Asp Val Ser
                165             170             175

His Glu Asp Pro Glu Val Lys Phe Asn Trp Tyr Val Asp Gly Val Glu
            180             185             190

Val His Asn Ala Lys Thr Lys Pro Arg Glu Glu Gln Tyr Asn Ser Thr
            195             200             205

Tyr Arg Val Val Ser Val Leu Thr Val Leu His Gln Asp Trp Leu Asn
210             215             220

Gly Lys Glu Tyr Lys Cys Lys Val Ser Asn Lys Ala Leu Pro Ala Pro
225             230             235             240

Ile Glu Lys Thr Ile Ser Lys Ala Lys Gly Gln Pro Arg Glu Pro Gln
                245             250             255

Val Tyr Thr Leu Pro Pro Ser Arg Asp Glu Leu Thr Lys Asn Gln Val
            260             265             270

Ser Leu Thr Cys Leu Val Lys Gly Phe Tyr Pro Ser Asp Ile Ala Val
            275             280             285

Glu Trp Glu Ser Asn Gly Gln Pro Glu Asn Asn Tyr Lys Thr Thr Pro
290             295             300

Pro Val Leu Asp Ser Asp Gly Ser Phe Phe Leu Tyr Ser Lys Leu Thr
305             310             315             320

Val Asp Lys Ser Arg Trp Gln Gln Gly Asn Val Phe Ser Cys Ser Val
                325             330             335

Met His Glu Ala Leu His Asn His Tyr Thr Gln Lys Ser Leu Ser Leu
            340             345             350

Ser Pro Gly Lys
        355

<210> SEQ ID NO 412
<211> LENGTH: 356
<212> TYPE: PRT
<213> ORGANISM: Artificial Sequence
<220> FEATURE:
<223> OTHER INFORMATION: AS06775VH11 synthesized HCAb

<400> SEQUENCE: 412

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
                20                  25                  30

Ala Val Gly Trp Phe Arg Gln Ala Pro Gly Lys Gly Leu Glu Phe Val
            35                  40                  45
```

Ser Gly Ile Arg Trp Ser Gly Gly Tyr Thr Asp Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 413
<211> LENGTH: 358
<212> TYPE: PRT
<213> ORGANISM: Artificial Sequence
<220> FEATURE:
<223> OTHER INFORMATION: AS06778 synthesized HCAb

<400> SEQUENCE: 413

Gln Val Gln Leu Val Glu Ser Gly Gly Gly Leu Val Gln Ala Gly Gly
 1               5                  10                  15

Ser Leu Lys Leu Ser Cys Ala Ala Ser Gly Arg Thr Phe Ile Thr Tyr
                20                  25                  30

Ala Met Gly Trp Phe Arg Gln Ala Pro Gly Lys Glu Arg Glu Leu Val
            35                  40                  45

Ala Ala Ile Ser Trp Ser Gly Ser Thr Tyr Ser Ala Asp Ser Val
            50              55                  60

Lys Gly Arg Phe Thr Ile Ser Arg Asp Asn Ala Lys Asn Thr Val Tyr
 65              70                  75                  80

Leu Gln Met Asn Ser Leu Lys Pro Glu Asp Thr Ala Val Tyr Tyr Cys
                 85                  90                  95

Ala Ala Glu Val Ser Ala Arg Thr Gly Glu His Leu Pro Lys Leu Met
            100                 105                 110

Gly Asp Tyr Trp Gly Gln Gly Thr Gln Val Thr Val Ser Ser Glu Pro
            115                 120                 125

Lys Ser Cys Asp Lys Thr His Thr Cys Pro Pro Cys Pro Ala Pro Glu
130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
            195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
            290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys
            355

<210> SEQ ID NO 414
<211> LENGTH: 356
<212> TYPE: PRT
<213> ORGANISM: Artificial Sequence
<220> FEATURE:
<223> OTHER INFORMATION: AS06791 synthesized HCAb

<400> SEQUENCE: 414

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
                20                  25                  30

Ala Ile Gly Trp Phe Arg Gln Ala Pro Gly Lys Glu Arg Glu Phe Val
            35                  40                  45

Thr Ala Ile Asn Trp Ser Gly Ser Met Thr Ser Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Ile Asn Gly Leu Lys Ser Glu Asp Thr Ala Val Tyr Tyr Cys
                 85                  90                  95

Ala Ala His Arg Gly Ala Ile Ala Pro Met Thr Gln Ser Val Tyr Asp
                100                 105                 110

Tyr Trp Gly Gln Gly Thr Gln Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 415
<211> LENGTH: 356
<212> TYPE: PRT
<213> ORGANISM: Artificial Sequence
<220> FEATURE:
<223> OTHER INFORMATION: AS11947 synthesized HCAb

<400> SEQUENCE: 415

Asp Val Gln Leu Val Glu Ser Gly Gly Gly Leu Val Gln Ala Gly Asp
1               5                   10                  15

Ser Leu Arg Leu Thr Cys Ser Ala Ser Gly Arg Thr Phe Ile Ser Tyr
                20                  25                  30

Ala Val Gly Trp Phe Arg Gln Ala Pro Gly Thr Glu Arg Glu Phe Val
                35                  40                  45

Ala Gly Ile Arg Trp Asn Gly Ile Ser Thr Asp Tyr Thr Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Ile Tyr Tyr Cys
                 85                  90                  95

Ala Ala His Arg Thr Ile Ala Thr Ile Pro Asn Lys Tyr Glu Tyr Asp
                100                 105                 110

His Trp Gly Gln Gly Thr Gln Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 416
<211> LENGTH: 356
<212> TYPE: PRT
<213> ORGANISM: Artificial Sequence
<220> FEATURE:
<223> OTHER INFORMATION: AS11948 synthesized HCAb

<400> SEQUENCE: 416

Glu Val Gln Leu Val Glu Ser Gly Gly Gly Leu Val Gln Ala Gly Asp
 1               5                  10                  15

Ser Leu Arg Leu Ser Cys Val Ala Ser Gly Arg Thr Phe Val Thr Tyr
                 20                  25                  30

Gly Met Gly Trp Phe Arg Gln Ala Pro Gly Lys Glu Arg Glu Phe Val
             35                  40                  45

Ala Ala Ile Asn Trp Ser Gly Ser Met Thr Ser Tyr Gly Asp Ser Val
            50                  55                  60

Lys Gly Arg Phe Ala Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110

Tyr Trp Gly Arg Gly Thr Gln Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 417
<211> LENGTH: 356
<212> TYPE: PRT
<213> ORGANISM: Artificial Sequence
<220> FEATURE:
<223> OTHER INFORMATION: AS12003 synthesized HCAb

<400> SEQUENCE: 417

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Leu Ser Tyr
                20                  25                  30

Ala Val Gly Trp Phe Arg Gln Ala Pro Gly Thr Glu Arg Glu Phe Val
                35                  40                  45

Ala Gly Ile Arg Trp Ser Gly Gly Ser Thr Asp Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala His Arg Thr Ile Ala Thr Val Pro Asn Lys Tyr Glu Tyr Asp
                100                 105                 110

Thr Trp Gly Gln Gly Thr Gln Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 418
<211> LENGTH: 356
<212> TYPE: PRT
<213> ORGANISM: Artificial Sequence
<220> FEATURE:
<223> OTHER INFORMATION: AS06730A synthesized HCAb

<400> SEQUENCE: 418

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ile Thr Tyr
                 20                  25                  30

Ala Ile Gly Trp Phe Arg Gln Ala Pro Gly Lys Glu Arg Glu Phe Val
                 35                  40                  45

Ser Ala Ile Ala Trp Ser Gly Ser Met Thr Ser Tyr Ala Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Gly Leu Lys Pro Glu Asp Thr Ala Val Tyr Tyr Cys
                 85                  90                  95

Ala Ala His Arg Gly Ala Ile Ala Pro Ile Ala Gln Ser Val Tyr Thr
                100                 105                 110

Asn Trp Gly Gln Gly Thr Gln Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 419
<211> LENGTH: 356
<212> TYPE: PRT
<213> ORGANISM: Artificial Sequence
<220> FEATURE:
<223> OTHER INFORMATION: AS06730S synthesized HCAb

<400> SEQUENCE: 419

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ile Thr Tyr
                 20                  25                  30

Ala Ile Gly Trp Phe Arg Gln Ala Pro Gly Lys Glu Arg Glu Phe Val
                 35                  40                  45

```
Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Gln Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355
```

<210> SEQ ID NO 420
<211> LENGTH: 356
<212> TYPE: PRT
<213> ORGANISM: Artificial Sequence
<220> FEATURE:
<223> OTHER INFORMATION: AS06730Q synthesized HCAb

<400> SEQUENCE: 420

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ile Thr Tyr
                20                  25                  30

Ala Ile Gly Trp Phe Arg Gln Ala Pro Gly Lys Glu Arg Glu Phe Val
            35                  40                  45
```

Ser Ala Ile Gln Trp Ser Gly Ser Met Thr Ser Tyr Ala Asp Ser Val
          50                  55                  60

Lys Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Ala His Arg Gly Ala Ile Ala Pro Ile Ala Gln Ser Val Tyr Thr
                100                 105                 110

Asn Trp Gly Gln Gly Thr Gln Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 421
<211> LENGTH: 356
<212> TYPE: PRT
<213> ORGANISM: Artificial Sequence
<220> FEATURE:
<223> OTHER INFORMATION: AS06730QVH1 synthesized HCAb

<400> SEQUENCE: 421

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
                20                  25                  30

Ala Ile Gly Trp Val Arg Gln Ala Pro Gly Lys Gly Leu Glu Trp Val
                35                  40                  45

Ser Ala Ile Gln Trp Ser Gly Ser Met Thr Ser Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Arg Gly Ala Ile Ala Pro Ile Ala Gln Ser Val Tyr Thr
            100                 105                 110

Asn Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 422
<211> LENGTH: 356
<212> TYPE: PRT
<213> ORGANISM: Artificial Sequence
<220> FEATURE:
<223> OTHER INFORMATION: AS06730QVH2 synthesized HCAb

<400> SEQUENCE: 422

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ile Thr Tyr
                 20                  25                  30

Ala Ile Gly Trp Phe Arg Gln Ala Pro Gly Lys Gly Leu Glu Trp Val
            35                  40                  45

Ser Ala Ile Gln Trp Ser Gly Ser Met Thr Ser Tyr Ala Asp Ser Val
    50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala His Arg Gly Ala Ile Ala Pro Ile Ala Gln Ser Val Tyr Thr
                100                 105                 110

Asn Trp Gly Gln Gly Thr Leu Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 423
<211> LENGTH: 356
<212> TYPE: PRT
<213> ORGANISM: Artificial Sequence
<220> FEATURE:
<223> OTHER INFORMATION: AS06730QVH3a synthesized HCAb

<400> SEQUENCE: 423

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ile Thr Tyr
                20                  25                  30

Ala Ile Gly Trp Phe Arg Gln Ala Pro Gly Lys Gly Leu Glu Phe Val
                35                  40                  45

Ser Ala Ile Gln Trp Ser Gly Ser Met Thr Ser Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser Glu Pro Lys Ser
        115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 424
<211> LENGTH: 356
<212> TYPE: PRT
<213> ORGANISM: Artificial Sequence
<220> FEATURE:
<223> OTHER INFORMATION: AS06730SVH12 synthesized HCAb

<400> SEQUENCE: 424

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala His Arg Gly Ala Ile Ala Pro Ile Ala Gln Ser Val Tyr Thr
                100                 105                 110

Asn Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 425
<211> LENGTH: 356
<212> TYPE: PRT
<213> ORGANISM: Artificial Sequence
<220> FEATURE:
<223> OTHER INFORMATION: AS06730SVH12M8 synthesized HCAb

<400> SEQUENCE: 425

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Ile Thr Ser Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala His Arg Gly Ala Ile Ala Pro Ile Ala Gln Ser Val Tyr Thr
                100                 105                 110

Asn Trp Gly Gln Gly Thr Leu Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 426
<211> LENGTH: 356
<212> TYPE: PRT
<213> ORGANISM: Artificial Sequence
<220> FEATURE:
<223> OTHER INFORMATION: AS06730SVH12M9 synthesized HCAb

<400> SEQUENCE: 426

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ile Thr Tyr
                 20                  25                  30

Ala Ile Gly Trp Phe Arg Gln Ala Pro Gly Lys Gly Arg Glu Phe Val
                 35                  40                  45

```
Ser Ala Ile Ser Trp Ser Gly Ser Leu Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Ala His Arg Gly Ala Ile Ala Pro Ile Ala Gln Ser Val Tyr Thr
                100                 105                 110

Asn Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 427
<211> LENGTH: 356
<212> TYPE: PRT
<213> ORGANISM: Artificial Sequence
<220> FEATURE:
<223> OTHER INFORMATION: AS06750VH1 synthesized HCAb

<400> SEQUENCE: 427

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
            20                  25                  30

Ala Val Gly Trp Val Arg Gln Ala Pro Gly Lys Gly Leu Glu Trp Val
        35                  40                  45
```

Ser Gly Ile Arg Trp Ser Gly Gly Tyr Thr Asp Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Arg Thr Ile Ala Thr Ile Pro Glu Lys Tyr Glu Tyr Glu
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 428
<211> LENGTH: 356
<212> TYPE: PRT
<213> ORGANISM: Artificial Sequence
<220> FEATURE:
<223> OTHER INFORMATION: AS06750VH2 synthesized HCAb

<400> SEQUENCE: 428

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Leu Thr Tyr
                 20                  25                  30

Ala Val Gly Trp Phe Arg Gln Ala Pro Gly Lys Gly Leu Glu Trp Val
            35                  40                  45

```
Ala Gly Ile Arg Trp Ser Gly Gly Tyr Thr Asp Tyr Ala Asp Ser Val
    50              55                  60
Lys Gly Arg Phe Thr Ile Ser Arg Asp Asn Ser Lys Asn Thr Val Tyr
 65              70                  75                      80
Leu Gln Met Asn Ser Leu Arg Ala Glu Asp Thr Ala Val Tyr Tyr Cys
                 85                  90                  95
Ala Ala His Arg Thr Ile Ala Thr Ile Pro Glu Lys Tyr Glu Tyr Glu
            100                 105                 110
Tyr Trp Gly Gln Gly Thr Leu Val Thr Val Ser Ser Glu Pro Lys Ser
            115                 120                 125
Cys Asp Lys Thr His Thr Cys Pro Pro Cys Pro Ala Pro Glu Leu Leu
130                 135                 140
Gly Gly Pro Ser Val Phe Leu Phe Pro Pro Lys Pro Lys Asp Thr Leu
145                 150                 155                 160
Met Ile Ser Arg Thr Pro Glu Val Thr Cys Val Val Val Asp Val Ser
                165                 170                 175
His Glu Asp Pro Glu Val Lys Phe Asn Trp Tyr Val Asp Gly Val Glu
            180                 185                 190
Val His Asn Ala Lys Thr Lys Pro Arg Glu Glu Gln Tyr Asn Ser Thr
            195                 200                 205
Tyr Arg Val Val Ser Val Leu Thr Val Leu His Gln Asp Trp Leu Asn
210                 215                 220
Gly Lys Glu Tyr Lys Cys Lys Val Ser Asn Lys Ala Leu Pro Ala Pro
225                 230                 235                 240
Ile Glu Lys Thr Ile Ser Lys Ala Lys Gly Gln Pro Arg Glu Pro Gln
                245                 250                 255
Val Tyr Thr Leu Pro Pro Ser Arg Asp Glu Leu Thr Lys Asn Gln Val
            260                 265                 270
Ser Leu Thr Cys Leu Val Lys Gly Phe Tyr Pro Ser Asp Ile Ala Val
            275                 280                 285
Glu Trp Glu Ser Asn Gly Gln Pro Glu Asn Asn Tyr Lys Thr Thr Pro
            290                 295                 300
Pro Val Leu Asp Ser Asp Gly Ser Phe Phe Leu Tyr Ser Lys Leu Thr
305                 310                 315                 320
Val Asp Lys Ser Arg Trp Gln Gln Gly Asn Val Phe Ser Cys Ser Val
                325                 330                 335
Met His Glu Ala Leu His Asn His Tyr Thr Gln Lys Ser Leu Ser Leu
            340                 345                 350
Ser Pro Gly Lys
            355

<210> SEQ ID NO 429
<211> LENGTH: 356
<212> TYPE: PRT
<213> ORGANISM: Artificial Sequence
<220> FEATURE:
<223> OTHER INFORMATION: AS06750VH3 synthesized HCAb

<400> SEQUENCE: 429

Glu Val Gln Leu Val Glu Ser Gly Gly Gly Leu Val Gln Pro Gly Gly
1               5                   10                  15
Ser Leu Arg Leu Ser Cys Ala Ala Ser Gly Arg Thr Phe Leu Thr Tyr
                20                  25                  30
Ala Val Gly Trp Phe Arg Gln Ala Pro Gly Lys Gly Leu Glu Phe Val
            35                  40                  45
```

Ala Gly Ile Arg Trp Ser Gly Gly Tyr Thr Asp Tyr Ala Asp Ser Val
            50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
            130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
            210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
            290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 430
<211> LENGTH: 356
<212> TYPE: PRT
<213> ORGANISM: Artificial Sequence
<220> FEATURE:
<223> OTHER INFORMATION: AS06750VHa synthesized HCAb

<400> SEQUENCE: 430

Glu Val Gln Leu Val Glu Ser Gly Gly Gly Leu Val Gln Pro Gly Gly
 1               5                  10                  15

Ser Leu Arg Leu Ser Cys Thr Ala Ser Gly Arg Thr Phe Leu Thr Tyr
                 20                  25                  30

Ala Val Gly Trp Phe Arg Gln Ala Pro Gly Lys Gly Leu Glu Phe Val
             35                  40                  45

Ala Gly Ile Arg Trp Ser Gly Gly Tyr Thr Asp Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala His Arg Thr Ile Ala Thr Ile Pro Glu Lys Tyr Glu Tyr Glu
                100                 105                 110

Tyr Trp Gly Gln Gly Thr Leu Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 431
<211> LENGTH: 356
<212> TYPE: PRT
<213> ORGANISM: Artificial Sequence
<220> FEATURE:
<223> OTHER INFORMATION: AS06750VH11 synthesized HCAb

<400> SEQUENCE: 431

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Leu Thr Tyr
                20                  25                  30

Ala Val Gly Trp Phe Arg Gln Ala Pro Gly Lys Gly Arg Glu Phe Val
                35                  40                  45

Ser Gly Ile Arg Trp Ser Gly Gly Tyr Thr Asp Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala His Arg Thr Ile Ala Thr Ile Pro Glu Lys Tyr Glu Tyr Glu
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
            165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
            245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
            290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
            325                 330                 335

Met His Glu Ala Leu His Asn His Tyr Thr Gln Lys Ser Leu Ser Leu
            340                 345                 350

Ser Pro Gly Lys
        355

<210> SEQ ID NO 432
<211> LENGTH: 356
<212> TYPE: PRT
<213> ORGANISM: Artificial Sequence
<220> FEATURE:
<223> OTHER INFORMATION: AS11948A synthesized HCAb

<400> SEQUENCE: 432

Glu Val Gln Leu Val Glu Ser Gly Gly Gly Leu Val Gln Ala Gly Asp
 1               5                  10                  15

Ser Leu Arg Leu Ser Cys Val Ala Ser Gly Arg Thr Phe Val Thr Tyr
                 20                  25                  30

Gly Met Gly Trp Phe Arg Gln Ala Pro Gly Lys Glu Arg Glu Phe Val
            35                  40                  45

Ala Ala Ile Ala Trp Ser Gly Ser Met Thr Ser Tyr Gly Asp Ser Val
            50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Arg Gly Thr Gln Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 433
<211> LENGTH: 356
<212> TYPE: PRT
<213> ORGANISM: Artificial Sequence
<220> FEATURE:
<223> OTHER INFORMATION: AS11948S synthesized HCAb

<400> SEQUENCE: 433

Glu Val Gln Leu Val Glu Ser Gly Gly Gly Leu Val Gln Ala Gly Asp
1               5                   10                  15

Ser Leu Arg Leu Ser Cys Val Ala Ser Gly Arg Thr Phe Val Thr Tyr
                20                  25                  30

Gly Met Gly Trp Phe Arg Gln Ala Pro Gly Lys Glu Arg Glu Phe Val
            35                  40                  45

Ala Ala Ile Ser Trp Ser Gly Ser Met Thr Ser Tyr Gly Asp Ser Val
        50                  55                  60

Lys Gly Arg Phe Ala Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Ala Leu Gly Ala Val Val Tyr Thr Thr Arg Glu Pro Tyr Thr
               100                 105                 110

Tyr Trp Gly Arg Gly Thr Gln Val Thr Val Ser Ser Glu Pro Lys Ser
               115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
               165                 170                 175

His Glu Asp Pro Glu Val Lys Phe Asn Trp Tyr Val Asp Gly Val Glu
               180                 185                 190

Val His Asn Ala Lys Thr Lys Pro Arg Glu Glu Gln Tyr Asn Ser Thr
               195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
               245                 250                 255

Val Tyr Thr Leu Pro Pro Ser Arg Asp Glu Leu Thr Lys Asn Gln Val
               260                 265                 270

Ser Leu Thr Cys Leu Val Lys Gly Phe Tyr Pro Ser Asp Ile Ala Val
               275                 280                 285

Glu Trp Glu Ser Asn Gly Gln Pro Glu Asn Asn Tyr Lys Thr Thr Pro
               290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
               325                 330                 335

Met His Glu Ala Leu His Asn His Tyr Thr Gln Lys Ser Leu Ser Leu
               340                 345                 350

Ser Pro Gly Lys
       355

<210> SEQ ID NO 434
<211> LENGTH: 356
<212> TYPE: PRT
<213> ORGANISM: Artificial Sequence
<220> FEATURE:
<223> OTHER INFORMATION: AS11948Q synthesized HCAb

<400> SEQUENCE: 434

Glu Val Gln Leu Val Glu Ser Gly Gly Gly Leu Val Gln Ala Gly Asp
 1               5                  10                  15

Ser Leu Arg Leu Ser Cys Val Ala Ser Gly Arg Thr Phe Val Thr Tyr
                20                  25                  30

Gly Met Gly Trp Phe Arg Gln Ala Pro Gly Lys Glu Arg Glu Phe Val
                35                  40                  45

Ala Ala Ile Gln Trp Ser Gly Ser Met Thr Ser Tyr Gly Asp Ser Val
         50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110

Tyr Trp Gly Arg Gly Thr Gln Val Thr Val Ser Ser Glu Pro Lys Ser
                115                 120                 125

Cys Asp Lys Thr His Thr Cys Pro Pro Cys Pro Ala Pro Glu Leu Leu
        130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
        340                 345                 350

Ser Pro Gly Lys
        355

<210> SEQ ID NO 435
<211> LENGTH: 356
<212> TYPE: PRT
<213> ORGANISM: Artificial Sequence
<220> FEATURE:
<223> OTHER INFORMATION: AS11948QVH1 synthesized HCAb

<400> SEQUENCE: 435

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
                20                  25                  30

Gly Met Gly Trp Val Arg Gln Ala Pro Gly Lys Gly Leu Glu Trp Val
        35                  40                  45

Ser Ala Ile Gln Trp Ser Gly Ser Met Thr Ser Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 436
<211> LENGTH: 356
<212> TYPE: PRT
<213> ORGANISM: Artificial Sequence
<220> FEATURE:
<223> OTHER INFORMATION: AS11948QVH2 synthesized HCAb

<400> SEQUENCE: 436

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Leu Glu Phe Val
        35                  40                  45

Ala Ala Ile Gln Trp Ser Gly Ser Met Thr Ser Tyr Gly Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110

Tyr Trp Gly Gln Gly Thr Leu Val Thr Val Ser Ser Glu Pro Lys Ser
                115                 120                 125

Cys Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 437
<211> LENGTH: 356
<212> TYPE: PRT
<213> ORGANISM: Artificial Sequence
<220> FEATURE:
<223> OTHER INFORMATION: AS11948QVHa synthesized HCAb

<400> SEQUENCE: 437

Glu Val Gln Leu Val Glu Ser Gly Gly Gly Leu Val Gln Pro Gly Gly
 1               5                  10                  15

Ser Leu Arg Leu Ser Cys Val Ala Ser Gly Arg Thr Phe Val Thr Tyr
                 20                  25                  30

Gly Met Gly Trp Phe Arg Gln Ala Pro Gly Lys Gly Arg Glu Phe Val
                 35                  40                  45

Ser Ala Ile Gln Trp Ser Gly Ser Met Thr Ser Tyr Gly Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110

Tyr Trp Gly Gln Gly Thr Leu Val Thr Val Ser Ser Glu Pro Lys Ser
                115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 438
<211> LENGTH: 356
<212> TYPE: PRT
<213> ORGANISM: Artificial Sequence
<220> FEATURE:
<223> OTHER INFORMATION: AS11948SVH12 synthesized HCAb

<400> SEQUENCE: 438

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
                20                  25                  30

Gly Met Gly Trp Phe Arg Gln Ala Pro Gly Lys Gly Arg Glu Phe Val
            35                  40                  45

Ser Ala Ile Ser Trp Ser Gly Ser Met Thr Ser Tyr Gly Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 439
<211> LENGTH: 356
<212> TYPE: PRT
<213> ORGANISM: Artificial Sequence
<220> FEATURE:
<223> OTHER INFORMATION: AS11948SVH12M8 synthesized HCAb

<400> SEQUENCE: 439

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Ile Thr Ser Tyr Gly Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Ala Leu Gly Ala Val Val Tyr Thr Arg Glu Pro Tyr Thr
                100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 440
<211> LENGTH: 356
<212> TYPE: PRT
<213> ORGANISM: Artificial Sequence
<220> FEATURE:
<223> OTHER INFORMATION: AS11948SVH12M9 synthesized HCAb

<400> SEQUENCE: 440

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Val Thr Tyr
                20                  25                  30

Gly Met Gly Trp Phe Arg Gln Ala Pro Gly Lys Gly Arg Glu Phe Val
            35                  40                  45

-continued

Ser Ala Ile Ser Trp Ser Gly Ser Leu Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Pro Lys Ser
            115                 120                 125

Cys Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 441
<211> LENGTH: 272
<212> TYPE: PRT
<213> ORGANISM: Artificial Sequence
<220> FEATURE:
<223> OTHER INFORMATION: PD-L1

<400> SEQUENCE: 441

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
                115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu Pro Leu Ala His Pro Pro Asn Glu Arg Thr His Leu Val
210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
                260                 265                 270

<210> SEQ ID NO 442
<211> LENGTH: 220
<212> TYPE: PRT
<213> ORGANISM: Artificial Sequence
<220> FEATURE:
<223> OTHER INFORMATION: PD-L1 ECD

<400> SEQUENCE: 442

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
                35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
                115                 120                 125

Val Thr Ser Glu His Glu Leu Thr Cys Gln Ala Glu Gly Tyr Pro Lys
130                 135                 140

```
Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg
        210                 215                 220

<210> SEQ ID NO 443
<211> LENGTH: 9
<212> TYPE: PRT
<213> ORGANISM: Artificial Sequence
<220> FEATURE:
<223> OTHER INFORMATION: Peptide Linker

<400> SEQUENCE: 443

Gly Gly Gly Gly Ser Gly Gly Gly Ser
1               5

<210> SEQ ID NO 444
<211> LENGTH: 15
<212> TYPE: PRT
<213> ORGANISM: Artificial Sequence
<220> FEATURE:
<223> OTHER INFORMATION: Peptide Linker

<400> SEQUENCE: 444

Gly Gly Gly Gly Ser Gly Gly Gly Gly Ser Gly Gly Gly Gly Ser
1               5                   10                  15

<210> SEQ ID NO 445
<211> LENGTH: 15
<212> TYPE: PRT
<213> ORGANISM: Artificial Sequence
<220> FEATURE:
<223> OTHER INFORMATION: Peptide Linker

<400> SEQUENCE: 445

Glu Pro Lys Ser Ser Asp Lys Thr His Thr Ser Pro Pro Ser Pro
1               5                   10                  15
```